(12) United States Patent
Bearss et al.

(10) Patent No.: US 8,901,120 B2
(45) Date of Patent: Dec. 2, 2014

(54) SUBSTITUTED N-PHENYLPYRIMIDIN-2-AMINE ANALOGS AS INHIBITORS OF THE AXL KINASE

(75) Inventors: David J. Bearss, Alpine, UT (US); Hariprasad Vankayalapati, Draper, UT (US); Alexis Mollard, Salt Lake City, UT (US); Steven L. Warner, Sandy, UT (US); Sunil Sharma, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 169 days.

(21) Appl. No.: 13/436,910

(22) Filed: Mar. 31, 2012

(65) Prior Publication Data

US 2012/0283261 A1 Nov. 8, 2012

Related U.S. Application Data

(60) Provisional application No. 61/471,090, filed on Apr. 1, 2011.

(51) Int. Cl.
| | | |
|---|---|---|
| C07D 239/42 | (2006.01) | |
| C07D 239/48 | (2006.01) | |
| A61K 31/506 | (2006.01) | |
| C07D 401/12 | (2006.01) | |
| C07D 403/12 | (2006.01) | |

(52) U.S. Cl.
CPC ............ *C07D 239/42* (2013.01); *A61K 31/506* (2013.01); *C07D 239/48* (2013.01); *C07D 401/12* (2013.01); *C07D 403/12* (2013.01)
USPC ................... 514/235.8; 514/252.14; 514/269; 514/275; 544/122; 544/295; 544/321; 544/330

(58) Field of Classification Search
CPC ... C07D 239/42; C07D 239/48; A61K 31/506
USPC .............. 544/122, 295, 321, 330; 514/235.8, 514/252.14, 269, 275
See application file for complete search history.

(56) References Cited

U.S. PATENT DOCUMENTS

| | | | |
|---|---|---|---|
| 5,958,935 A | 9/1999 | Davis et al. .................... 514/275 |
| 7,655,649 B2 | 2/2010 | Bilodeau et al. ............ 514/227.8 |
| 7,741,330 B1 | 6/2010 | Chen et al. ................. 514/262.1 |
| 8,133,900 B2 | 3/2012 | Hood et al. .................... 514/275 |
| 8,138,199 B2 | 3/2012 | Noronha et al. .............. 514/275 |
| 8,268,850 B2 | 9/2012 | Li et al. .......................... 514/275 |
| 8,338,439 B2 | 12/2012 | Singh et al. ................... 514/275 |
| 2005/0171134 A1 | 8/2005 | Davis et al. ..................... 544/60 |
| 2008/0182852 A1* | 7/2008 | Johnson et al. .......... 514/252.14 |
| 2009/0298830 A1* | 12/2009 | Mann et al. ................. 514/235.8 |
| 2010/0190770 A1 | 7/2010 | Li et al. ..................... 514/210.21 |
| 2010/0204221 A1 | 8/2010 | Vankayalapati et al. ... 514/234.2 |

FOREIGN PATENT DOCUMENTS

| | | | |
|---|---|---|---|
| WO | WO 2007/053452 | * | 5/2007 |
| WO | WO 2012/135800 | | 10/2012 |
| WO | WO 2012/135801 | | 10/2012 |

OTHER PUBLICATIONS

Hughes et al., 4-Aryl-5-cyano-2-aminopyrimidines as VEGF-R2 inhibitors: Synthesis and biological evaluation, Bioorganic & Medicinal Chemistry Letters 17 (2007), pp. 3266-3270.*
Ulrich, Crystallization—4 Crystal Characteristics, Kirk-Othmer Encyclopedia of Chemical Technology, pp. 1-7, 2002.*
Vippagunta et al., Crystalline Solids, Advanced Drug Delivery Reviews 48 (2001), pp. 3-26.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Fry, Review: Phosphoinositide 3-kinase signaling in breast cancer: how big a role might it play?, Breast Cancer Res 2001, 3:304-312.*
Simone, Oncology: Introduction, Cecil Textbook of Medicine, 20th Edition, vol. 1, pp. 1004-101 O, 1996.*
International Search Report issued Jun. 27, 2012 by the International Searching Authority for Application PCT/US2012/031768 filed Mar. 31, 2012 and later published as WO 2012/135800 on Oct. 4, 2012 (Applicant—University of Utah Research Foundation // Inventor—David J. Bearss, et al.) (2 pages).
Written Opinion issued Jun. 27, 2012 by the International Searching Authority for Application PCT/US2012/031768 filed Mar. 31, 2012 and later published as WO 2012/135800 on Oct. 4, 2012 (Applicant—University of Utah Research Foundation // Inventor—David J. Bearss, et al.) (4 pages).
International Search Report issued Jul. 24, 2012 by the International Searching Authority for Application PCT/US2012/031772 filed Apr. 1, 2012 and later published as WO 2012/135801 on Oct. 4, 2012 (Applicant—University of Utah Research Foundation // Inventor—David J. Bearss, et al.) (2 pages).

(Continued)

*Primary Examiner* — Deepak Rao
(74) *Attorney, Agent, or Firm* — Seed IP Law Group PLLC

(57) ABSTRACT

In one aspect, the invention relates to substituted N-phenylpyrimidin-2-amine analogs, derivatives thereof, and related compounds, which are useful as inhibitors of Axl kinase; synthetic methods for making the compounds; pharmaceutical compositions comprising the compounds; and methods of using the compounds and compositions for treating disorders associated with dysfunction of the Axl kinase. This abstract is intended as a scanning tool for purposes of searching in the particular art and is not intended to be limiting of the present invention.

31 Claims, 15 Drawing Sheets

(56) References Cited

OTHER PUBLICATIONS

Written Opinion issued Jul. 24, 2012 by the International Searching Authority for Application PCT/US2012/031772 filed Apr. 1, 2012 and later published as WO 2012/135801 on Oct. 4, 2012 (Applicant—University of Utah Research Foundation // Inventor—David J. Bearss, et al.) (5 pages).

Alessi, et al., "Mechanism of Activation of Protein Kinase B by Insulin and IGF-1," The EMBO Journal, 1996. 15(23): pp. 6541-6551.

Angelillo-Scherrer, et al., "Role of Gas6 in Erythropoiesis and Anemia in Mice," J. Chin. Invest, 2008. 118(2): pp. 583-596.

Bellido-Martin and de Frutos. "Vitamin K-dependent actions of Gas6," Vitam Horm, 2008. 78: pp. 185-209.

Bellosta, et al., "Signaling Through the ARK Tyrosine Kinase Receptor Protects From Apoptosis in the Absence of Growth Stimulation," Oncogene, 1997. 15: pp. 2387-2397.

Bellosta, et al., "The Receptor Tyrosine Kinase ARK Mediates Cell Aggregation by Homophilic Binding," Molecular and Cellular Biology, 1995. 15(2): pp. 614-625.

Blume-Jensen et al., "Oncogenic Kinase Signaling," Nature, 2001. 411: pp. 355-365.

Braunger, et al., "Intracellular Signaling the Ufo/Axl Receptor Tyrosine Kinase Is Mediated Mainly by a Multi-Substrate Docking Site," Oncogene, 1997. 14(22): pp. 2619-2631.

Fridell, et al., "GAS 6 induced ASL-Mediated Chemotaxis of Vascular Smooth Muscle Cells," The Journal of Biological Chemistry, 1998. 273: pp. 7123-7126.

Fruman, et al., "Xid-like phenotypes: a B cell signalosome takes shape," Immunity, 2000. 13(1): pp. 1-3.

Gould, et al., "Gas6 Receptor Tyrosine Kinase, Mediates Flow-induced Vascular Remodeling," Journal of Thrombosis and Haemostasis, 2005. 3(4): pp. 733-741.

Graham, et al., "Cloning and mRNA Expression Analysis of a Novel Human Protooncogene, C-mer," Cell Growth and Differentiation, 1994. 5: pp. 647-657.

Green, et al., "Overexpression of the Axl Tyrosine Kinase Receptor in Cutaneous SCC-derived Cell Lines and Tumor," Journal of Cancer, 2006. 94: pp. 1446-1451.

Hafizi, et al., "Interaction of Axl Receptor Tyrosine Kinase with C1-TEN, a Novel C1 Domain-containing Protein with Homology to Tension," Biochemical and Biophysical Research Communications, 2002. 299(5): pp. 793-800.

Hafizi, et al., "Signaling and Functional Diversity Within the Axl Subfamily of receptor Tyrosine Kinase," Cytokine & Growth Factor Review, 2006. 178: pp. 295-304.

Hafizi and Dahlback, "Gas6 and protein S. Vitamin K-dependent ligands for the Axl receptor tyrosine kinase subfamily," FEBS J., 2006. 273(23): pp. 5231-5344.

Hanada, et al., "Structure, Regulation and Function of PKB/AKI—a Major Therapeutic Target," Biochim Biophys Acta, 2004. 1697(1-2): pp. 3-16.

Hendriks, "Drug Discovery: New Btk inhibitor holds promise," Nat. Chem. Biol., 2011. 7(1): pp. 4-5.

Hubbard, et al., "Protein Tyrosine Kinase Structure and Function," Annual Review of Biochemistry, 2000. 69: p. 377.

Keating, et al., "Lymphoblastic Leukemia/Lymphoma in Mice Overexpressing the Mer (Mer TK) Receptor Tyrosine Kinase," Oncogene, 2006. 25: pp. 6092-6100.

Korshunov, et al., "Axl, A Receptor Tyrosine Kinase, Mediated Flow-induced Vascular Remodeling," Circulation Research, 2006. 98: pp. 1446-1452.

Korshunov, et al., "Axl Mediates Vascular Remodeling Induced by Deoxycorticosterone Acetate Salt Hypertension," Hypertension, 2007. 50: pp. 1057-1062.

Kurosaki, "Functional dissection of BCR signaling pathways," Curr. Opin. Immunol., 2000. 12: pp. 276-281.

Lemke, et al., "Immunobiology of the TAM Receptors," Nature Reviews Immunology, 2008. 8: pp. 327-336.

Li, et al., "Axl as a Potential Therapeutic Target in Cancer, Role of Axl in Tumor Growth, Metastasis and Angiogenesis," Oncogene, 2009. 28: pp. 3442-3455.

Linger, et al., "TAM receptor tyrosine kinases: biologic functions, signaling, and potential therapeutic targeting in human cancer," Adv Cancer Res, 2008. 100: pp. 35-83.

Manfioletti, et al., "The protein Encoded by a Growth Arrest-specific Gene (GAS 6) is a New Member of the Vitamin K-Dependent Protein Related to Protein S, a Negative Coregulator in the Blood Coagulation Cascade," Molecular and Cellular Biology, 1993. 13(8): pp. 4976-4985.

Manning, et al., "Evolution of Protein Kinase Signaling from Yeast to Man," TRENDS in Biochemical Sciences, 2002. 27(1): pp. 514-520.

Mark, et al., "Rse, a Novel Receptor-type Tyrosine Kinase with Homology to Axl/Ufo, is Expressed at High Levels in the Brain," Journal of Biological Chemistry, 1994. 269: pp. 10720-10728.

Mollard, et al., "Design Synthesis and Biological Evaluation of a Series of Novel Axl Kinase Inhibitors," ACS Medicinal Chemistry Letters, 2011. 2: pp. 907-912.

Rescigno, et al., "A Putative Receptor Tyrosine Kinase With Unique Structural Topology," Oncogene, 1991. 6(10): pp. 1909-1913.

Robinson, et al., "The Protein Tyrosine Family of the Human Genome," Oncogene, 2000. 19: p. 5555.

Rothlin, et al., "TAM Receptors Are Pleiotropic Inhibitors of the Innate Immune Response," Cell, 2007. 131: pp. 1124-1136.

Sainaghi, et al., "Gas6 Induced Proliferation in Prostate Carcinoma Cell Lines Expressing the Axl Receptor," Journal of Cell Physiology, 2005. 204(1): pp. 36-44.

Sawabu, et al., "Growth Arrest-Specific Gene 6 and Axl Signaling Enhances Gastric Cancer Cell Survival Via AKT Pathway," Mol. Carcinog, 2007. 46(2): pp. 155-164.

Schaeffer, et al., "Tec family kinases in lymphocyte signaling and function," Curr. Opin. Immunol., 2000. 12(3): pp. 282-288.

Shankar, et al., "Gas6/Axl Signaling Activates the Phosphatidylinositol 3-Kinase/ALK1 Pathway to Protect Oligodendracytes From Tumor Necrosis Factor Alpha-induced Apoptosis," The Journal of Neuroscience, 2006. 26(21): pp. 5638-5648.

Sharif, et al., "Twist Mediates Suppression of Inflammation by Type I IFNs and Axl," The Journal of Experimental Medicine, 2006. 203(8): pp. 1891-1901.

Shieh, et al., "Expression of Axl in Lung Adenocarcinoma and Correlation with Tumor Progression," Neoplasia, 2005. 7(12): pp. 1058-1064.

Sun, et al., "Clinical Implications of Coexpression of Growth Arrest-specific Gene 6 and Receptor Tyrosine Kinases Axl and Sky in Human Uterine Leiomyoma," Molecular Human Reproduction, 2003. 9(11): pp. 701-707.

Vajkoczy, et al., "Dominant-negative Inhibition of the Axl Receptor Tyrosine Kinase Suppresses Brian Tumor Cell Growth and Invasion and Prolongs Survival," Proceedings of the National Academy of Sciences of the United States of America, 2006. 103(15): pp. 5799-5804.

* cited by examiner

Figure 2

Cell Viability (2-D Culture) — IC$_{50}$ Values (µM)

| | TC1 | TC2 | TC3 | TC4 | TC5 | TC6 | TC7 |
|---|---|---|---|---|---|---|---|
| PSN-1 | 0.005 | 0.061 | 0.009 | 0.003 | 0.009 | 0.003 | 0.256 |
| PANC-1 | 0.025 | 0.116 | 0.079 | 0.317 | 0.093 | 0.019 | 0.480 |
| PL45 | 0.009 | 0.020 | 0.005 | 0.005 | 0.017 | 0.005 | 0.230 |

Cell Viability (3-D Culture) — IC$_{50}$ Values (µM)

| | TC1 | TC2 | TC3 | TC4 | TC5 | TC6 | TC7 |
|---|---|---|---|---|---|---|---|
| PSN-1 | 0.073 | 0.270 | 0.218 | 0.179 | 0.074 | 0.150 | |
| PANC-1 | 0.027 | 0.055 | 0.043 | 0.036 | 0.015 | 0.044 | |
| PL45 | 0.017 | 0.026 | 0.004 | 0.006 | 0.004 | 0.036 | |

Figure 12

SUBSTITUTED N-PHENYLPYRIMIDIN-2-AMINE ANALOGS AS INHIBITORS OF THE AXL KINASE

CROSS-REFERENCE TO RELATED APPLICATIONS

This application claims the benefit of U.S. Provisional Application No. 61/471,090, filed on Apr. 1, 2011, which is incorporated herein by reference in its entirety.

BACKGROUND

The receptor tyrosine kinases represent a superfamily of transmembrane proteins that relay signals from the extracellular environment into the cell. The signals are conveyed by ligands which bind the extracellular domains of these kinases, thereby activating a signaling pathway. In this superfamily, frequently the ligand is a type of growth factor. One subfamily of kinases within this superfamily are the TAM subfamily of kinases, which comprise the tyrosine receptor kinases Axl, Tyro3 and Mer (Hafizi S and Dahlback B. Cytokine Growth Factor Rev 2006; 17: 295-304; Linger R M, et al. Adv Cancer Res 2008; 100: 35-83). This subfamily of kinases have in common a unique extracellular domain with N-terminal immunoglobulin domains and two fibronectin type III repeat structures. The structure of the fibronection type III repeats bears structural similarity to neural cell adhesion molecules (NCAMs). Although initially characterized as a single transmembrane protein, Axl can also exist as a soluble protein (sAxl) which is generated by ADAM10 (a metalloproteinase) mediated proteolysis. The role of sAxl is less well-characterized than intact, transmemberane Axl.

The natural ligand common to the TAM kinases is Gas6, a product of the growth arrest-specific gene 6 (Hafizi S and Dahlback B. FEBS J 2006; 273:5231-44; Bellido-Martin L and de Frutos P G. Vitam Horm 2008; 78:185-209.). The protein called protein S is also a potential natural ligand of the TAM kinases. Both of these proteins, Gas6 and protein S, are vitamin K-dependent proteins and share about 43% homology and several distinct protein domains. Binding of Gas6 to Axl leads to Axl autophosphorylation and activation of downstream signaling pathways including MAPK and PI3K/Akt pathways (Angelillo-Scherrer A, et al. J Clin Invest 2008; Shankar S L, et al. J Neuorosci 2006, 26: 5638-5648; Keating A K, et al. Oncogene 2006, 25:6092-6100), although the JAK/STAT pathway may be important for TAM-mediated immune responses (Rothlin C V, et al. Cell 2007, 131: 1124-1136).

The oncogenic potential of Axl was first discovered in chronic myelogenous leukemia (CML), but it has been demonstrated to play a role in the progression and metastasis of other cancer types. The increased expression of Axl and/or Axl ligand, Gash, has been shown in a number of human malignancies, including ovarian, melanoma, renal cell carcinoma, uterine leiomyoma, uterine endometrial cancer, thyroid carcinoma, gastric cancer, breast cancer, NSCLC, CML, AML, colorectal carcinoma, prostate cancer, various lymphomas, and esophageal cancer. The biochemical effects of increased expression of Axl is associated with increased oncogenic transformation, cell survival, proliferation, migration, angiogenesis, and cellular adhesion. Target validation studies of in vivo cancer models show that inhibition of Axl expression by RNAi blocked tumor growth in those models (e.g. see Li, Y. et al. Oncogene 2009, 28:3442-3455).

In addition to the association with cancer and tumorigenesis, TAM family kinases are implicated in a number of other cell and physiological functions. These include regulation of vascular smooth muscle homeostasis (Korshunov V A, et al. Hypertension 2007, 50: 1057-1062; Korshunov V A, et al. Circ Res 2006, 98: 1446-1452), platelet function, thrombus stabilization (Angelillo-Scherrer A, et al. J Clin Invest 2008, 118: 583-596; Gould W R, et al. J Thromb Haemost 2005, 3: 733-741), innate immunity (Lemke G and Rothlin CV. Nat Rev Immunol 2008, 8: 327-336) and inflammation (Rothlin C V, et al. Cell 2007, 131: 1124-1136; Sharif M N, et al. J. Exp Med 2006, 203: 1891-1901).

In summary, the Axl protein appears to have a key role in a number of human disorders, including cancer. The expression of the protein and/or the ligand is altered in these cancer cells. Thus, Axl protein is an attractive and valuable target for the discovery and development of new therapeutic agents to treat cancer and other conditions. There is a need for the design of specific and selective inhibitors for the treatment of disorders mediated and/or associated with Axl kinase.

SUMMARY

In accordance with the purpose(s) of the invention, as embodied and broadly described herein, the invention, in one aspect, relates to compounds useful as inhibitors of the PI3K/Akt pathway, compounds useful as inhibitors of Axl, methods of making same, pharmaceutical compositions comprising same, and methods of treating disorders of uncontrolled cellular proliferation using same.

Disclosed are compounds having a structure represented by a formula:

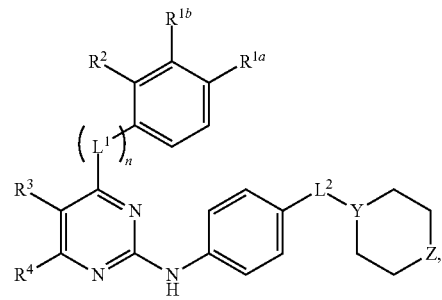

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein R⁴ is selected from hydrogen, halogen, Ar¹, C1-C6 alkyl, C3-C6 cycloalkyl, and C3-C6 heterocycloalkyl; wherein Ar¹ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof.

In various aspects, the invention relates to a compound having a structure represented by a formula:

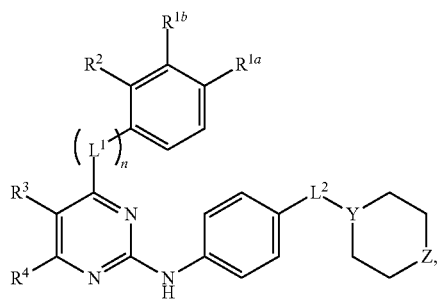

wherein L¹ is selected from O and NR⁵, wherein n is 0 or 1; wherein R⁵ is selected from is selected from hydrogen and C1-C6 alkyl; wherein L² is selected from $CH_2$ and $NCH_3$, provided that L² is $CH_2$ when Y is N; wherein Y is selected from CH or N; wherein Z is selected from O, NR⁶ and $CH_2$; wherein R⁶ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R⁷; wherein R⁷ is selected from hydrogen and C1-C6 alkyl; wherein R² is selected from hydrogen, C1-C6 alkyl, $SO_2R^8$, and (C=O)R⁸; wherein R⁸ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein R³ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein R⁴ is selected from hydrogen, halogen, Ar¹, C1-C6 alkyl, C3-C6 cycloalkyl, and C3-C6 heterocycloalkyl; wherein Ar¹ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof.

Also disclosed are pharmaceutical compositions comprising an effective amount of a disclosed compound and a pharmaceutically acceptable carrier.

Also disclosed are synthetic methods comprising the steps of: providing a first compound having a structure represented by a formula:

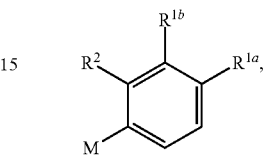

wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R⁷; wherein R⁷ is selected from hydrogen and C1-C6 alkyl; wherein R² is selected from hydrogen, C1-C6 alkyl, $SO_2R^8$, and (C=O)R⁸; wherein R⁸ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein M is selected from:

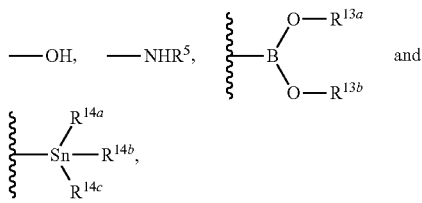

wherein each of $R^{13a}$ and $R^{13b}$ is independently selected from hydrogen, and C1-C6 alkyl; or $R^{13a}$ and $R^{13b}$ are covalently bonded and, together with the intermediate atoms, comprise an optionally substituted heterocyclic ring; and wherein each of $R^{14a}$, $R^{14b}$, and $R^{14c}$ is independently C1-C6 alkyl; and coupling with a second compound having a structure represented by a formula:

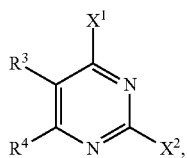

wherein R³ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein R⁴ is selected from hydrogen, halogen, Ar¹, C1-C6 alkyl, C3-C6 cycloalkyl, and C3-C6 heterocycloalkyl; wherein Ar¹ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino; wherein R$^{12}$ is selected from C1-C6 alkyl and C3-C6 cycloalkyl; wherein X¹ is halide or pseudohalide; wherein X² is halide, pseudohalide, or a group having a structure represented by the formula:

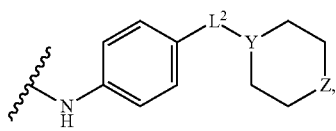

wherein L² is selected from CH$_2$ and NCH$_3$, provided that L² is CH$_2$ when Y is N; wherein Y is selected from CH or N; wherein Z is selected from O, NR$^6$ and CH$_2$; wherein R$^6$ is selected from hydrogen and CH$_3$; wherein coupling is performed for a time and at a temperature sufficient to provide a product having a structure represented by a formula:

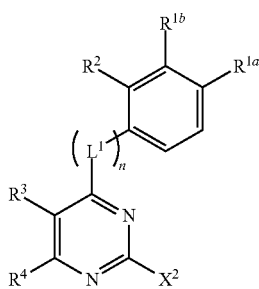

wherein L¹ is selected from O and NR$^5$, wherein n is 0 or 1; wherein R$^5$ is selected from is selected from hydrogen and C1-C6 alkyl.

Also disclosed are synthetic methods comprising the steps of providing a compound having a structure represented by a formula:

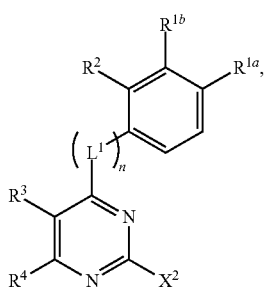

wherein L¹ is selected from O and NR$^5$, wherein n is 0 or 1; wherein R$^5$ is selected from is selected from hydrogen and C1-C6 alkyl; wherein each of R$^{1a}$ and R$^{1b}$ is independently selected from hydrogen, halogen, OH, CN, SO$_2$CH$_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R$^7$; wherein R$^7$ is selected from hydrogen and C1-C6 alkyl; wherein R² is hydrogen; wherein R³ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; wherein R$^4$ is selected from hydrogen, halogen, Ar¹, C1-C6 alkyl, C3-C6 cycloalkyl, and C3-C6 heterocycloalkyl; wherein Ar¹ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino; wherein R$^{12}$ is selected from C1-C6 alkyl and C3-C6 cycloalkyl; and wherein X² is halide, pseudohalide, or a group having a structure represented by the formula:

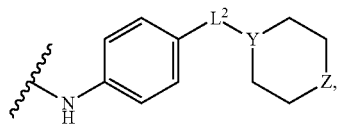

wherein L² is selected from CH$_2$ and NCH$_3$, provided that L² is CH$_2$ when Y is N; wherein Y is selected from CH or N; wherein Z is selected from O, NR$^6$ and CH$_2$; wherein R$^6$ is selected from hydrogen and CH$_3$; halosulfonation to provide a compound having a structure represented by a formula:

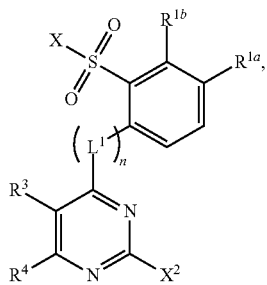

wherein X is halogen.

Also disclosed are synthetic methods comprising the steps of: providing a compound having a structure represented by a formula:

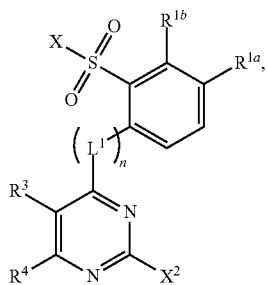

wherein L¹ is selected from O and NR$^5$, wherein n is 0 or 1; wherein R$^5$ is selected from is selected from hydrogen and C1-C6 alkyl; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)$R^7$; wherein $R^7$ is selected from hydrogen and C1-C6 alkyl; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; and wherein $X^2$ is halide, pseudohalide, or a group having a structure represented by the formula:

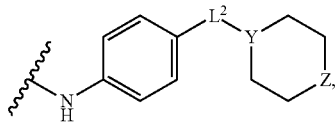

wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; reacting the compound with an amine having a structure represented by a formula:

wherein $R^{10}$ is selected from hydrogen, C1-C6 alkyl, and C3-C6 cycloalkyl; and wherein $R^{11}$ is selected from hydrogen and C1-C6 alkyl; or wherein $R^{10}$ and $R^{11}$ are covalently bonded and, together with the intermediate nitrogen, comprise an optionally substituted 3-7 membered heterocycloalkyl ring; thereby providing a product having a structure represented by a formula:

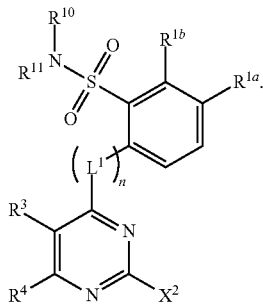

Also disclosed are synthetic methods comprising the steps of: providing a first compound having a structure represented by a formula:

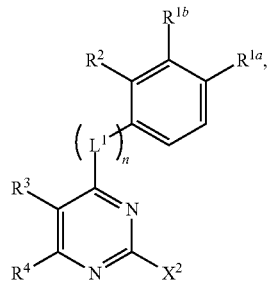

wherein $L^1$ is selected from O and $NR^5$, wherein n is 0 or 1; wherein $R^5$ is selected from is selected from hydrogen and C1-C6 alkyl; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)$R^7$; wherein $R^7$ is selected from hydrogen and C1-C6 alkyl; wherein $R^2$ is selected from hydrogen, C1-C6 alkyl, $SO_2R^8$, and (C=O)$R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; and wherein $X^2$ is halide or pseudohalide; reacting the compound with an amine having a structure represented by a formula:

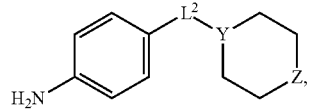

in the presence of a palladium(0) catalyst for a time and at a temperature sufficient to provide a product having a structure represented by a formula:

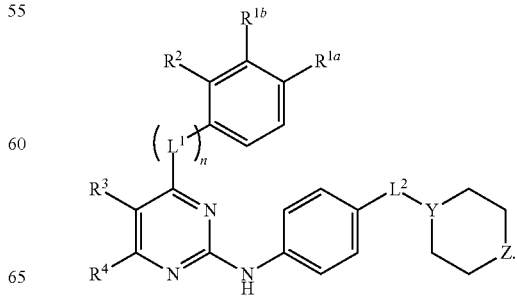

Also disclosed are the products of the disclosed methods.

Also disclosed are pharmaceutical compositions comprising a therapeutically effective amount of the product of a disclosed method and a pharmaceutically acceptable carrier.

Also disclosed are methods for the treatment of a disorder of uncontrolled cellular proliferation disorder in a mammal, the method comprising the step of administering to the mammal an effective amount of least one compound having a structure represented by a formula:

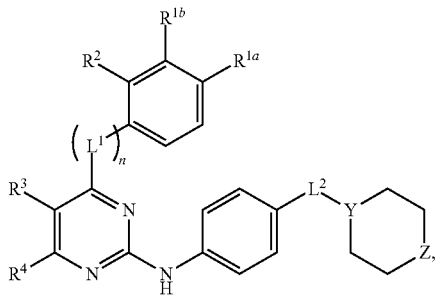

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof.

Also disclosed are methods for decreasing kinase activity in a mammal, the method comprising the step of administering to the mammal a therapeutically effective amount of at least one compound having a structure represented by a formula:

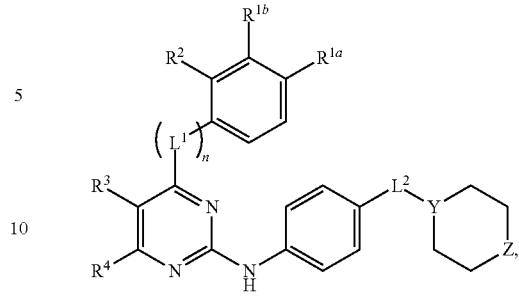

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof.

Also disclosed are methods for decreasing kinase activity in at least one cell, the method comprising the step of contacting the at least one cell with an effective amount of least one compound having a structure represented by a formula:

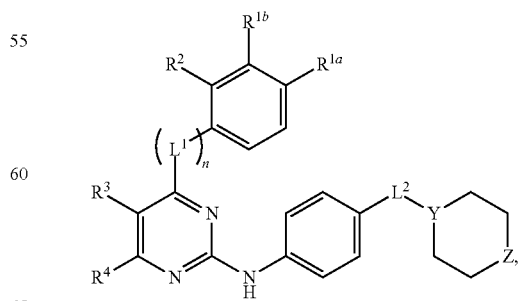

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof.

Also disclosed are methods for manufacturing a medicament comprising combining at least one disclosed compound or at least one product of a disclosed method with a pharmaceutically acceptable carrier or diluent.

Also disclosed are uses of a disclosed compound or a disclosed product in the manufacture of a medicament for the treatment of a disorder associated with a kinase dysfunction.

Also disclosed are kits comprising at least one compound having a structure represented by a formula:

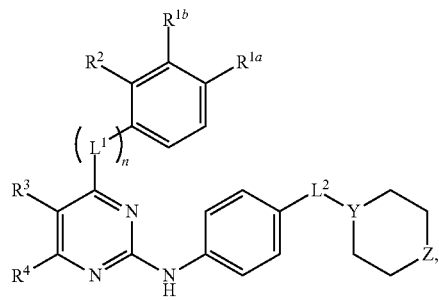

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof; and one or more of: (a) at least one agent known to increase kinase activity; (b) at least one agent known to decrease kinase activity; (c) at least one agent known to treat a disorder of uncontrolled cellular proliferation; or (d) instructions for treating a disorder associated with uncontrolled cellular proliferation.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 2 shows a multiple sequence alignment used to develop a homology model of Axl kinase.

FIG. 12 shows representative data on inhibition of cell viability by representative disclosed compounds.

Figure 1:
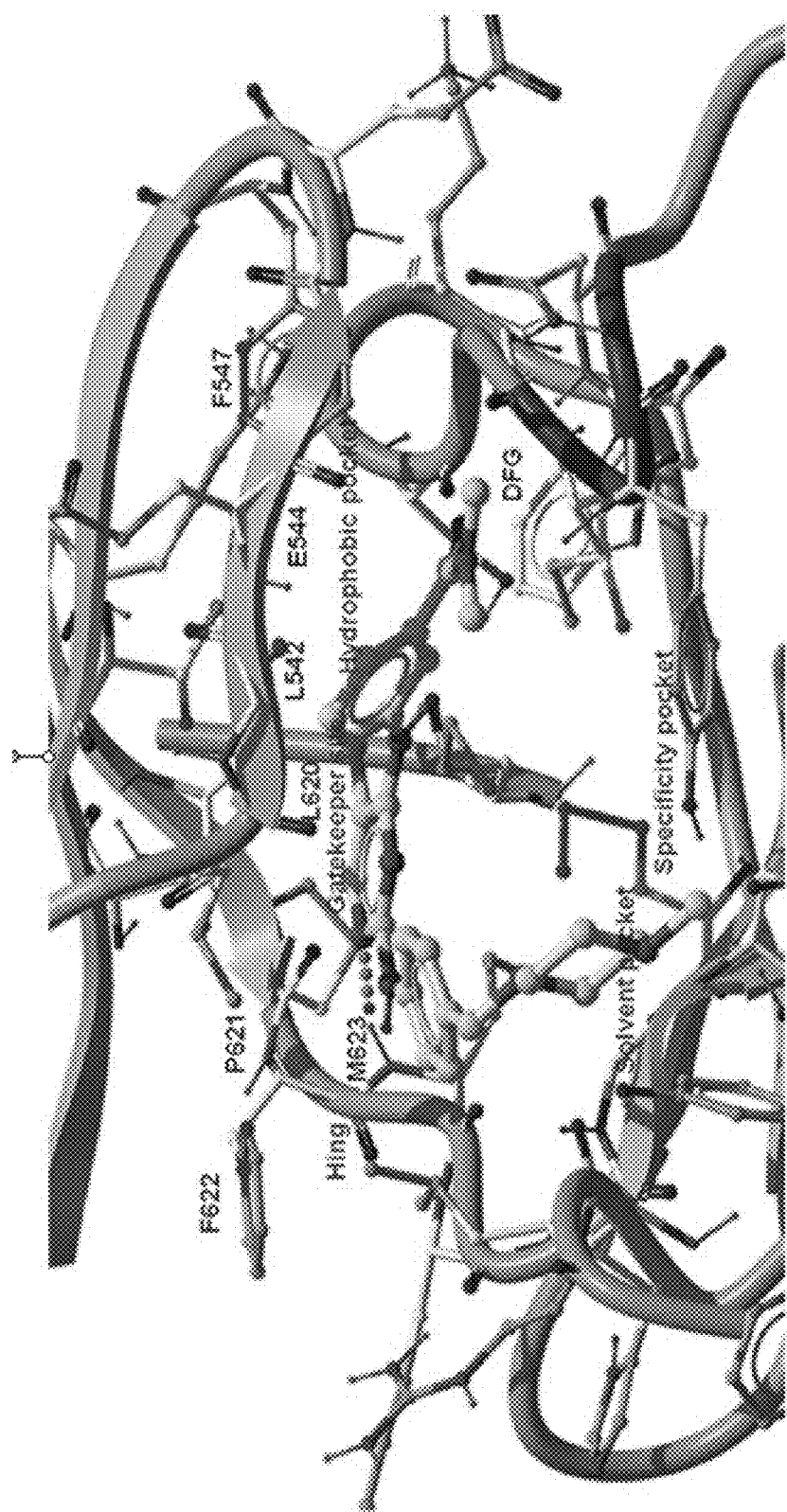
FIG. 1 shows a docking study for compounds of the present invention with a homology model of Axl kinase.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound 1f given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the terms "Axl," "AXL," "receptor tyrosine kinase Axl," and "AXL receptor tyrosine kinase" can be used interchangeably and refer to a protein kinase encoded by the AXL gene, which has a gene map locus of 19q13.1-q13.2. The larger isoform of Axl has 894 amino acids, inclusive of the signal peptide. There are two isoforms of the protein product resulting from mRNA splice isoforms ("isoform long" and "isoform short"). The EC number for this kinase is 2.7.10.1. The term Axl is inclusive of the splice isoforms, and also is inclusive such alternative designations as tyrosine-protein kinase receptor UFO, Axl oncogene, Axl protooncogene, AXL receptor tyrosine kinase, AXL transforming sequence/gene, UFO, oncogene AXL, and JTK11 by those skilled in the art.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of a disorder of uncontrolled cellular proliferation associated with a protein kinase dysfunction prior to the administering step. In some aspects of the disclosed method, the subject has been diagnosed with a need for inhibition of a protein kinase prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder of uncontrolled cellular proliferation" means having been subjected to a physical examination by a person of skill, for example, a physician, and found to have a condition that can be diagnosed or treated by a compound or composition that can inhibit a protein kinase. As a further example, "diagnosed with a need for inhibition of a protein kinase" refers to having been subjected to a physical examination by a person of skill, for example, a physician, and found to have a condition characterized by a protein kinase dysfunction. Such a diagnosis can be in reference to a disorder, such as a disorder of uncontrolled cellular proliferation, cancer and the like, as discussed herein. For example, the term "diagnosed with a need for inhibition of protein kinase activity" refers to having been subjected to a physical examination by a person of skill, for example, a physician, and found to have a condition that can be diagnosed or treated by inhibition of protein kinase activity. For example, "diagnosed with a need for treatment of one or more disorders of uncontrolled cellular proliferation associated with a protein kinase dysfunction" means having been subjected to a physical examination by a person of skill, for example, a physician, and found to have one or more disorders of uncontrolled cellular proliferation associated with a protein kinase dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a dysfunction of protein kinase activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target protein kinase, or other biological entity together in such a manner that the compound can affect the activity of the target (e.g., spliceosome, cell, etc.), either directly; i.e., by interacting with the target itself, or indirectly; i.e., by interacting with another molecule, cofactor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14 th edition), the Physicians' Desk Reference (64 th edition), and The Pharmacological Basis of Therapeutics (12 th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$EC_{50}$," is intended to refer to the concentration of a substance (e.g., a compound or a drug) that is required for 50% agonism or activation of a biological process, or component of a process, including a protein, subunit, organelle, ribonucleoprotein, etc. In one aspect, an $EC_{50}$ can refer to the concentration of a substance that is required for 50% agonism or activation in vivo, as further defined elsewhere herein. In a further aspect, $EC_{50}$ refers to the concentration of agonist or activator that provokes a response halfway between the baseline and maximum response.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, an $IC_{50}$ can refer to the concentration of a substance that is required for 50% inhibition in vivo or the inhibition is measured in vitro, as further defined elsewhere herein. Alternatively, $IC_{50}$ refers to the half maximal (50%) inhibitory concentration (IC) of a substance. The inhibition can be measured in a cell-line such as K562, MCF-7, PL-45, PANC-1, PSN-1, HepG2, or A549 cells. In a yet further aspect, the inhibition is measured in a cell-line, e.g. HEK-293 or HeLa, transfected with a mutant or wild-type mammalian protein kinase, e.g. Axl.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

For example, a "C1-C3 alkyl" group can be selected from methyl, ethyl, n-propyl, i-propyl, and cyclopropyl, or from a subset thereof. In certain aspects, the "C1-C3 alkyl" group can be optionally further substituted. As a further example, a "C1-C4 alkyl" group can be selected from methyl, ethyl, n-propyl, i-propyl, cyclopropyl, n-butyl, i-butyl, s-butyl, t-butyl, and cyclobutyl, or from a subset thereof. In certain aspects, the "C1-C4 alkyl" group can be optionally further substituted. As a further example, a "C1-C6 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, and cyclohexane, or from a subset thereof. In certain aspects, the "C1-C6 alkyl" group can be optionally further substituted. As a further example, a "C1-C8 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, and cyclooctane, or from a subset thereof. In certain aspects, the "C1-C8 alkyl" group can be optionally further substituted. As a further example, a "C1-C12 alkyl" group can be selected from methyl, ethyl, n-propyl, i-propyl, cyclopropyl, n-butyl, i-butyl, s-butyl, t-butyl, cyclobutyl, n-pentyl, i-pentyl, s-pentyl, t-pentyl, neopentyl, cyclopentyl, n-hexyl, i-hexyl, 3-methylpentane, 2,3-dimethylbutane, neohexane, cyclohexane, heptane, cycloheptane, octane, cyclooctane, nonane, cyclononane, decane, cyclodecane, undecane, cycloundecane, dodecane, and cyclododecane, or from a subset thereof. In certain aspects, the "C1-C12 alkyl" group can be optionally further substituted.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. The term "cyanoalkyl" specifically refers to an alkyl group that is substituted with one or more cyano groups. When "alkyl" is used in one instance and a specific term such as "calkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The cycloalkyl group can be substituted or unsubstituted. The cycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The cycloalkenyl group can be substituted or unsubstituted. The cycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The cycloalkynyl group can be substituted or unsubstituted. The cycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2)π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formulas —NH(-alkyl) and —N(-alkyl)$_2$, and where alkyl is as described herein. The alkyl group can be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like, up to and including a C1-C24 alkyl. Representative examples include, but are not limited to, methylamino group, ethylamino group, propylamino group, isopropylamino group, butylamino group, isobutylamino group, (sec-butyl) amino group, (tert-butyl)amino group, pentylamino group, isopentylamino group, (tert-pentyl)amino group, hexylamino group, N-ethyl-N-methylamino group, N-methyl-N-propylamino group, and N-ethyl-N-propylamino group. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group, and the like.

The term "monoalkylamino" as used herein is represented by the formula —NH(-alkyl), where alkyl is as described herein. The alkyl group can be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like, up to and including a C1-C24 alkyl. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$, where alkyl is as described herein. The alkyl group can be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like, up to and including a C1-C24 alkyl. It is understood that each alkyl group can be independently varied, e.g. as in the representative compounds such as N-ethyl-N-methylamino group, N-methyl-N-propylamino group, and N-ethyl-N-propylamino group. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group, and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O) C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted, and the heteroaryl group can be monocyclic, bicyclic or multicyclic aromatic ring. The heteroaryl group can be substituted with one or more groups including, but not limited to, alkyl, cycloalkyl, alkoxy, amino, ether, halide, hydroxy, nitro, silyl, sulfo-oxo, or thiol as described herein. It is understood that a heteroaryl group may be bound either through a heteroatom in the ring, where chemically possible, or one of carbons comprising the heteroaryl ring.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Non-limiting examples of heteroaryl rings include furyl, pyrrolyl, pyrazolyl, imidazolyl, triazolyl, pyridyl, pyridazinyl, pyrimidinyl, pyrazinyl, azepinyl, triazinyl, thienyl, oxazolyl, thiazolyl, oxadiazolyl, oxatriazolyl, oxepinyl, thiepinyl, diazepinyl, benzofuranyl, thionapthene, indolyl, benzazolyl, pyranopyrrolyl, isoindazolyl, indoxazinyl, benzoxazolyl, quinolinyl, isoquinolinyl, benzodiazonyl, naphthyridinyl, benzothienyl, pyridopyridinyl, acridinyl, carbazolyl and purinyl rings.

The term "monocyclic heteroaryl," as used herein, refers to a monocyclic ring system which is aromatic and in which at least one of the ring atoms is a heteroatom. Monocyclic heteroaryl groups include, but are not limited to, the following exemplary groups: pyridine, pyrimidine, furan, thiophene, pyrrole, isoxazole, isothiazole, pyrazole, oxazole, thiazole, imidazole, oxadiazole, including, 1,2,3-oxadiazole, 1,2,5-oxadiazole and 1,3,4-thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3, 4-tetrazole and 1,2,4,5-tetrazole, pyridazine, pyrazine, triazine, including 1,2,4-triazine and 1,3,5-triazine, tetrazine, including 1,2,4,5-tetrazine, and the like. Monocyclic heteroaryl groups are numbered according to standard chemical nomenclature.

The term "bicyclic heteroaryl," as used herein, refers to a ring system comprising a bicyclic ring system in which at least one of the two rings is aromatic and at least one of the two rings contains a heteroatom. Bicyclic heteroaryl encompasses ring systems wherein an aromatic ring is fused with another aromatic ring, or wherein an aromatic ring is fused with a non-aromatic ring. Bicyclic heteroaryl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Examples of bicyclic heteroaryl groups include without limitation indolyl, isoindolyl, indolyl, indolinyl, indolizinyl, quinolinyl, isoquinolinyl, benzofuryl, bexothiophenyl, indazolyl, benzimidazolyl, benzothiazinyl, benzothiazolyl, purinyl, quinolizyl, quinolyl, isoquinolyl, cinnolinyl, phthalazinyl, quinazolizinyl, quinoxalyl, naphthyridinyl, and pteridyl. Bicyclic heteroaryls are numbered according to standard chemical nomenclature.

The term "heterocycloalkyl" as used herein refers to an aliphatic, partially unsaturated or fully saturated, 3- to 14-membered ring system, including single rings of 3 to 8 atoms and bi- and tricyclic ring systems where at least one of the carbon atoms of the ring is replaced with a heteroatom such as, but not limited to, nitrogen, oxygen, sulfur, or phosphorus. A heterocycloalkyl can include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, the following exemplary groups: pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. The term heterocycloalkyl group can also be a C2 heterocycloalkyl, C2-C3 heterocycloalkyl, C2-C4 heterocycloalkyl, C2-C5 heterocycloalkyl, C2-C6 heterocycloalkyl, C2-C7 heterocycloalkyl, C2-C8 heterocycloalkyl, C2-C9 heterocycloalkyl, C2-C10 heterocycloalkyl, C2-C11 heterocycloalkyl, and the like up to and including a C2-C14 heterocycloalkyl. For example, a C2 heterocycloalkyl comprises a group which has two carbon atoms and at least one heteroatom, including, but not limited to, aziridinyl, diazetidinyl, oxiranyl, thiiranyl, and the like. Alternatively, for example, a C5 heterocycloalkyl comprises a group which has five carbon atoms and at least one heteroatom, including, but not limited to, piperidinyl, tetrahydropyranyl, tetrahydrothiopyranyl, diazepanyl, and the like. It is understood that a heterocycloalkyl group may be bound either through a heteroatom in the ring, where chemically possible, or one of carbons comprising the heterocycloalkyl ring. The heterocycloalkyl group can be substituted or unsubstituted. The heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "hydroxyl" or "hydroxyl," as used herein can be used interchangeably and refers to a group represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido," as used herein can be used interchangeably and refers to a group represented by the formula —$N_3$.

The term "nitro" as used herein is represented by the formula —$NO_2$.

The term "nitrile" or "cyano," as used herein can be used interchangeably and refers to a group represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R^{\circ}$; —$(CH_2)_{0-4}OR^{\circ}$; —$O(CH_2)_{0-4}R^{\circ}$, —O—$(CH_2)_{0-4}C(O)OR^{\circ}$; —$(CH_2)_{0-4}$; —$CH(OR^{\circ})_2$; —$(CH_2)_{0-4}SR^{\circ}$; —$(CH_2)_{0-4}Ph$, which may be substituted with $R^{\circ}$; —$(CH_2)_{0-4}O(CH_2)_{0-1}Ph$ which may be substituted with $R^{\circ}$; —CH=CHPh, which may be substituted with $R^{\circ}$; —$(CH_2)_{0-4}O(CH_2)_{0-1}$-pyridyl which may be substituted with $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)N(R^{\circ})_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —C(S)$R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}OC(O)R^{\circ}$; —$OC(O)(CH_2)_{0-4}SR$—, —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —$SC(S)SR^{\circ}$, —$(CH_2)_{0-4}OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; $SiR^{\circ}_3$; —$(C_{1-4}$ straight or branched alkylene)O—$N(R^{\circ})_2$; or —$(C_{1-4}$ straight or branched)alkylene)C(O)O—$N(R^{\circ})_2$, wherein each $R^{\circ}$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —$O(haloR^{\bullet})$, —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —$(C_{1-4}$ straight or branched alkylene)$C(O)OR^{\bullet}$, or —$SSR^{\bullet}$ wherein each $R^{\bullet}$ is unsubstituted or where preceded by "halo" is substituted only with one or more halogens, and is independently selected from $C_1$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include =O and =S.

Suitable divalent substituents on a saturated carbon atom of an "optionally substituted" group include the following: =O, =S, =$NNR^*_2$, =$NNHC(O)R^{\bullet}$, =$NNHC(O)OR^{\bullet}$, =$NNHS(O)_2R^{\bullet}$, =$NR^{\bullet}$, =$NOR^{\bullet}$, —$O(C(R^*_2))_{2-3}O$—, or —$S(C(R^*_2))_{2-3}S$—, wherein each independent occurrence of $R^{\bullet}$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^{\bullet}$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^{\bullet}$ include halogen, —$R^{\bullet}$, -(halo$R^{\bullet}$), —OH, —$OR^{\bullet}$, —$O(haloR^{\bullet})$, —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^{\dagger}$, —$NR^{\dagger}_2$, —$C(O)R^{\dagger}$, —$C(O)OR^{\dagger}$, —$C(O)C(O)R^{\dagger}$, —$C(O)CH_2C(O)R^{\dagger}$, —$S(O)_2R^{\dagger}$, —$S(O)_2NR^{\dagger}_2$, —$C(S)NR^{\dagger}_2$, —$C(NH)NR^{\dagger}_2$, or —$N(R^{\dagger})S(O)_2R^{\dagger}$; wherein each $R^{\dagger}$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^{\bullet}$ are independently halogen, —$R^{\bullet}$, -(halo$R^{\bullet}$), —OH, —$OR^{\bullet}$, —$O(haloR^{\bullet})$, —CN, —C(O)OH, —$C(O)OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides—including chloro, bromo, and iodo—and pseudohalides (sulfonate esters)—including triflate, mesylate, tosylate, and brosylate. It is also contemplated that a hydroxyl moiety can be converted into a leaving group via Mitsunobu reaction.

The term "protecting group" means a group which protects one or more functional groups of a compound giving rise to a protected derivative of the specified compound. Functional groups which may be protected include, by way of example, amino groups, hydroxyl groups, and the like. Protecting groups are well-known to those skilled in the art and are described, for example, in T. W. Greene and G. M. Wuts, Protecting Groups in Organic Synthesis, Third Edition, Wiley, New York, 1999, and references cited therein.

The term "amino-protecting group" means a protecting group suitable for preventing undesired reactions at an amino group, include, but are not limited to, tert-butoxycarbonyl (BOC), trityl (Tr), benzyloxycarbonyl (Cbz), 9-fluorenylmethoxycarbonyl (FMOC), formyl, trimethylsilyl (TMS), tert-butyldimethylsilyl (TBS), benzyl, p-methoxybenzyl, p-fluorobenzyl, p-chlorobenzyl, p-bromobenzyl, diphenylmethyl naphtylmethyl, and the like.

The term "hydroxyl-protecting group" means a protecting group suitable for preventing undesirable reactions at a hydroxyl group. Representative hydroxyl-protecting groups include, but are not limited to, silyl groups including tri(1-6C)-alkylsilyl groups, such as trimethylsilyl (TMS), triethylsilyl (TES), tert-butyldimethylsilyl (TBS), and the like; esters (acyl groups) including (1-6C)-alkanoyl groups, such as formyl, acetyl, and the like; arylmethyl groups, such as benzyl (Bn), p-methoxybenzyl (PMB), 9-fluorenylmethyl (Fm), diphenylmethyl (benzhydryl, DPM), and the like.

The terms "hydrolysable group" and "hydrolysable moiety" refer to a functional group capable of undergoing hydrolysis, e.g., under basic or acidic conditions. Examples of hydrolysable residues include, without limitatation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

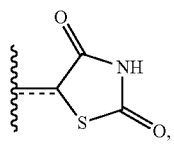

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound. For example, a compound prefixed with (−) or l meaning that the compound is levorotatory or a compound prefixed with (+) or d is dextrorotatory. For a given chemical structure, these compounds, called stereoisomers, are identical except that they are non-superimposable minor images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labelled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $14_C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures below, by substituting a readily available isotopically labelled reagent for a non-isotopically labelled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

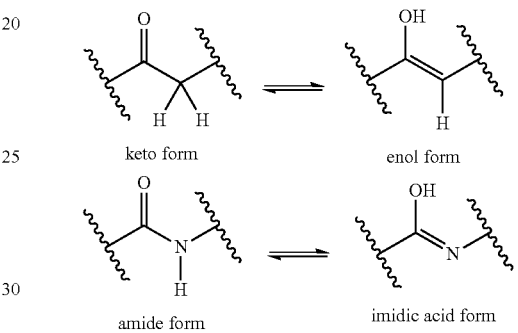

keto form             enol form amide form            imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

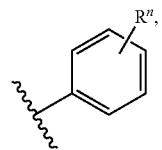

which is understood to be equivalent to a formula:

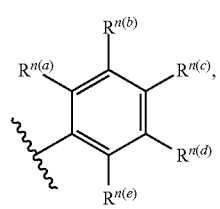

wherein n is typically an integer. That is, R″ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C—F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the compounds are useful as inhibitors of protein kinases. In a still further aspect, the compound exhibits inhibition of a protein kinase selected from c-abl oncogene 1 kinase, c-abl oncogene 1 kinase (T315I form), ALK tyrosine kinase receptor, aurora kinase A, AXL receptor tyrosine kinase, cyclin-dependent kinase 1, cyclin-dependent kinase 2, serine/threonine-protein kinase Chk1, macrophage colony-stimulating factor 1 receptor kinase, ephrin type-A receptor 1 kinase, tyrosine-protein kinase Fer, tyrosine-protein kinase Fes/Fps, fibroblast growth factor receptor 1, tyrosine-protein kinase Fgr, insulin-like growth factor 1 receptor, macrophage-stimulating protein receptor kinase, proto-oncogene tyrosine-protein kinase receptor Ret, proto-oncogene tyrosine-protein kinase ROS, proto-oncogene tyrosine-protein kinase Src, proto-oncogene tyrosine-protein kinase Yes, PTK2B protein tyrosine kinase 2 beta, serine/threonine-protein kinase MST4, serine/threonine-protein kinase PAK 4, yyrosine-protein kinase JAK1, tyrosine-protein kinase JAK2, tyrosine-protein kinase JAK3, tyrosine-protein kinase Lck, tyrosine-protein kinase Lyn, tyrosine-protein kinase Mer, tyrosine-protein kinase SYK, vascular endothelial growth factor receptor 2, and vascular endothelial growth factor receptor 3. In a yet further aspect, the compound exhibits inhibition of receptor tyrosine kinase Axl ("Axl").

In a further aspect, the invention relates to compounds useful as inhibitors of the PI3K/Akt pathway. In a yet further aspect, the compound exhibits inhibition of phosphorylation of Akt in a cell.

In one aspect, the compounds of the invention are useful in the treatment of disorders of uncontrolled cellular proliferation. In a further aspect, the disorder of uncontrolled cellular proliferation is a cancer or a tumor. In a still further aspect, the disorder of uncontrolled cellular proliferation is associated with a dysfunction in the PI3K/Akt pathway and other diseases in which an Axl dysfunction is involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

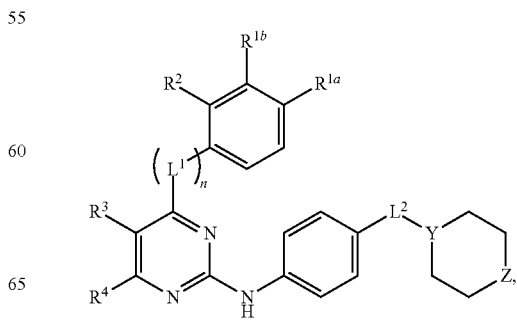

wherein L¹ is selected from O and NR⁵, wherein n is 0 or 1; wherein R⁵ is selected from is selected from hydrogen and C1-C6 alkyl; wherein L² is selected from CH₂ and NCH₃, provided that L² is CH₂ when Y is N; wherein Y is selected from CH or N; wherein Z is selected from O, NR⁶ and CH₂; wherein R⁶ is selected from hydrogen and CH₃; wherein each of R¹ᵃ and R¹ᵇ is independently selected from hydrogen, halogen, OH, CN, SO₂CH₃, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R⁷; wherein R⁷ is selected from hydrogen and C1-C6 alkyl; wherein R² is selected from hydrogen, C1-C6 alkyl, SO₂R⁸, and (C=O)R⁸; wherein R⁸ is selected from hydrogen, C1-C6 alkyl, C3-C6 cycloalkyl, C3-C6 heterocycloalkyl, and NR¹⁰R¹¹; wherein R¹⁰ is selected from hydrogen, C1-C6 alkyl, and C3-C6 cycloalkyl; and wherein R¹¹, when present, is selected from hydrogen and C1-C6 alkyl; or R¹⁰ and R¹¹ are covalently bonded and, together with the intermediate nitrogen, comprise an optionally substituted 3-7 membered heterocycloalkyl ring; wherein R³ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein R⁴ is selected from hydrogen, halogen, Ar¹, C1-C6 alkyl, C3-C6 cycloalkyl, and C3-C6 heterocycloalkyl; wherein Ar¹ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, SO₂R¹², C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, SO₂R¹², C1-C3 alkyl, C1-C3 alkylamine, and C1-C3 dialkylamino; wherein R¹² is selected from C1-C6 alkyl and C3-C6 cycloalkyl; or a pharmaceutically acceptable salt, hydrate, solvate, or polymorph thereof.

In various aspects, the invention relates to a compound having a structure represented by a formula:

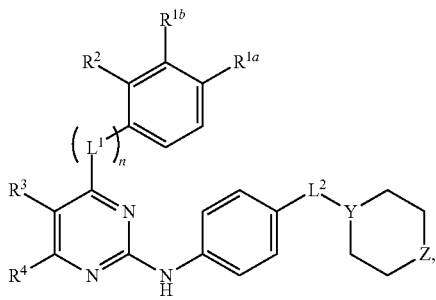

wherein L¹ is selected from O and NR⁵, wherein n is 0 or 1; wherein R⁵ is selected from is selected from hydrogen and C1-C6 alkyl; wherein L² is selected from CH₂ and NCH₃, provided that L² is CH₂ when Y is N; wherein Y is selected from CH or N; wherein Z is selected from O, NR⁶ and CH₂; wherein R⁶ is selected from hydrogen and CH₃; wherein each of R¹ᵃ and R¹ᵇ is independently selected from hydrogen, halogen, OH, CN, SO₂CH₃, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R⁷; wherein R⁷ is selected from hydrogen and C1-C6 alkyl; wherein R² is selected from hydrogen, C1-C6 alkyl, SO₂R⁸, and (C=O)R⁸; wherein R⁸ is selected from hydrogen, C1-C6 alkyl, C3-C6 cycloalkyl, C3-C6 heterocycloalkyl, and NR¹⁰R¹¹; wherein R¹⁰ is selected from hydrogen, C1-C6 alkyl, and C3-C6 cycloalkyl; and wherein R¹¹, when present, is selected from hydrogen and C1-C6 alkyl; or R¹⁰ and R¹¹ are covalently bonded and, together with the intermediate nitrogen, comprise an optionally substituted 3-7 membered heterocycloalkyl ring; wherein R³ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein R⁴ is selected from hydrogen, halogen, Ar¹, C1-C6 alkyl, C3-C6 cycloalkyl, and C3-C6 heterocycloalkyl; wherein Ar¹ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, SO₂R¹², C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, SO₂R¹², C1-C3 alkyl, C1-C3 alkylamine, and C1-C3 dialkylamino; wherein R¹² is selected from C1-C6 alkyl and C3-C6 cycloalkyl; or a pharmaceutically acceptable salt, hydrate, solvate, or polymorph thereof.

In one aspect, n is 0 or 1. In a further aspect, n is 0. In a further aspect, n is 1.

In a further aspect, the compound has a structure represented by a formula:

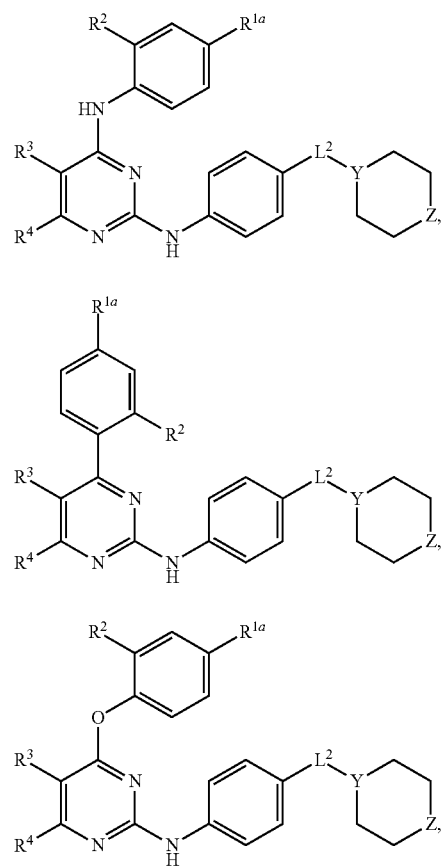

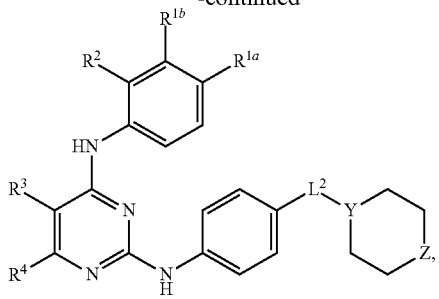
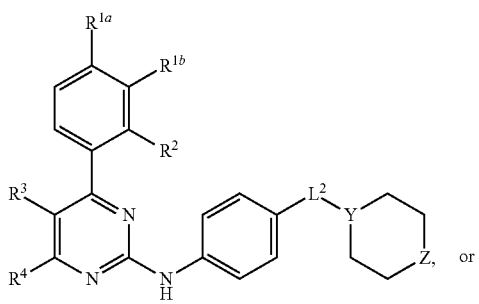
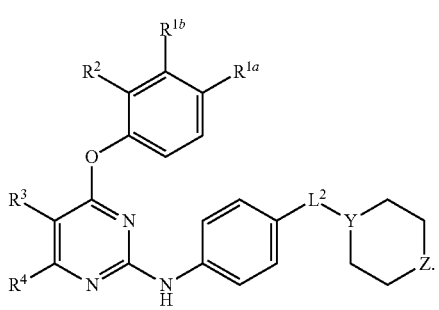
In a further aspect, the compound has a structure represented by a formula:
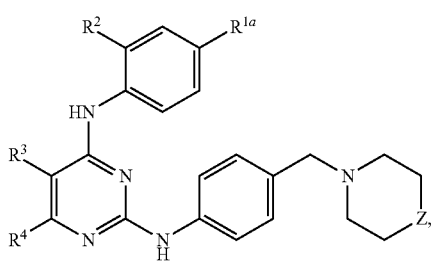
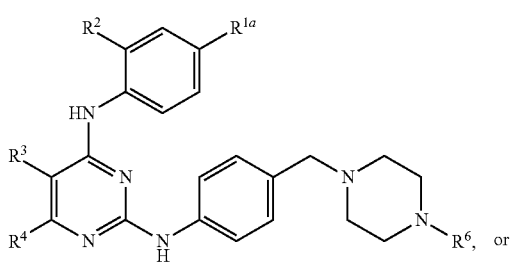
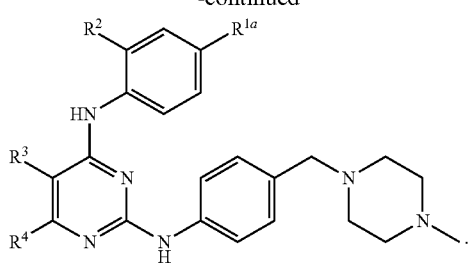
In a further aspect, the compound has a structure represented by a formula:
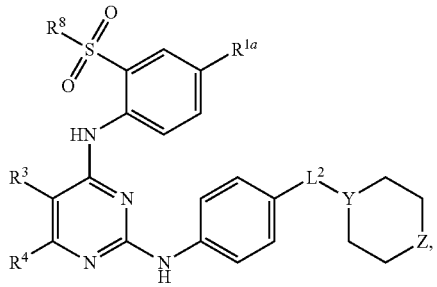
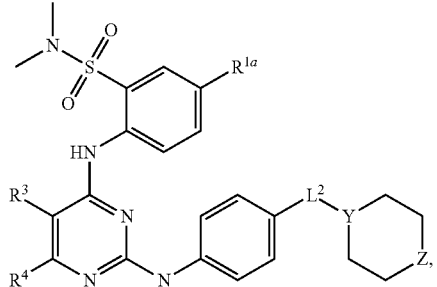
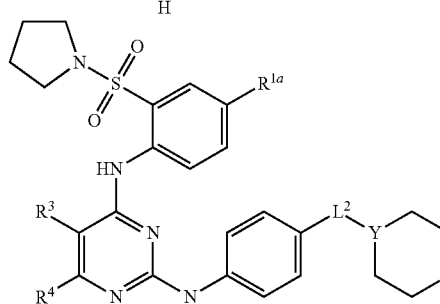
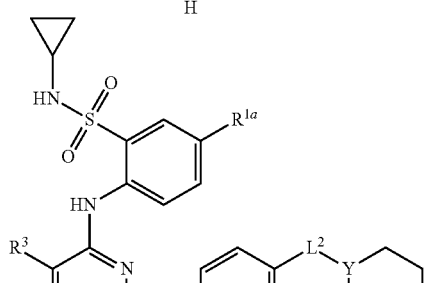
In a further aspect, the compound has a structure represented by a formula:

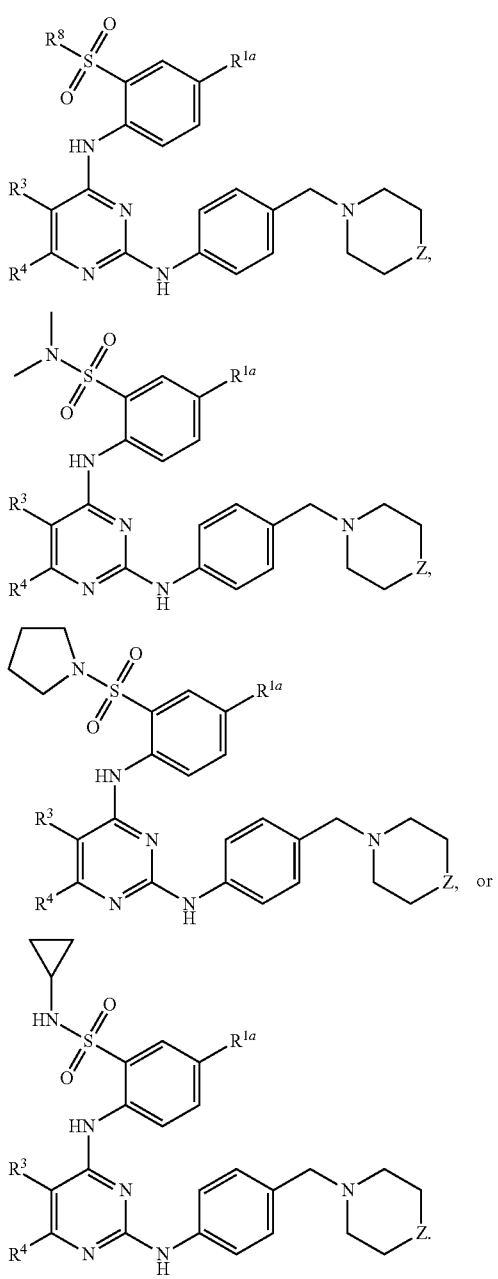
In a further aspect, the compound has a structure represented by a formula:
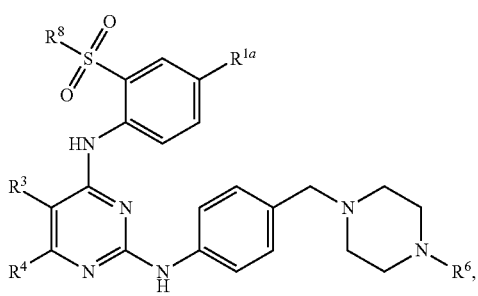
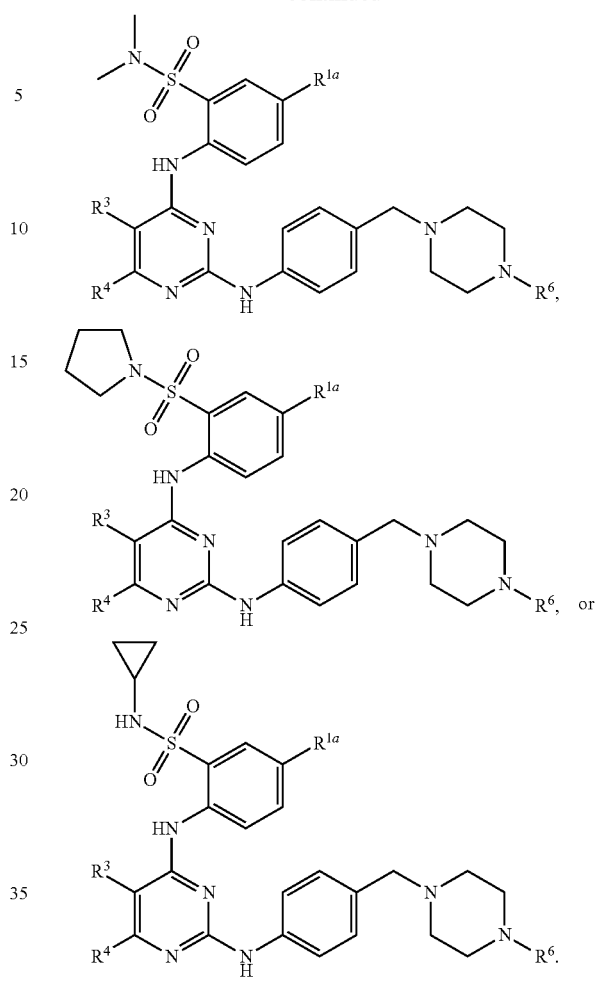
In a further aspect, the compound has a structure represented by a formula:
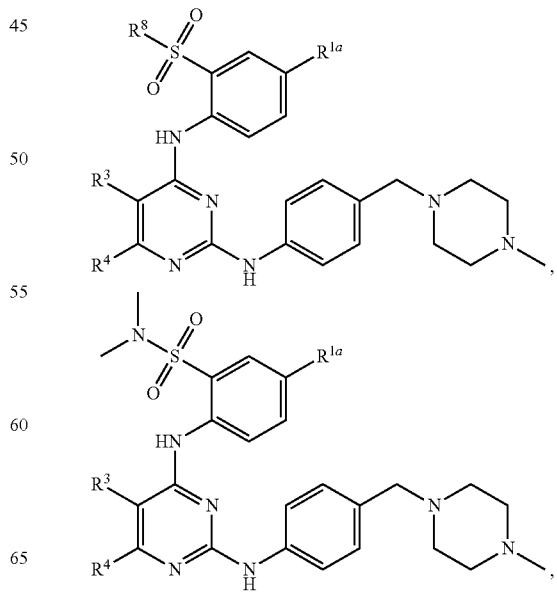

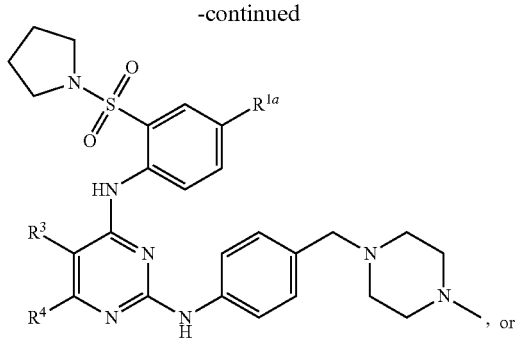
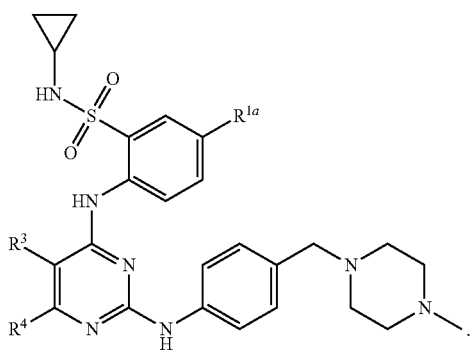
In a further aspect, the compound has a structure represented by a formula:
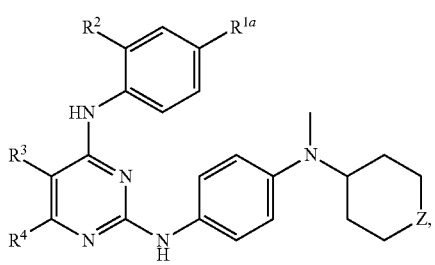
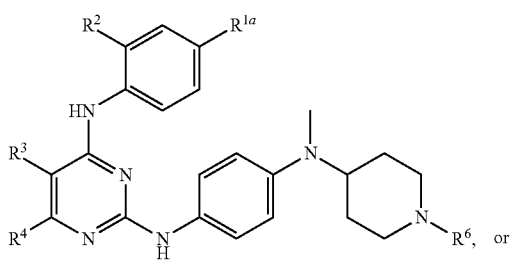
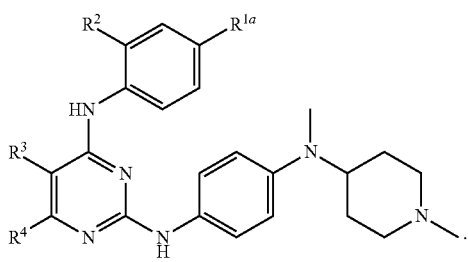
In a further aspect, the compound has a structure represented by a formula:
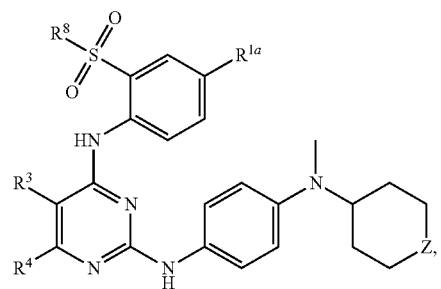
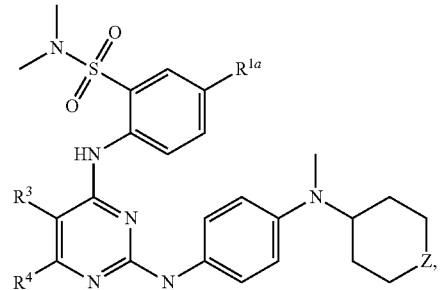
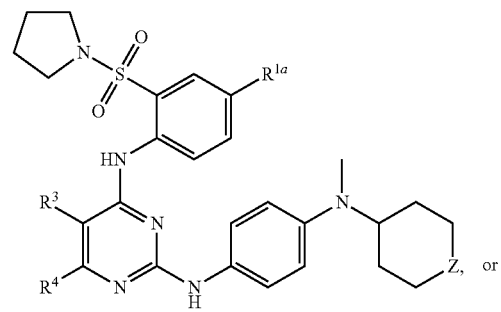
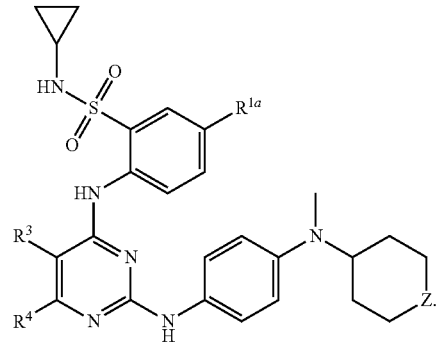
In a further aspect, the compound has a structure represented by a formula:
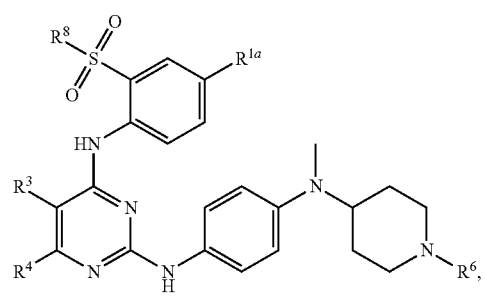

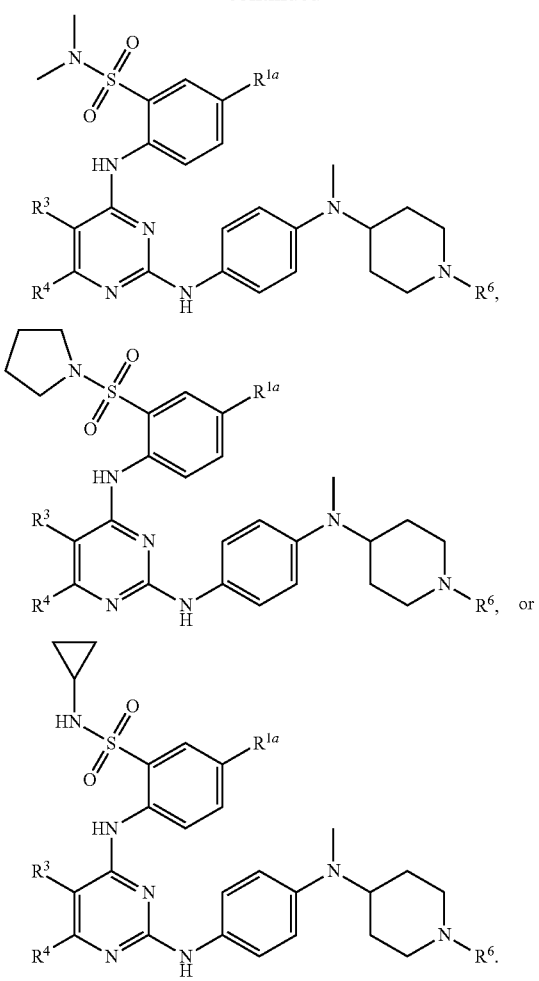
In a further aspect, the compound has a structure represented by a formula:
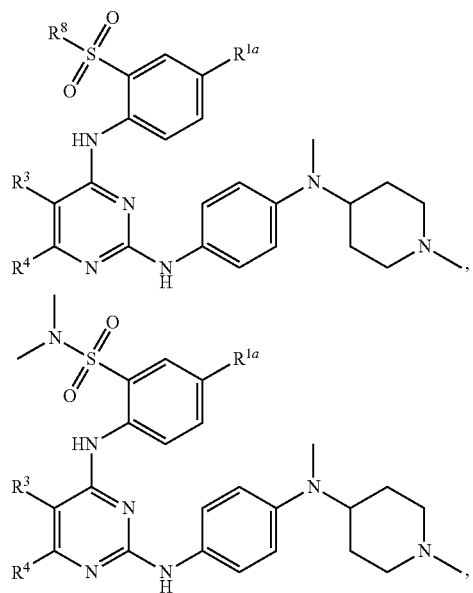
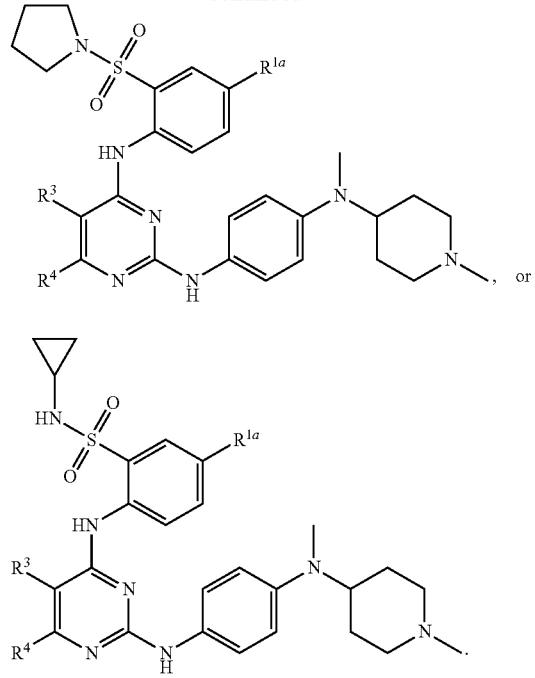
In a further aspect, the compound has a structure represented by a formula:
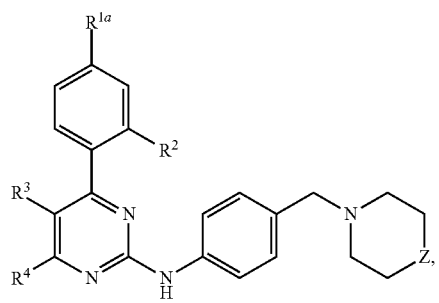

In a further aspect, the compound has a structure represented by a formula:
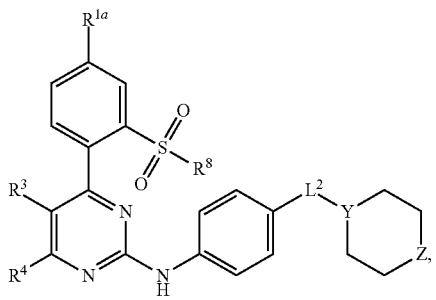
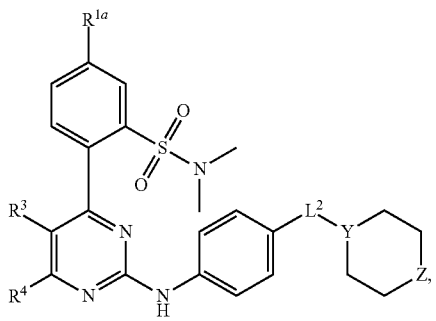
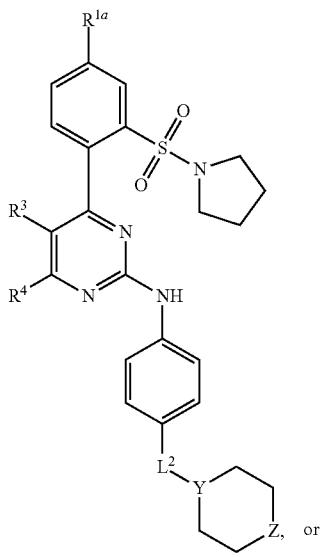
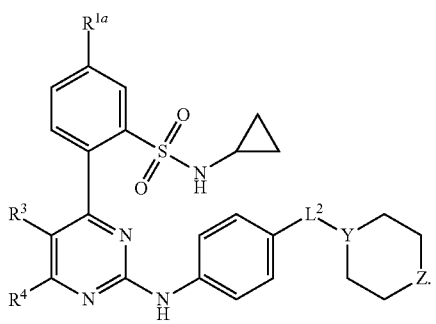
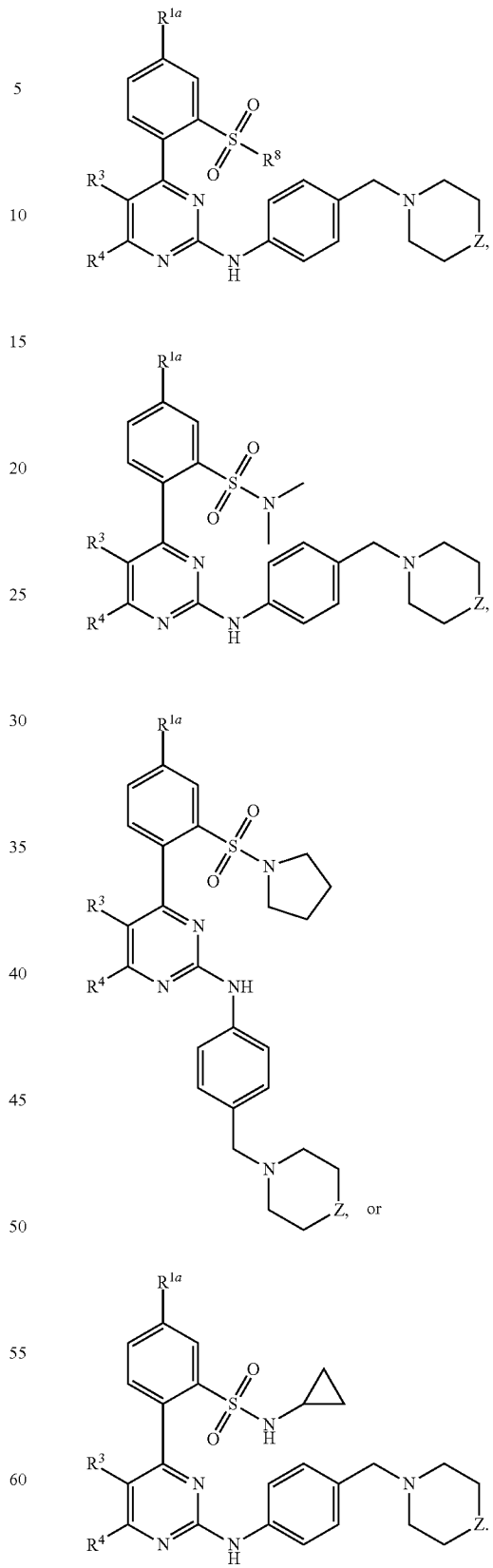
In a further aspect, the compound has a structure represented by a formula:
In a further aspect, the compound has a structure represented by a formula:

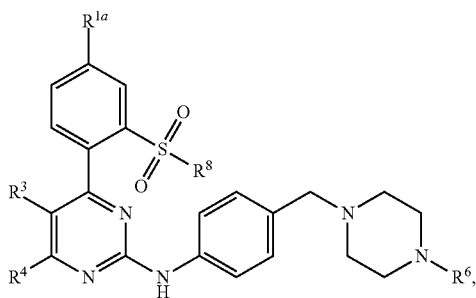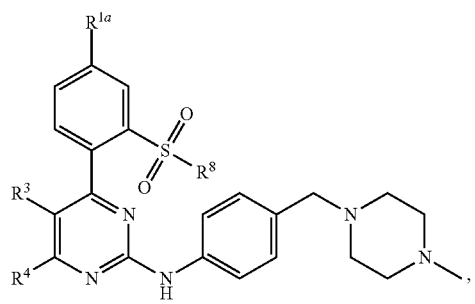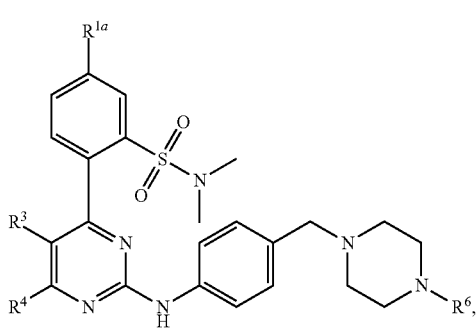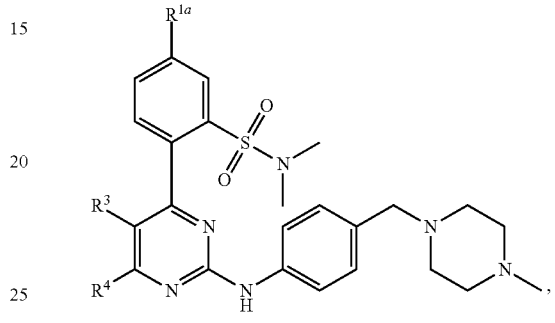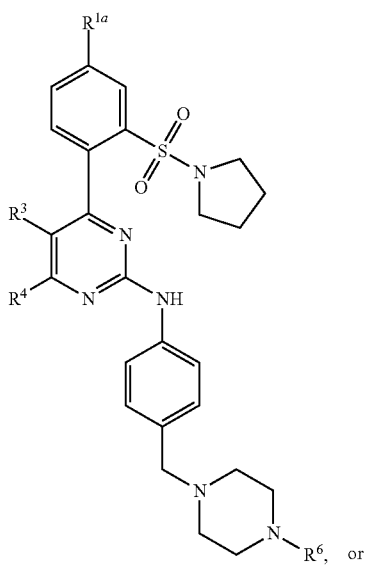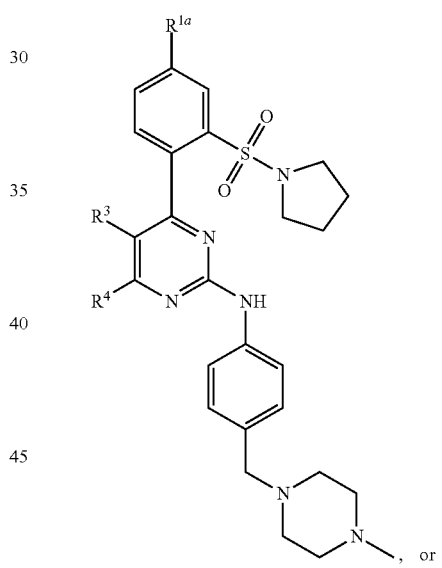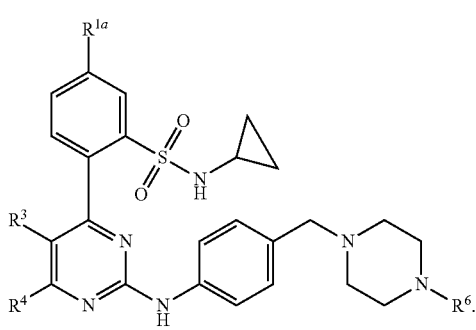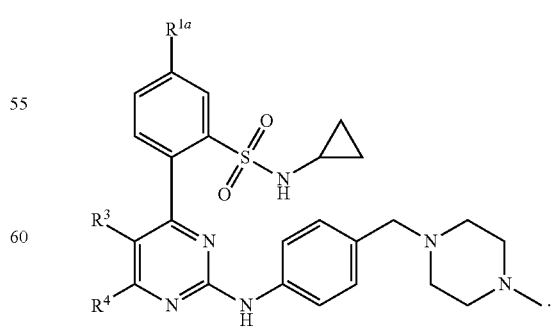
In a further aspect, the compound has a structure represented by a formula:
In a further aspect, the compound has a structure represented by a formula:

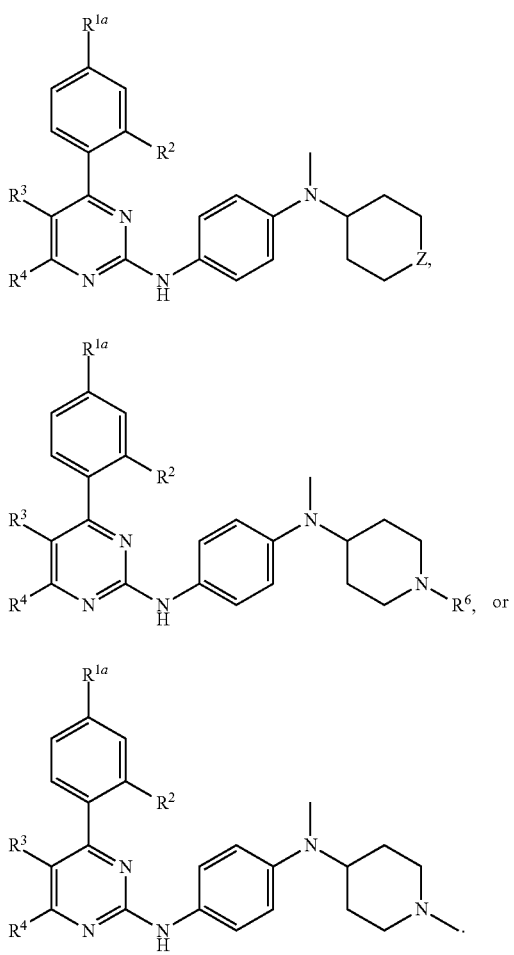
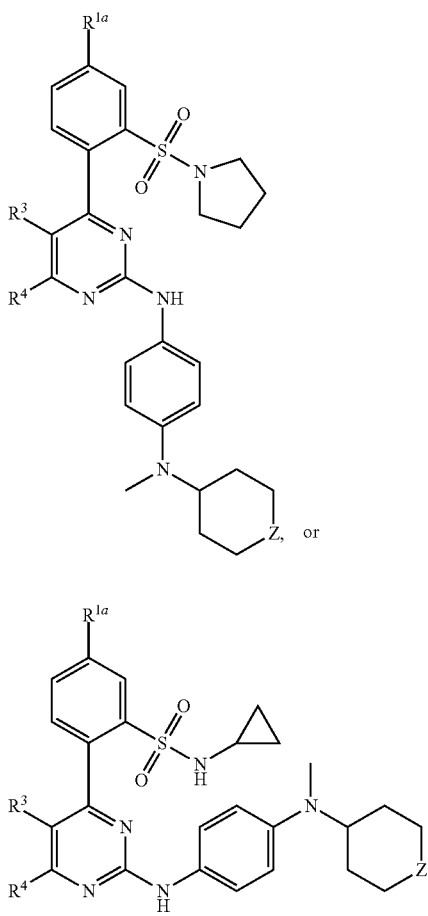
In a further aspect, the compound has a structure represented by a formula:
In a further aspect, the compound has a structure represented by a formula:
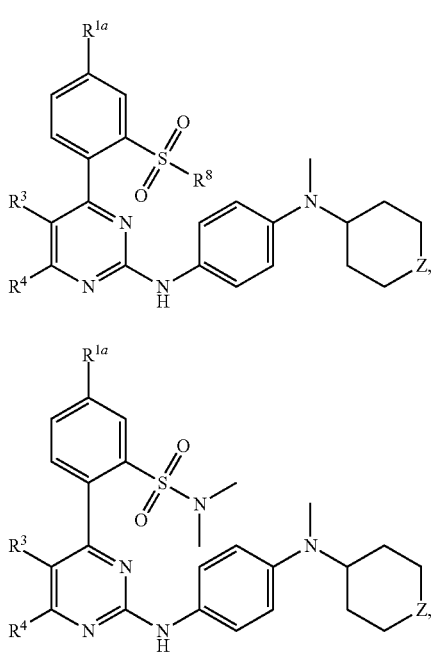
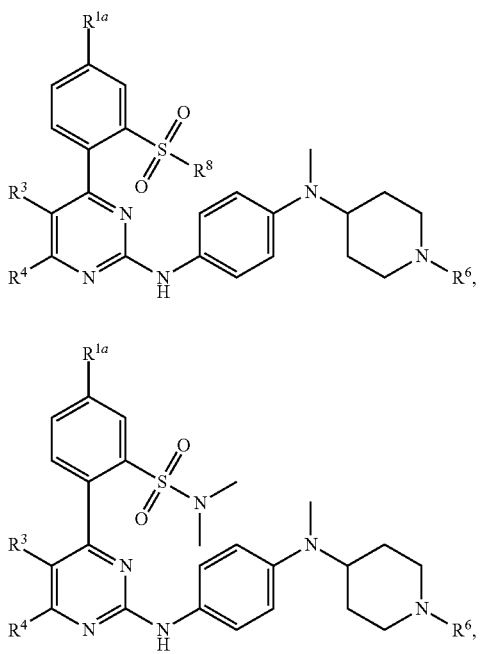

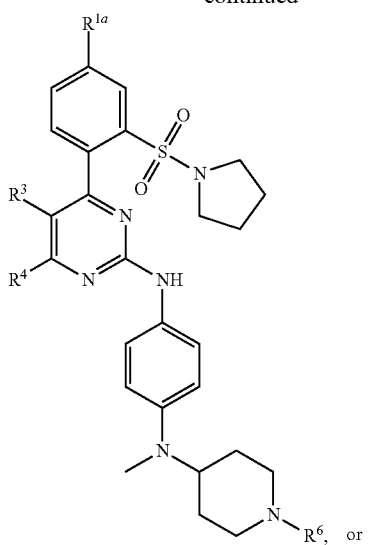
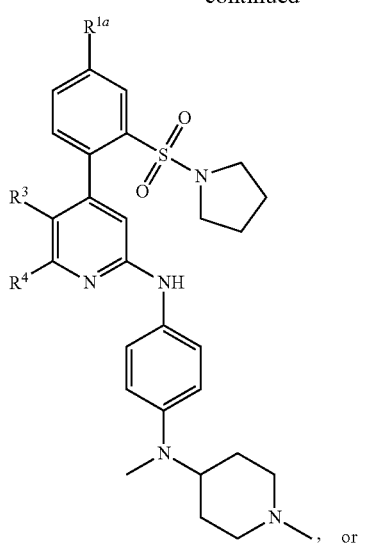
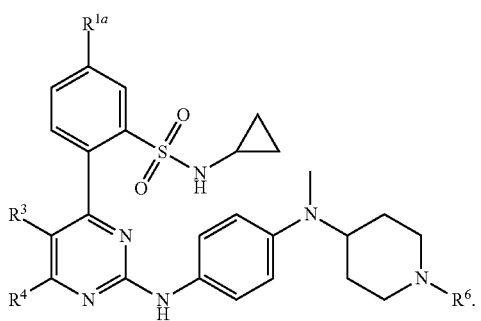
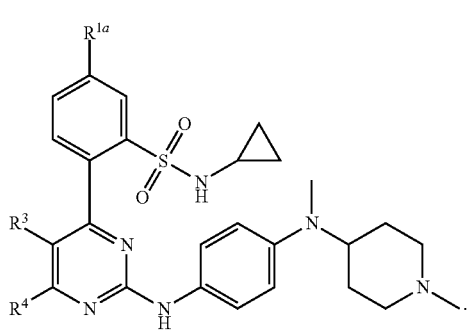
In a further aspect, the compound has a structure represented by a formula:
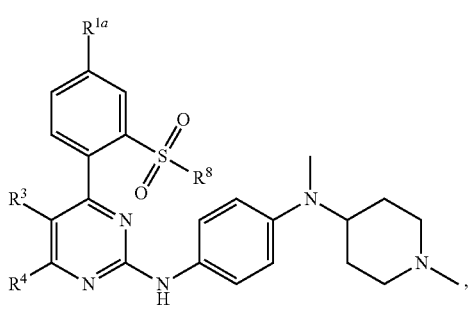
In a further aspect, the compound has a structure represented by a formula:
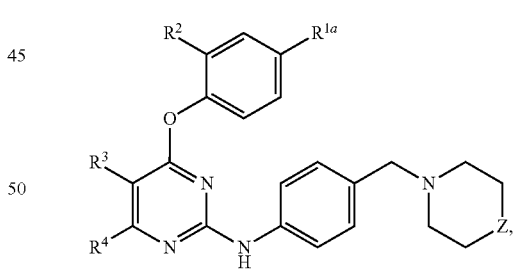
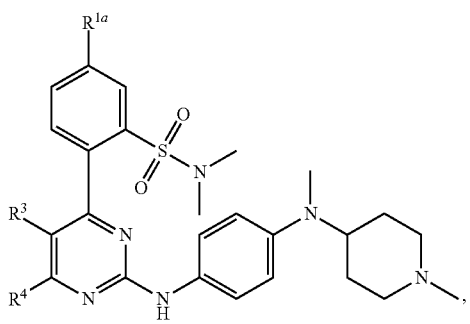
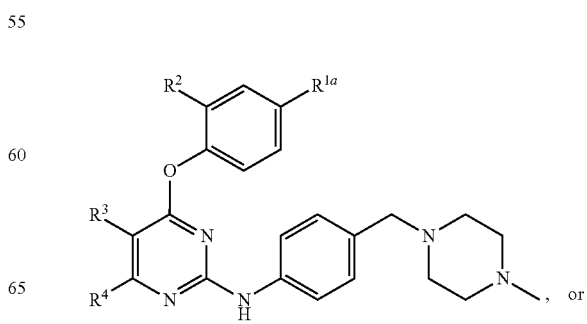

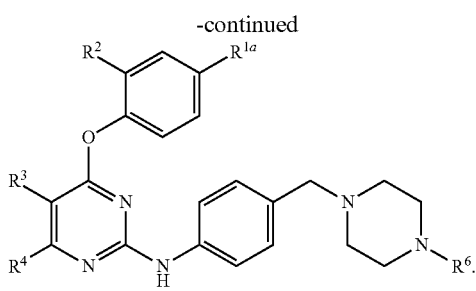
In a further aspect, the compound has a structure represented by a formula:
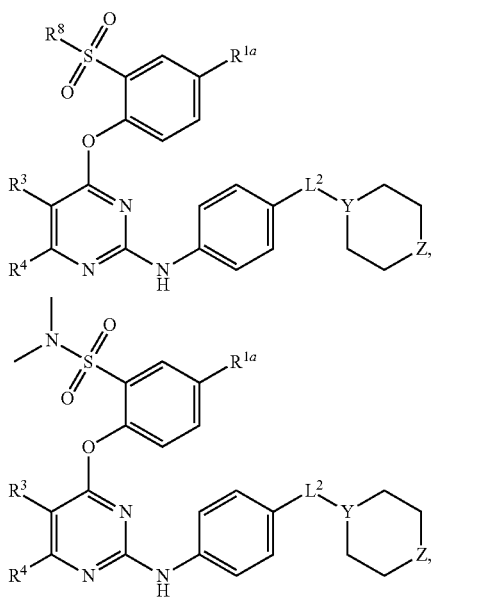
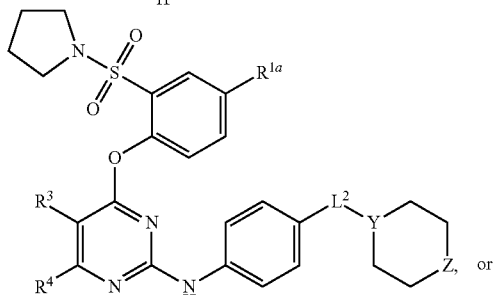
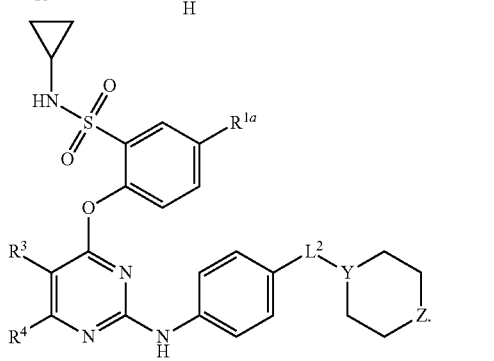
In a further aspect, the compound has a structure represented by a formula:
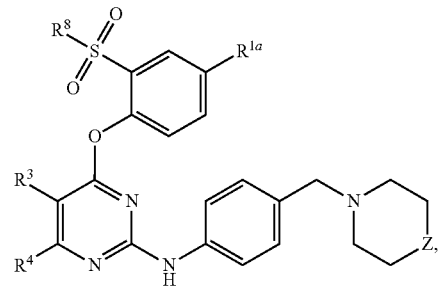
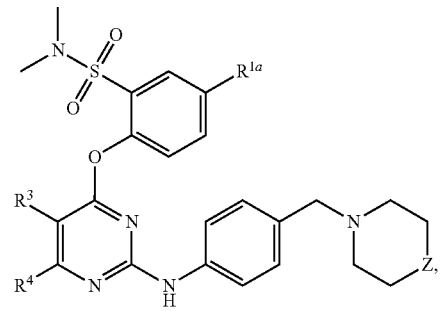
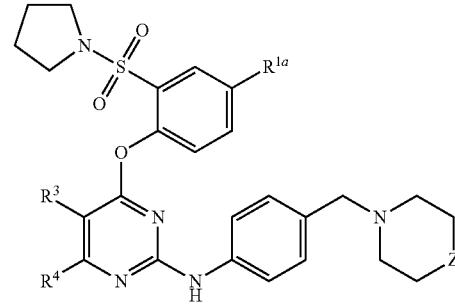
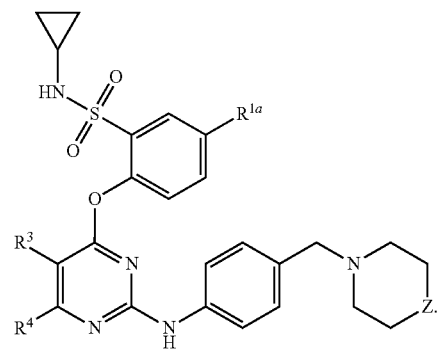
In a further aspect, the compound has a structure represented by a formula:
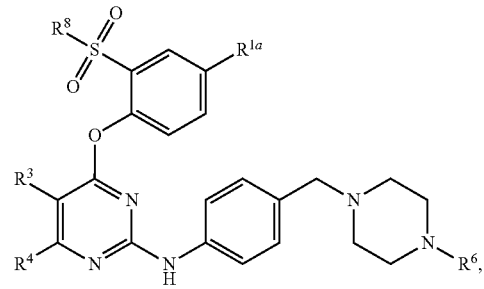

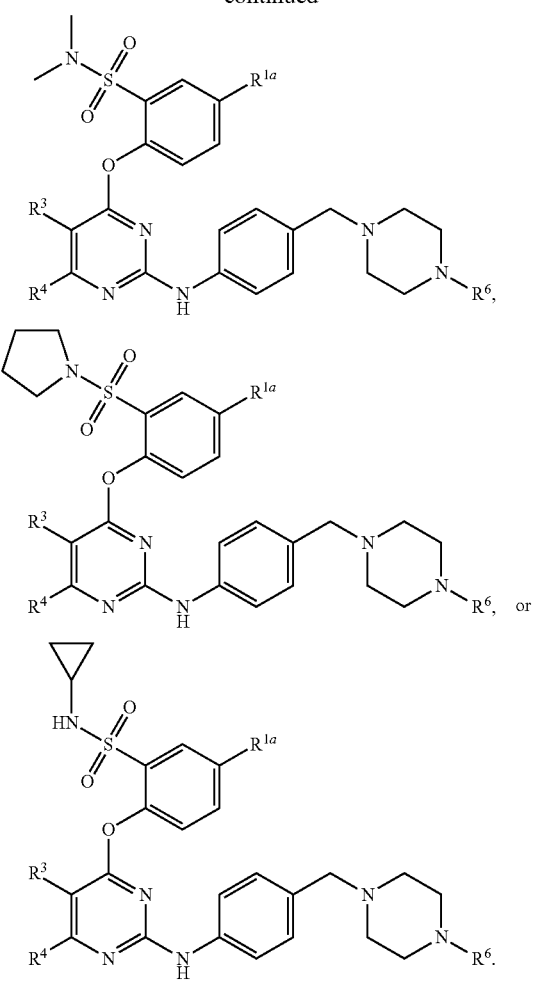
In a further aspect, the compound has a structure represented by a formula:
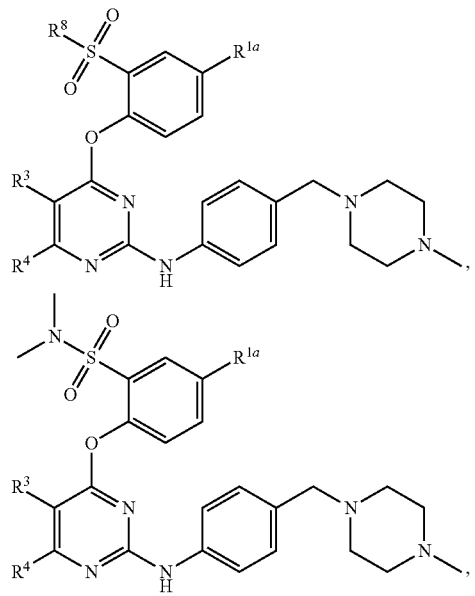
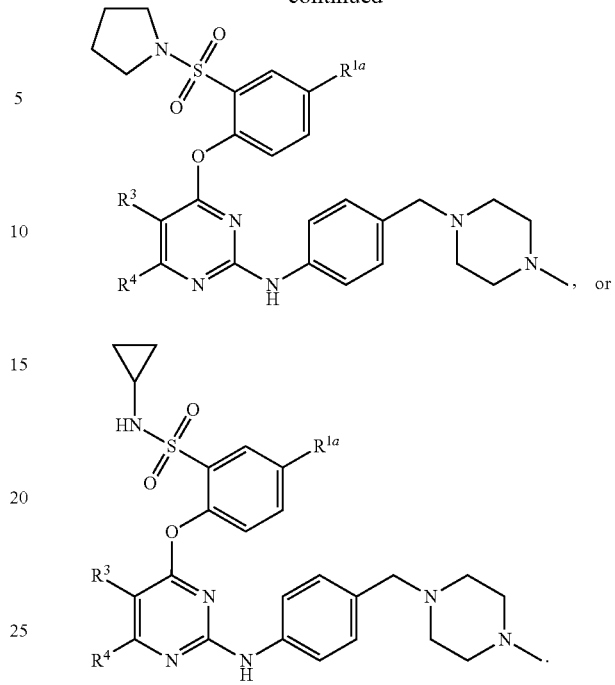
In a further aspect, the compound has a structure represented by a formula:
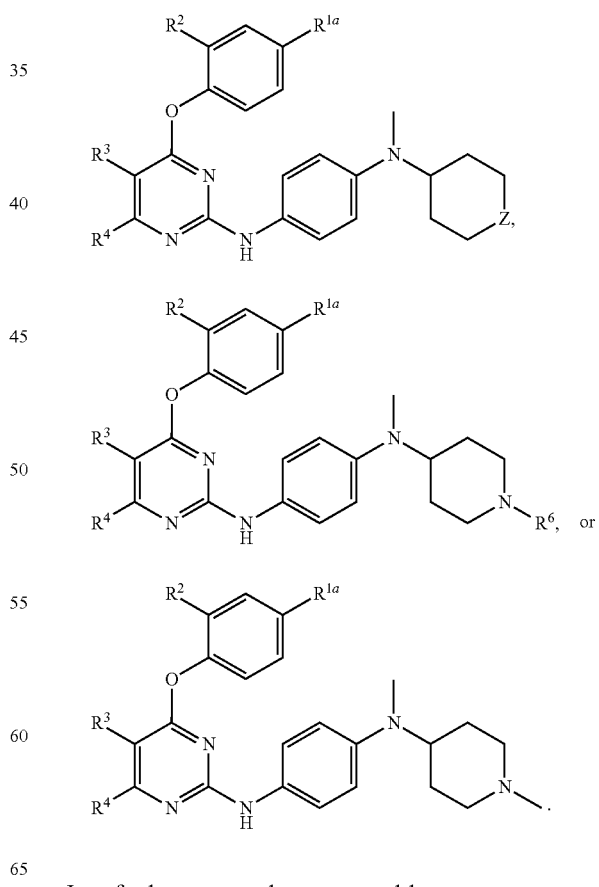
In a further aspect, the compound has a structure represented by a formula:

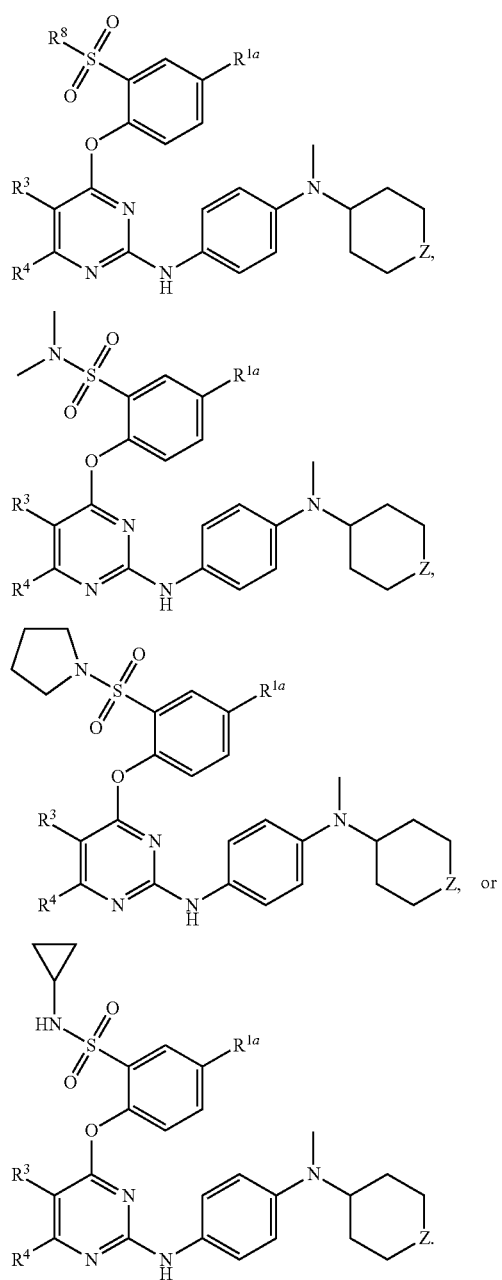
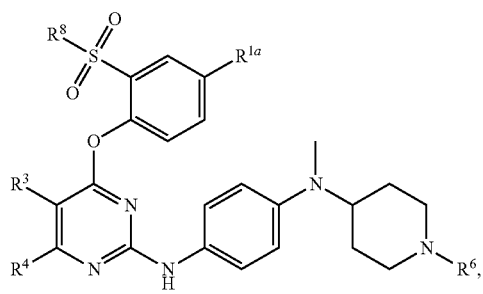
In a further aspect, the compound has a structure represented by a formula:
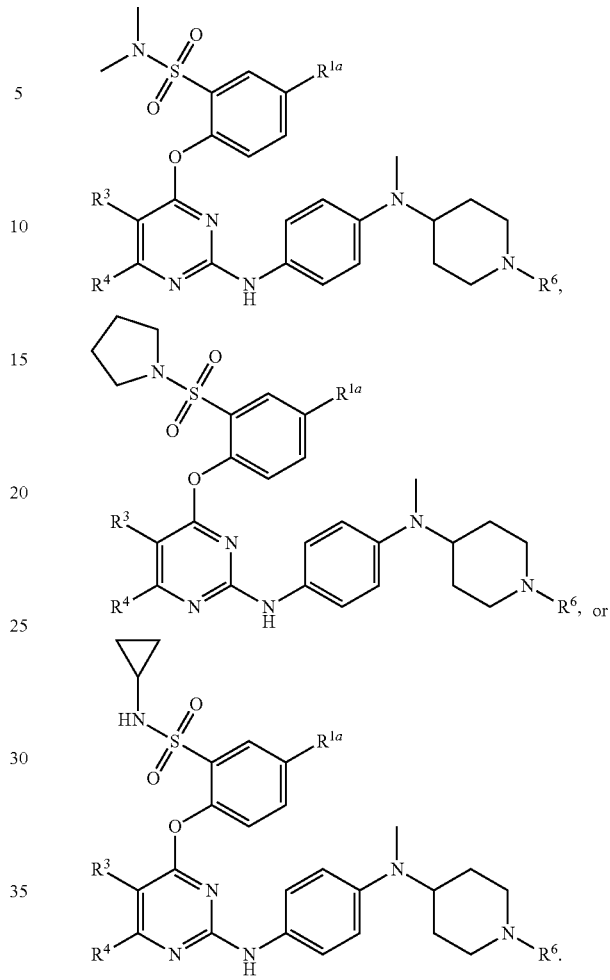
In a further aspect, the compound has a structure represented by a formula:
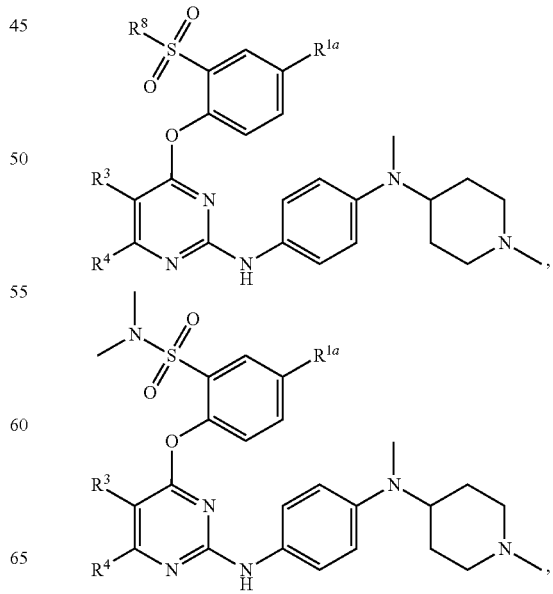

-continued
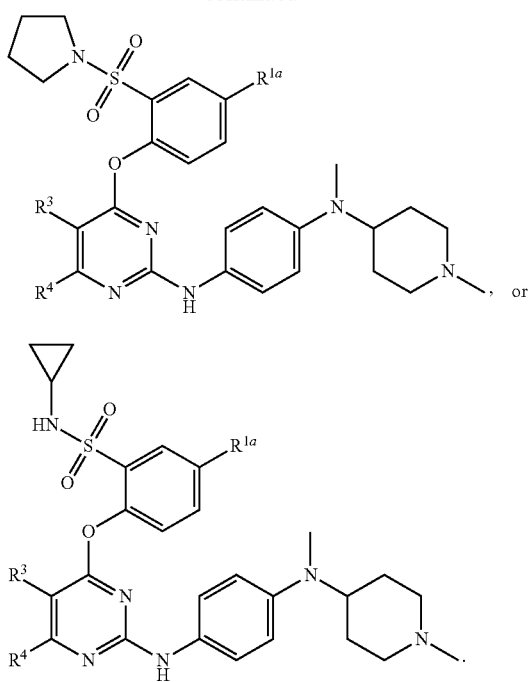
In a further aspect, the compound has a structure represented by a formula:
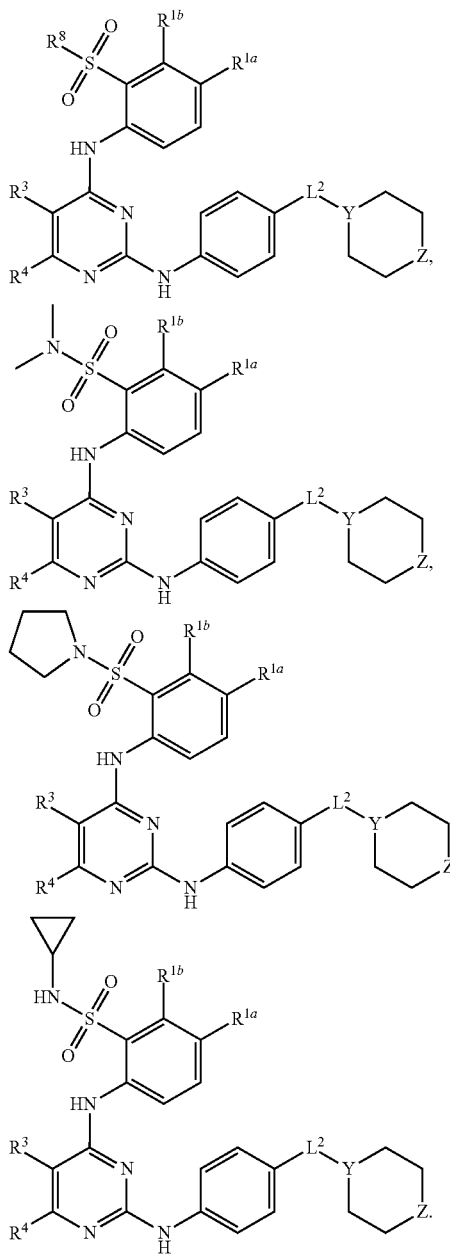
In a further aspect, the compound has a structure represented by a formula:
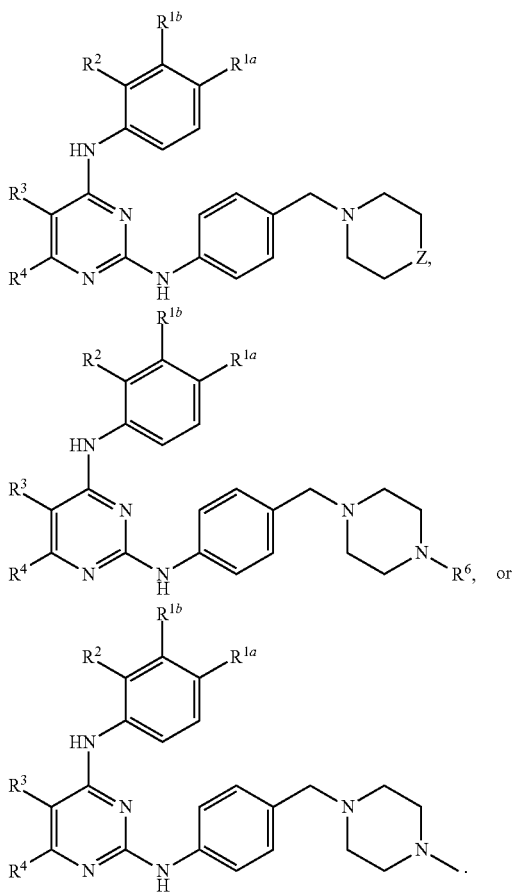
In a further aspect, the compound has a structure represented by a formula:
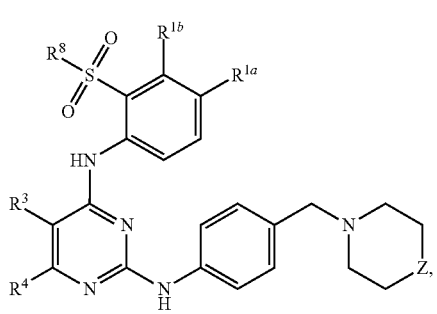

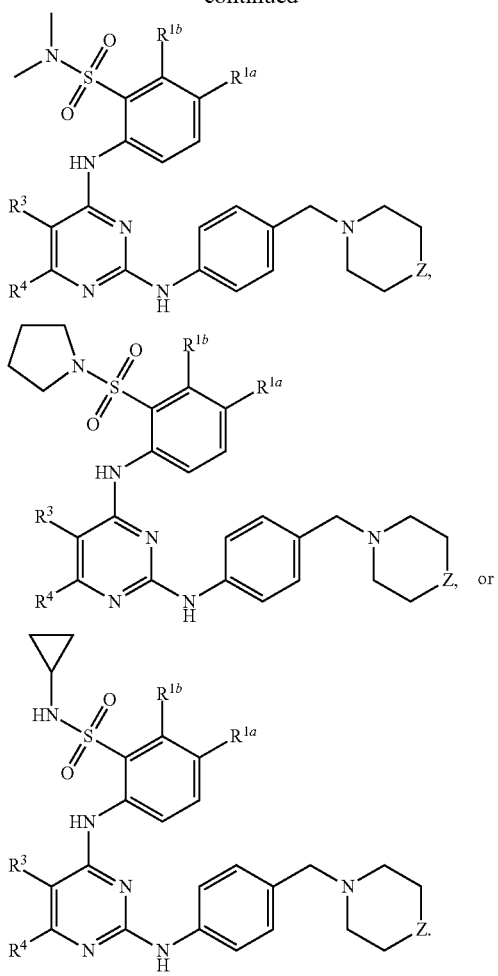
In a further aspect, the compound has a structure represented by a formula:
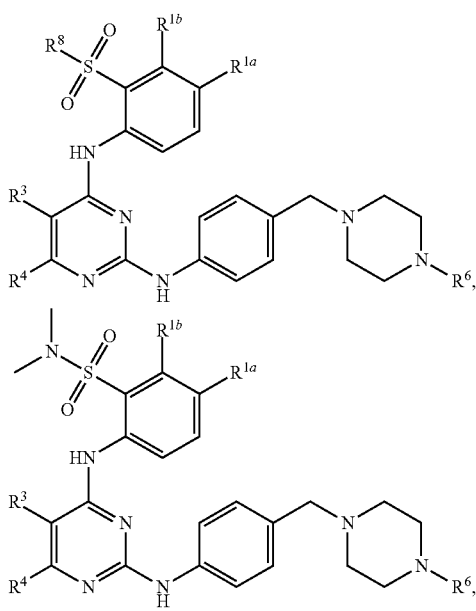
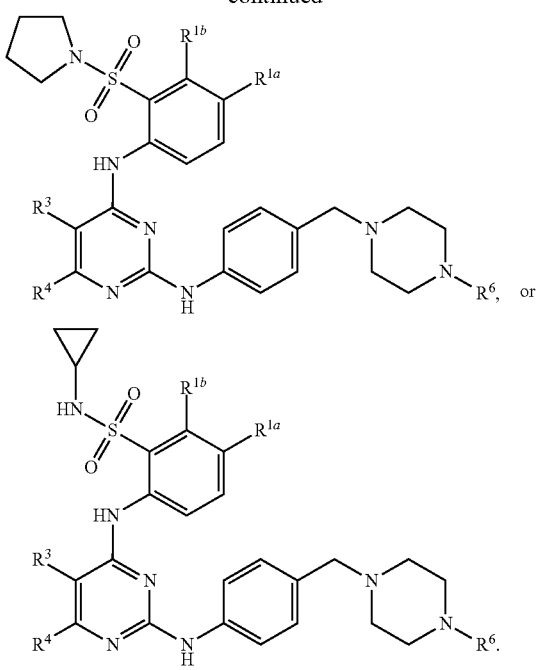
In a further aspect, the compound has a structure represented by a formula:
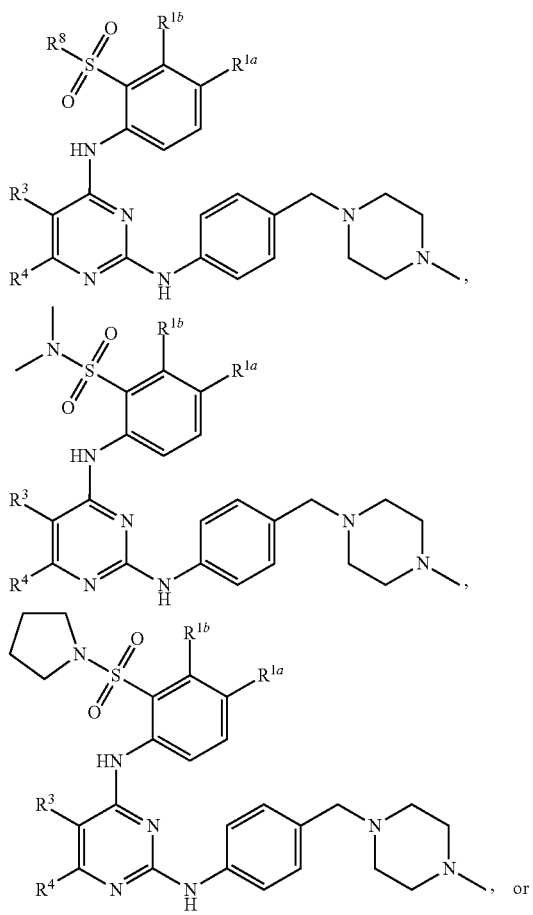

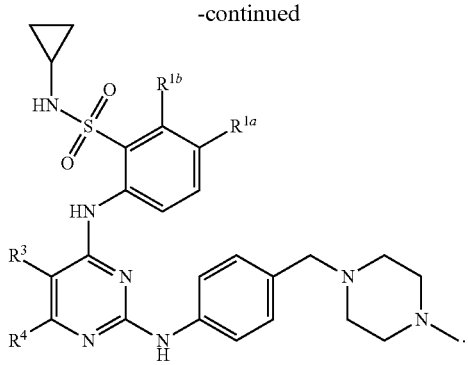
In a further aspect, the compound has a structure represented by a formula:
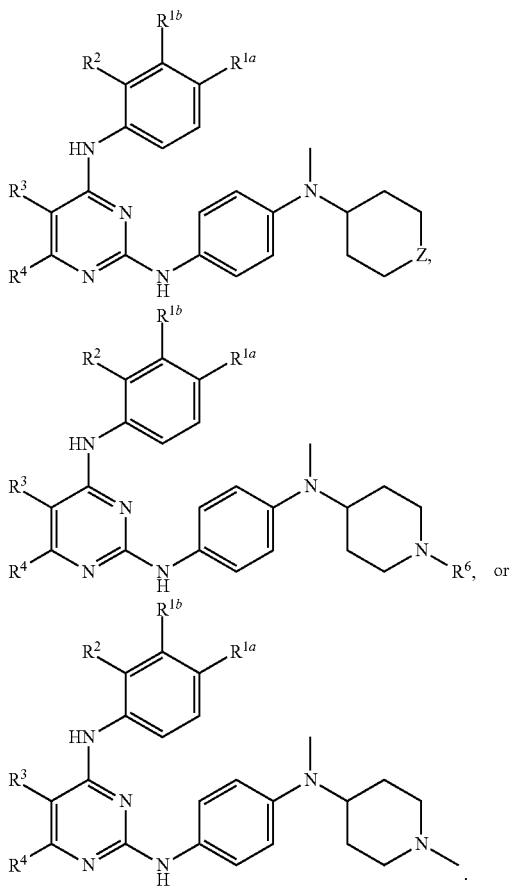
In a further aspect, the compound has a structure represented by a formula:
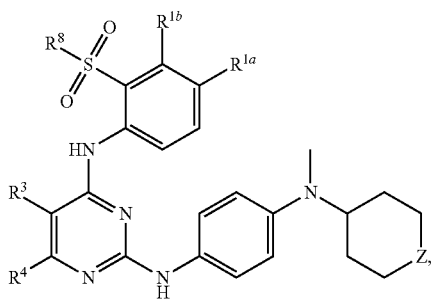
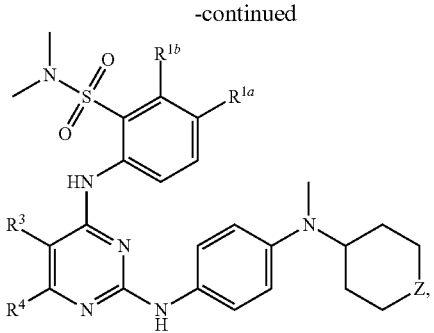
In a further aspect, the compound has a structure represented by a formula:
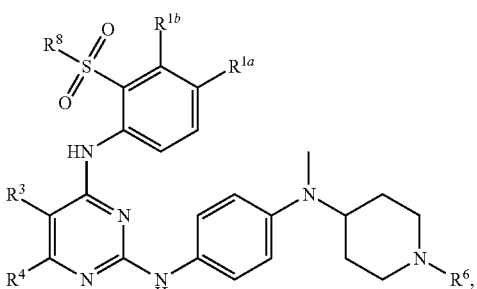

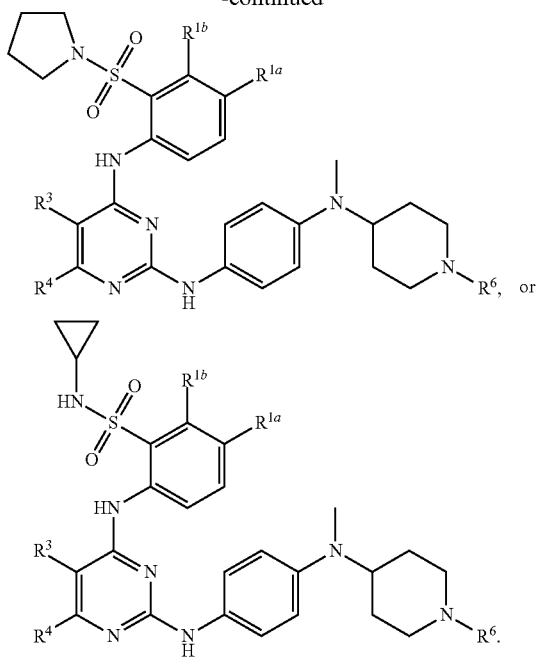
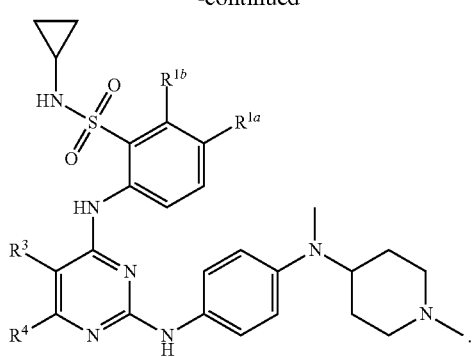
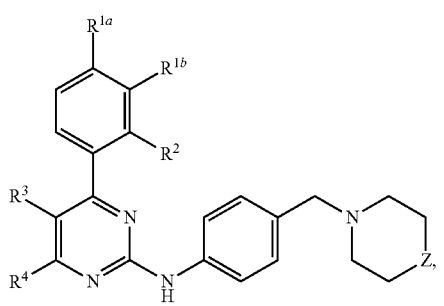
In a further aspect, the compound has a structure represented by a formula:
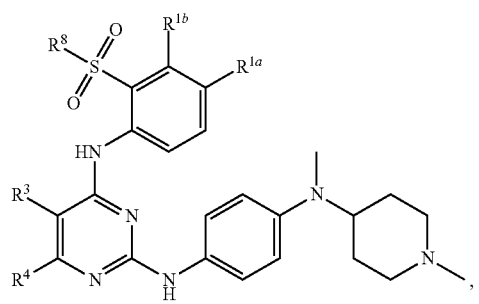
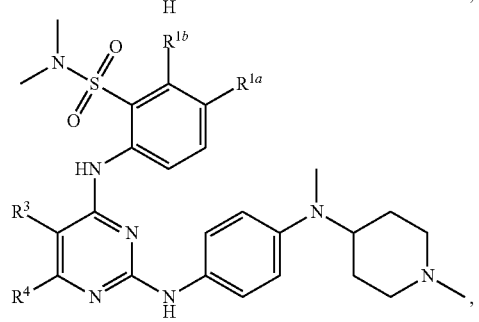
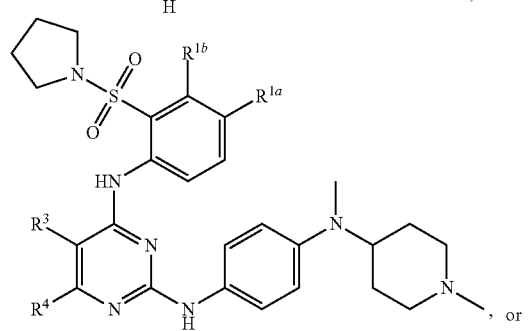
In a further aspect, the compound has a structure represented by a formula:
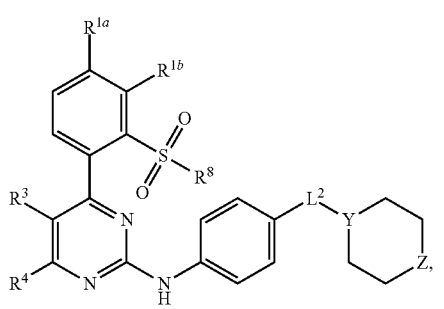

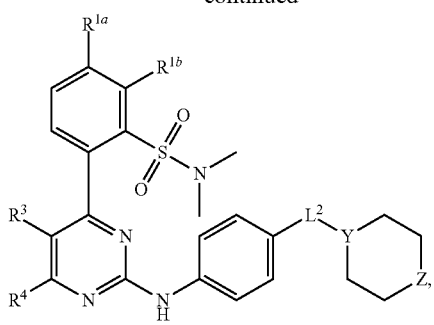
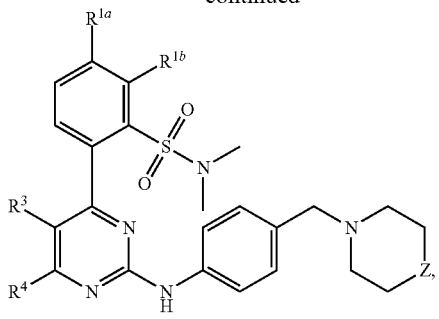
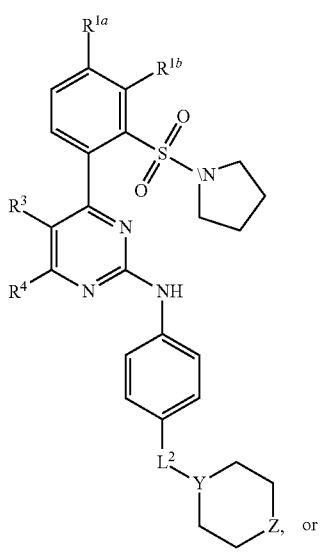
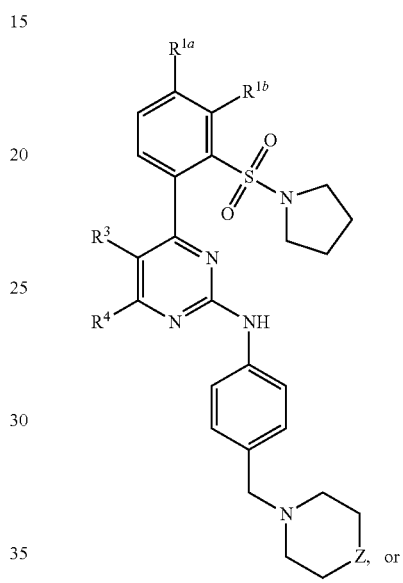
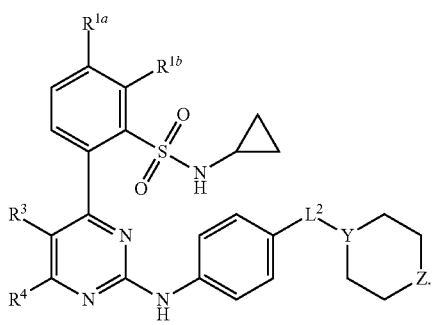
In a further aspect, the compound has a structure represented by a formula:
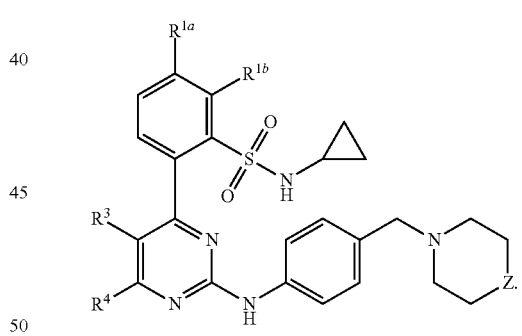
In a further aspect, the compound has a structure represented by a formula:
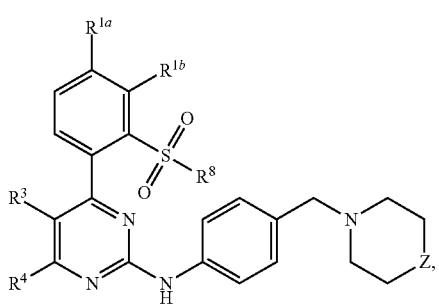
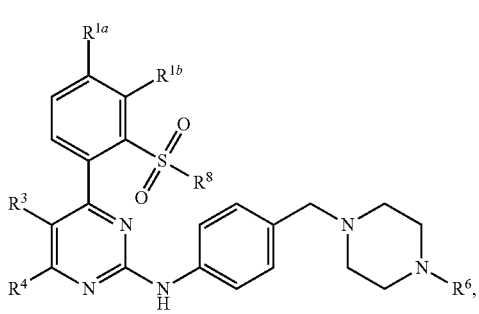

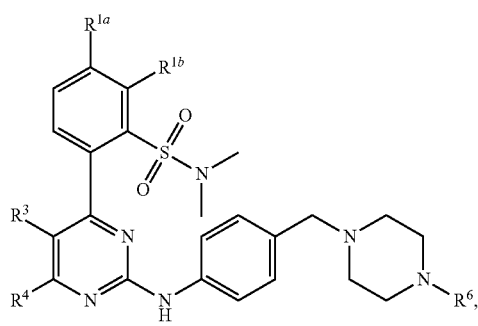
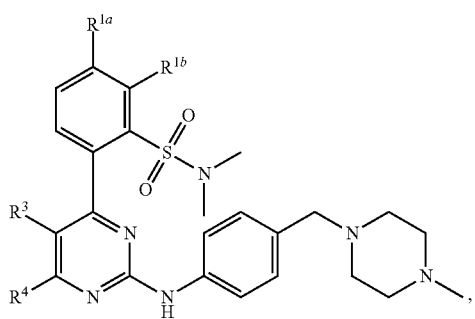
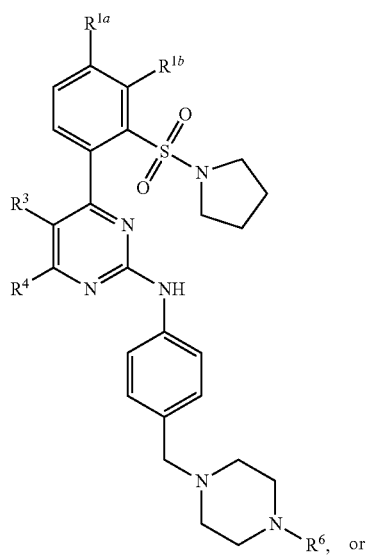
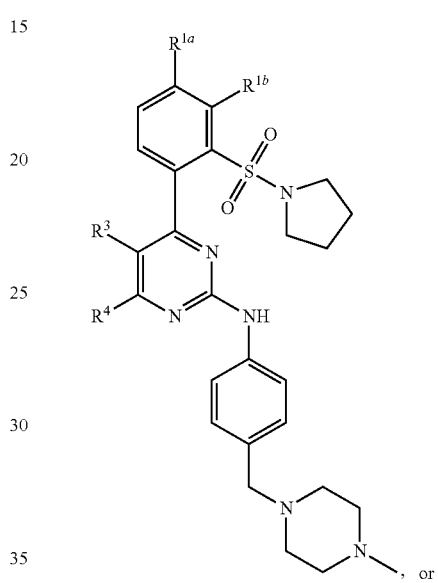
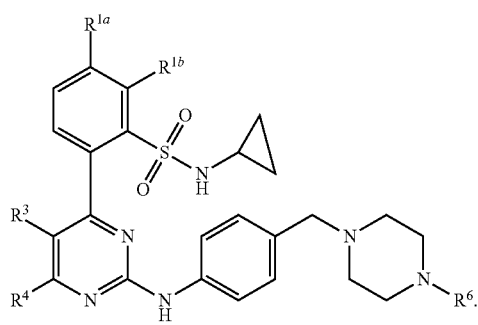
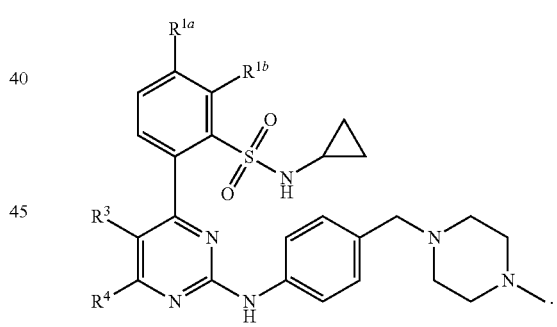
In a further aspect, the compound has a structure represented by a formula:
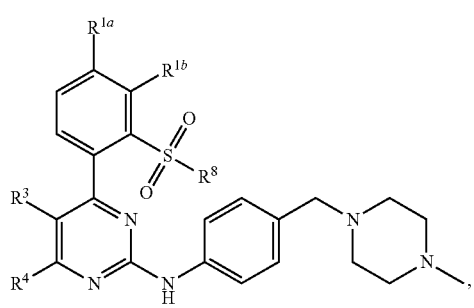
In a further aspect, the compound has a structure represented by a formula:
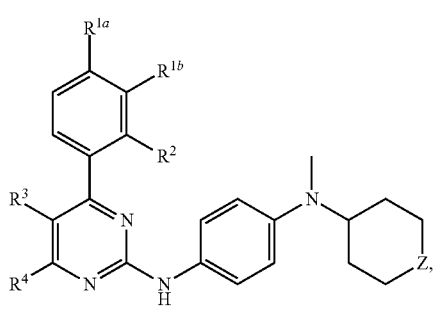

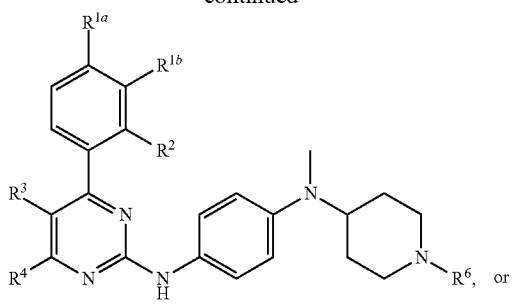
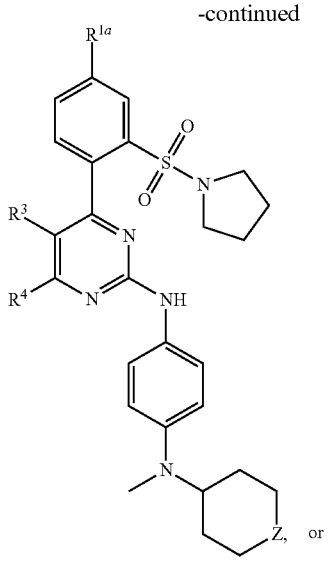
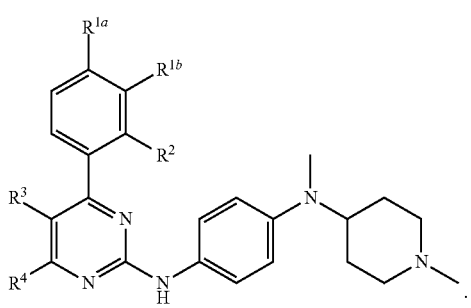
In a further aspect, the compound has a structure represented by a formula:
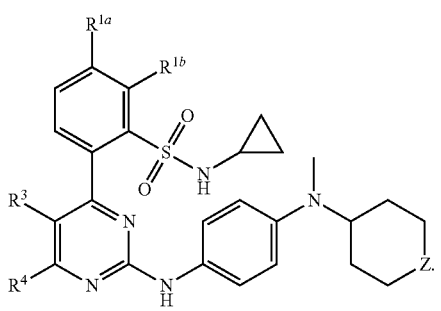
In a further aspect, the compound has a structure represented by a formula:
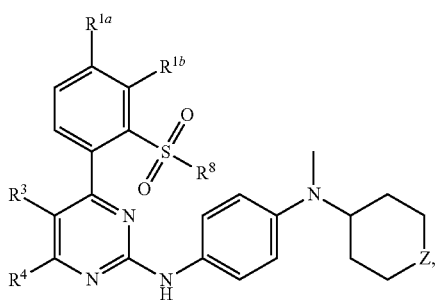
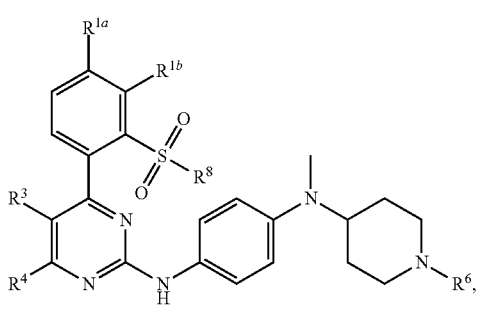
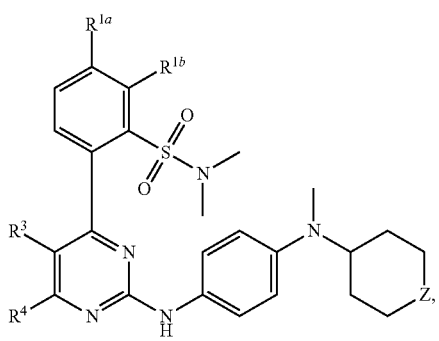
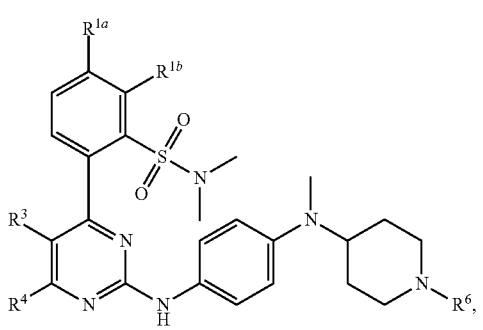

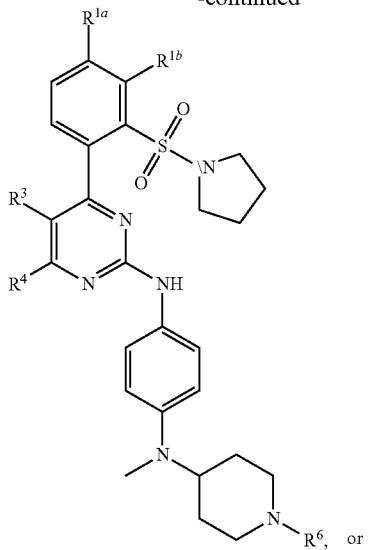
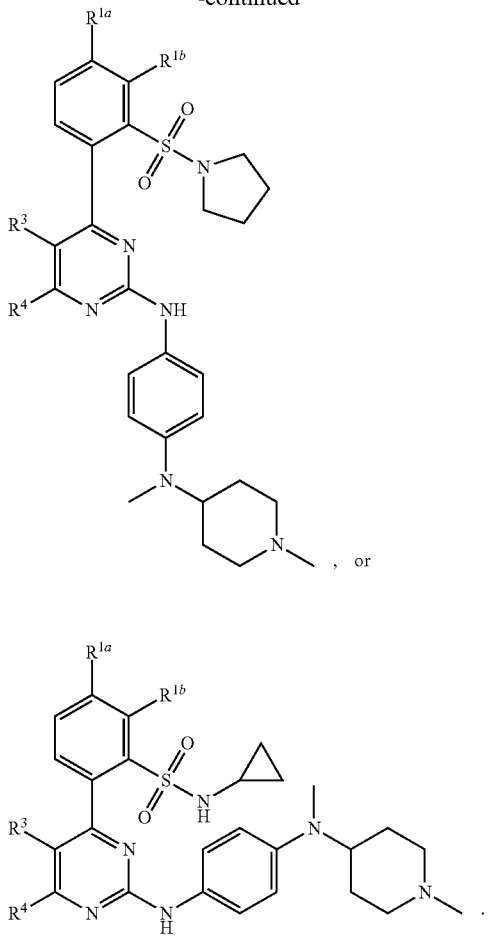
In a further aspect, the compound has a structure represented by a formula:
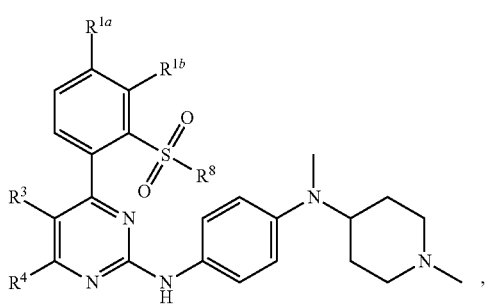
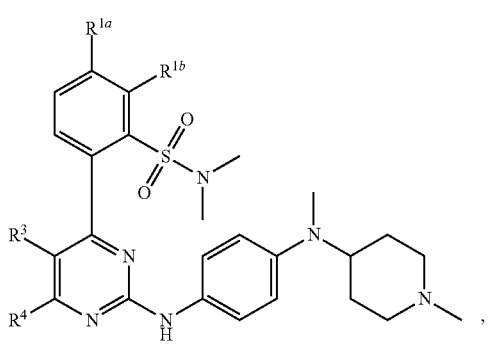
In a further aspect, the compound has a structure represented by a formula:
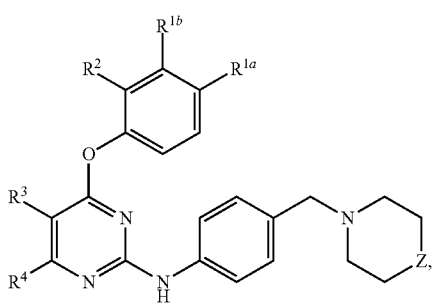
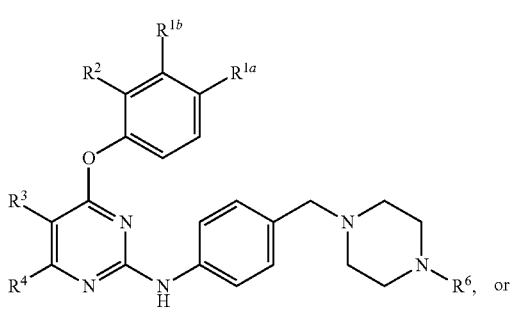

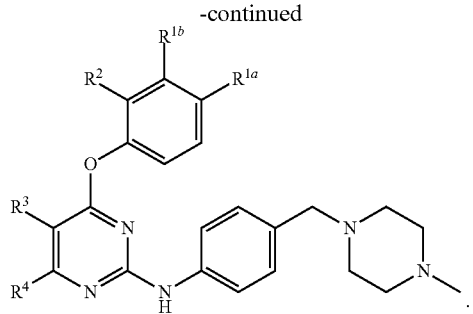
In a further aspect, the compound has a structure represented by a formula:
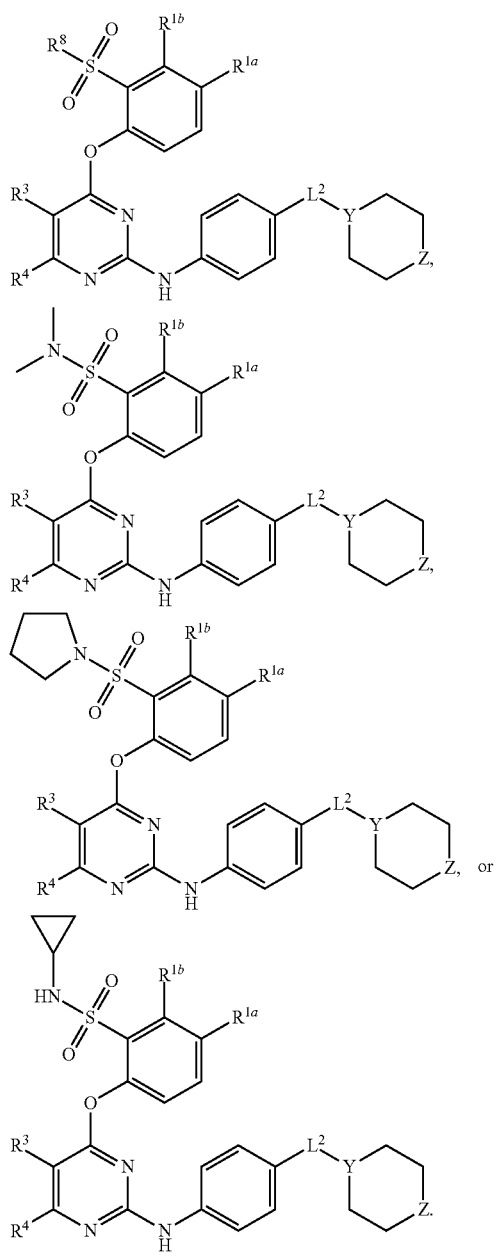
In a further aspect, the compound has a structure represented by a formula:
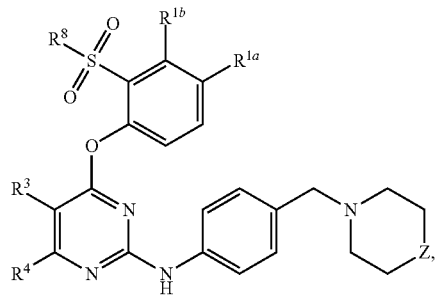
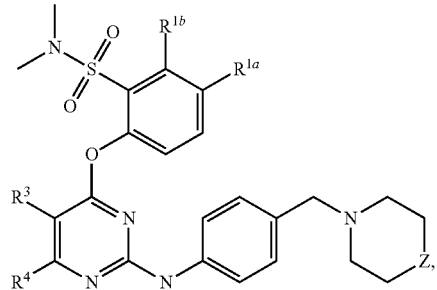
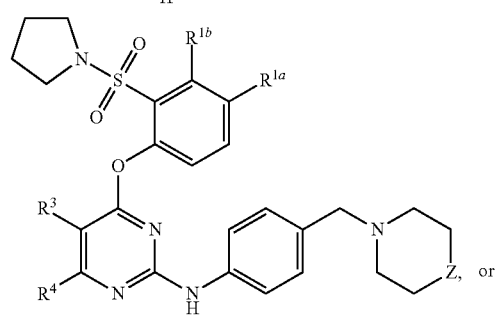
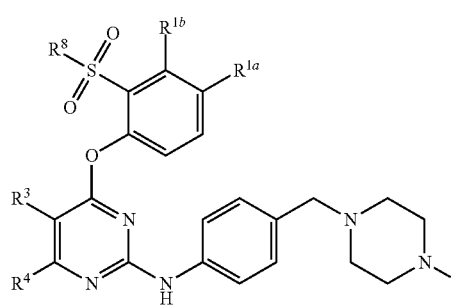
In a further aspect, the compound has a structure represented by a formula:
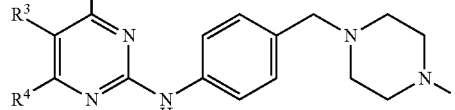

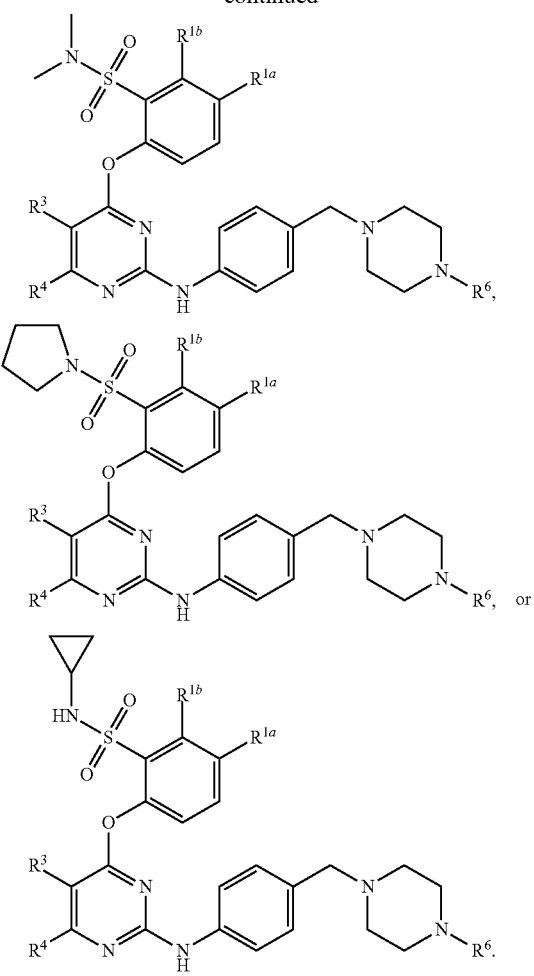
In a further aspect, the compound has a structure represented by a formula:
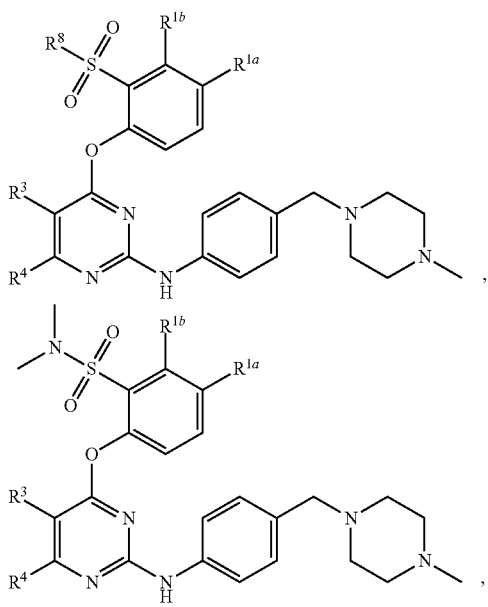
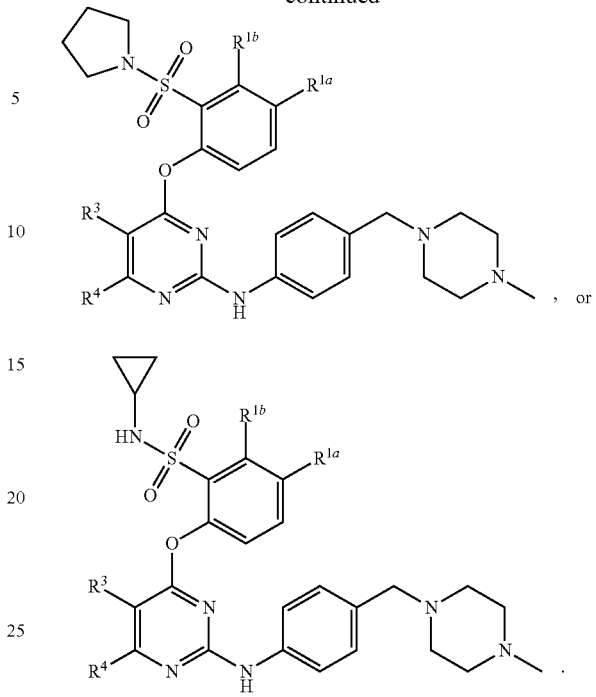
In a further aspect, the compound has a structure represented by a formula:
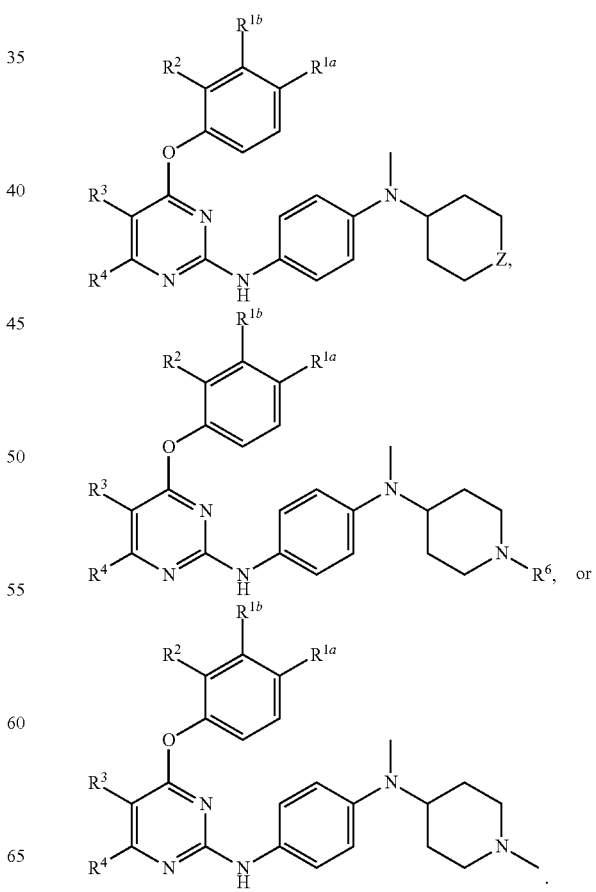

In a further aspect, the compound has a structure represented by a formula:
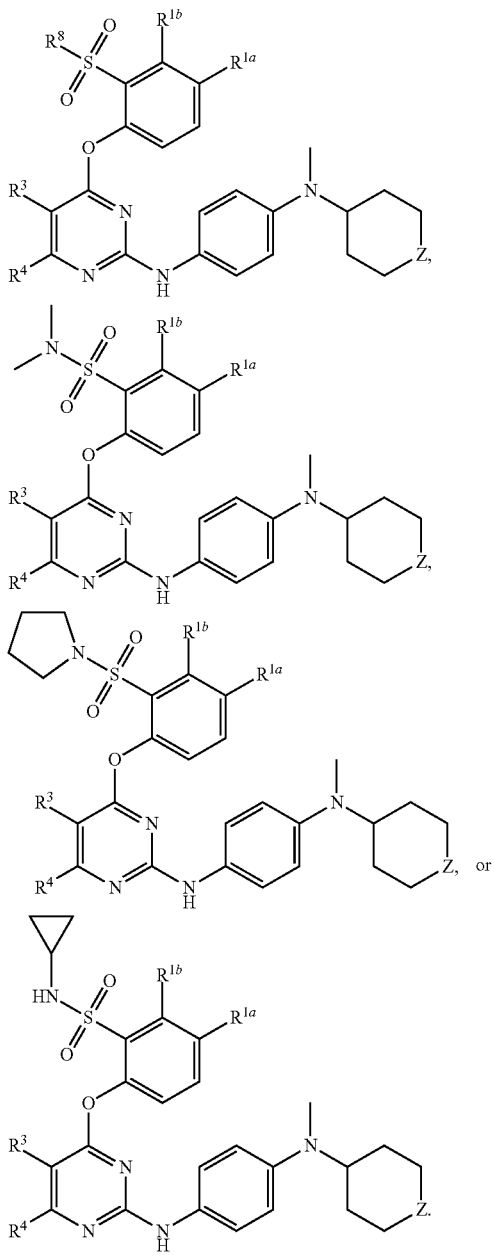
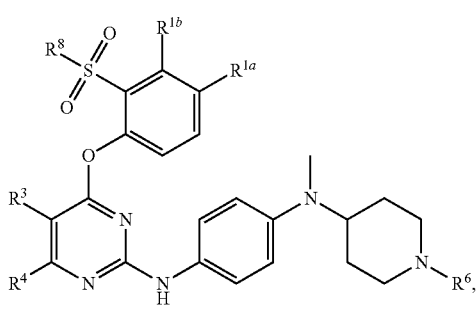
In a further aspect, the compound has a structure represented by a formula:
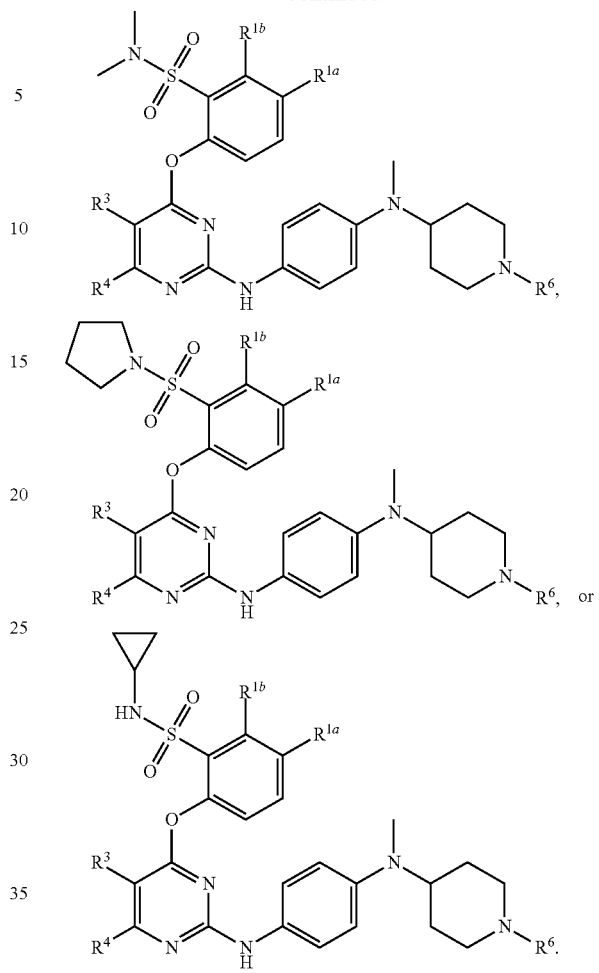
In a further aspect, the compound has a structure represented by a formula:
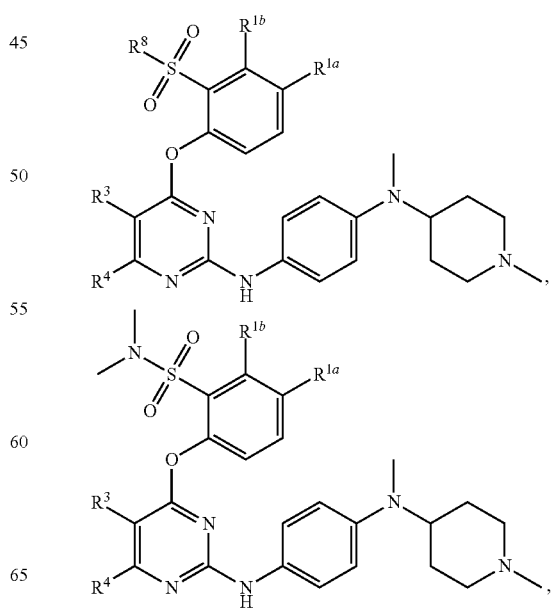

a. L¹ groups

In one aspect, L¹ is selected from O and NR⁵. In a further aspect, L¹ is O. In a further aspect, L¹ is NR⁵. In a further aspect, L¹ is O, and n is 1. In a further aspect, L¹ is NR⁵, and n is 1.

b. L² Groups

In one aspect, L² is selected from CH₂ and NCH₃, provided that L² is CH₂ when Y is N. In a further aspect, L² is CH₂. In a further aspect, wherein L² is NCH₃.

c. Y Groups

In one aspect, Y is selected from CH or N. In a further aspect, Y is CH. In a further aspect, Y is N.

d. Z Groups

In one aspect, Z is selected from O, NR⁶ and CH₂. In a further aspect, Z is selected from O and NR⁶. In a further aspect, Z is selected from O and CH₂. In a further aspect, Z is selected from CH₂ and NR⁶. In a further aspect, Z is O. In a further aspect, Z is CH₂. In a further aspect, Z is NR⁶. In a further aspect, Z is NH. In a further aspect, Z is NCH₃.

e. AR¹ Groups

In one aspect, Ar¹ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, SO₂R¹², C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, SO₂R¹², C1-C3 alkyl, C1-C3 alkylamine, and C1-C3 dialkylamino. In a further aspect, Ar¹ is unsubstituted. In a further aspect, Ar¹ has 1, 2 or 3 substituents.

In a further aspect, Ar¹ is phenyl. In a further aspect, Ar¹ is phenyl substituted with 1-3 substituents independently selected from cyano, C1-C6 alkyl, C1-C6 haloalkyoxy, C1-C6 haloalkyl, C1-C6 polyhaloalkyl, C1-C6 cyanoalkyl, SO₂R¹², C1-C3 alkyl, C1-C3 alkylamine, and C1-C3 dialkylamino. In a further aspect, Ar¹ is phenyl substituted with 0-3 substituents independently selected from cyano, C1-C6 haloalkyoxy, C1-C6 haloalkyl, C1-C6 polyhaloalkyl, C1-C6 cyanoalkyl, and SO₂R¹². In a further aspect, Ar¹ is phenyl monosubstituted with a substituent selected from cyano, C1-C6 haloalkyoxy, C1-C6 haloalkyl, C1-C6 polyhaloalkyl, C1-C6 cyanoalkyl, and SO₂R¹².

In a further aspect, Ar¹ is heteroaryl. In a further aspect, Ar¹ is pyridinyl, pyridazinyl, pyrimidinyl, or pyrazinyl. In a further aspect, Ar¹ is pyridinyl, pyridazinyl, pyrimidinyl, or pyrazinyl substituted with 0-3 substituents independently selected from halo, cyano, C1-C6 alkyl, C1-C6 haloalkyoxy, C1-C6 haloalkyl, C1-C6 polyhaloalkyl, C1-C6 cyanoalkyl, SO₂R¹², C1-C3 alkyl, C1-C3 alkylamine, and C1-C3 dialkylamino. In a further aspect, Ar¹ is heteroaryl substituted with 0-3 substituents independently selected from halo, cyano, C1-C6 alkyl, C1-C6 haloalkyoxy, C1-C6 haloalkyl, C1-C6 polyhaloalkyl, C1-C6 cyanoalkyl, SO₂R¹². In a further aspect, Ar¹ is heteroaryl substituted with 0-3 substituents independently selected from halo, cyano, C1-C6 haloalkyoxy, C1-C6 haloalkyl, C1-C6 polyhaloalkyl, C1-C6 cyanoalkyl, and SO₂R¹². In a further aspect, Ar¹ is heteroaryl monosubstituted with a substituent selected from halo, cyano, C1-C6 haloalkyoxy, C1-C6 haloalkyl, C1-C6 polyhaloalkyl, C1-C6 cyanoalkyl, and SO₂R¹².

f. R¹ Groups

In one aspect, each R¹ group (i.e., R¹ᵃ and R¹ᵇ) is independently selected from hydrogen, halogen, OH, CN, SO₂CH₃, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R⁷.

In a further aspect, R¹ᵃ is hydrogen. In a further aspect, R¹ᵃ is halogen. In a further aspect, R¹ᵃ is selected from hydrogen and halogen. In a further aspect, R¹ᵃ is selected from hydrogen, halogen, OH, CN, and C1-C6 alkyl. In a further aspect, R¹ᵃ is selected from hydrogen, halogen, OH, CN, methyl, ethyl, and propyl. In a further aspect, R¹ᵃ is selected from hydrogen, halogen, OH, methyl, ethyl, and propyl. In a further aspect, R¹ᵃ is selected from hydrogen, halogen, OH, and CN. In a further aspect, R¹ᵃ is selected from hydrogen, halogen, and OH. In a further aspect, R¹ᵃ is selected from hydrogen, methyl, ethyl, and propyl. In a further aspect, R¹ᵃ is selected from methyl, ethyl, and propyl. In a further aspect, R¹ᵃ is selected from hydrogen, halogen, methyl, ethyl, and propyl. In a further aspect, R¹ᵃ is selected from halogen, OH, CN, methyl, ethyl, and propyl. In a further aspect, R¹ᵃ is selected from halogen, OH, methyl, ethyl, and propyl. In a further aspect, R¹ᵃ is selected from halogen, methyl, ethyl, and propyl.

In a further aspect, R¹ᵃ is selected from halogen, OH, and CN. In a further aspect, R¹ is selected from hydrogen, halogen, OH, CN, C1-C6 alkyl, C1-C6 haloalkyl, and C1-C6 polyhaloalkyl. In a further aspect, R¹ᵃ is selected from hydrogen, CN, methyl, and CF₃. In a further aspect, R¹ᵃ is selected from hydrogen, halogen, methyl, and CF₃. In a further aspect, R¹ᵃ is selected from hydrogen, OH, CN, methyl, and CF₃. In a further aspect, R¹ᵃ is selected from hydrogen, halogen, OH, methyl, and CF₃. In a further aspect, R¹ᵃ is selected from halogen, CN, methyl, and CF₃. In a further aspect, R¹ᵃ is selected from halogen, OH, CN, methyl, and CF₃. In a further aspect, R¹ᵃ is selected from hydrogen, halogen, OH, CN, and C1-C6 cyanoalkyl. In a further aspect, R¹ᵃ is selected from hydrogen, OH, CN, and C1-C6 cyanoalkyl. In a further aspect, R¹ᵃ is selected from hydrogen, CN, and C1-C6 cyanoalkyl. In a further aspect, R¹ᵃ is selected from hydrogen, OH, and C1-C6 cyanoalkyl. In a further aspect, R¹ᵃ is selected from hydrogen, CN, and C1-C6 cyanoalkyl. In a further aspect, R¹ᵃ is selected from hydrogen, CN, cyanomethyl, cyanoethyl, cyanopropyl, and 2-cyanopropyl. In a further aspect, R¹ᵃ is selected from halogen, OH, CN, and C1-C6 cyanoalkyl. In a further aspect, R¹ᵃ is selected from halogen, CN, and C1-C6 cyanoalkyl. In a further aspect, $R^{1a}$ is selected from halogen, OH, and C1-C6 cyanoalkyl. In a further aspect, $R^{1a}$ is selected from halogen, CN, cyanomethyl, cyanoethyl, cyanopropyl, and 2-cyanopropyl.

In a further aspect, $R^{1b}$ is hydrogen. In a further aspect, $R^{1b}$ is halogen. In a further aspect, $R^{1b}$ is selected from hydrogen and halogen. In a further aspect, $R^{1b}$ is selected from hydrogen, halogen, CN, $SO_2CH_3$, C1-C6 alkoxy, and $NH(C=O)R^7$. In a further aspect, $R^{1b}$ is selected from hydrogen, CN, $SO_2CH_3$, C1-C6 alkoxy, C1-C6 haloalkoxy, C1-C6 polyhaloalkoxy, and $NH(C=O)R^7$. In a further aspect, $R^{1b}$ is selected from hydrogen, halogen, CN, and $SO_2CH_3$. In a further aspect, $R^{1b}$ is selected from hydrogen, halogen, C1-C6 alkoxy, C1-C6 haloalkoxy, C1-C6 polyhaloalkoxy, and $NH(C=O)R^7$. In a further aspect, $R^{1b}$ is selected from hydrogen, halogen, and $NH(C=O)R^7$. In a further aspect, $R^{1b}$ is selected from hydrogen, halogen, C1-C6 alkoxy, C1-C6 haloalkoxy, and C1-C6 polyhaloalkoxy.

In a further aspect, $R^{1b}$ is selected from hydrogen, halogen, OH, CN, and C1-C6 cyanoalkyl. In a further aspect, $R^{1b}$ is selected from hydrogen, halogen, CN, and C1-C6 cyanoalkyl. In a further aspect, $R^{1b}$ is selected from hydrogen, halogen, OH, and C1-C6 cyanoalkyl. In a further aspect, $R^{1b}$ is selected from hydrogen, OH, CN, and C1-C6 cyanoalkyl. In a further aspect, $R^{1b}$ is selected from hydrogen, OH, and C1-C6 cyanoalkyl. In a further aspect, $R^{1b}$ is selected from hydrogen, CN, and C1-C6 cyanoalkyl. In a further aspect, $R^{1b}$ is selected from halogen, OH, CN, and C1-C6 cyanoalkyl. In a further aspect, $R^{1b}$ is selected from halogen, OH, and C1-C6 cyanoalkyl. In a further aspect, $R^{1b}$ is selected from halogen, CN, and C1-C6 cyanoalkyl.

In one aspect, each of $R^{1a}$ and $R^{1b}$ is independently selected from hydrogen and halogen. In a further aspect, each of $R^{1a}$ and $R^{1b}$ is hydrogen. In a further aspect, each of $R^{1a}$ and $R^{1b}$ is independently selected from halogen. In a further aspect, each of $R^{1a}$ and $R^{1b}$ is independently selected from hydrogen, halogen, OH, CN, C1-C6 alkyl, C1-C6 cyanoalkyl, and C1-C6 alkoxy. In a further aspect, $R^{1a}$ is selected from hydrogen, halogen, CN, C1-C6 cyanoalkyl, and C1-C6 alkyl, and $R^{1b}$ is selected from hydrogen, halogen, CN, OH, $SO_2CH_3$, $NH(C=O)R^7$, and C1-C6 alkoxy.

In one aspect, C1-C6 cyanoalkyl is selected from cyanomethyl, cyanoethyl, cyanopropyl, and 2-cyanopropyl. In a further aspect, C1-C6 alkoxy is selected from methoxy, ethoxy, and propoxy. In a further aspect, C1-C6 polyhaloalkoxy is selected from trifluoromethoxy, 2,2,2-trifluoroethoxy, and 3,3,3-trifluoropropoxy. In a further aspect, the halogen is selected from fluoro or chloro.

g. $R^2$ Groups

In one aspect, $R^2$ is selected from hydrogen, C1-C6 alkyl, $SO_2R^8$, and $(C=O)R^8$. In a further aspect, $R^2$ is selected from hydrogen and C1-C6 alkyl. In a further aspect, $R^2$ is selected from C1-C6 alkyl, $(C=O)R^8$, and $SO_2R^8$. In a further aspect, $R^2$ is selected from hydrogen, $(C=O)R^8$, and $SO_2R^8$. In a further aspect, $R^2$ is selected from $(C=O)R^8$ and $SO_2R^8$. In a further aspect, $R^2$ is selected from hydrogen and $SO_2R^8$. In a further aspect, $R^2$ is selected from hydrogen and $(C=O)R^8$. In a further aspect, $R^2$ is $(C=O)R^8$. In a further aspect, $R^2$ is $SO_2R^8$. In a further aspect, $R^2$ is $SO_2NR^{10}R^{11}$. In a further aspect, $R^2$ is $(C=O)NR^{10}R^{11}$. In a further aspect, $R^2$ is hydrogen. In a further aspect, $R^2$ is $(C=O)R^8$. $R^2$ is selected from hydrogen, C1-C6 alkyl, $SO_2R^8$, and $(C=O)R^8$;

h. $R^3$ Groups

In one aspect, $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl. In a further aspect, $R^3$ is hydrogen.

In a further aspect, $R^3$ is halogen. In a further aspect, $R^3$ is selected from hydrogen, halogen, and CN. In a further aspect, $R^3$ is selected from hydrogen, halogen, CN, and OH. In a further aspect, $R^3$ is selected from hydrogen, C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl. In a further aspect, $R^3$ is selected from halogen, C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl. In a further aspect, $R^3$ is selected from hydrogen, halogen, C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl. In a further aspect, $R^3$ is selected from hydrogen, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl. In a further aspect, $R^3$ is selected from hydrogen, halogen, C1-C3 alkyl, C1-C3 haloalkyl, C1-C3 polyalkyl, C3 cycloalkyl, C3 haloalkyl, and C3 polyhaloalkyl. In a further aspect, $R^3$ is selected from hydrogen, C1-C3 alkyl, C1-C3 haloalkyl, C1-C3 polyalkyl, C3 cycloalkyl, C3 haloalkyl, and C3 polyhaloalkyl. In a further aspect, $R^3$ is selected from halogen, C1-C3 alkyl, C1-C3 haloalkyl, C1-C3 polyalkyl, C3 cycloalkyl, C3 haloalkyl, C3 polyhaloalkyl, and C3 heterocycloalkyl. In a further aspect, $R^3$ is selected from hydrogen, halogen, CN, $CH_3$, $CH_2F$, $CHF_2$, and $CF_3$. In a further aspect, $R^3$ is selected from hydrogen, halogen, CN, $CH_3$, $CH_2F$, $CHF_2$, $CF_3$, cyclopropyl, 2,3-difluorocyclopropyl, 2,2-difluorocyclopropyl, and aziridine. In a further aspect, $R^3$ is selected from hydrogen, halogen, $CH_3$, $CH_2F$, $CHF_2$, $CF_3$, cyclopropyl, 2,3-difluorocyclopropyl, 2,2-difluorocyclopropyl, and aziridine. In a further aspect, $R^3$ is selected from hydrogen, halogen, $CH_3$, $CH_2F$, $CHF_2$, $CF_3$, cyclopropyl, 2,3-difluorocyclopropyl, and 2,2-difluorocyclopropyl. In a further aspect, $R^3$ is selected from hydrogen, halogen, $CH_3$, $CH_2F$, $CHF_2$, $CF_3$, and cyclopropyl. In a further aspect, $R^3$ is selected from hydrogen, halogen, $CH_3$, $CH_2F$, $CHF_2$, and $CF_3$.

In a further aspect, the halogen is selected from fluoro or chloro.

i. $R^4$ Groups

In one aspect, $R^4$ is selected from hydrogen, halogen, $Ar^1$, C1-C6 alkyl, C3-C6 cycloalkyl, and C3-C6 heterocycloalkyl. In a further aspect, $R^4$ is hydrogen. In a further aspect, $R^4$ is halogen. In a further aspect, $R^4$ is CN. In a further aspect, $R^4$ is $Ar^1$. In a further aspect, $R^4$ is selected from hydrogen, halogen, C1-C6 alkyl, C3-C6 cycloalkyl, and C3-C6 heterocycloalkyl. In a further aspect, $R^4$ is selected from hydrogen, halogen, aryl, and heteroaryl. In a further aspect, $R^4$ is selected from hydrogen and $Ar^1$. In a further aspect, $R^4$ is selected from halogen and $Ar^1$. In a further aspect, $R^4$ is selected from hydrogen, C1-C6 alkyl, C3-C6 cycloalkyl, C3-C6 heterocycloalkyl, and $Ar^1$. In a further aspect, $R^4$ is selected from halogen, C1-C6 alkyl, C3-C6 cycloalkyl, C3-C6 heterocycloalkyl, and $Ar^1$. In a further aspect, $R^4$ is selected from hydrogen, halogen, C3-C6 cycloalkyl, C3-C6 heterocycloalkyl, and $Ar^1$. In a further aspect, $R^4$ is selected from hydrogen, halogen, $CH_3$, aziridinyl, cyclopropyl, morpholinyl, piperidinyl, piperazinyl, hexahydropyrimidinyl, hexahydropyridazinyl, pyrrolidinyl, oxazolidinyl, imidazolidinyl, pyrazolidinyl, 1,3-oxazinanyl, thiomorpholinyl 1,1-dioxide, and 1-(C1-C6 alkylsulfonyl)piperazinyl.

In a further aspect, the halogen is selected from fluoro or chloro.

j. $R^5$ Groups

In one aspect, $R^5$ is selected from is selected from hydrogen and C1-C6 alkyl. In a further aspect, $R^5$ is hydrogen. In a further aspect, $R^5$ is C1-C6 alkyl, for example, C1-C4 alkyl. In a further aspect, $R^5$ is selected from hydrogen, methyl and ethyl.

k. $R^6$ Groups

In one aspect, $R^6$ is selected from hydrogen and $CH_3$. In a further aspect, $R^6$ is hydrogen. In a further aspect, $R^6$ is $CH_3$.

l. $R^7$ Groups

In one aspect, $R^7$ is selected from hydrogen and C1-C6 alkyl. In a further aspect, $R^7$ is hydrogen. In a further aspect, $R^7$ is C1-C6 alkyl, for example C1-C4 alkyl. In a further aspect, $R^7$ is selected from hydrogen, methyl, ethyl and propyl. In a further aspect, $R^7$ is selected from methyl, ethyl and propyl.

m. $R^8$ Groups

In one aspect, $R^8$ is selected from hydrogen, C1-C6 alkyl, C3-C6 cycloalkyl, C3-C6 heterocycloalkyl, and $NR^{10}R^{11}$. In a further aspect, $R^8$ is selected from C1-C6 alkyl, C3-C6 cycloalkyl, C3-C6 heterocycloalkyl, and $NR^{10}R^{11}$. In a further aspect, $R^8$ is selected from C1-C6 alkyl, C3-C6 cycloalkyl, and C3-C6 heterocycloalkyl. In a further aspect, $R^8$ is selected from hydrogen, methyl, aziridinyl, cyclopropyl, morpholinyl, piperidinyl, piperazinyl, pyrrolidinyl, oxazolidinyl, imidazolidinyl, and pyrazolidinyl. In a further aspect, $R^8$ is selected from hydrogen, aziridinyl, morpholinyl, piperidinyl, piperazinyl, pyrrolidinyl, oxazolidinyl, imidazolidinyl, and pyrazolidinyl. In a further aspect, $R^8$ is selected from hydrogen, aziridinyl, piperidinyl, and pyrrolidinyl. In a further aspect, $R^8$ is selected from methyl, aziridinyl, cyclopropyl, morpholinyl, piperidinyl, piperazinyl, pyrrolidinyl, oxazolidinyl, imidazolidinyl, and pyrazolidinyl. In a further aspect, $R^8$ is selected from aziridinyl, morpholinyl, piperidinyl, piperazinyl, pyrrolidinyl, oxazolidinyl, imidazolidinyl, and pyrazolidinyl. In a further aspect, $R^8$ is selected from aziridinyl, piperidinyl, and pyrrolidinyl. In a further aspect, $R^8$ is piperidinyl. In a further aspect, $R^8$ is pyrrolidinyl. In a further aspect, $R^8$ is selected from hydrogen and $NR^{10}R^{11}$. In a further aspect, $R^8$ is $NR^{10}R^{11}$.

n. $R^{10}$ Groups

In one aspect, $R^{10}$ is selected from hydrogen, C1-C6 alkyl, and C3-C6 cycloalkyl. In a further aspect, $R^{10}$ is hydrogen. In a further aspect, $R^{10}$ is selected from hydrogen and C1-C6 alkyl. In a further aspect, $R^{10}$ is C1-C6 alkyl, for example, C1-C4 alkyl. In a further aspect, $R^{10}$ is C3-C6 cycloalkyl, for example, cyclopropyl, cyclobutyl, cyclopentyl, or cyclohexyl. In a further aspect, $R^{10}$ is selected from hydrogen, methyl, ethyl, propyl and cyclopropyl. In a further aspect, $R^{10}$ is selected from hydrogen, methyl, ethyl, and propyl. In a further aspect, $R^{10}$ is selected from hydrogen, methyl, and ethyl.

o. $R^{11}$ GROUPS

In one aspect, $R^{11}$ is selected from hydrogen and C1-C6 alkyl; or $R^{10}$ and $R^{11}$ are covalently bonded and, together with the intermediate nitrogen, comprise an optionally substituted 3-7 membered heterocycloalkyl ring. In a further aspect, $R^{11}$ is hydrogen. In a further aspect, $R^{11}$ is selected from hydrogen and C1-C6 alkyl. In a further aspect, $R^{11}$ is selected from hydrogen, methyl, ethyl, propyl and cyclopropyl. In a further aspect, $R^{11}$ is selected from hydrogen, methyl, ethyl, and propyl.

In a further aspect, each of $R^{10}$ and $R^{11}$ is hydrogen. In a further aspect, each of $R^{10}$ and $R^{11}$ is methyl. In a further aspect, each of $R^{10}$ and $R^{11}$ is ethyl. In a further aspect, each of $R^{10}$ and $R^{11}$ is cyclopropyl. In a further aspect, $R^{10}$ is hydrogen, and $R^{11}$ is methyl. In a further aspect, $R^{10}$ is hydrogen, and $R^{11}$ is ethyl. In a further aspect, $R^{10}$ is hydrogen, and $R^{11}$ is cyclopropyl. In a further aspect, each of $R^{10}$ and $R^{11}$ is selected from hydrogen, methyl, and ethyl. In a further aspect, $R^{10}$ is selected from hydrogen, C1-C6 alkyl, and C3-C6 cycloalkyl, and $R^{11}$ is hydrogen. In a further aspect, $R^{10}$ is selected from C1-C6 alkyl, and C3-C6 cycloalkyl, and $R^{11}$ is C1-C6 alkyl. In a further aspect, $R^{10}$ is selected from hydrogen, C1-C6 alkyl, and C3-C6 cycloalkyl; and $R^{11}$ is selected from hydrogen and C1-C6 alkyl. In a further aspect, $R^{10}$ is selected from hydrogen, methyl, ethyl, propyl, and cyclopropyl, and $R^{11}$ is hydrogen. In a further aspect, $R^{10}$ is selected from methyl, ethyl, propyl, and cyclopropyl, and $R^{11}$ is selected from methyl, ethyl, and propyl. In a further aspect, $R^{10}$ is selected from hydrogen, methyl, ethyl, propyl, and cyclopropyl, and $R^{11}$ is selected from hydrogen, methyl, ethyl, and propyl.

In one aspect, $R^{10}$ and $R^{11}$ are covalently bonded and, together with the intermediate carbons, comprise an optionally substituted 3-7 membered heterocycloalkyl ring with the nitrogen. In a further aspect, the optionally substituted 3-7 membered heterocycloalkyl ring with nitrogen is selected from optionally substituted aziridinyl, pyrollidinyl, oxazolidinyl, imidazolidinyl, pyrazolidinyl, piperidinyl, piperazinyl, hexahydropiperidinyl, hexahydropyridazinyl, morpholinyl, 1,3-oxazinanyl and azepanyl. In a further aspect, the optionally substituted 3-7 membered heterocycloalkyl ring with the nitrogen is selected from optionally substituted aziridinyl, pyrrolidinyl, morpholinyl, and piperidinyl. In a further aspect, the optionally substituted 3-7 membered heterocycloalkyl ring with nitrogen is selected from optionally substituted aziridinyl, pyrollidinyl, and piperidinyl. In a further aspect, the optionally substituted 3-7 membered heterocycloalkyl ring with the nitrogen is optionally substituted aziridinyl. In a further aspect, the optionally substituted 3-7 membered heterocycloalkyl ring with the nitrogen is optionally substituted pyrrolidinyl. In a further aspect, the optionally substituted 3-7 membered heterocycloalkyl ring with the nitrogen is morpholinyl. In a further aspect, the optionally substituted 3-7 membered heterocycloalkyl ring with the nitrogen is piperidinyl. In a further aspect, the optionally substituted 3-7 membered heterocycloalkyl ring with nitrogen is optionally substituted with 0-3 substituents selected halogen, CN, OH, C1-C3 alkylamine, C1-C3 alkyl, and cyclopropyl. In a further aspect, the 0-3 substituents are selected from halogen, CN, methyl, ethyl and propyl. In a further aspect, the 0-3 substituents are halogen. In one aspect, halogen is selected from fluoro and chloro. In one aspect, the halogen is fluoro. In a further aspect, the optionally substituted 3-7 membered heterocycloalkyl ring is unsubstituted.

In one aspect, $NR^{10}R^{11}$ is selected from $NH_2$, $NHCH_3$, $N(CH_3)_2$, $N(CH_2CH_3)_2$, $NH(C_3H_5)$, aziridinyl, pyrrolidinyl, morpholinyl, and piperidinyl. In a further aspect, $NR^{10}R^{11}$ is selected from $N(CH_3)_2$, $N(CH_2CH_3)_2$, $NH(C_3H_5)$, pyrrolidinyl, morpholinyl, and piperidinyl. In a further aspect, $NR^{10}R^{11}$ is selected $N(CH_3)_2$, $NH(C_3H_5)$, $N(CH_2CH_3)_2$, aziridinyl, cyclopropylamino, pyrrolidinyl, and piperidinyl. In a further aspect, $NR^{10}OR^{11}$ is selected from $N(CH_3)_2$, $NH(C_3H_5)$, aziridinyl, cyclopropylamino, and pyrrolidinyl. In a further aspect, $NR^{10}R^{11}$ is $N(CH_3)_2$. In a further aspect, $NR^{10}R^{11}$ is $NH(CH_3H_5)$. In a further aspect, $NR^{10}R^{11}$ is pyrrolidinyl.

p. $R^{12}$ Groups

In one aspect, $R^{12}$ is selected from C1-C6 alkyl and C3-C6 cycloalkyl. In a further aspect, $R^{12}$ is C1-C6 alkyl, for example, C1-C4 alkyl. In a further aspect, $R^{12}$ is C3-C6 cycloalkyl, for example, cyclopropyl, cyclobutyl, cyclopentyl, or cyclohexyl. In a further aspect, $R^{12}$ is selected from methyl, ethyl, propyl, and cyclopropyl. In a further aspect, $R^{12}$ is selected from methyl, ethyl, and propyl. In a further aspect, $R^{12}$ is methyl.

q. $R^{13}$ GROUPS

In one aspect, each $R^{13}$ group (i.e., $R^{13a}$ and $R^{13b}$) is independently selected from hydrogen, and C1-C6 alkyl; or $R^{13a}$ and $R^{13b}$ are covalently bonded and, together with the intermediate atoms, comprise an optionally substituted heterocyclic ring. In a further aspect, $R^{13a}$ is hydrogen or C1-C6 alkyl. In a further aspect, $R^{13a}$ is hydrogen or C1-C6 alkyl, for example, C1-C4 alkyl. In a further aspect, $R^{13b}$ is hydrogen or C1-C6 alkyl. In a further aspect, $R^{13b}$ is hydrogen or C1-C6 alkyl, for example, C1-C4 alkyl. In a further aspect, $R^{13a}$ and $R^{13b}$ are both hydrogen. In a further aspect, $R^{13a}$ and $R^{13b}$ are both C1-C6 alkyl, for example, C1-C4 alkyl.

In a further aspect, $R^{13a}$ and $R^{13b}$ are covalently bonded and, together with the intermediate atoms, comprise an optionally substituted heterocyclic ring. In a further aspect, $R^{13a}$ and $R^{13b}$ are covalently bonded and, together with the intermediate boron, comprise boronic acid pinacol ester, boronic acid trimethylene glycol ester, or 9-borabicyclo[3.3.1]nonane (9-BBN).

r. $R^{14}$ Groups

In one aspect, each $R^{14}$ group (i.e., $R^{14a}$, $R^{14b}$, and $R^{14c}$) is independently selected from C1-C6 alkyl, for example, C1-C4 alkyl. In a further aspect, $R^{14a}$, $R^{14b}$, and $R^{14c}$ are all butyl.

s. $X^1$ Groups

In one aspect, $X^1$ is halide or pseudohalide. In a further aspect, $X^1$ is halogen, for example, fluororo, chloro, bromo, or iodo. In a further aspect, $X^1$ is chloro, bromo, or iodo. In a further aspect, $X^1$ is bromo or iodo. In a further aspect, $X^1$ is chloro. In one aspect, $X^1$ is pseudohalide, for example, triflate, mesylate, tosylate, or brosylate. In a further aspect, $X^1$ is a group capable of undergoing a transition-metal mediated coupling reaction, for example a transition-metal mediated coupling reaction.

t. $X^2$ Groups

In one aspect, $X^2$ is halide, pseudohalide, or a group having a structure represented by the formula:

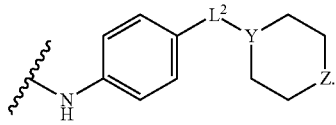

In a further aspect, $X^2$ is halide or pseudohalide. In a further aspect, $X^2$ is halogen, for example, fluororo, chloro, bromo, or iodo. In a further aspect, $X^2$ is chloro, bromo, or iodo. In a further aspect, $X^2$ is bromo or iodo. In a further aspect, $X^2$ is chloro. In one aspect, $X^2$ is pseudohalide, for example, triflate, mesylate, tosylate, or brosylate. In a further aspect, $X^2$ is a group capable of undergoing a coupling reaction, for example a transition-metal mediated coupling reaction.

In a further aspect, $X^2$ is a group having a structure represented by the formula:

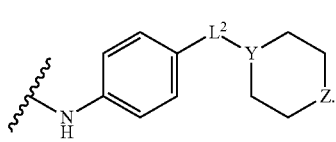

In a further aspect, both $X^1$ and $X^2$ are halide. In a further aspect, both $X^1$ and $X^2$ are chloro.

u. M Groups

In one aspect, M is a group capable of undergoing a coupling reaction, for example a transition-metal mediated coupling reaction. In a further aspect, M is selected from:

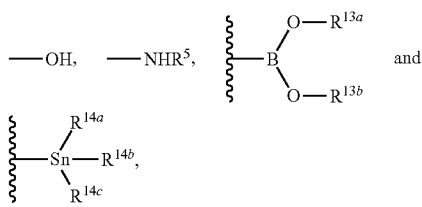

wherein each of $R^{13a}$ and $R^{13b}$ is independently selected from hydrogen, and C1-C6 alkyl; or $R^{13a}$ and $R^{13b}$ are covalently bonded and, together with the intermediate atoms, comprise an optionally substituted heterocyclic ring; and wherein each of $R^{14a}$, $R^{14b}$, and $R^{14c}$ is independently C1-C6 alkyl.

In a further aspect, M is —OH. In a further aspect, M is —$NHR^5$.

In a further aspect, M is a group having a structure

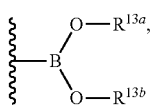

wherein each of $R^{13a}$ and $R^{13b}$ is independently selected from hydrogen, and C1-C6 alkyl; or $R^{13a}$ and $R^{13b}$ are covalently bonded and, together with the intermediate atoms, comprise an optionally substituted heterocyclic ring.

In a further aspect, M is a group having a structure:

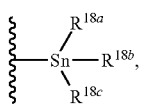

wherein each of $R^{14a}$, $R^{14b}$, and $R^{14c}$ is independently C1-C6 alkyl.

2. Example Compounds

In one aspect, a compound can be present as:

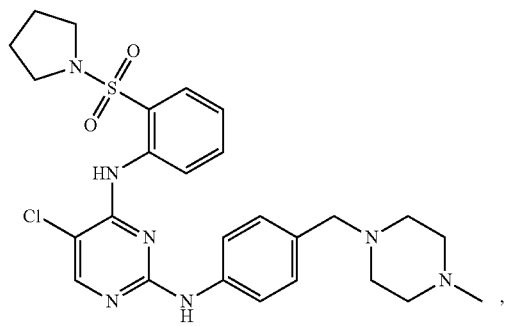

89
-continued
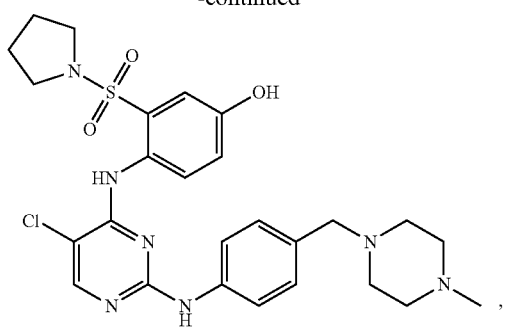
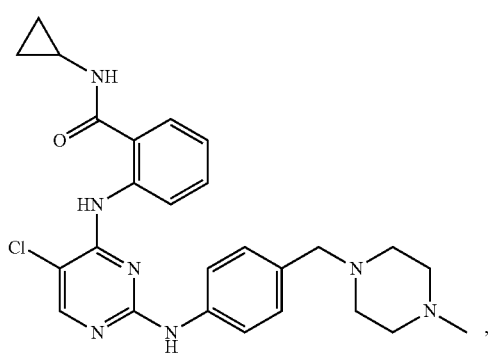
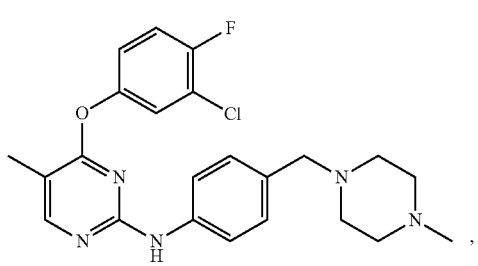
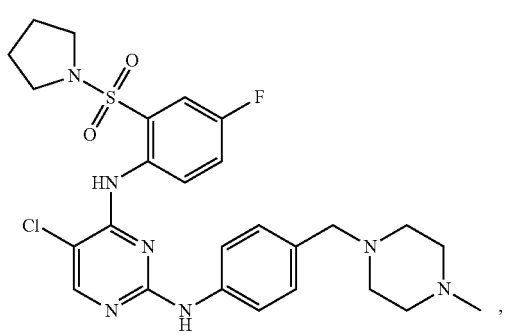
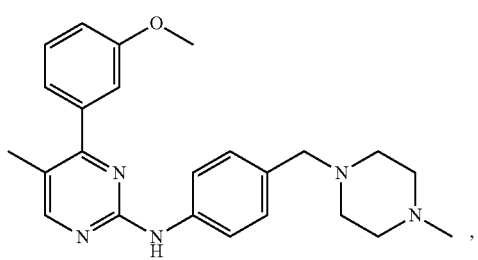
90
-continued
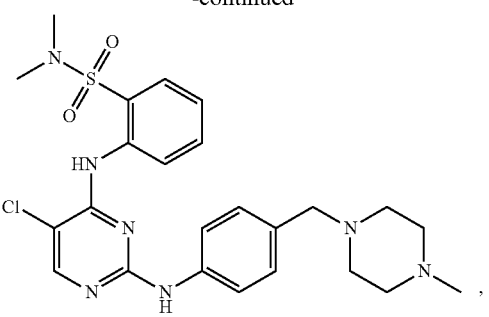
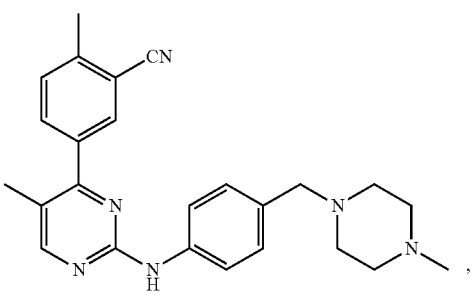
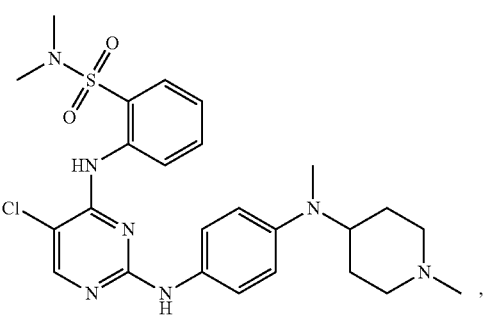
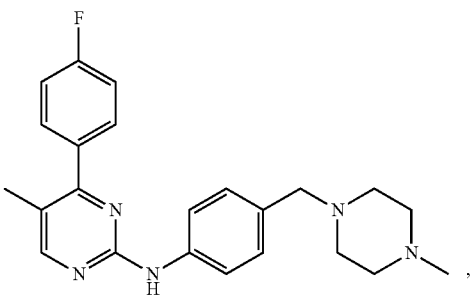
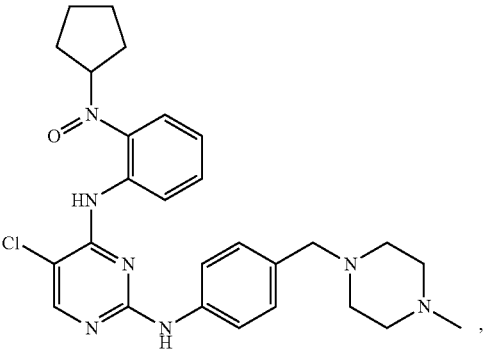

-continued
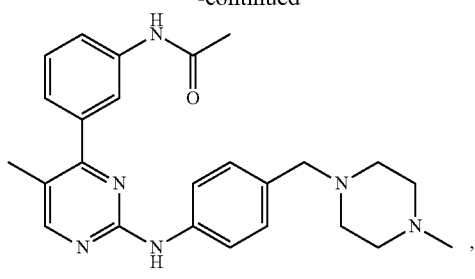
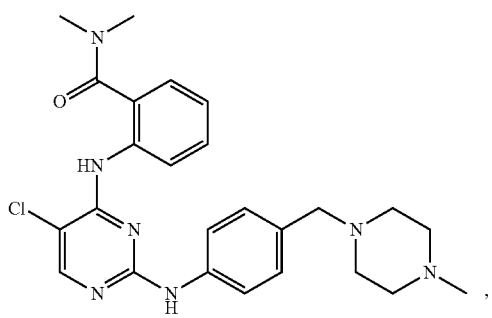
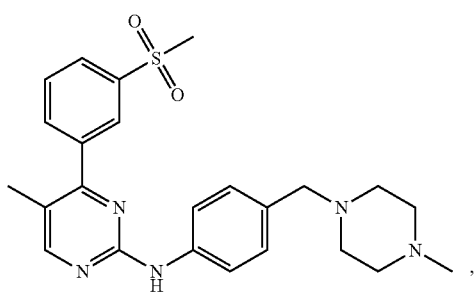
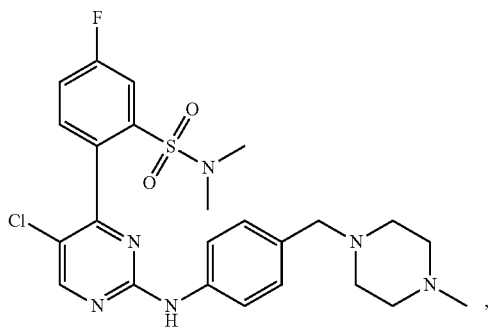
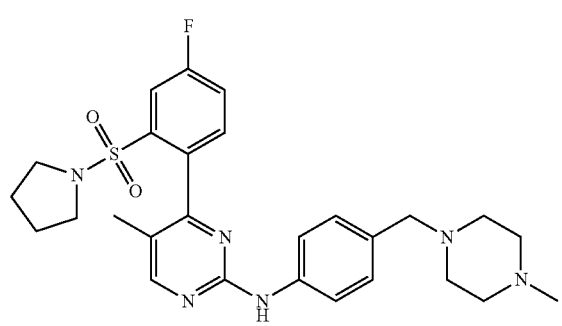
-continued
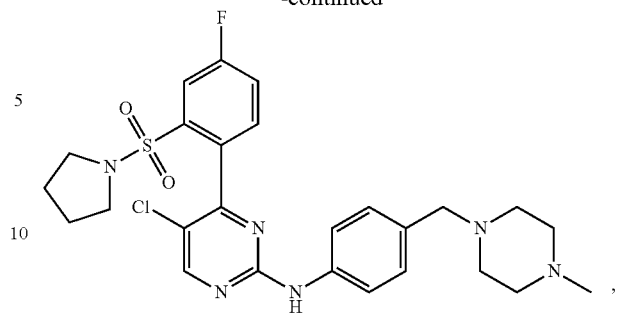
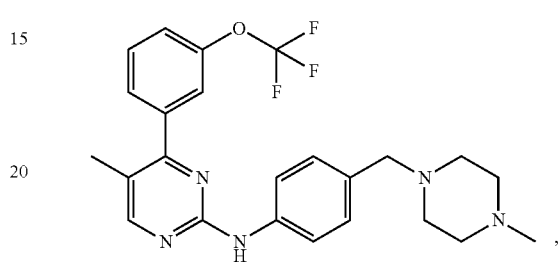
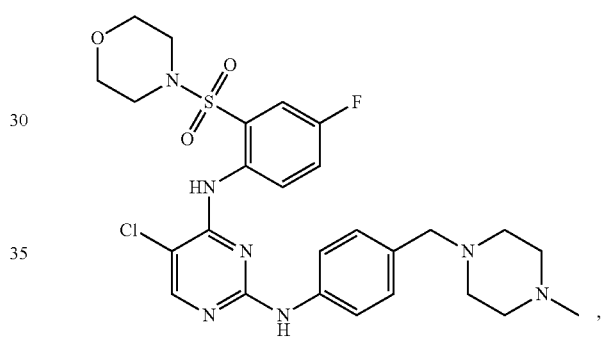
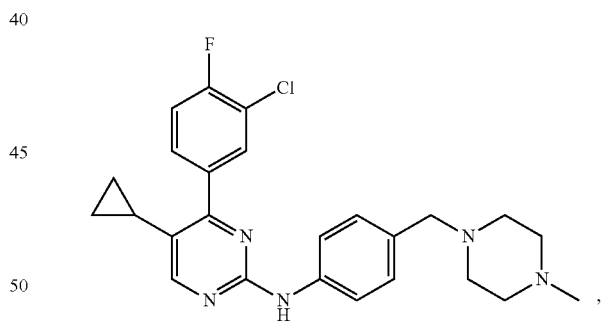
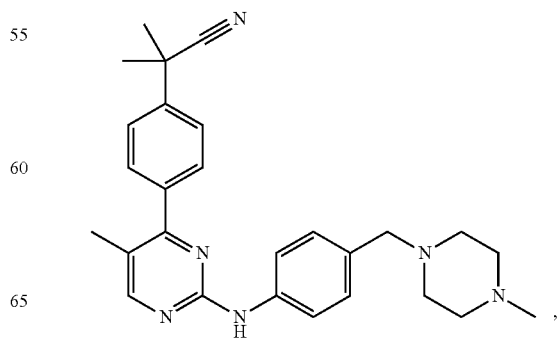

-continued
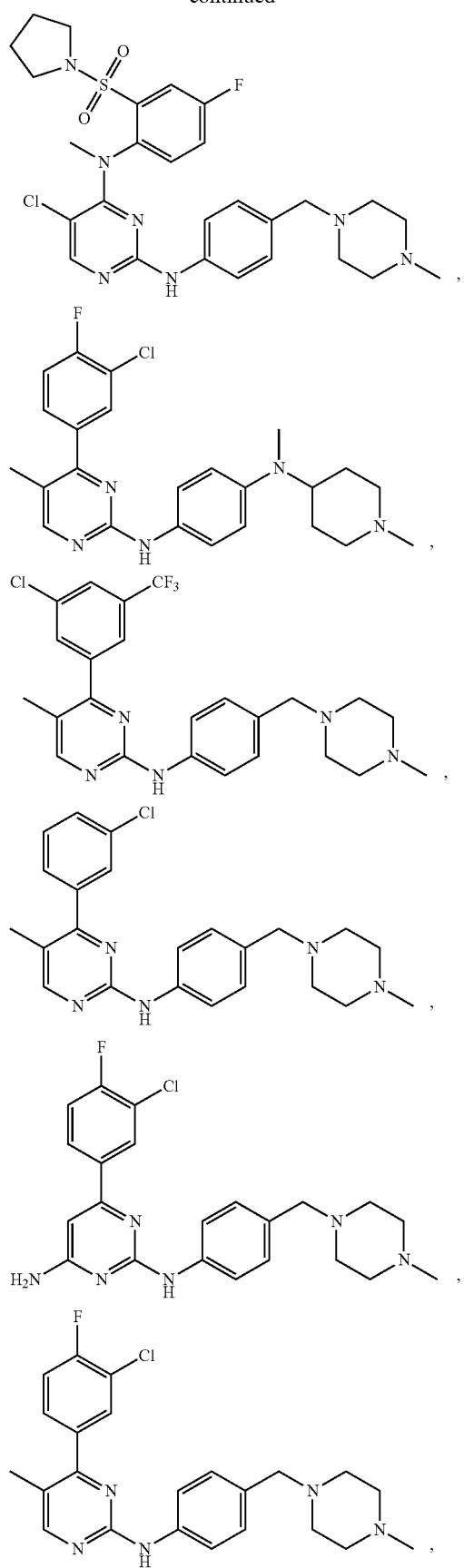
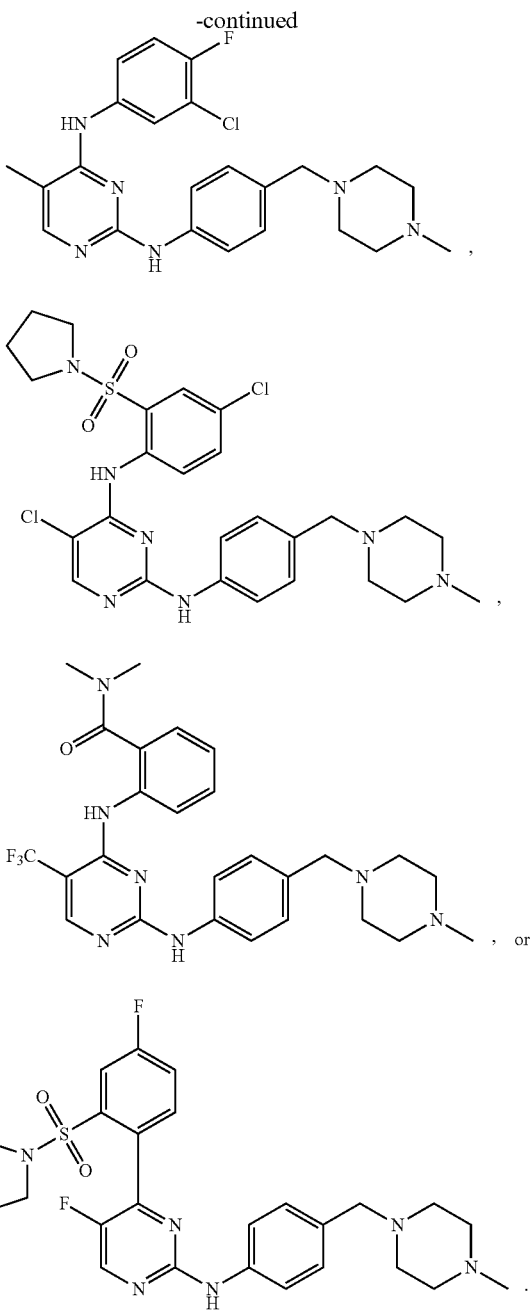
In one aspect, a compound can be present as:
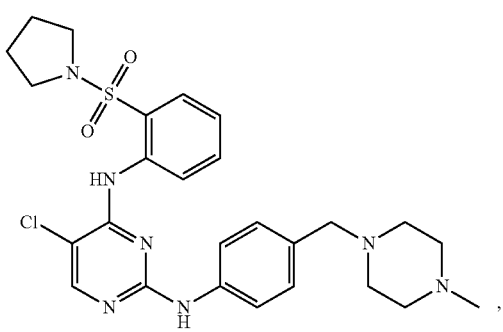

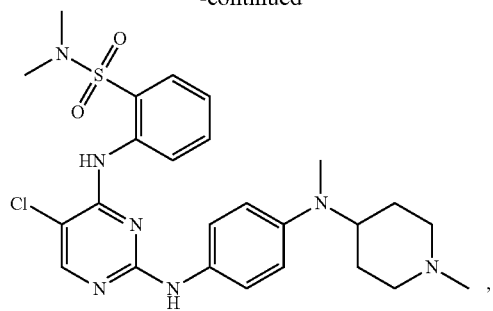
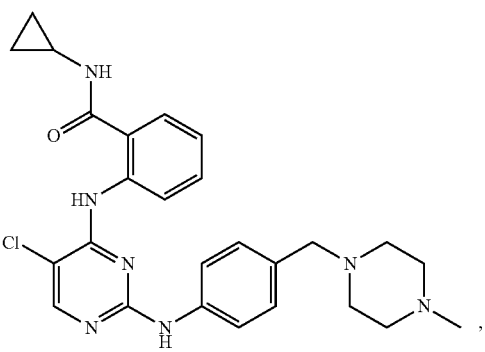
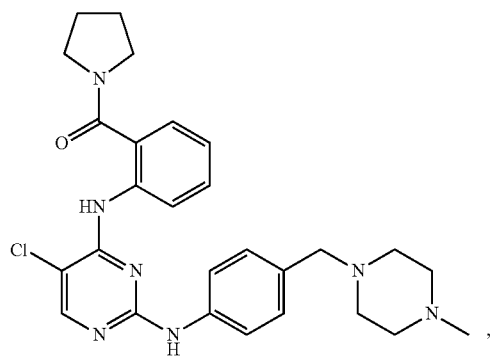
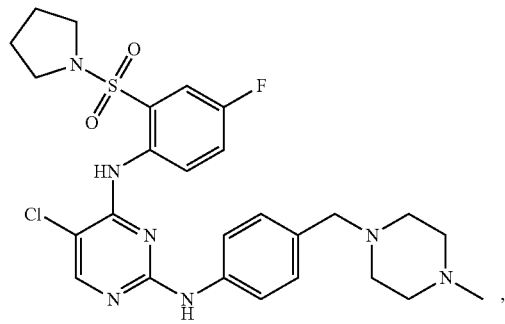
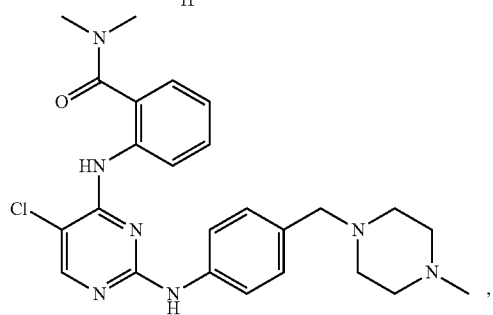
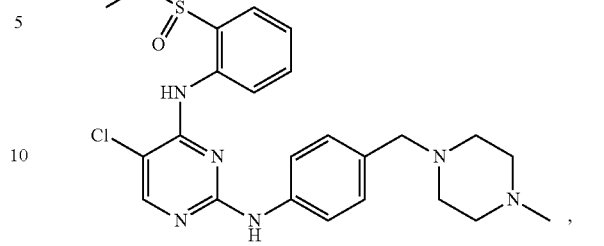
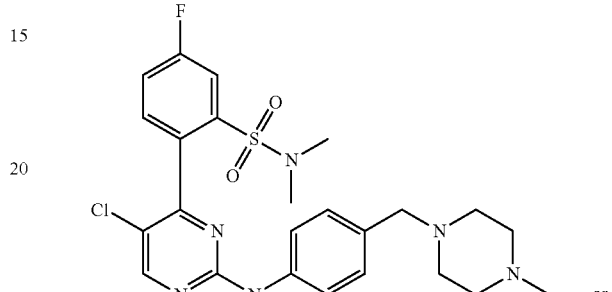
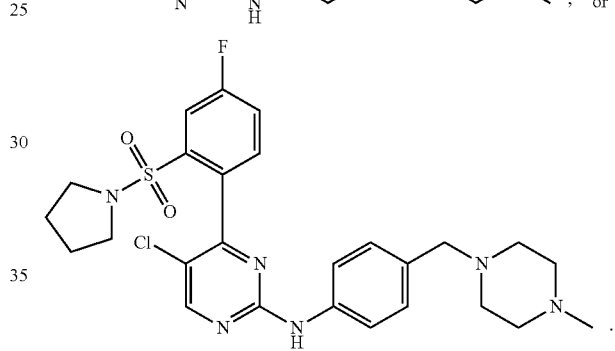
In one aspect, a compound can be present as:
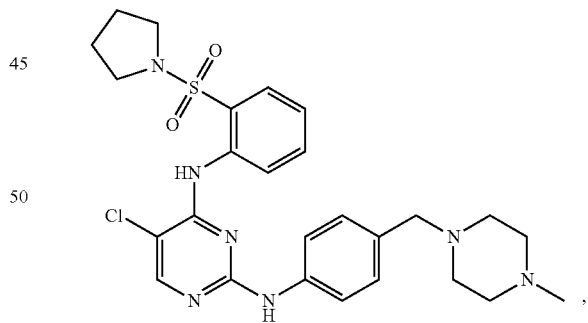
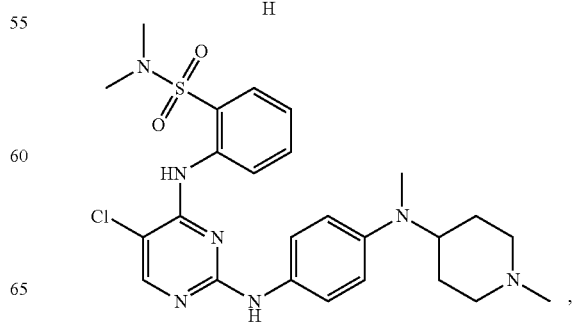

97
-continued
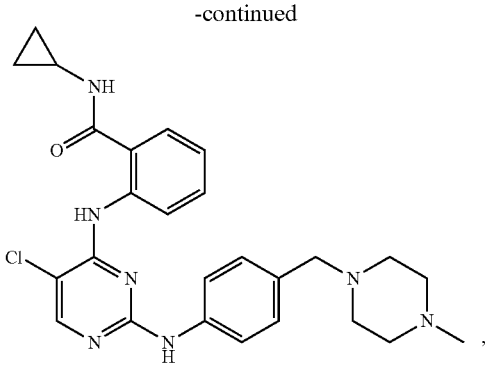
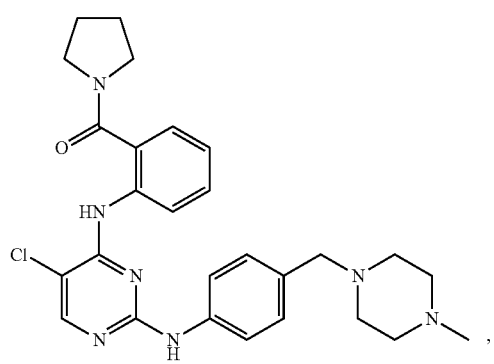
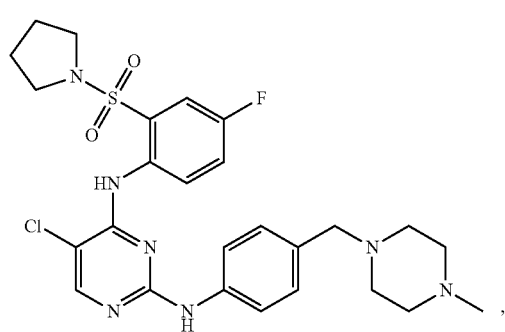
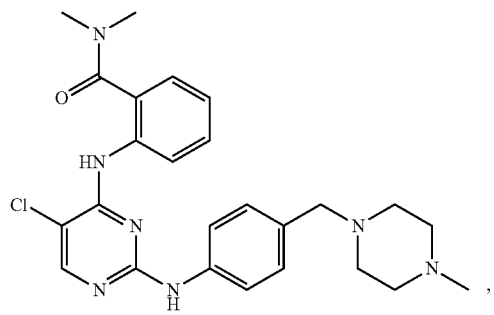
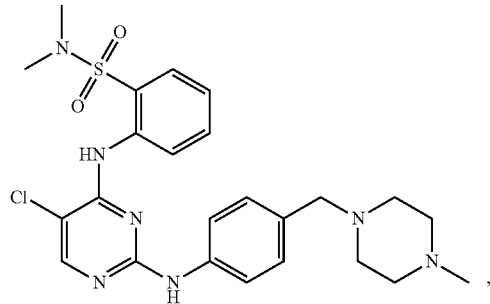
98
-continued
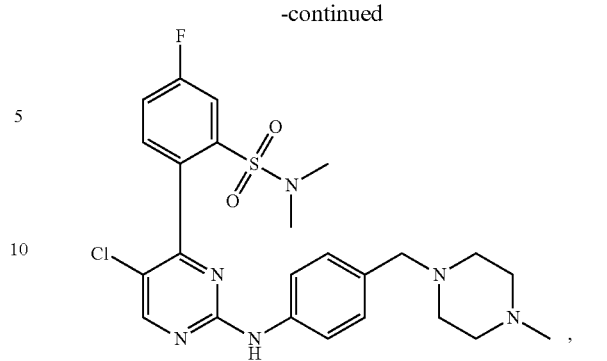
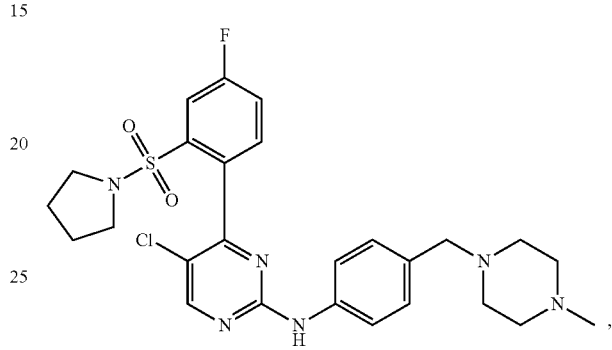
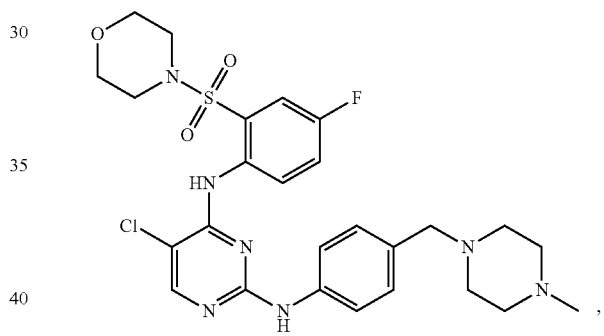
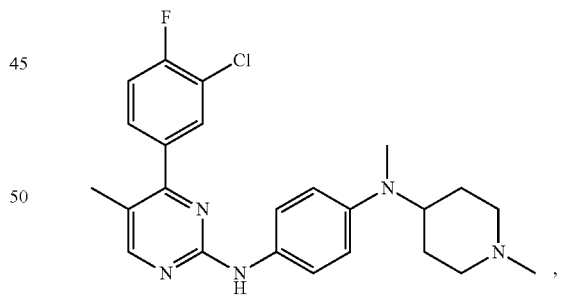
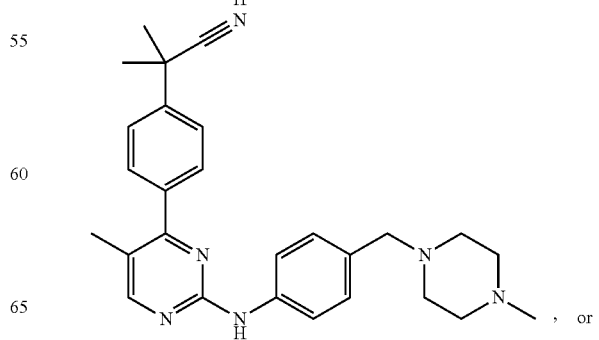, or 99
-continued
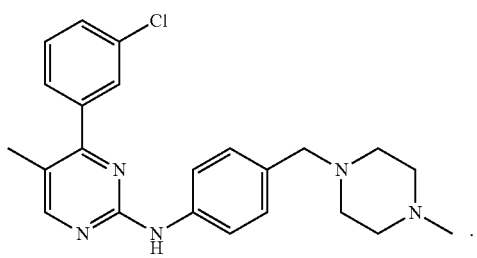
In one aspect, a compound can be present as:
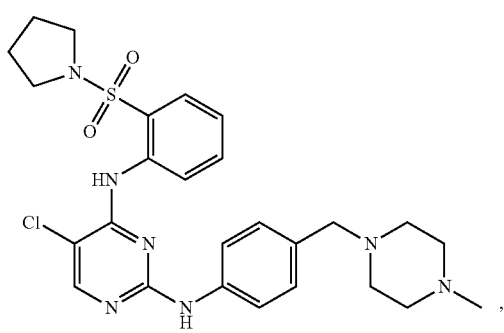
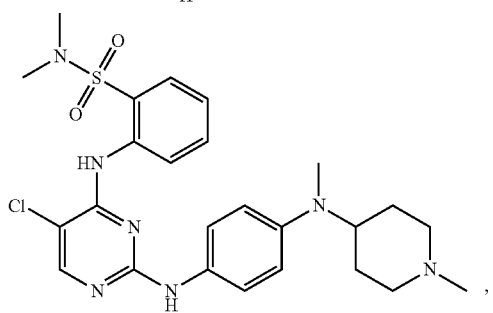
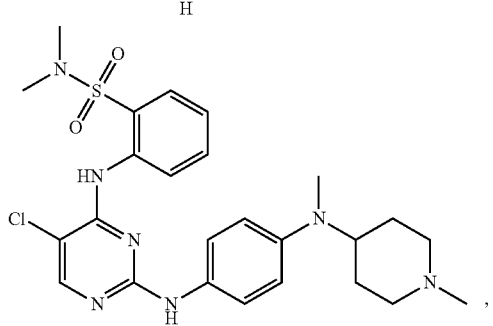
100
-continued
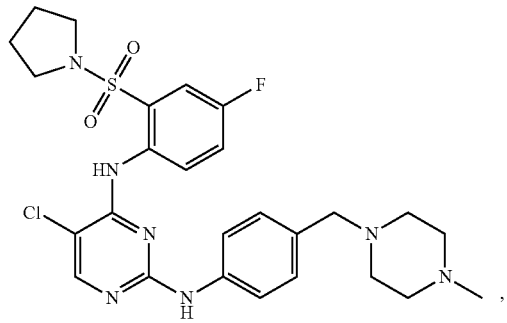
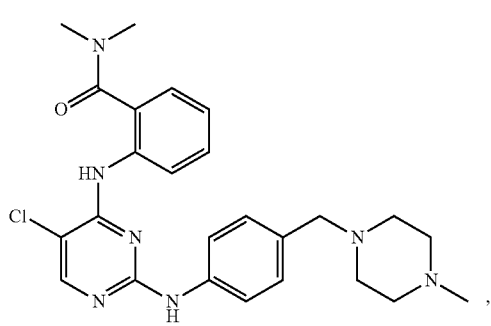
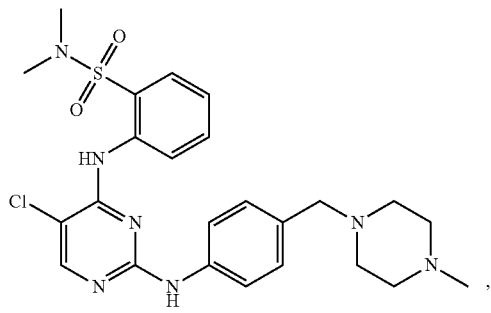

-continued
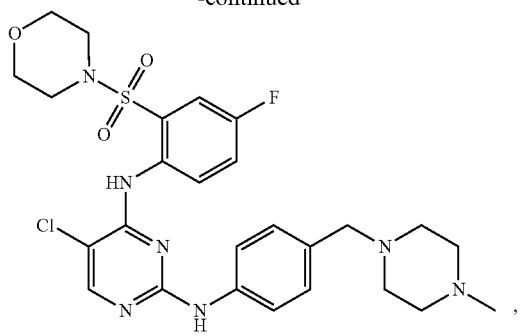
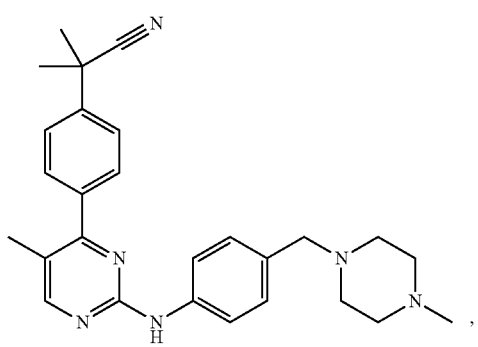
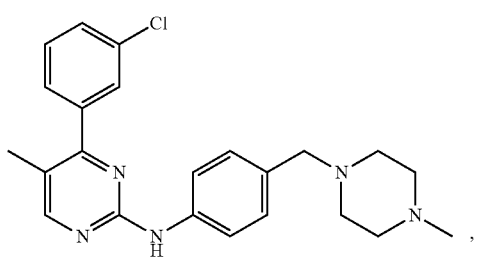
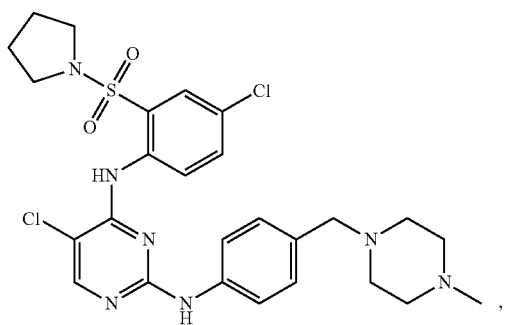
-continued
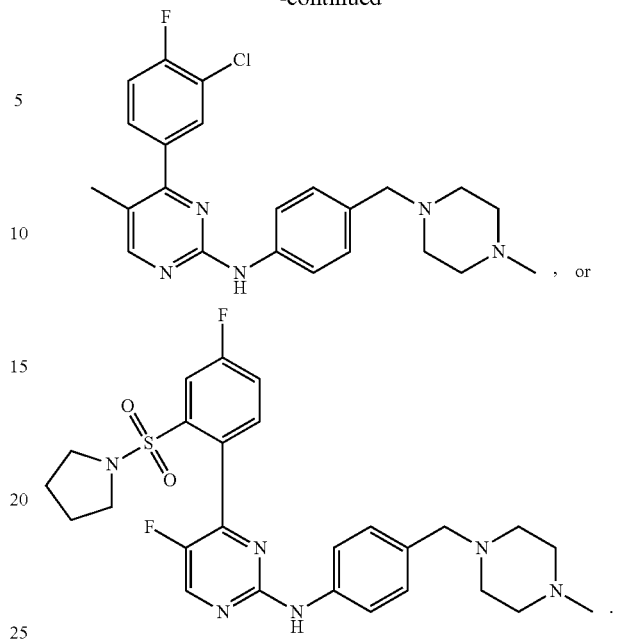
, or
.
In one aspect, a compound can be present as:
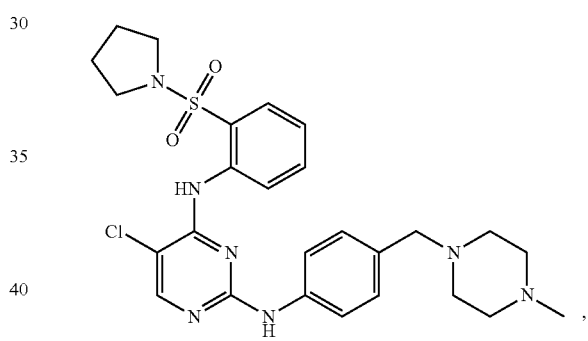
,
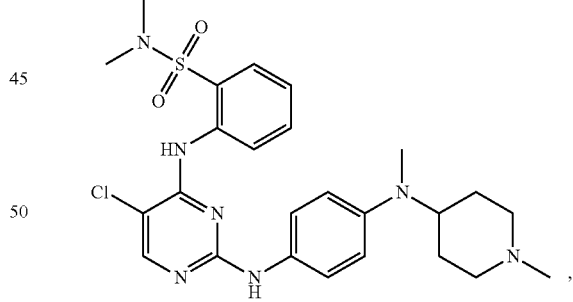
,
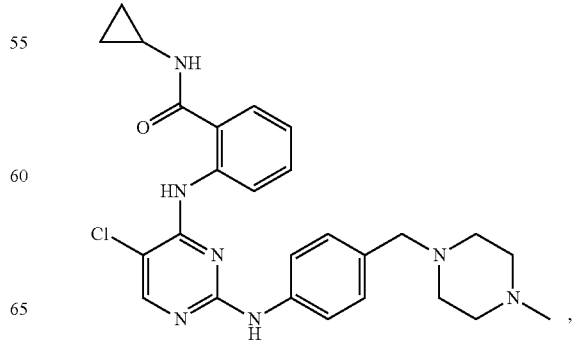
, 103
-continued
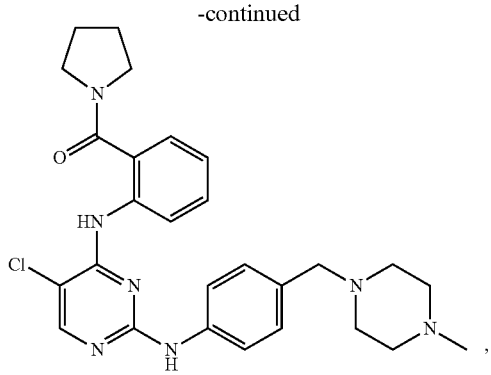
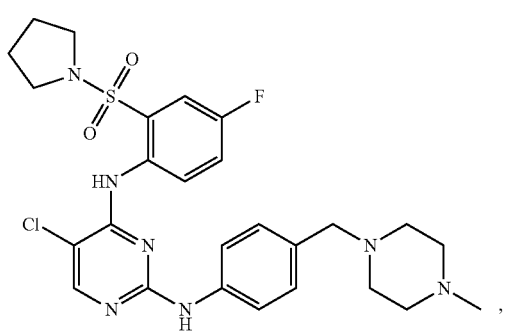
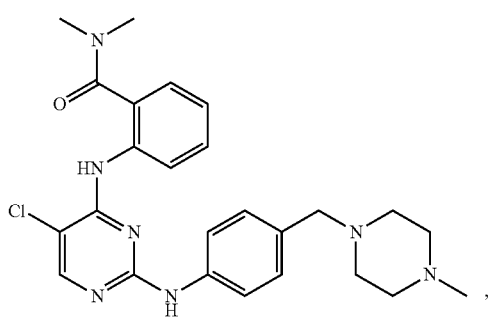
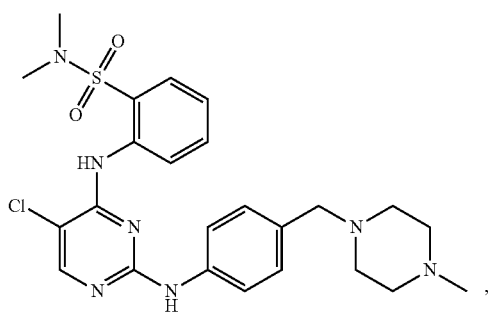
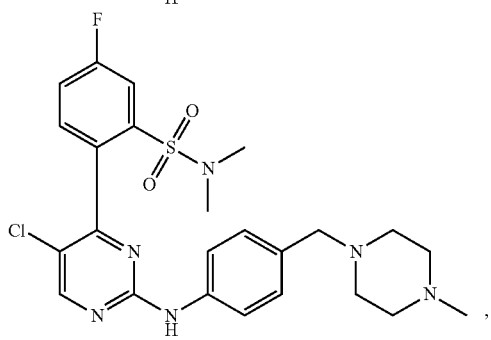
104
-continued
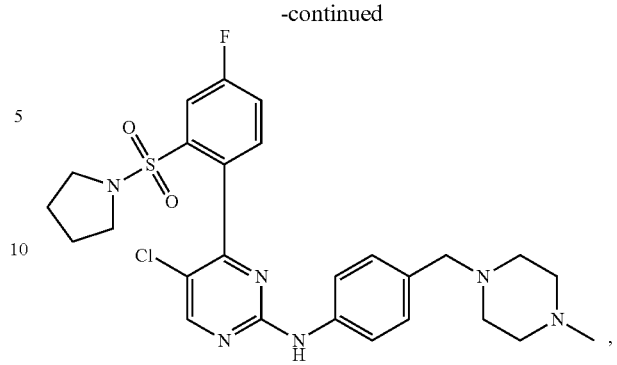
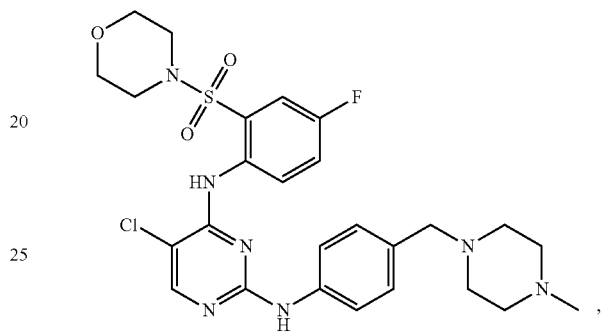
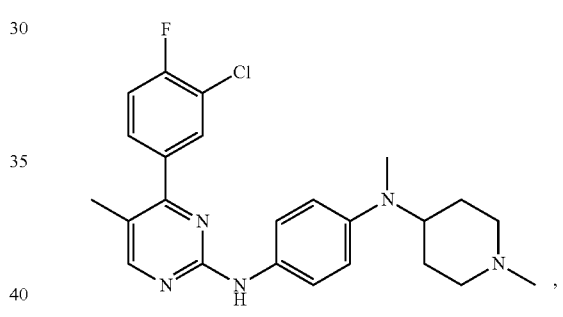
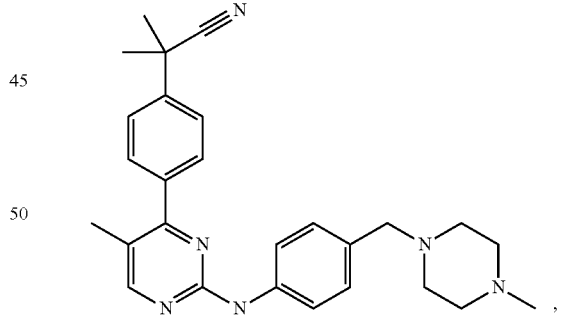
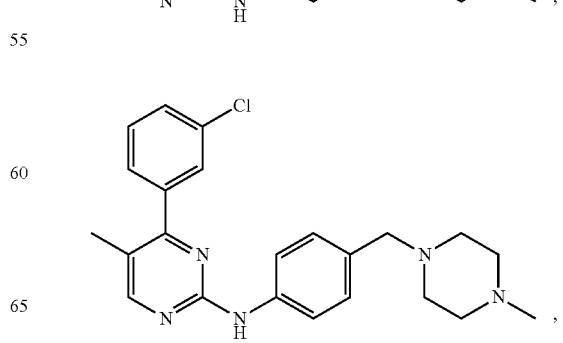

105
-continued
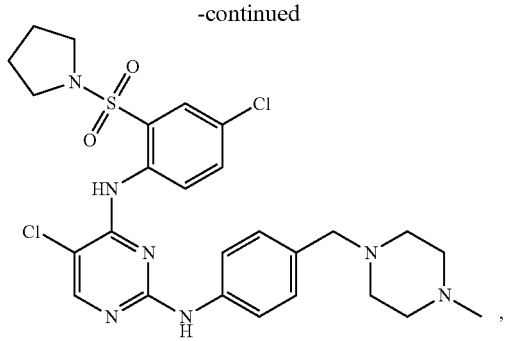
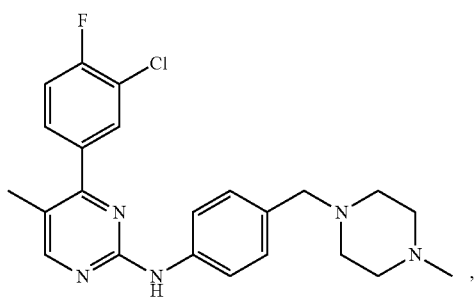
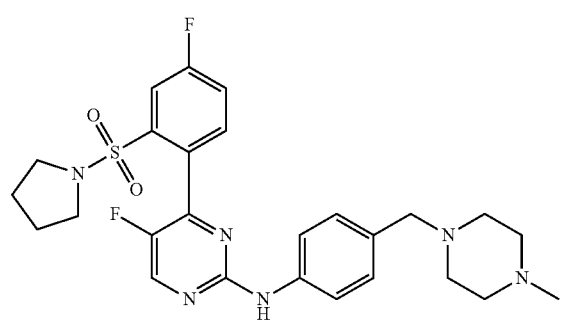
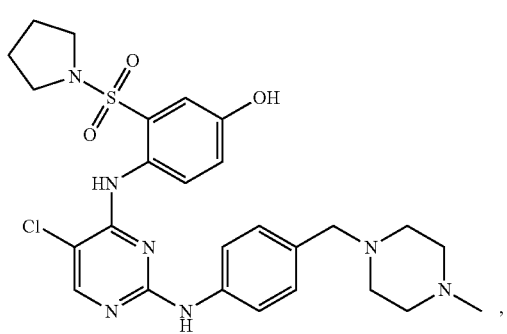
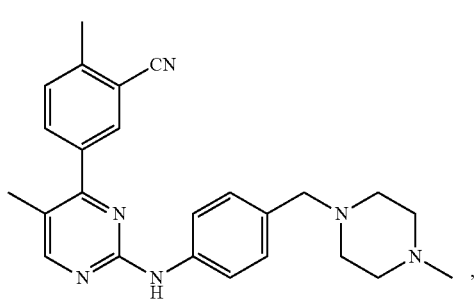
106
-continued
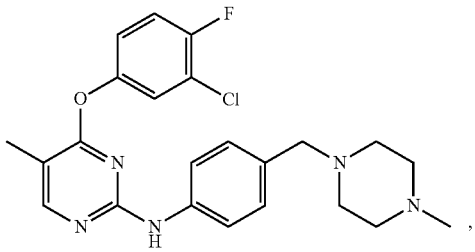
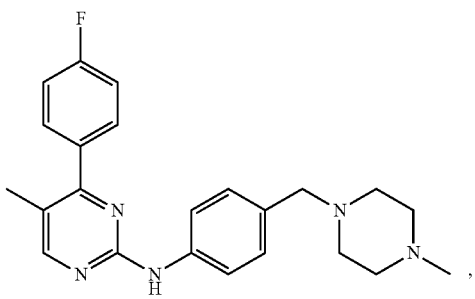
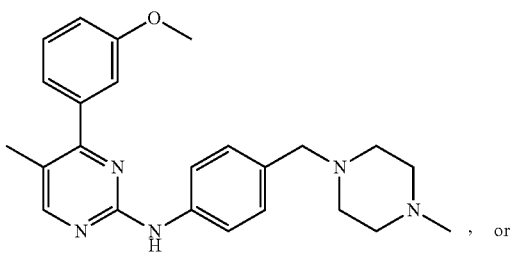
, or
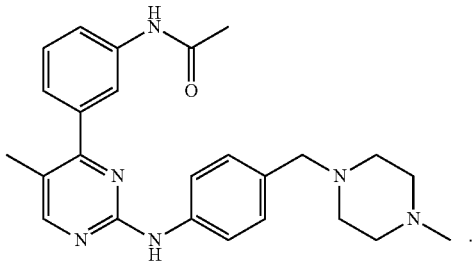
.
In one aspect, a compound can be present as:
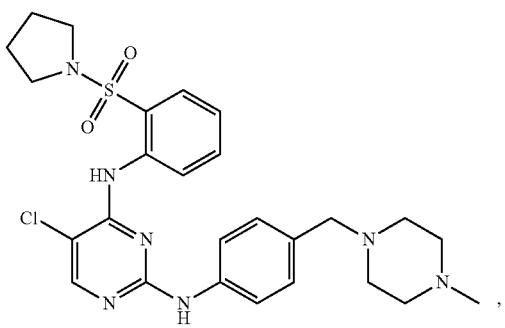
,

107
-continued
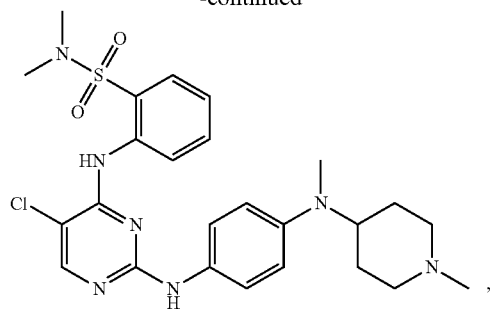
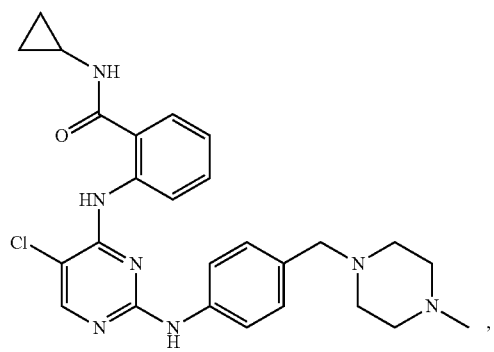
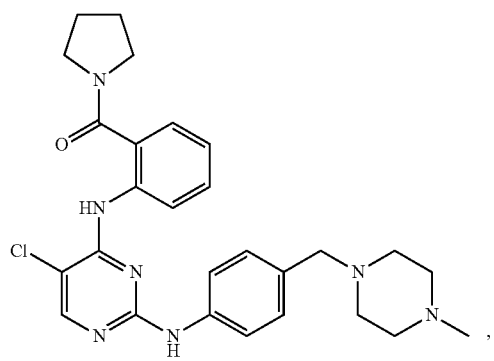
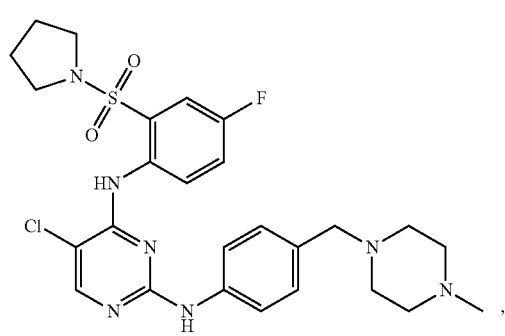
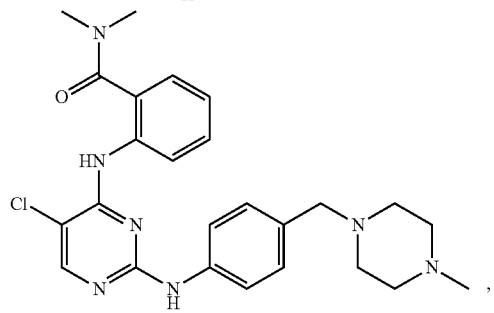
108
-continued
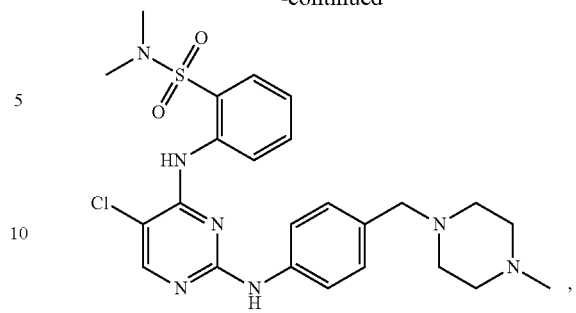
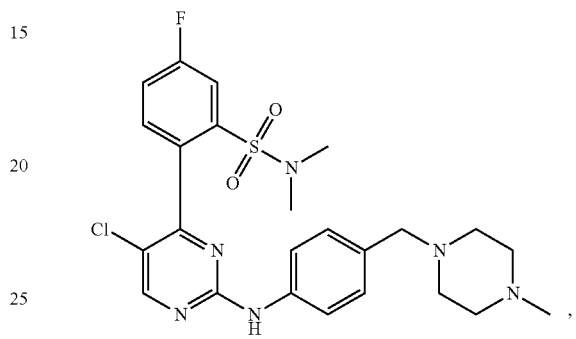
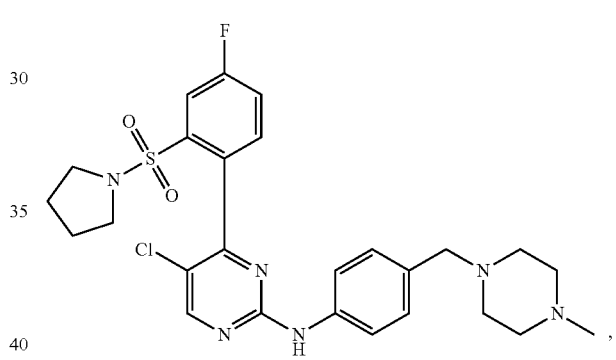
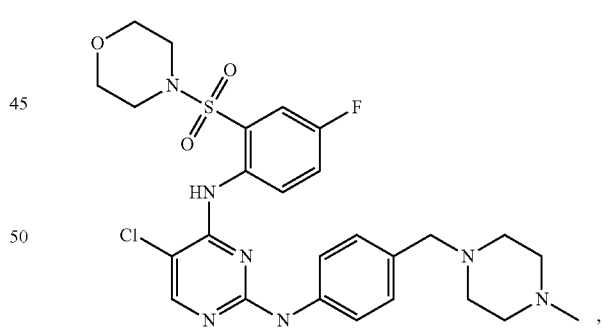
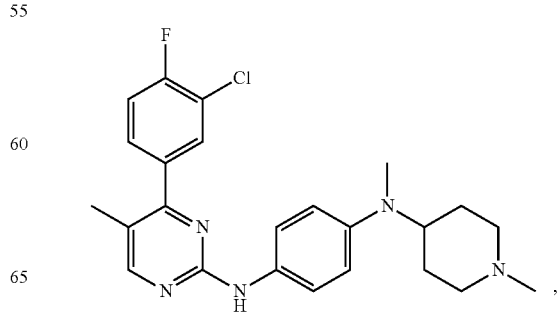

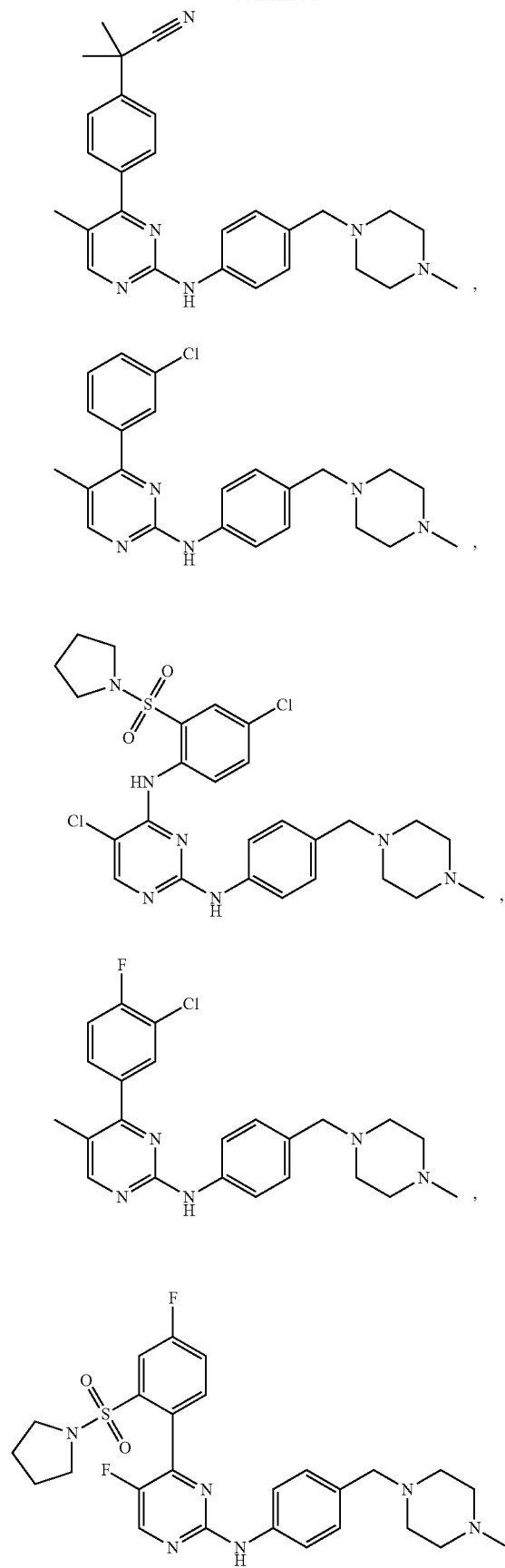
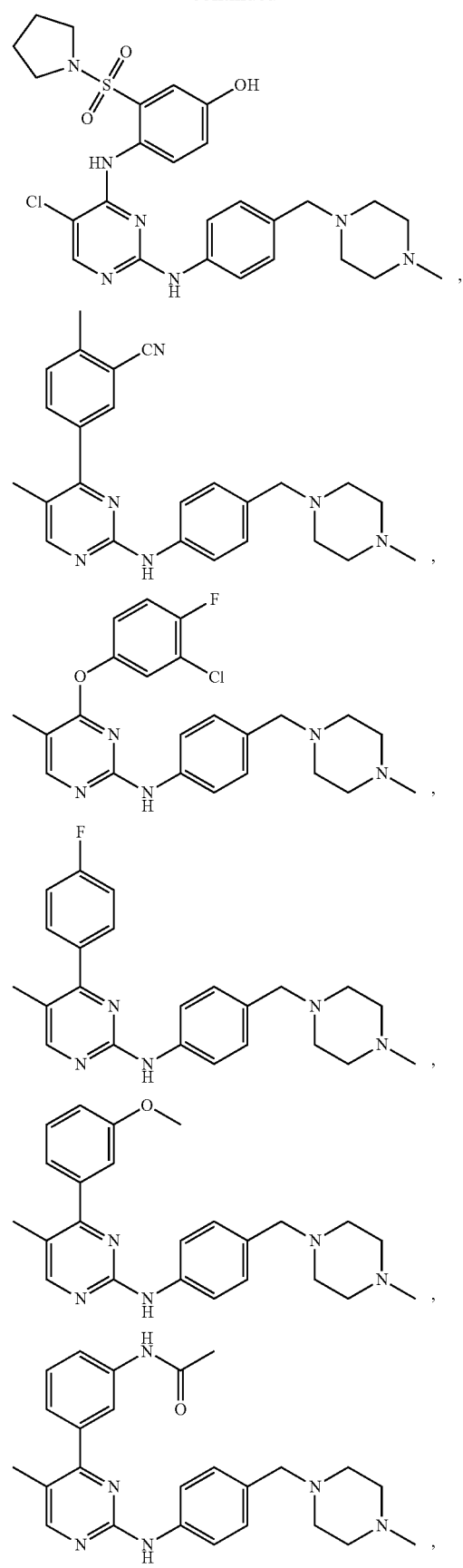

111
-continued
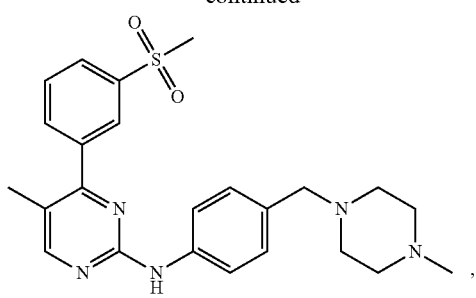
,
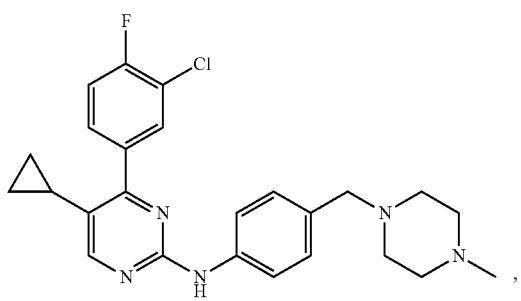
,
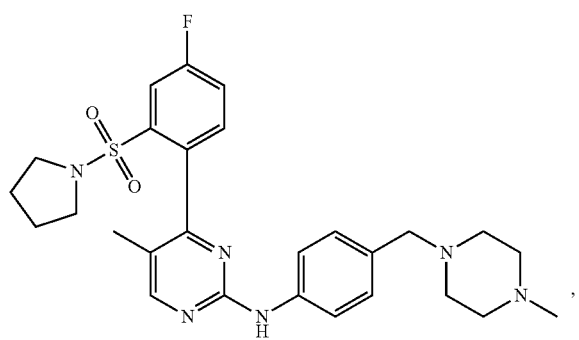 [SMILES: CN1CCN(Cc2ccc(Nc3ncc(F)c(-c4ccc(F)cc4S(=O)(=O)N4CCCC4)n3)cc2)CC1 ; "."]
,
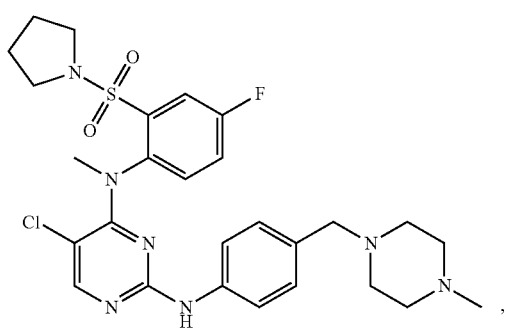
,
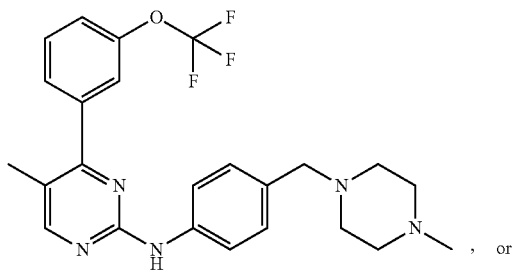
, or
112
-continued
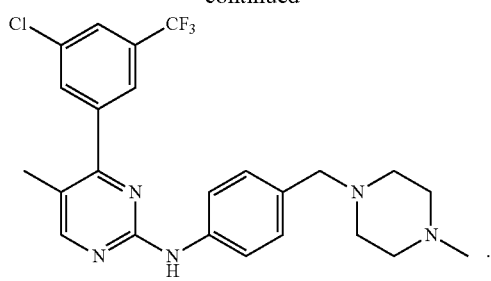
.
In one aspect, a compound can be present as:
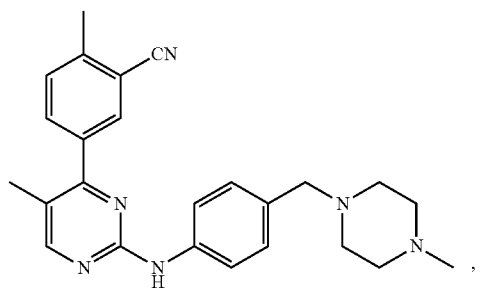
,
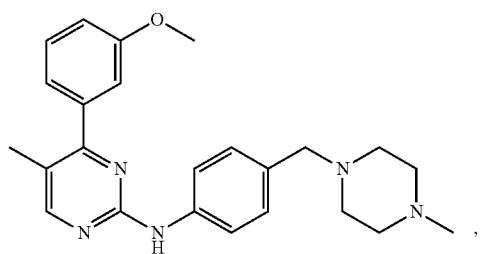
,
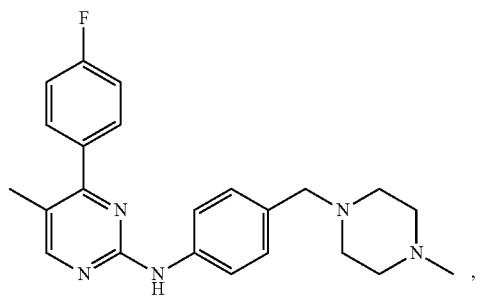
,
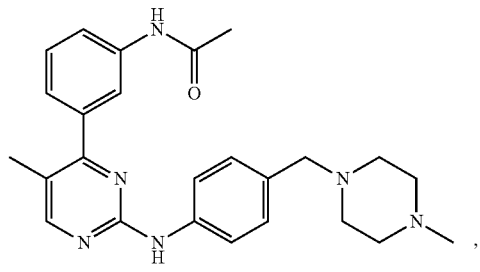
,

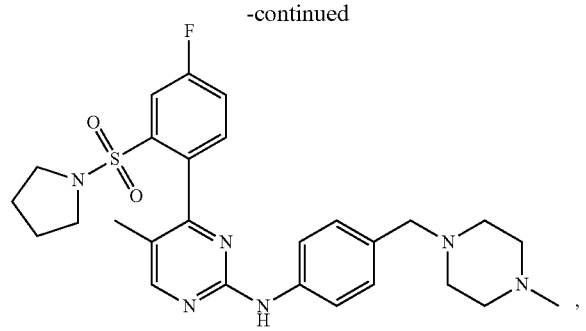
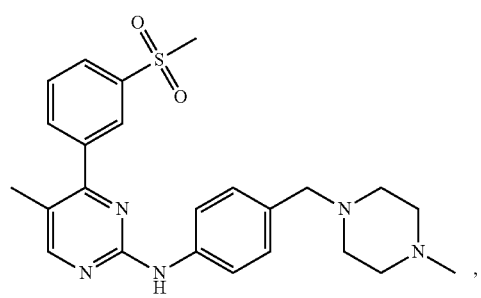
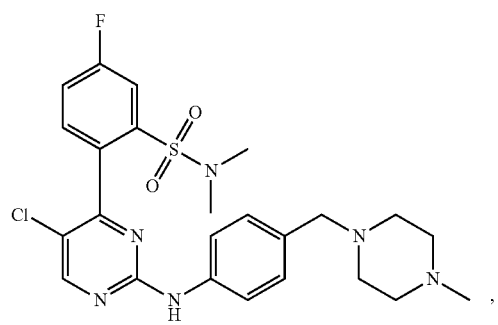
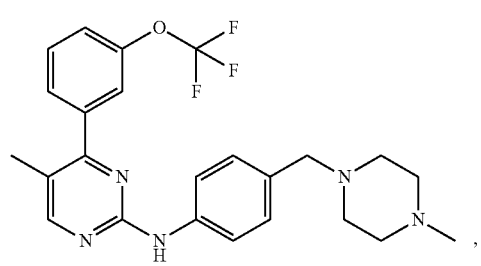
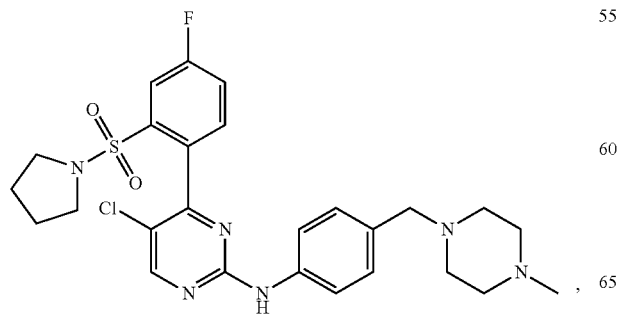
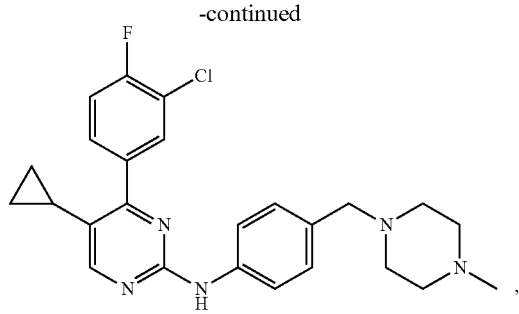
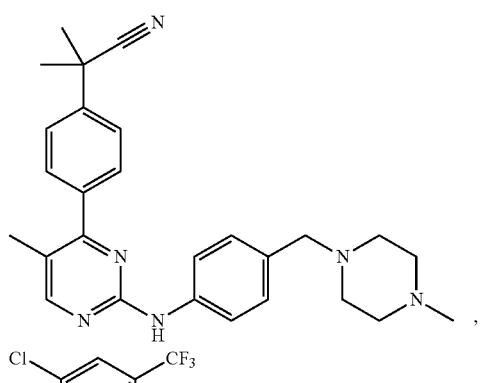
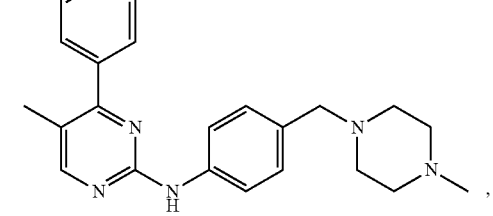
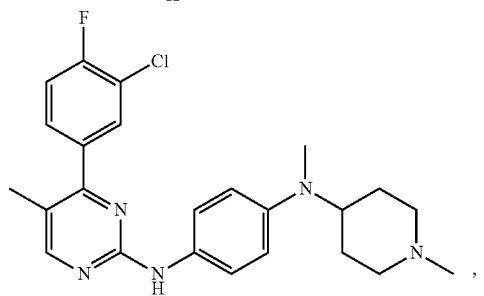
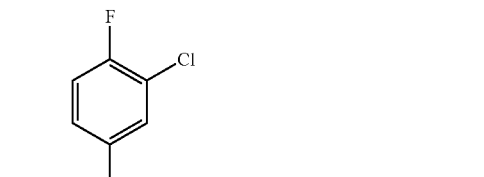
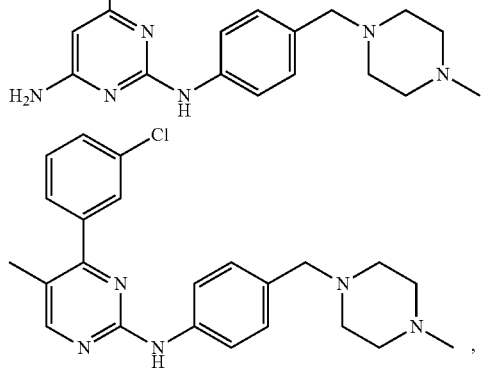

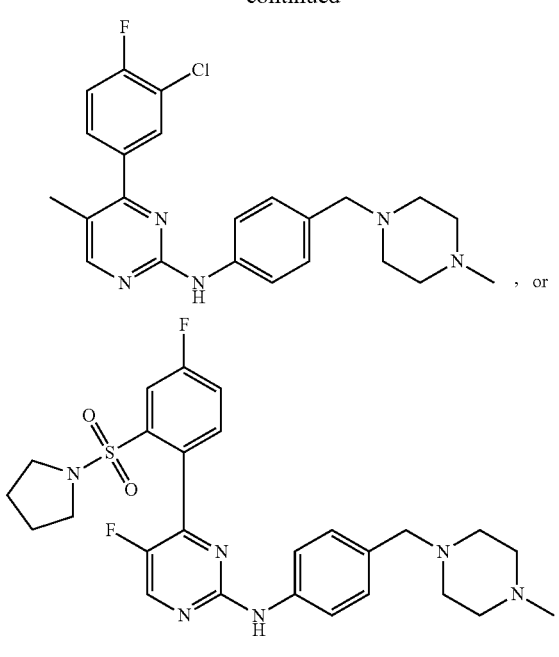
In one aspect, a compound can be present as:
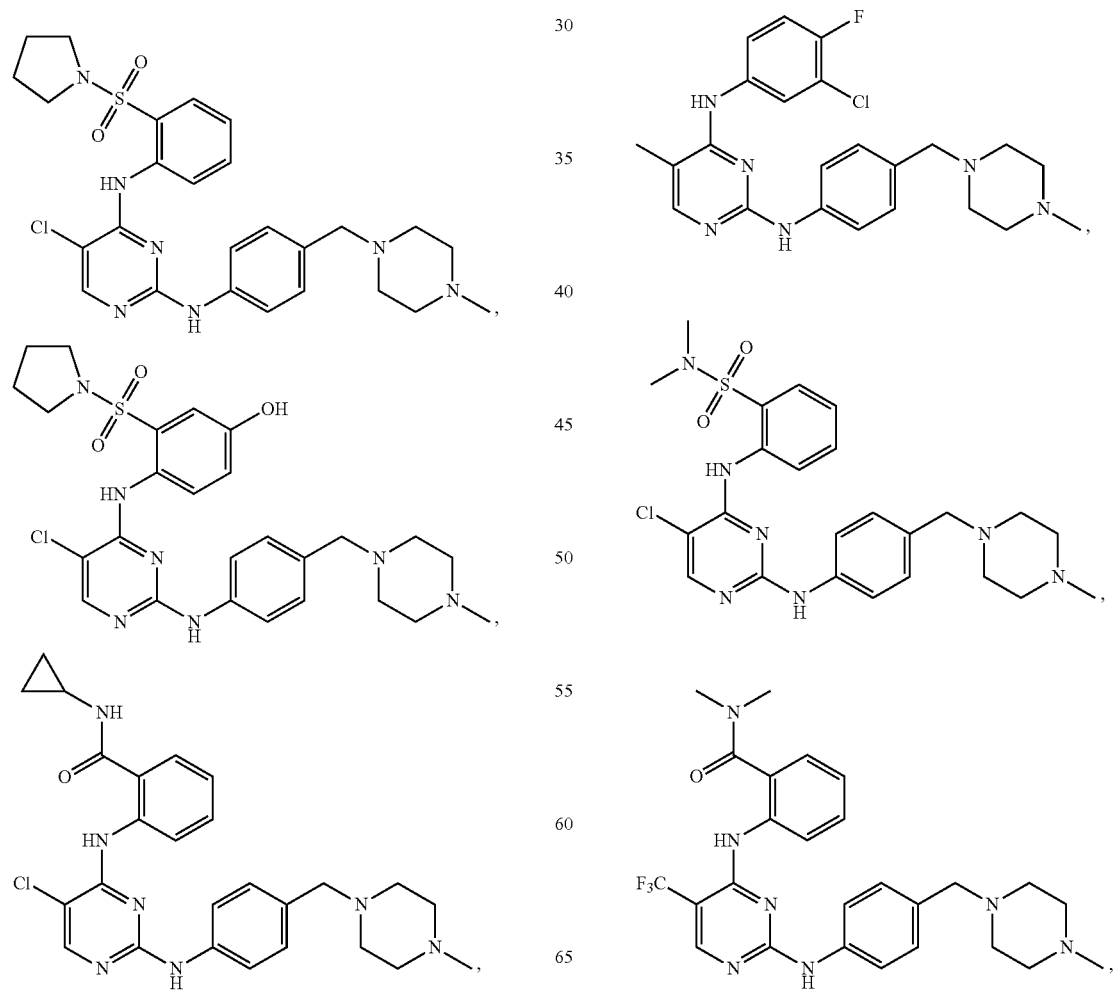

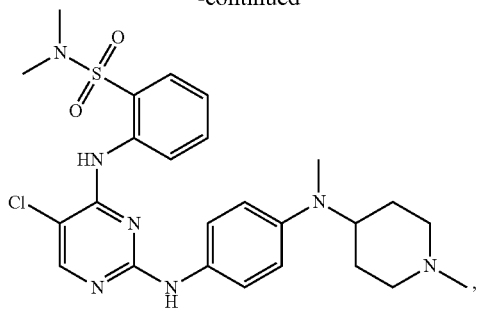
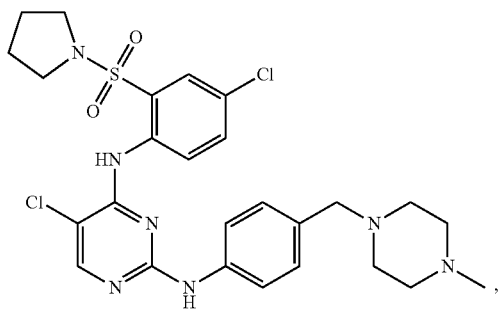
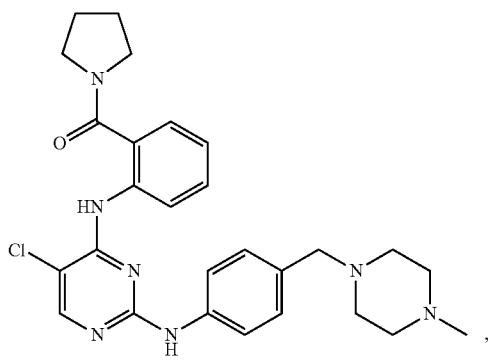
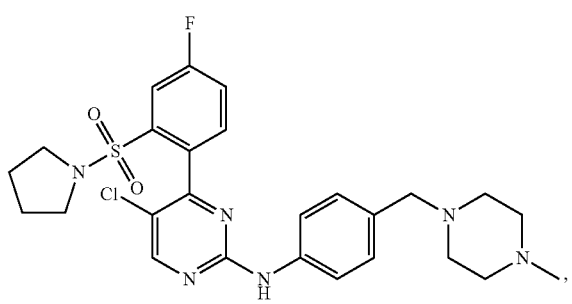
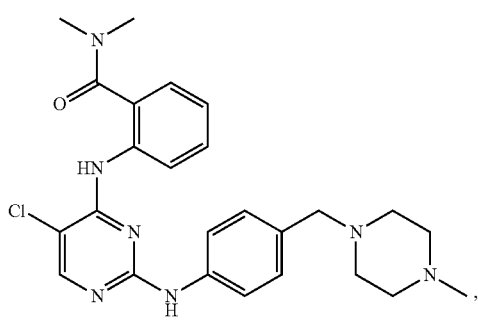
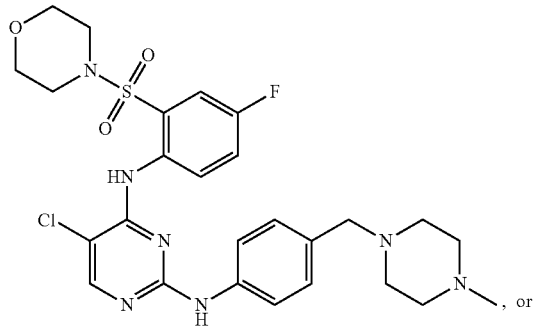
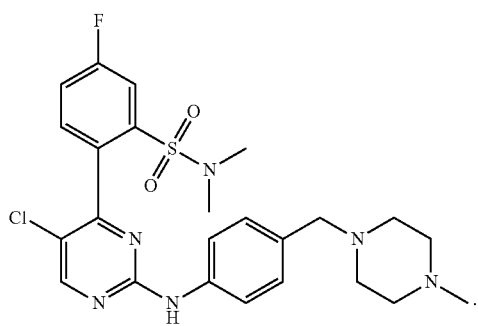
In one aspect, a compound can be present as:
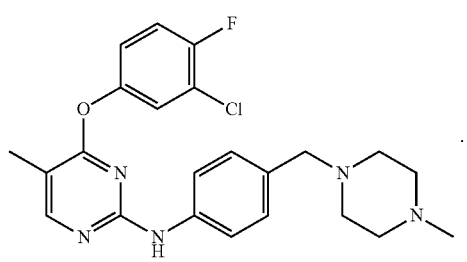
In one aspect, a compound can be present as:
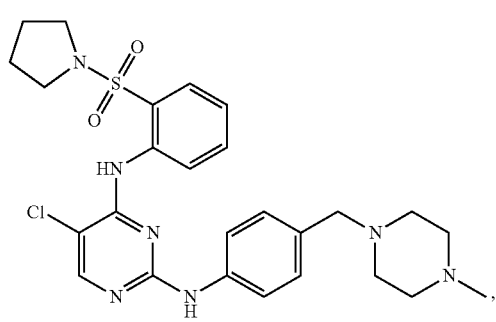
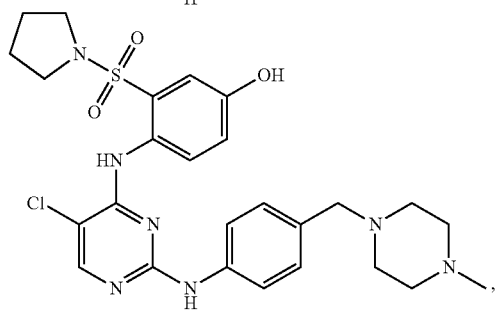

119
-continued
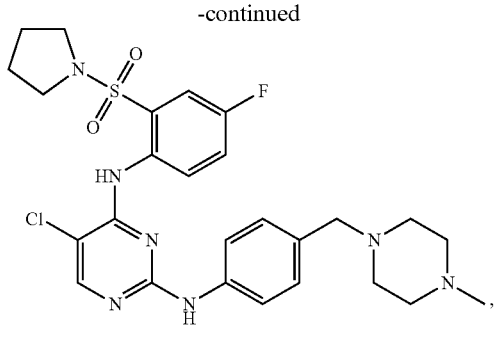
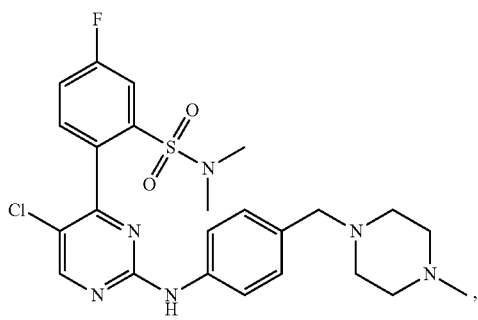
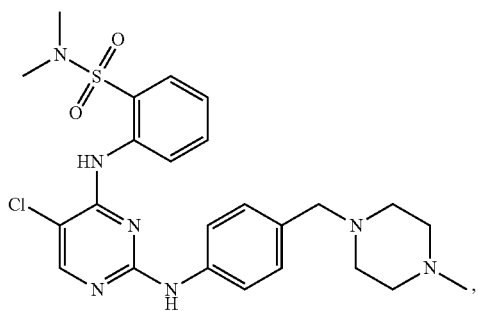
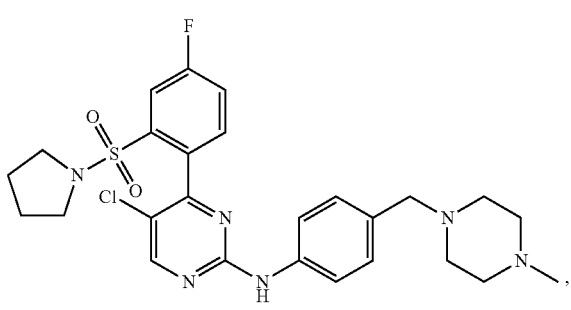
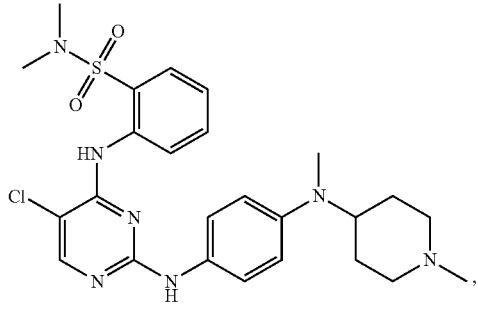
120
-continued
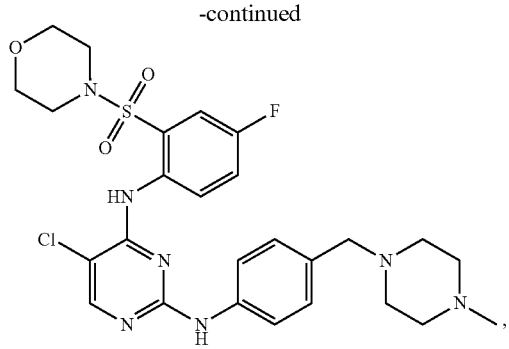
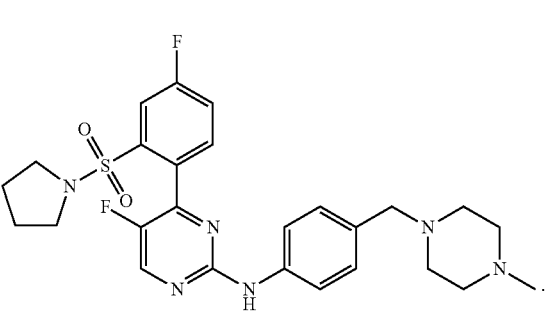

In one aspect, a compound can be present as:
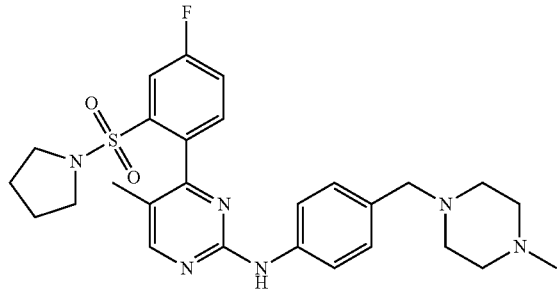
,
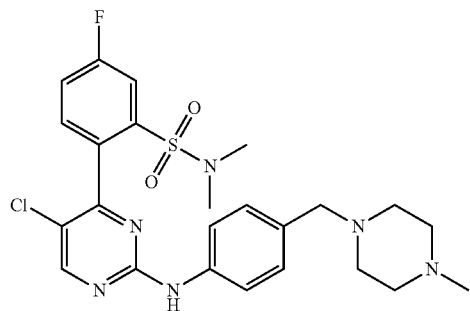
,
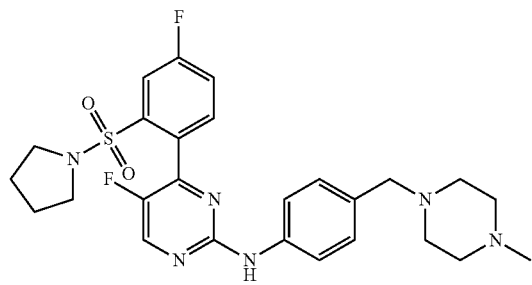
, or
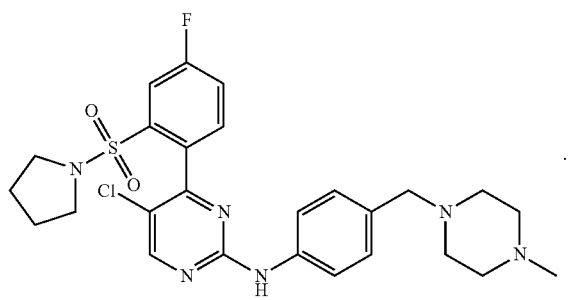
.
In one aspect, a compound can be present as:
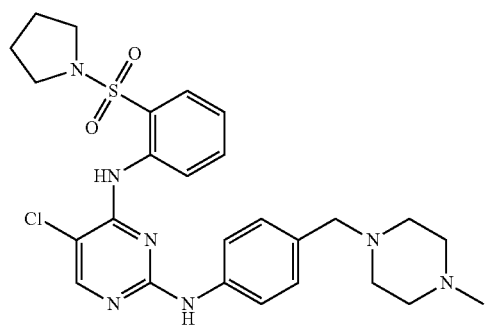
,
-continued
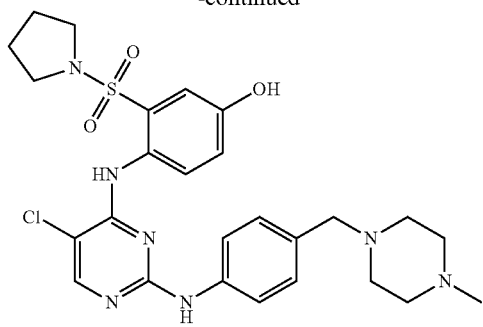
,
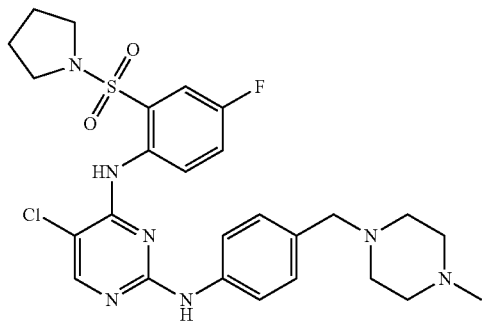
,
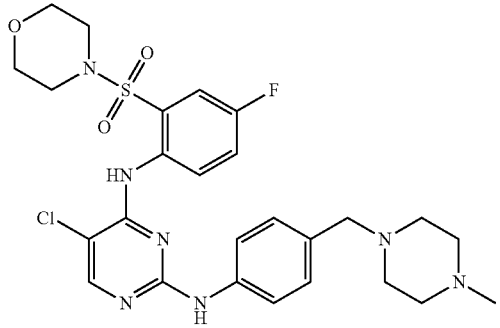
,
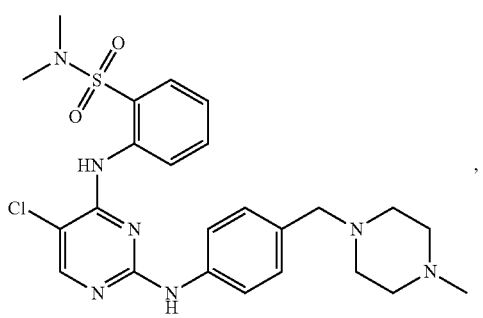
,
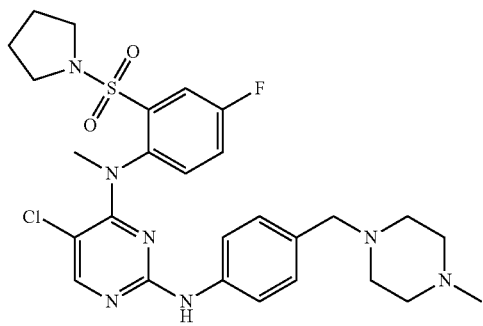
,

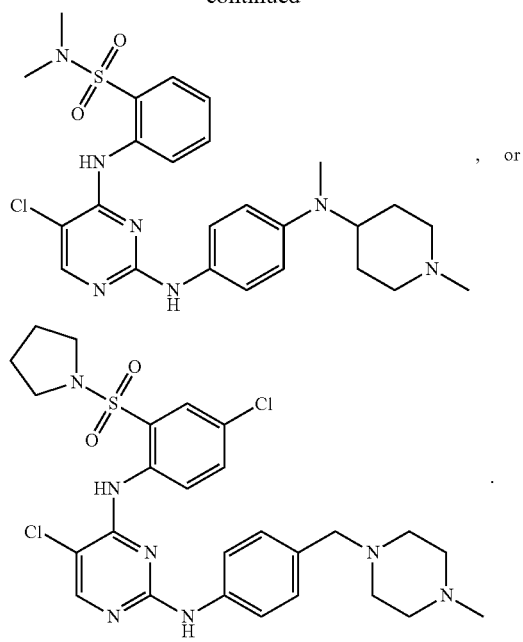
In one aspect, a compound can be present as:
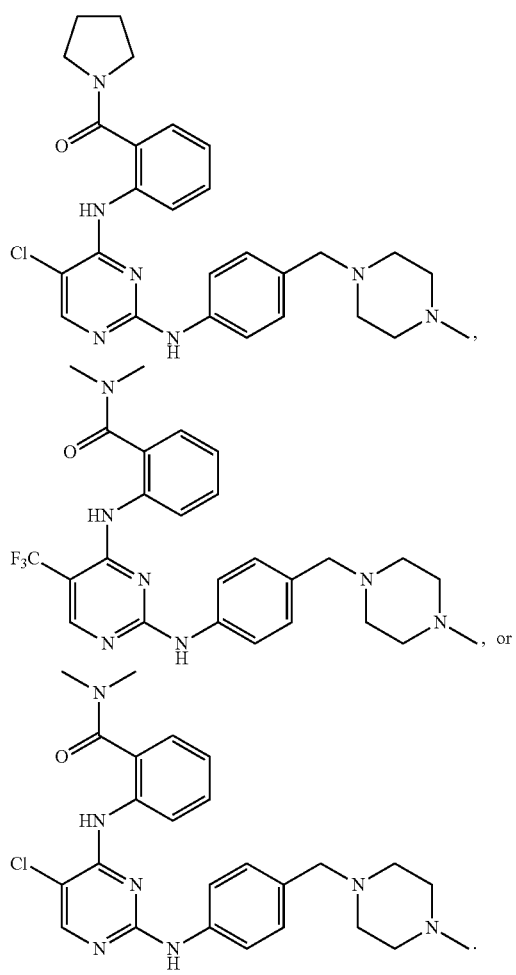
In one aspect, a compound can be present as:
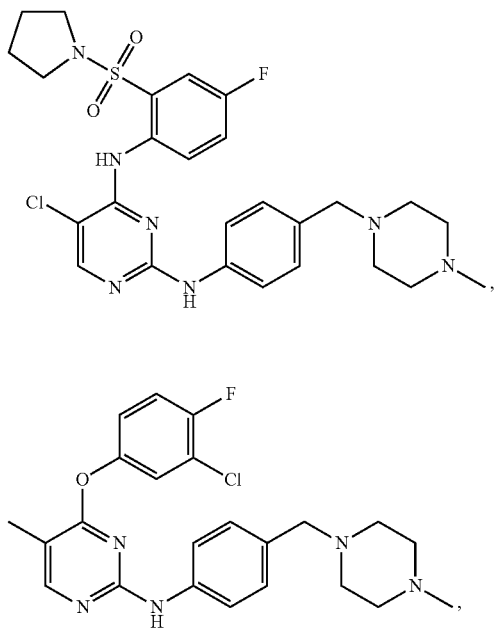
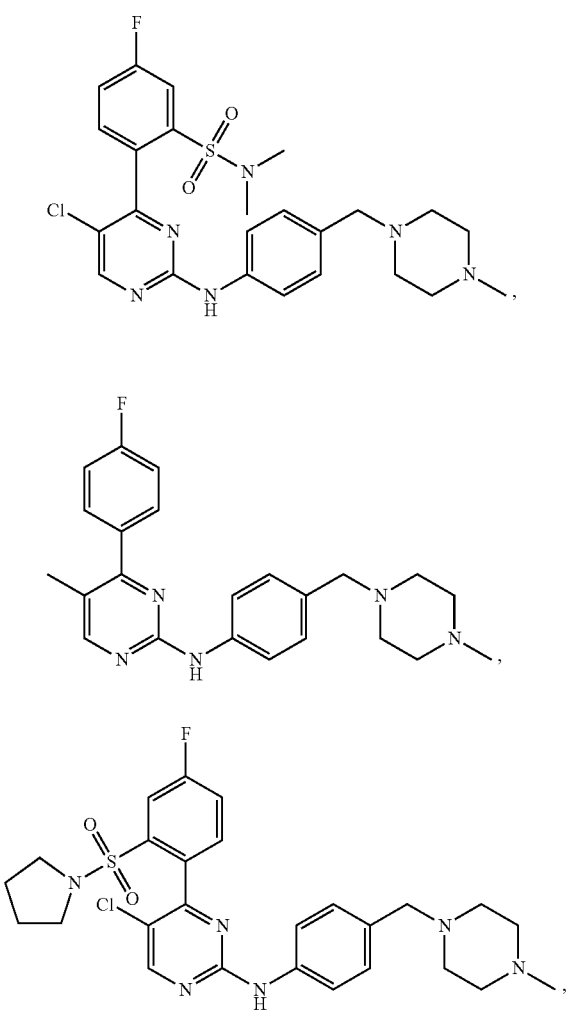

125
-continued
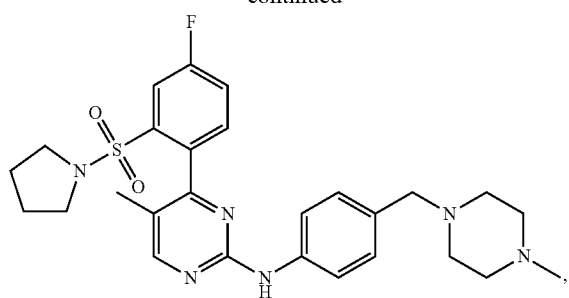
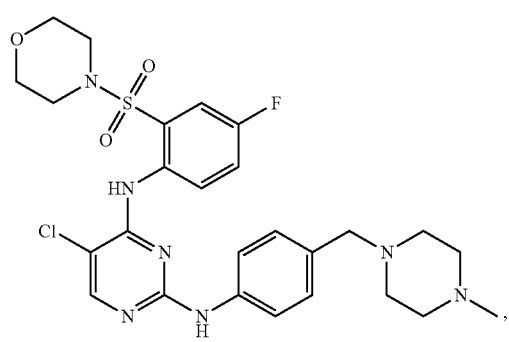
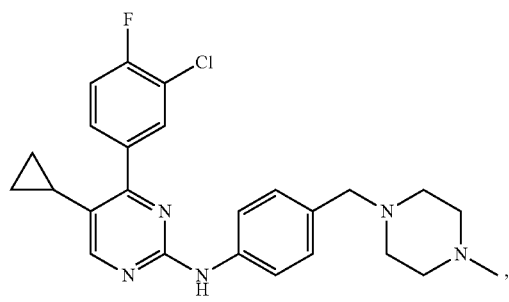
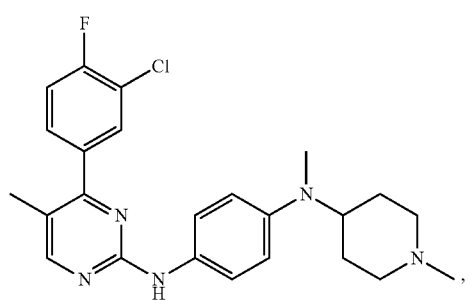
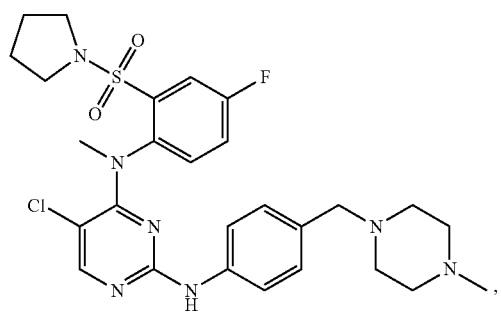
126
-continued
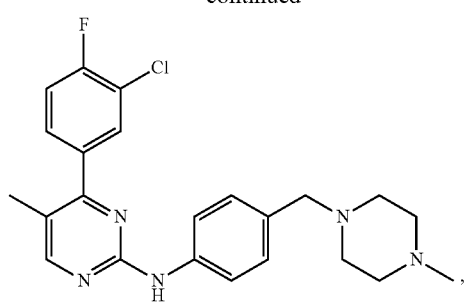
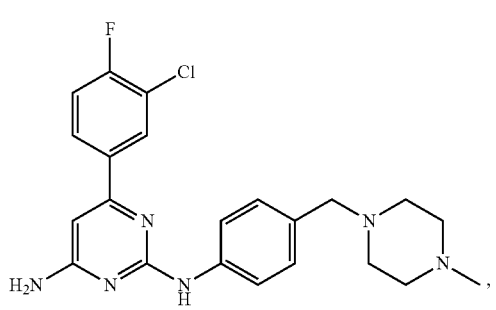
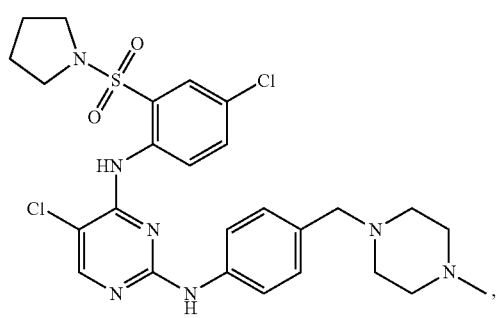
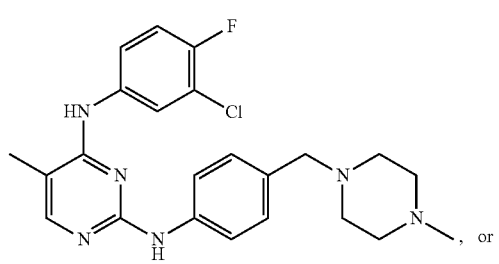, or
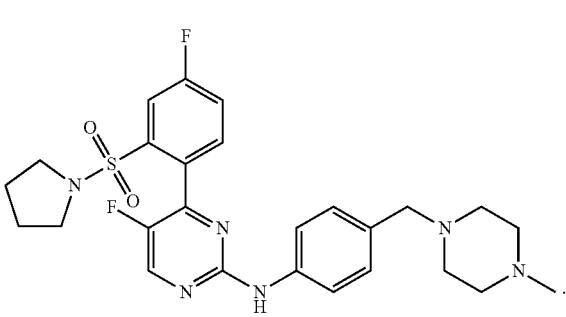

In one aspect, a compound can be present as:
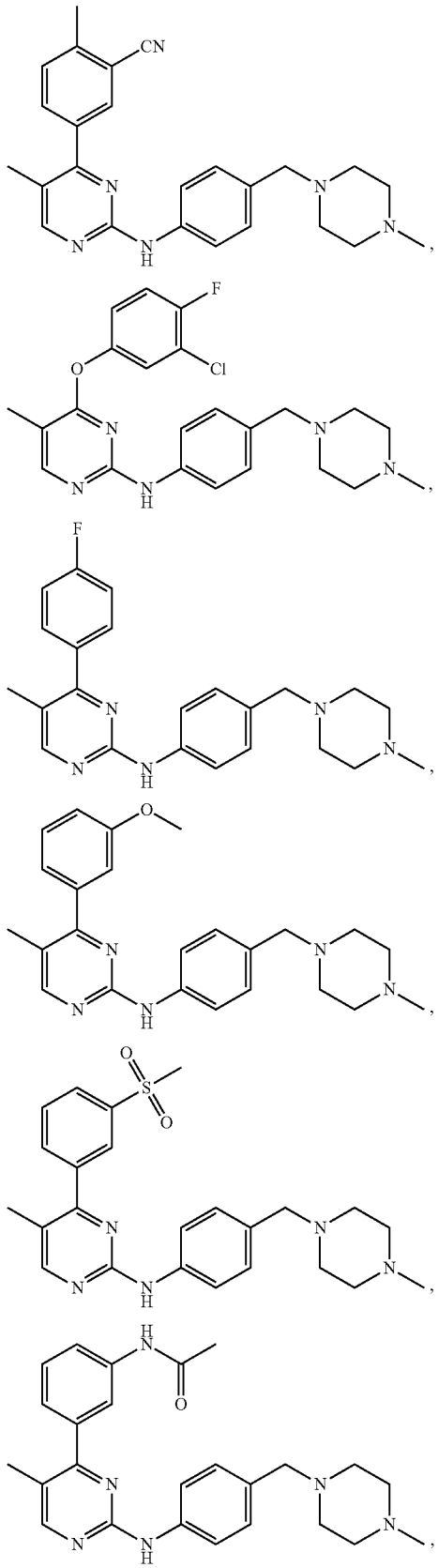
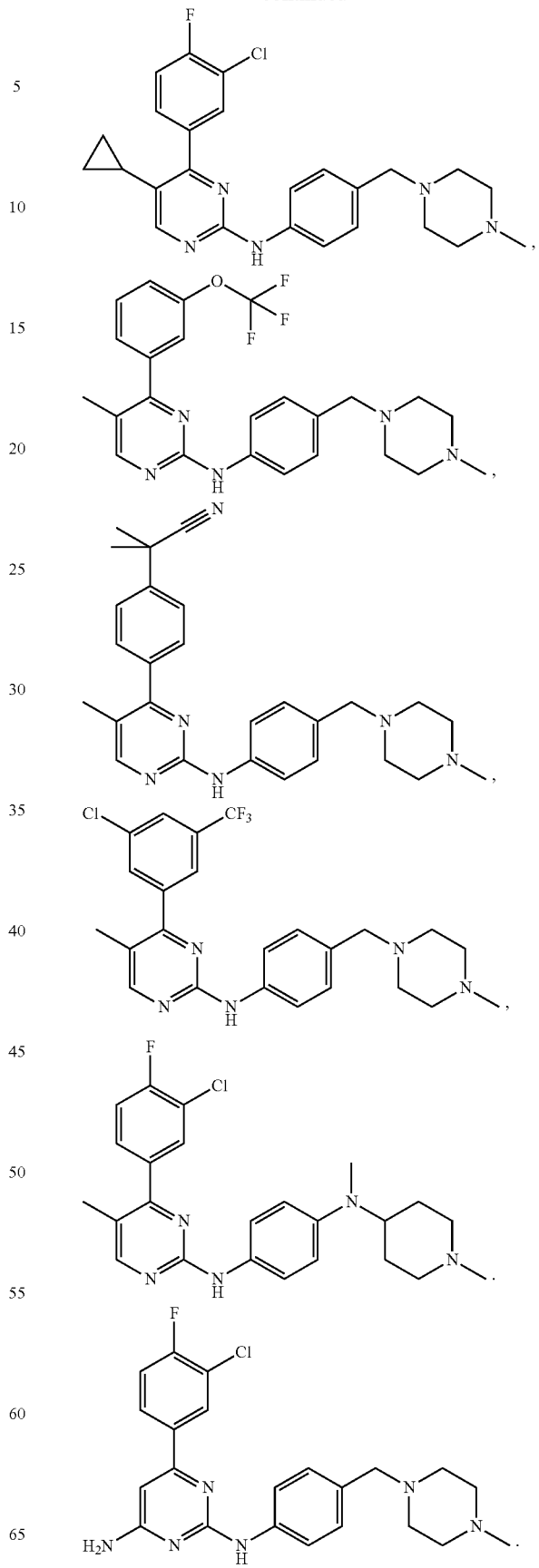

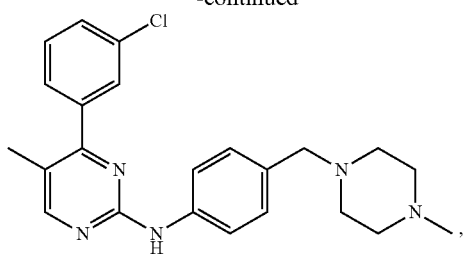
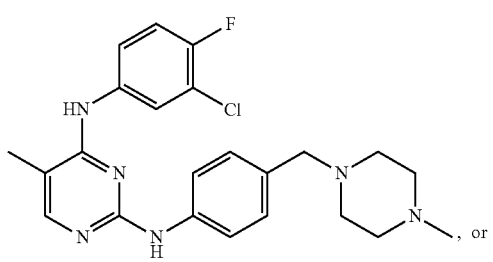, or
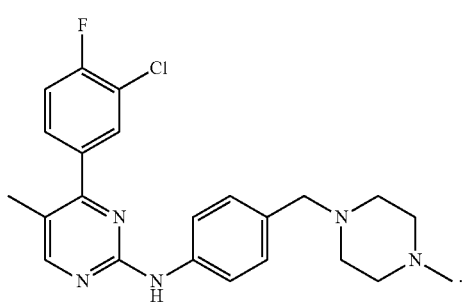.
In one aspect, a compound can be present as:
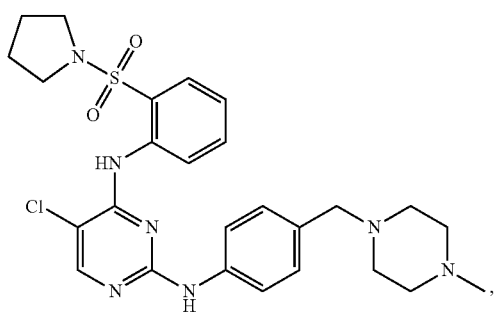,
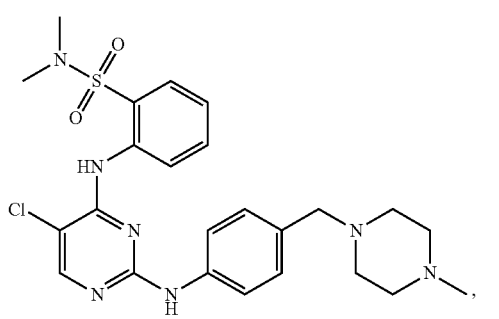,
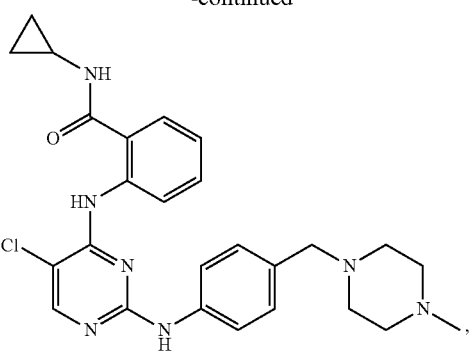,
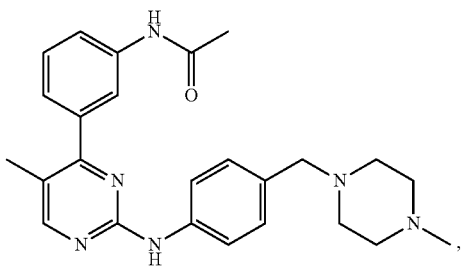,
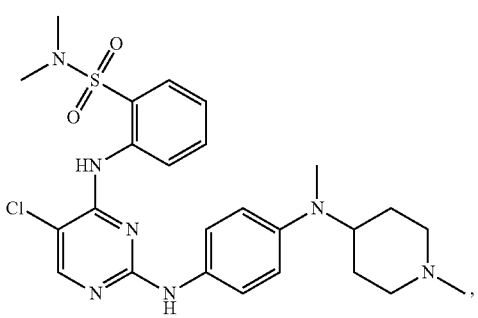,
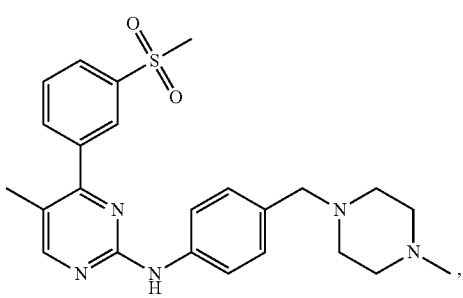,
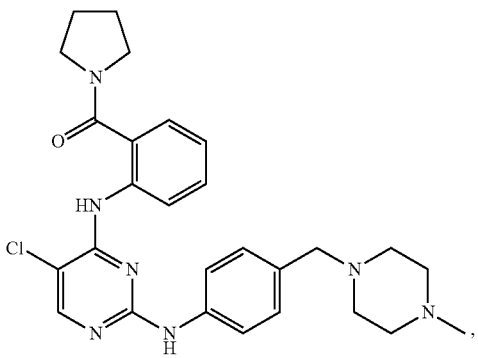, 131
-continued
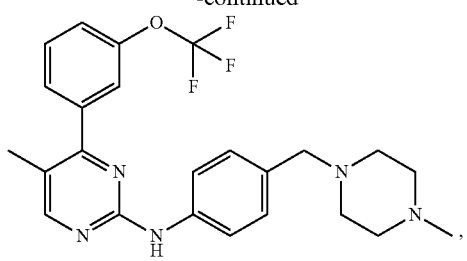
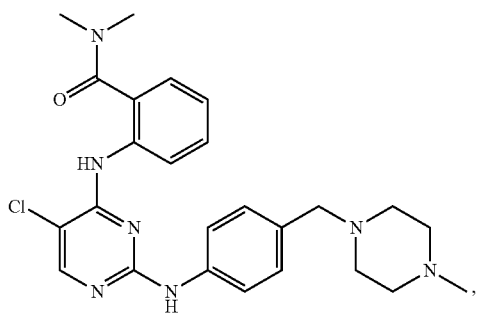
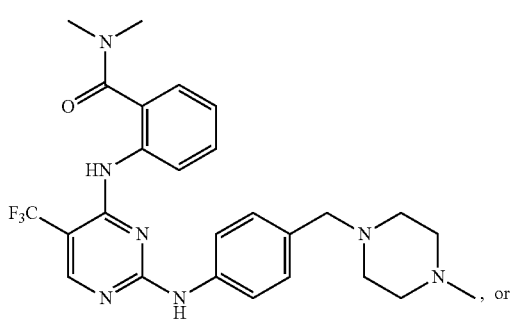, or
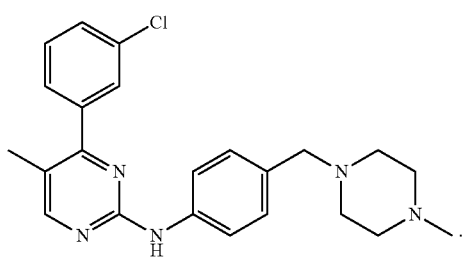
In one aspect, a compound can be present as:
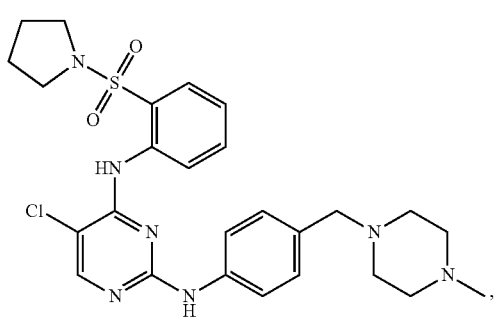
132
-continued
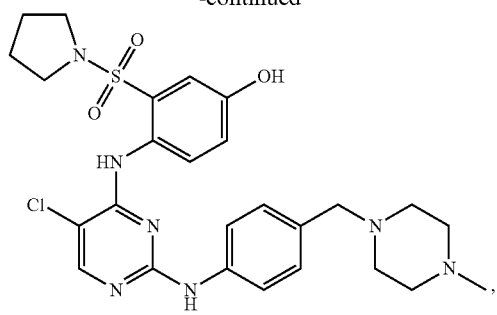
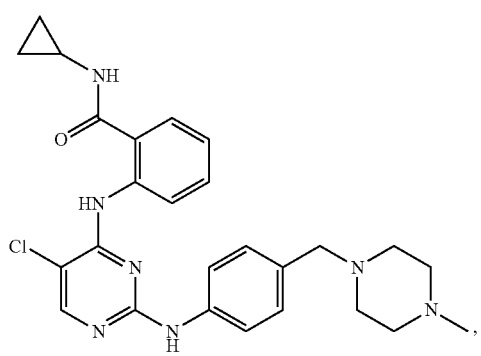
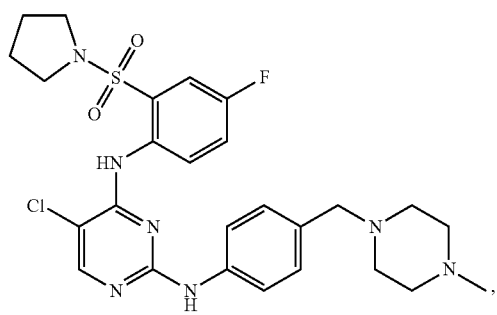
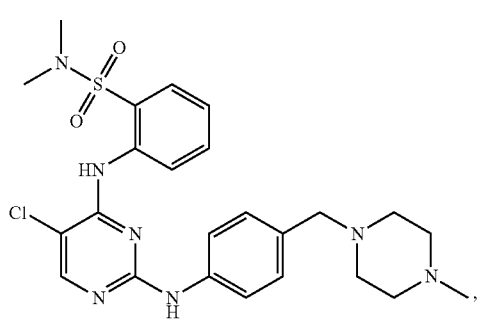
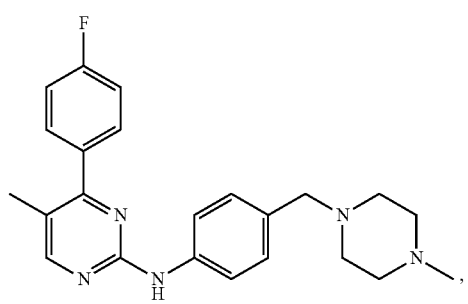

133
-continued
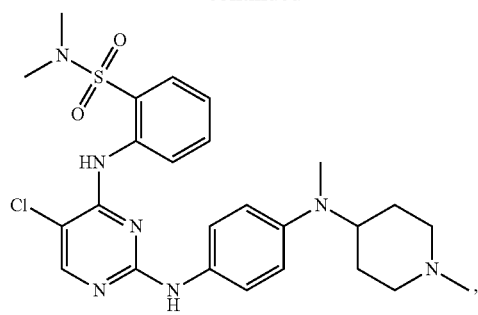
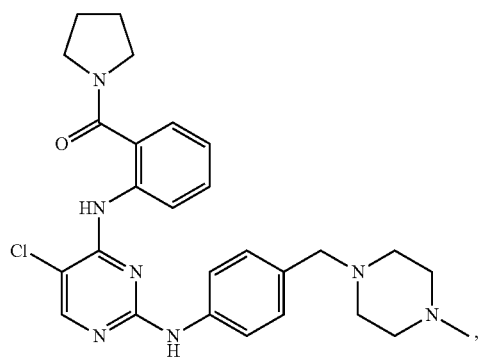
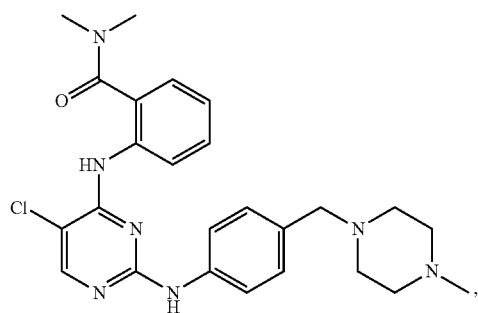
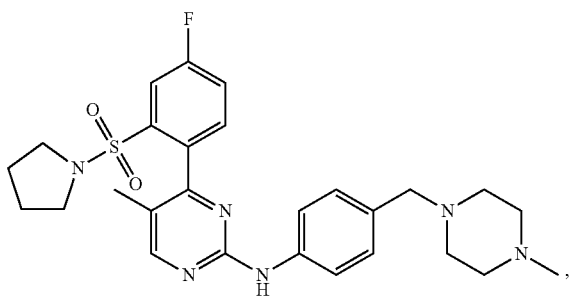
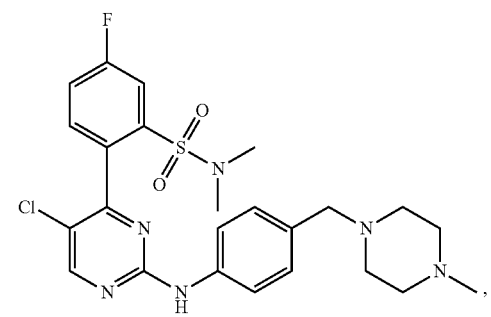
134
-continued
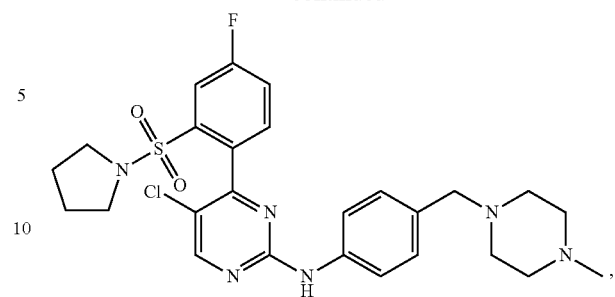
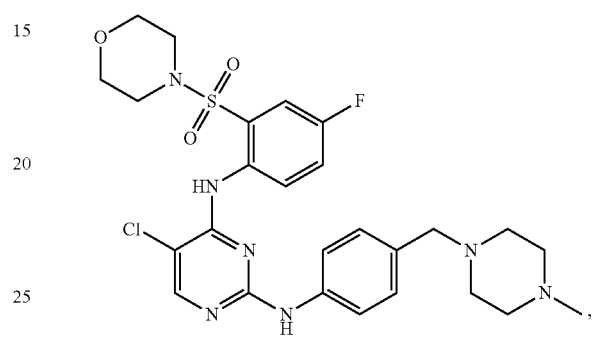
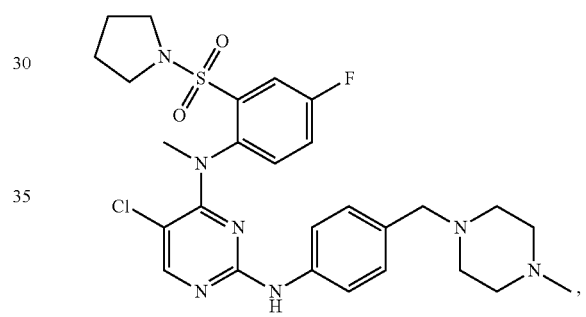
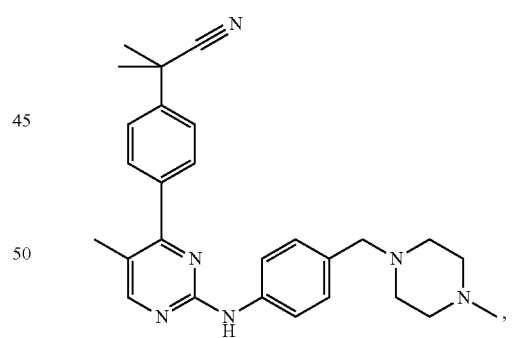
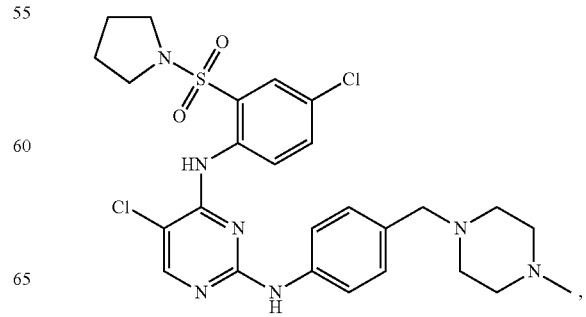

-continued
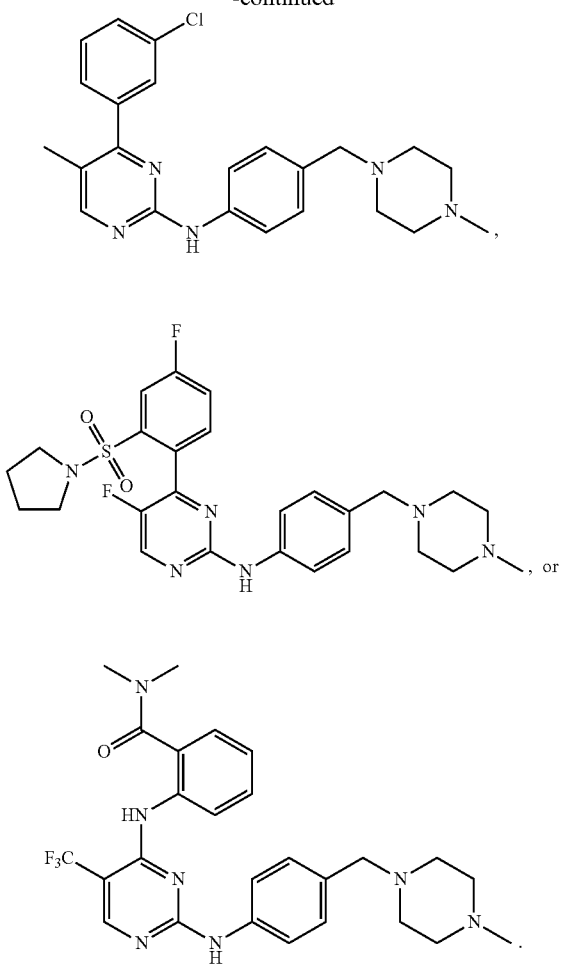
In one aspect, a compound can be present as:
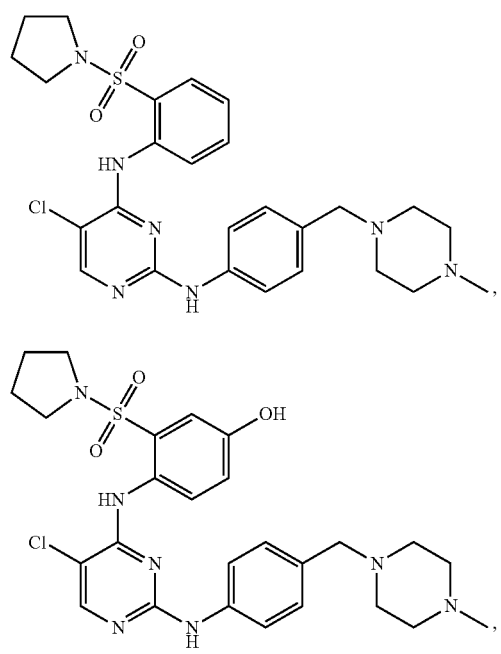
-continued
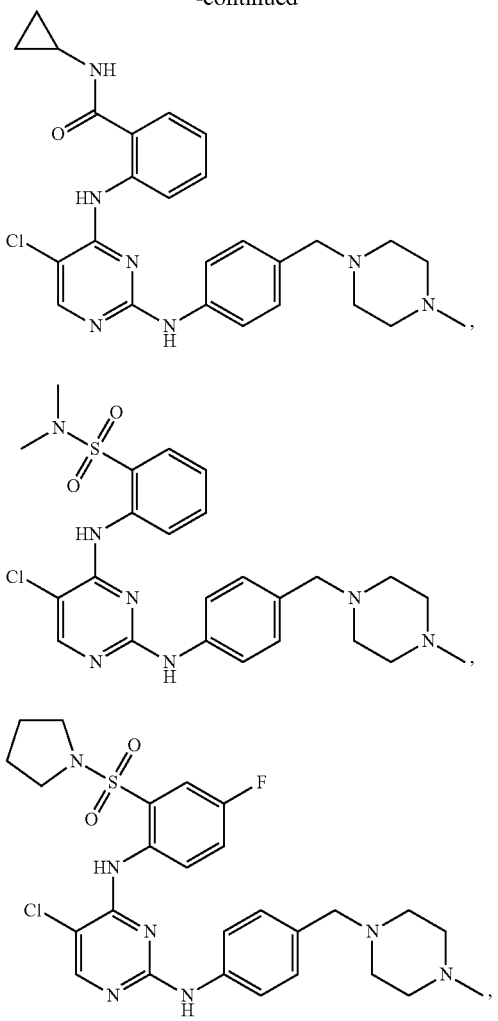
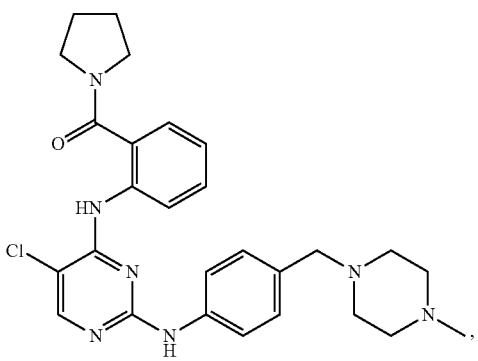

137
-continued
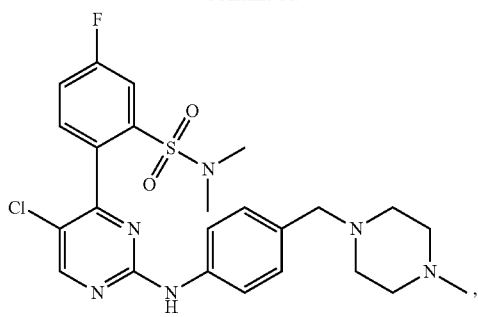
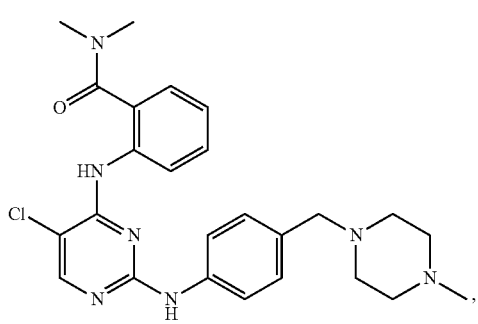
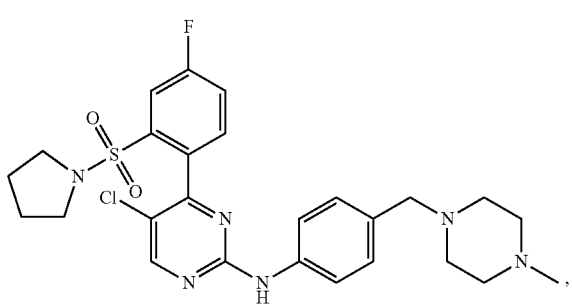
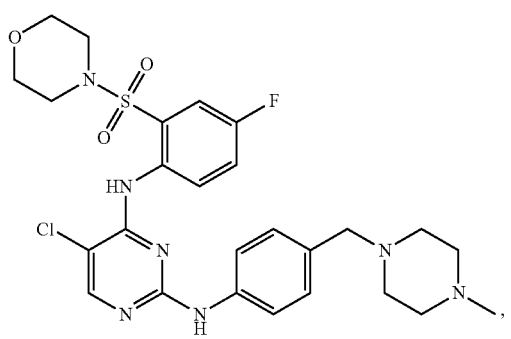
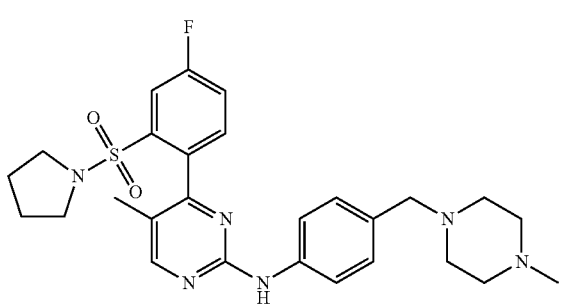
138
-continued
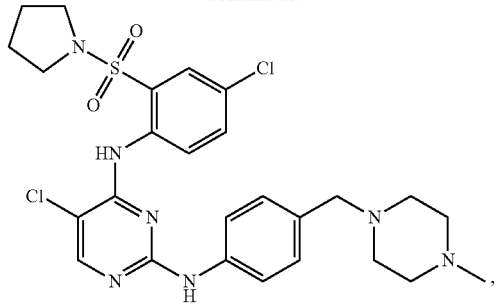
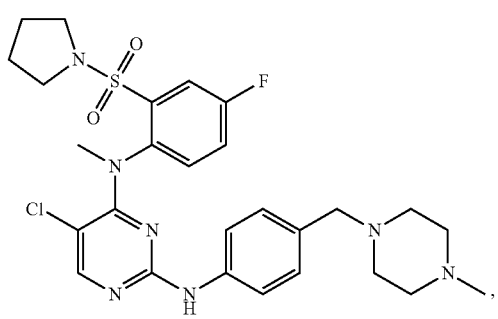
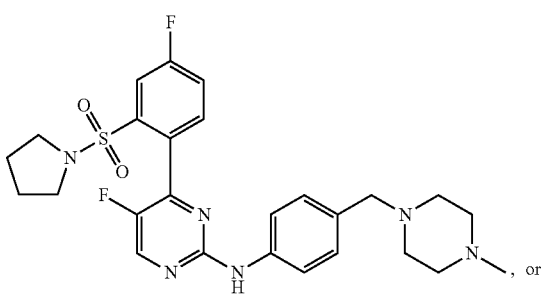, or
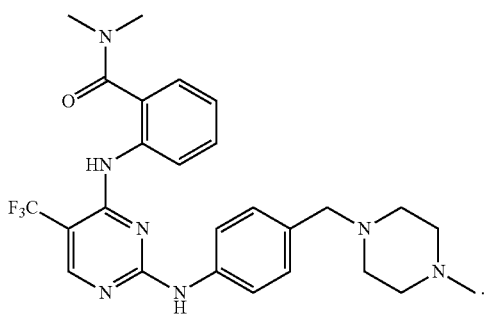 [SMILES: CN1CCN(Cc2ccc(Nc3ncc(C(F)(F)F)c(Nc4ccccc4C(=O)N(C)C)n3)cc2)CC1]
In one aspect, a compound can be present as:
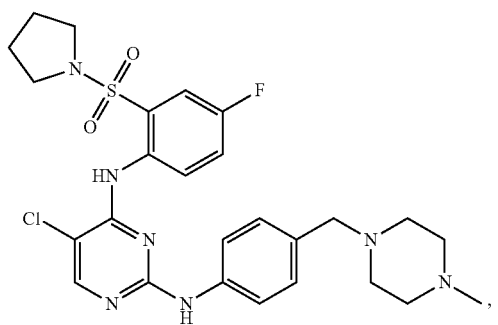

139
-continued
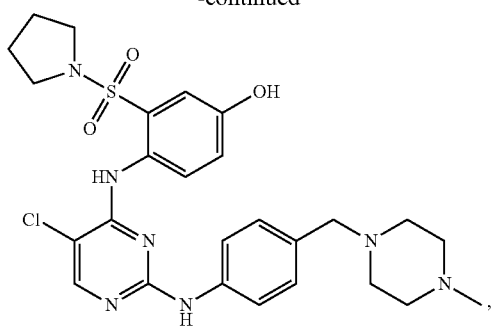
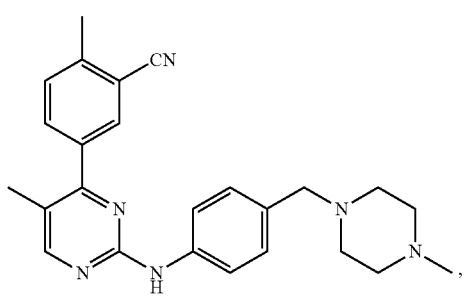
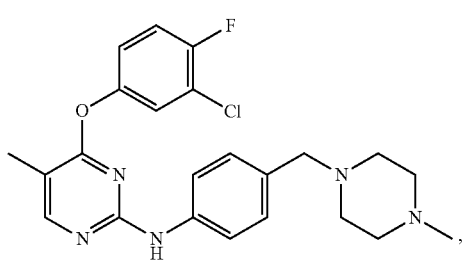
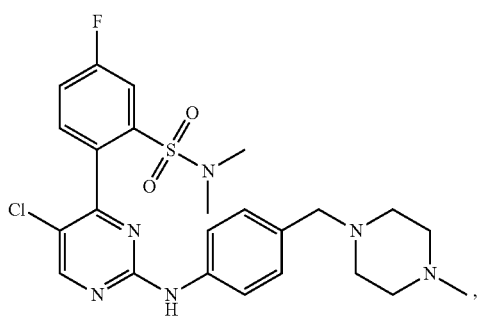
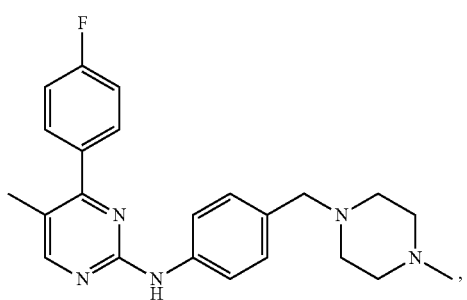
140
-continued
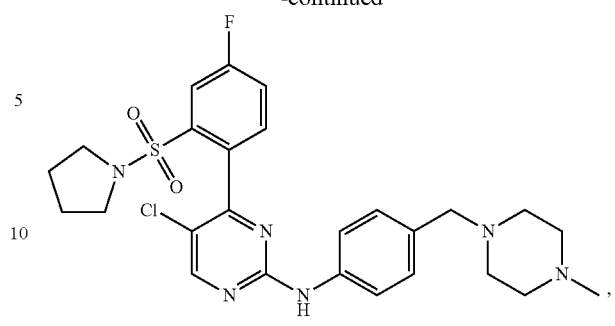
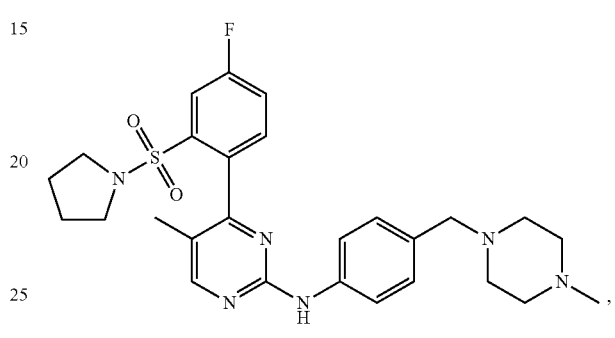
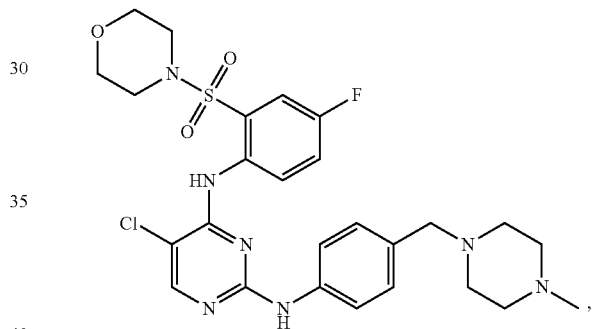
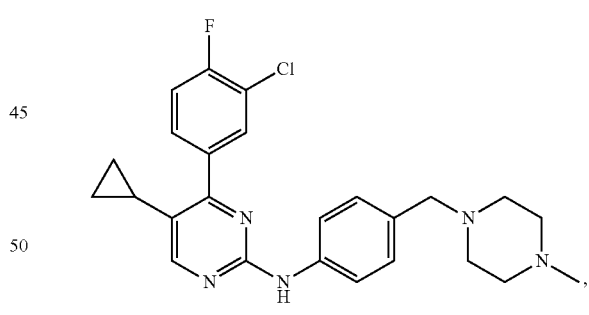
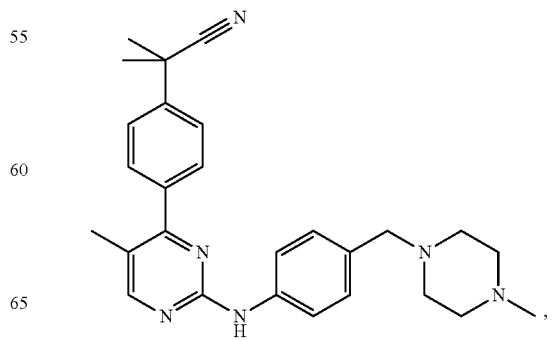

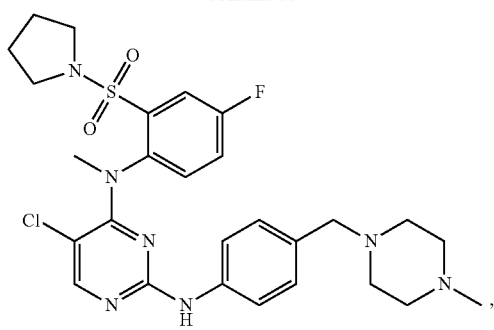
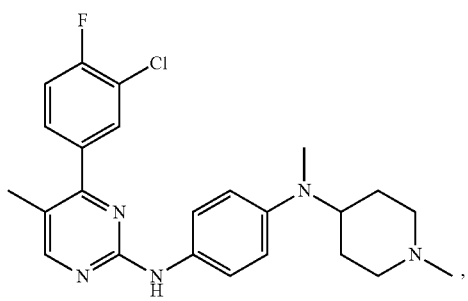
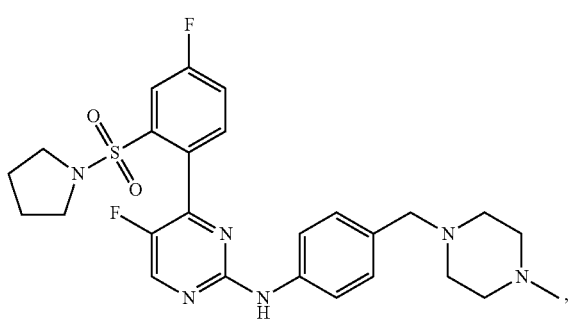
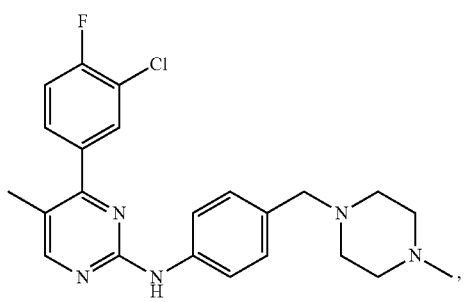
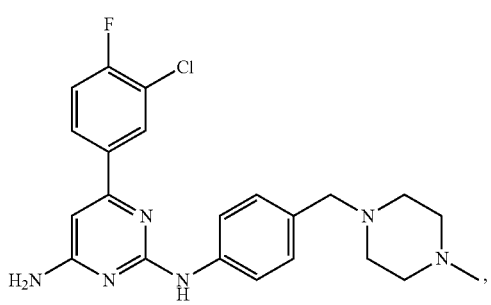
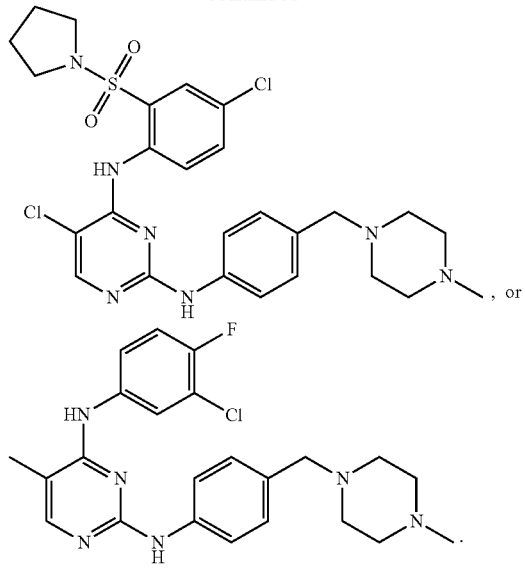
, or
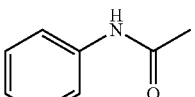
In one aspect, a compound can be present as:
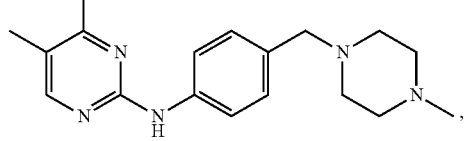
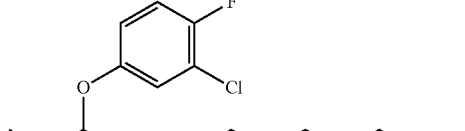
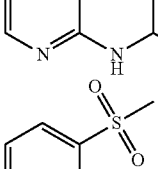
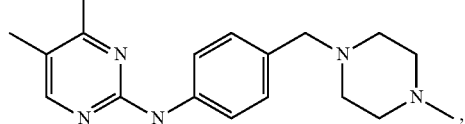
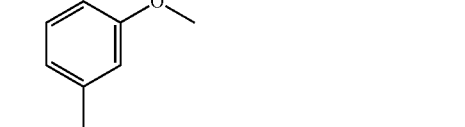
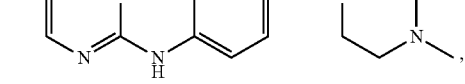

-continued
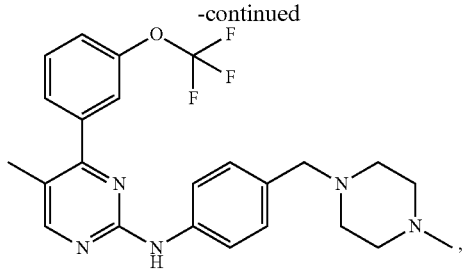
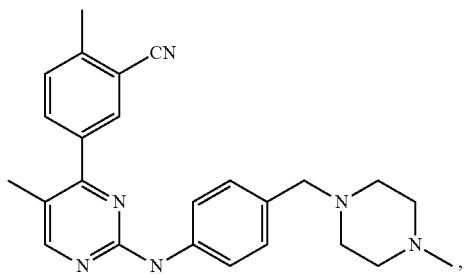
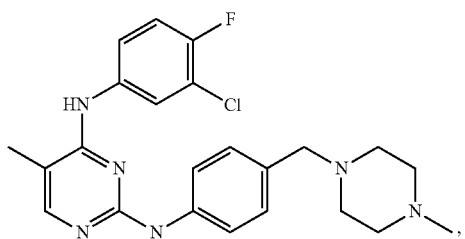
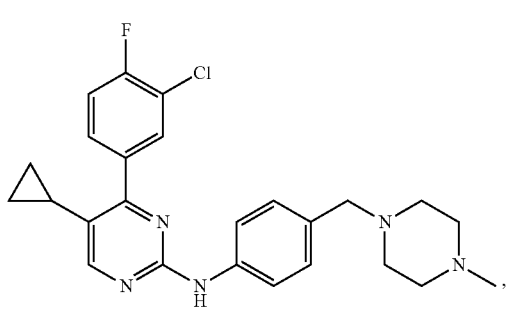
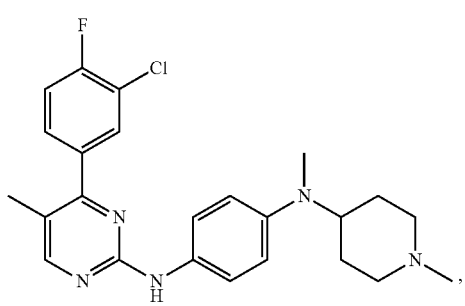
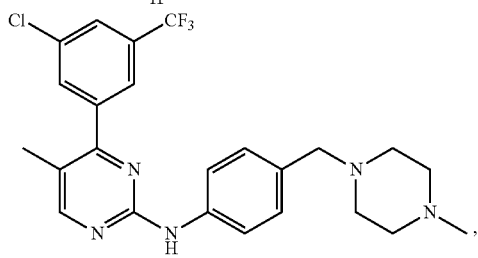
-continued
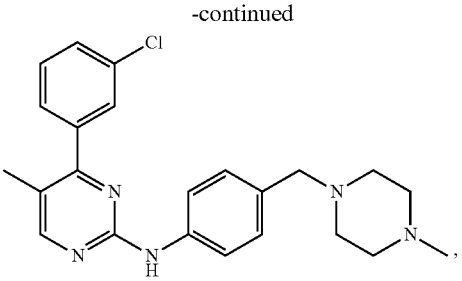
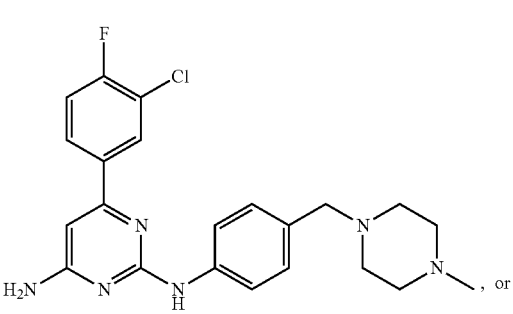
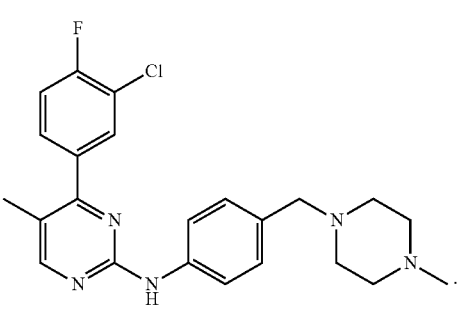
In one aspect, a compound can be present as:
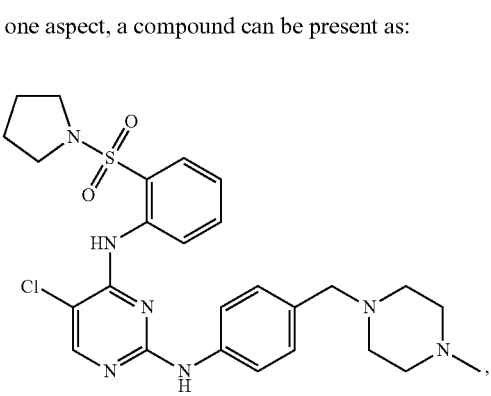
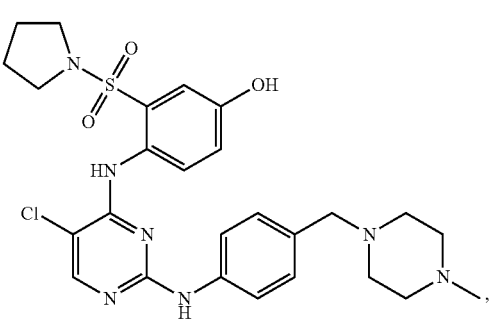

145
-continued
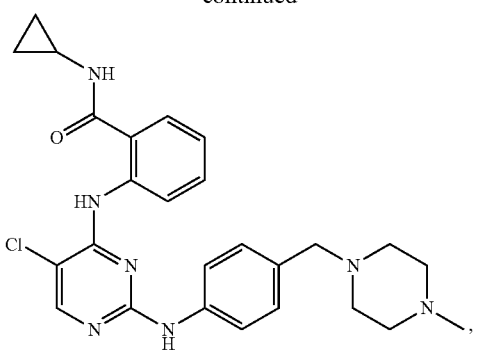
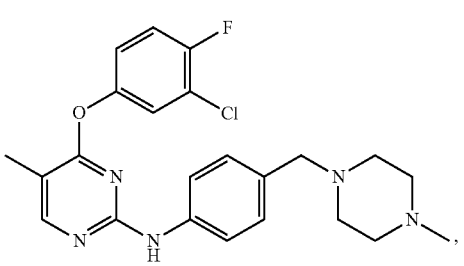
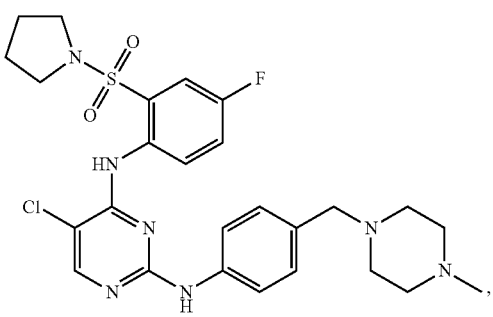
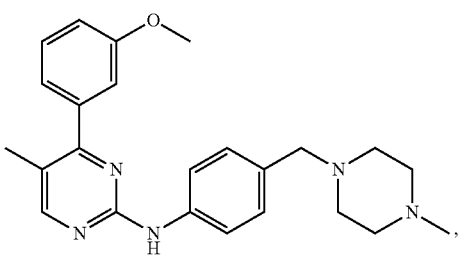
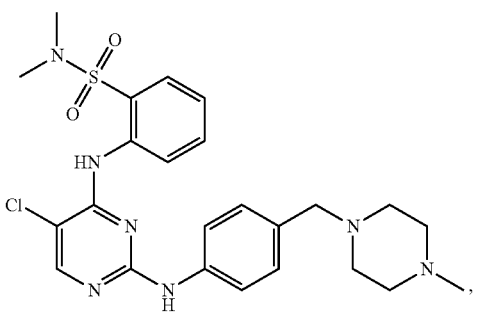
146
-continued
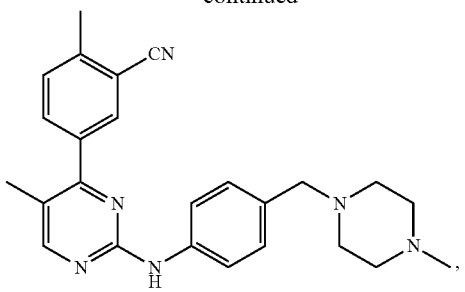
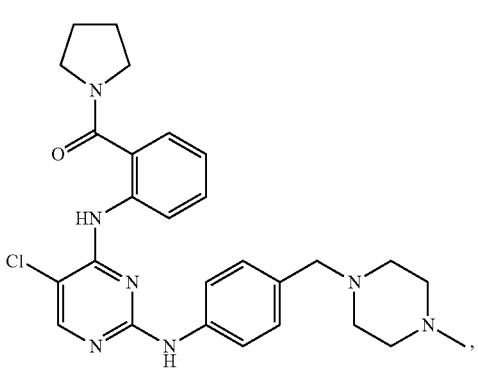
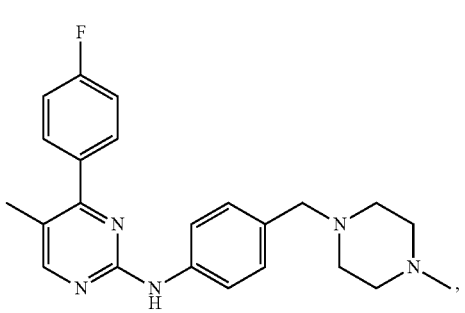
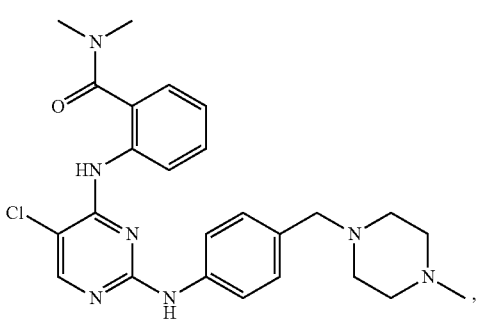
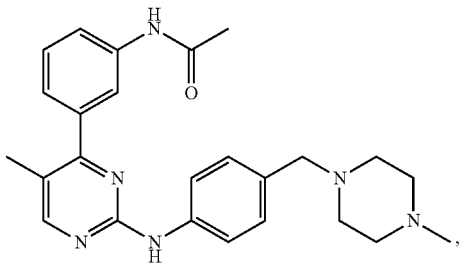

147
-continued
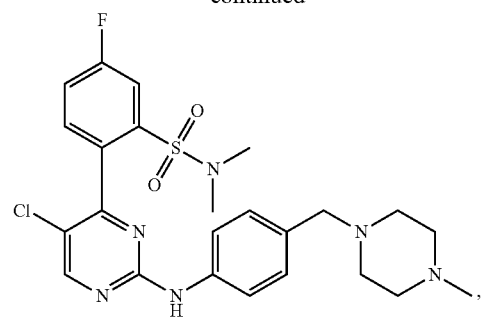
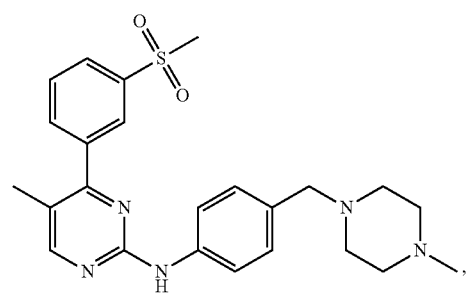
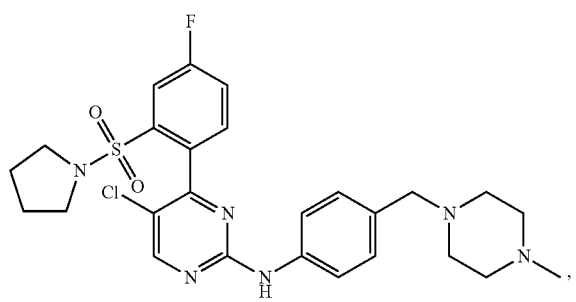
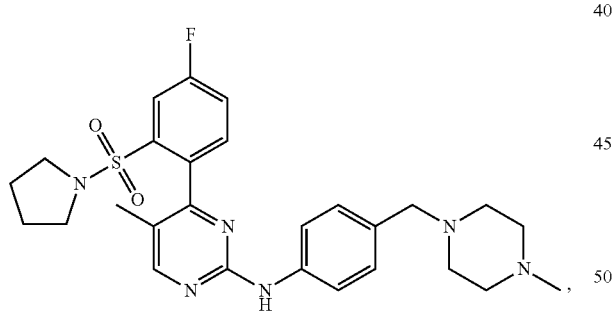
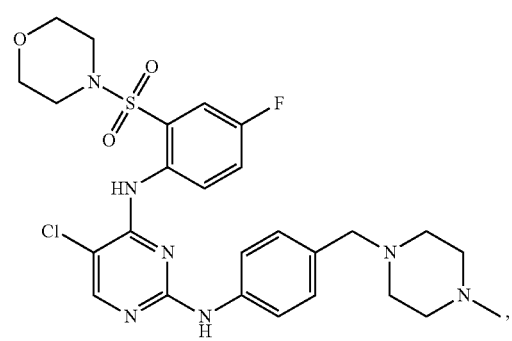
148
-continued
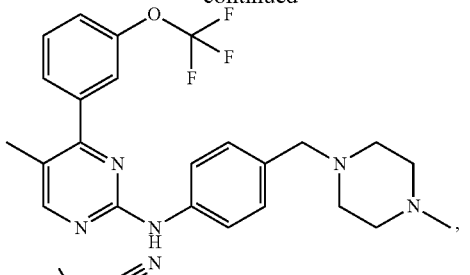
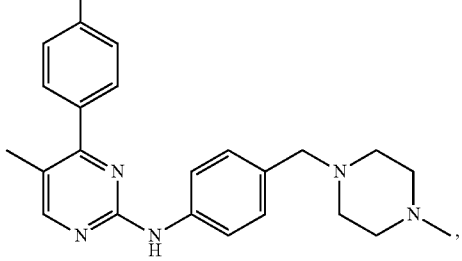
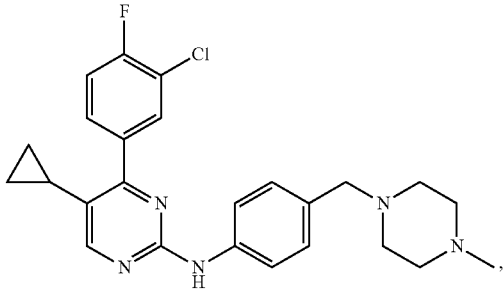
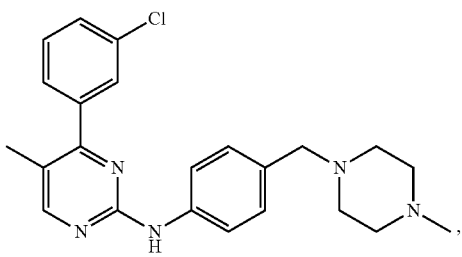
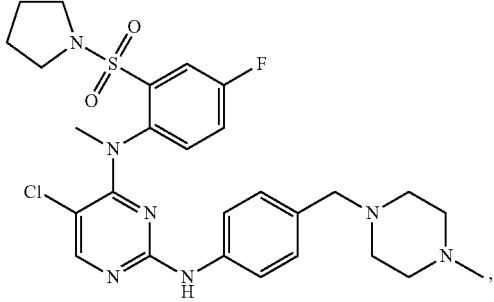
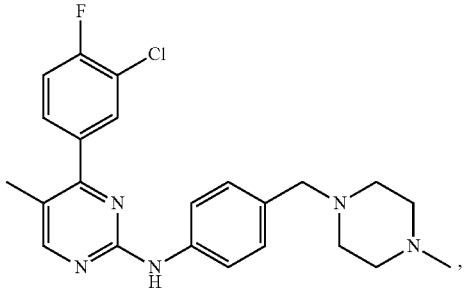

-continued

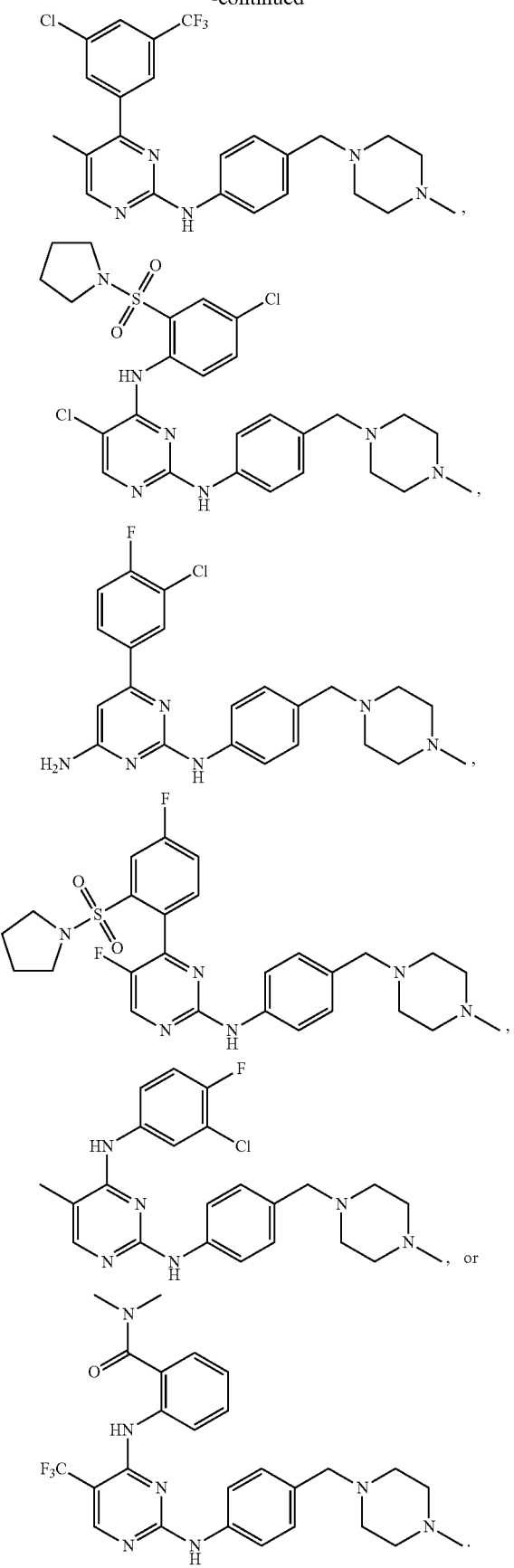

In one aspect, a compound can be present as:

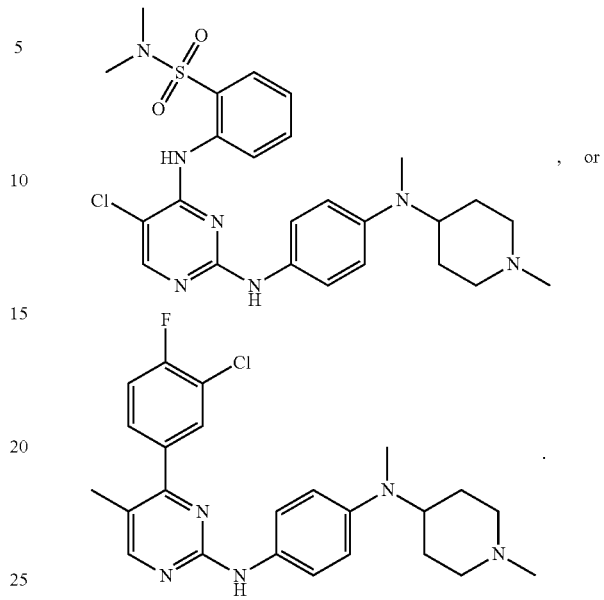

In a further aspect, the compound exhibits inhibition of a protein kinase. In a further aspect, the compound exhibits inhibition of a protein kinase. In a still further aspect, the compound exhibits inhibition of a protein kinase selected from c-abl oncogene 1 kinase, c-abl oncogene 1 kinase (T315I form), ALK tyrosine kinase receptor, aurora kinase A, AXL receptor tyrosine kinase, cyclin-dependent kinase 1, cyclin-dependent kinase 2, serine/threonine-protein kinase Chk1, macrophage colony-stimulating factor 1 receptor kinase, ephrin type-A receptor 1 kinase, tyrosine-protein kinase Fer, tyrosine-protein kinase Fes/Fps, fibroblast growth factor receptor 1, tyrosine-protein kinase Fgr, insulin-like growth factor 1 receptor, macrophage-stimulating protein receptor kinase, proto-oncogene tyrosine-protein kinase receptor Ret, proto-oncogene tyrosine-protein kinase ROS, proto-oncogene tyrosine-protein kinase Src, proto-oncogene tyrosine-protein kinase Yes, PTK2B protein tyrosine kinase 2 beta, serine/threonine-protein kinase MST4, serine/threonine-protein kinase PAK 4, yyrosine-protein kinase JAK1, tyrosine-protein kinase JAK2, tyrosine-protein kinase JAK3, tyrosine-protein kinase Lck, tyrosine-protein kinase Lyn, tyrosine-protein kinase Mer, tyrosine-protein kinase SYK, vascular endothelial growth factor receptor 2, and vascular endothelial growth factor receptor 3. In a yet further aspect, the compound exhibits inhibition of receptor tyrosine kinase Axl ("Axl").

In a further aspect, the invention relates to compounds useful as inhibitors of the PI3K/Akt pathway. In a yet further aspect, the compound exhibits inhibition of phosphorylation of Akt in a cell.

In a further aspect, the disclosed compounds exhibit inhibition with an $IC_{50}$ of less than about $1.0 \times 10^4$ M. In a still further aspect, the disclosed compounds exhibit inhibition with an $IC_{50}$ of less than about $1.0 \times 10^{-5}$ M. In a yet further aspect, the disclosed compounds exhibit inhibition with an $IC_{50}$ of less than about $1.0 \times 10^{-6}$ M. In an even further aspect, the compounds exhibit inhibition with an $IC_{50}$ of less than about $1.0 \times 10^{-7}$ M. In a still further aspect, the compounds exhibit inhibition with an $IC_{50}$ of less than about $1.0 \times 10^{-8}$ M.

In a yet further aspect, the compounds exhibit inhibition with an $IC_{50}$ of less than about $1.0 \times 10^{-9}$ M.

It is contemplated that one or more compounds can optionally be omitted from the disclosed invention.

It is contemplated that one or more compounds can optionally be omitted from the disclosed invention.

3. Inhibition of Protein Kinase Activity

Generally, the disclosed compounds exhibit inhibition of the PI3K/Akt pathway. In a further aspect, the compound exhibits inhibition of a protein kinase. In a still further aspect, the compound exhibits inhibition of a protein kinase selected a protein kinase selected from c-abl oncogene 1 kinase, c-abl oncogene 1 kinase (T315I form), ALK tyrosine kinase receptor, aurora kinase A, AXL receptor tyrosine kinase, cyclin-dependent kinase 1, cyclin-dependent kinase 2, serine/threonine-protein kinase Chk1, macrophage colony-stimulating factor 1 receptor kinase, ephrin type-A receptor 1 kinase, tyrosine-protein kinase Fer, tyrosine-protein kinase Fes/Fps, fibroblast growth factor receptor 1, tyrosine-protein kinase Fgr, insulin-like growth factor 1 receptor, macrophage-stimulating protein receptor kinase, proto-oncogene tyrosine-protein kinase receptor Ret, proto-oncogene tyrosine-protein kinase ROS, proto-oncogene tyrosine-protein kinase Src, proto-oncogene tyrosine-protein kinase Yes, PTK2B protein tyrosine kinase 2 beta, serine/threonine-protein kinase MST4, serine/threonine-protein kinase PAK 4, yyrosine-protein kinase JAK1, tyrosine-protein kinase JAK2, tyrosine-protein kinase JAK3, tyrosine-protein kinase Lck, tyrosine-protein kinase Lyn, tyrosine-protein kinase Mer, tyrosine-protein kinase SYK, vascular endothelial growth factor receptor 2, and vascular endothelial growth factor receptor 3. In a further aspect, a disclosed compound can exhibit inhibition of one of these kineases with an $IC_{50}$ of less than about 10 µM, of less than about 1 µM, of less than about 500 nM, of less than about 100 nM, or of less than about 10 nM.

In one aspect, the disclosed compounds exhibit inhibition of kinases which are members of the receptor tyrosine kinase subfamily TAM. In a further aspect, the receptor tyrosine kinase is selected from Axl, Tyro3 and Mer. For example, a disclosed compound can exhibit inhibition of Tyro3 with an $IC_{50}$ of less than about 10 µM, of less than about 1 µM, of less than about 500 nM, of less than about 100 nM, or of less than about 10 nM. Alternatively, a disclosed compound can exhibit inhibition of Mer with an $IC_{50}$ of less than about 10 µM, of less than about 1 µM, of less than about 500 nM, of less than about 100 nM, or of less than about 10 nM.

In one aspect, the disclosed compounds exhibit inhibition of receptor tyrosine kinase Axl ("Axl"). For example, a disclosed compound can exhibit inhibition of Axl with an $IC_{50}$ of less than about 10 µM, of less than about 1 µM, of less than about 500 nM, of less than about 100 nM, or of less than about 10 nM.

In a further aspect, the inhibition is determined in an in vitro assay that measures catalytic activity of the protein kinase, e.g. disappearance of ATP substrate or conversion of ATP to ADP using methods known in the art. In a yet further aspect, the assay uses a recombinant protein kinase. In a still further aspect, the recombinant protein kinase is Axl. In some instances, it can be useful for the recombinant protein kinase to tagged with an affinity tag. An example of a useful affinity tags is the His6 tag. One suitable assay is the Lathascreen™ Axl kinase assay (Invitrogen), the use of which is described in the examples. For example, a disclosed compound can exhibit inhibition of the catalytic activity of the protein kinase with an $IC_{50}$ of less than about 10 µM, of less than about 1 µM, of less than about 500 nM, of less than about 100 nM, or of less than about 10 nM.

In a further aspect, the in vitro assay measures inhibition by a disclosed compound of binding of an ATP competitive inhibitor to the active site of the protein kinase. In a yet further aspect, the assay uses a recombinant protein kinase. In a still further aspect, the recombinant protein kinase is Axl. In a still further aspect, a disclosed compound can exhibit inhibition of binding at the ATP binding site of the protein kinase with an $IC_{50}$ of less than about 10 µM, of less than about 1 µM, of less than about 500 nM, of less than about 100 nM, or of less than about 10 nM. An example of such an assay is LanthaScreen™ Eu Kinase Binding Assay (Invitrogen Corporation, Carlsbad, Calif.) which is based on the binding and displacement of the Alexa Fluor® 647-labeled, ATP-competitive kinase inhibitor scaffold (kinase tracer) to the kinase of interest. Binding of the tracer to the kinase is detected using a europium-labeled anti-tag antibody, which binds to the kinase of interest. Simultaneous binding of both the tracer and antibody to the kinase results in a high degree of FRET (fluorescence resonance energy transfer) from the europium (Eu) donor fluorophore to the Alexa Fluor® 647 acceptor fluorophore on the kinase tracer. Binding of an inhibitor to the kinase competes for binding with the tracer, resulting in a loss of FRET. This type of assay allows detection of multiple modes of interaction with the target kinase at the ATP binding site, including "Type II" inhibitors, which bind to both the ATP site and a second site often referred to as the "allosteric" site, compounds which bind to either active or non-activated forms of a target kinase, and compounds with slow binding kinetics.

C. Inhibition of the PI3K/Akt Pathway

The utility of the compounds in accordance with the present invention as inhibitors of the PI3K/Akt signaling pathway, in particular by inhibition of Axl activity, can be demonstrated by methodology known in the art. For example, inhibition of specific steps in a signaling pathway can be determined. In one aspect, the compounds of the present invention inhibit the phosphorylation of Akt. In a further aspect, phosphorylation of Akt at Ser473 can be determined as a measure of inhibition of the signaling pathway. For example, a compound can exhibit inhibition of Akt phosphorylation with an $IC_{50}$ of less than about 10 µM, of less than about 1 µM, of less than about 500 nM, of less than about 100 nM, or of less than about 10 nM. In a further aspect, the inhibition is of phosphorylation at Thr308 of Akt.

In one aspect, the disclosed compounds exhibit inhibition of cell viability. For example, cells derived from tumors with increased expression of Axl and/or Gas6 are suitable for determination of cell viability. In a further aspect, inhibition is determined using a cell-line selected from PSN-1, PL45, and PANC-1 cells. In a still further aspect, the cell-line is selected from K562, MCF-7, PL-45, PANC-1, PSN-1, HepG2, A549AN3-CA, RL95-2, SK-OV-3, NCCIT, HCT-116, AGS, BT549, RKO, Hec-1A,786-O, HCT-15, U87-MG, PC-3, MCF-7, H1975, HT-29, T47D, BT-20, and LNCap cells. For example, a compound can exhibit inhibition of cell viability in one of these cell-lines with an $IC_{50}$ of less than about 10 µM, of less than about 1 µM, of less than about 500 nM, of less than about 100 nM, or of less than about 10 nM. Methods to measure cell viability are known in the art and described herein.

In vivo efficacy for disclosed compounds can be measured in a number of preclinical models where known, clinically useful therapeutics display similar positive responses. For example, disclosed compounds can assess in tumor xenograft models in laboratory animals at doses ranging from 1 to 100 mg/kg administered orally, by intravenous injection, subcutaneous injection, or intraperitoneal injection. Although, nude mice are most frequently used in the tumor xenograft model, other laboratory animals may used as needed for convenience or the goals of the study. In the tumor xenograft model, the tumor volume at various points post-implantation of the tumor and/or mortality can be used as efficacy endpoints in the study. Suitable cell-lines for establishing tumor xenografts include the following: PL45, PANC-1 or PSN-1. In a still further aspect, the cell-line is selected from K562, MCF-7, PL-45, PANC-1, PSN-1, HepG2, A549AN3-CA, RL95-2, SK-OV-3, NCCIT, HCT-116, AGS, BT549, RKO, Hec-1A, 786-0, HCT-15, U87-MG, PC-3, MCF-7, H1975, HT-29, T47D, BT-20, and LNCap.

D. Structure-Based Identification of Axl Inhibitors

A structure-based design strategy was used in identifying potential pharmacophores useful as Axl inhibitors. Virtual docking experiments identified 2,4,6-trisubstituted pyrimidines 2,4-diamines as active fragments. A representative docking study is shown in FIG. 1, which shows the docking of 2-((5-chloro-2-((4-((4-methylpiperazin-1-yl)methyl)phenyl) amino)pyrimidin-4-yl)amino)-N,N-dimethylbenzamide with a homology based model of Axl kinase. The critical residues are labeled and the hinge, gatekeeper, hydrophobic and solvent sites are highlighted with surface representation. As shown, the pyrimidine nitrogen takes part in a hydrogen bonding interaction in the hinge region of the kinase with the Met623 amide NH. For discussion of the structure-based approach, reference is made to the chemical structure given below. The pyrimidine substituents extend in the solvent-exposed region ($R^b$ position) and occupy the hydrophobic cavity ($R^d$ position).

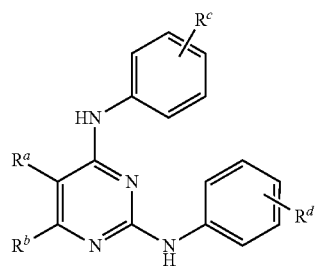

Figure 2:
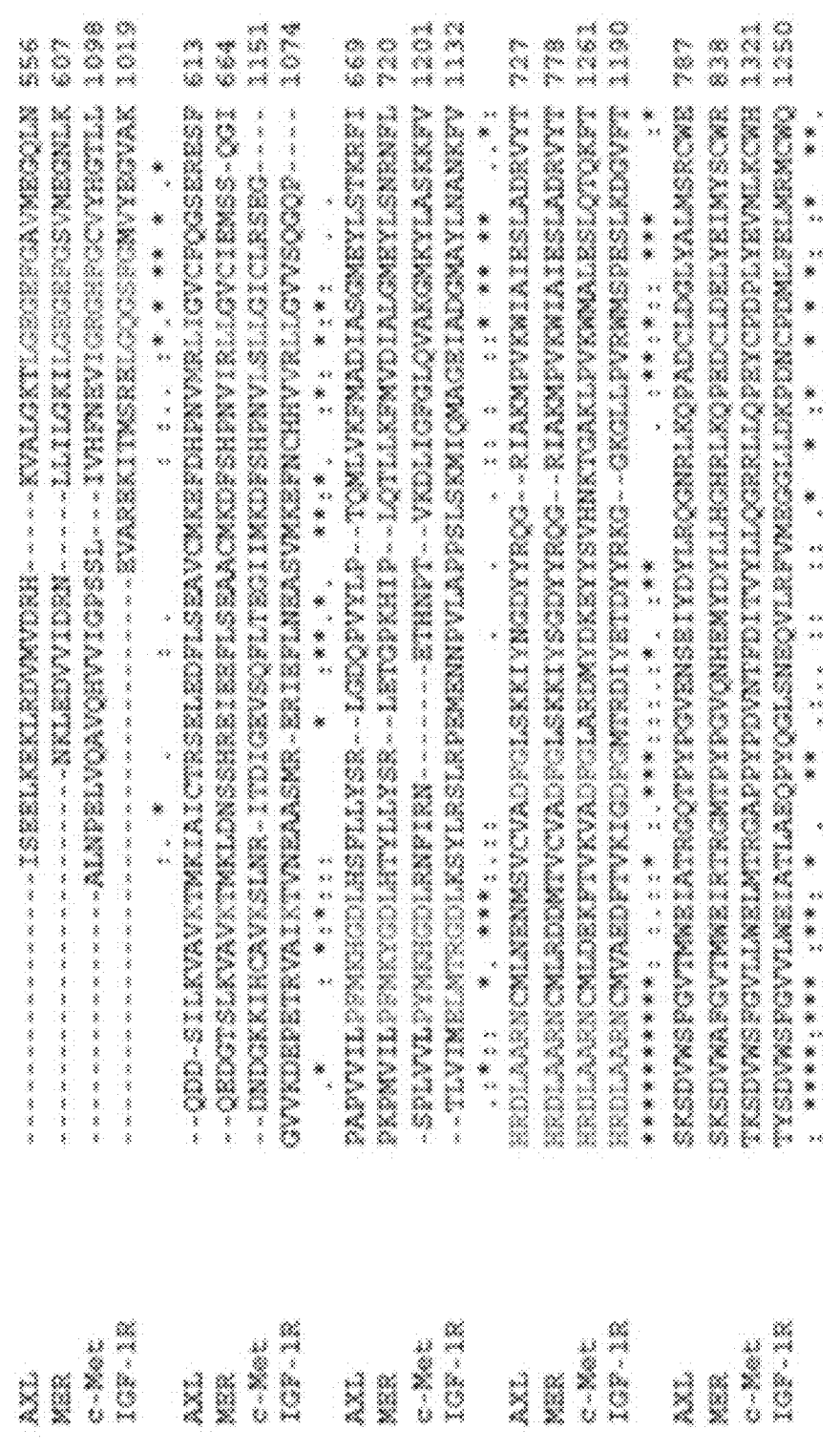

A homology model was used since there currently does not exist a solved crystal structure of the catalytic domain of Axl kinase. The homology model was developed from multiple sequence alignment using CLUSTAL 2.0.11 multiple sequence alignment software of three related proteins with solved x-ray crystal structures. The sequences used in the alignment, and forming the basis of the homology model, were: MER (69/83% sequence identity/similarity, 1% gaps), c-Met (46% identity) and IGF-1R (41% identity). The alignment is shown in FIG. 2, and residues are highlighted as follows: identical residues indicated with a single raised dot; highly conserved residues with aligned double dots; and similar residues with a lower single dot. The amino acid residues highlighted in with lighter gray lettering are the critical active site residues and the residue in red is the kinase gatekeeper.

In one synthetic approach to improved Axl inhibitors, anilines bearing heterocycles with desirable pharmacokinetic properties were installed in the 2-position and electron-deficient aryl groups were attached in the $R^d$ position. The compounds synthesized in this series resulted in compounds with activities in the 10 µM range. It was found that substitution at the 6-position ($R^b$) disrupted binding in the hinge region due to steric clash with the Leu620 gate-keeper, resulting in loss of activity.

A $2^{nd}$ generation of compounds prepared with small hydrophobic or basic $R^a$ groups (alkyl, halogens, CN) exhibited activities as low as 750 nm. The hydrophobic $R^d$ substituent was further varied with polarizable oxygens and hydrophobic alkyl groups (e.g. dialkylamide) to enhance $Mg^{2+}$ coordination and favor hydrophobic interactions with the DFG loop, yielding a 3rd generation of compounds with activities as low as 20 nm.

Further optimization of activity and selectivity of Axl inhibitors can proceed by synthesis of compounds which take into further account the gate keeper, DFG loop, and 13 hydrophobic sheet (see FIG. 1). For example, multiple sequence alignment for AXL and Aurora A & B showing a high degree of sequence identity/similarity as shown below.

```
Axl        LGEGEFGVMRLILPFMGNDFG

Aurora A   LGKGKFGVLRLYLEYAGNDFG

Aurora B   LGKGKFGVLRMYLEFAGNDFG
           **:*:***:*: * : *****
```

The residues which are bolded are believed to be involved as the kinase gate keeper. AXL and Auroras share a Leu gate keeper, however the next residue is a polar acidic Glu (Auroras) or hydrophobic Pro (Axl). Without wishing to be bound by a particular theory, bulkier more hydrophobic 5-substituents could destabilize the hinge region of Aurora. It was found that trifluoromethane excessive bulk also destabilized Axl but the smaller CN substituents could improve selective kinase activity.

Figure 3:
FIG. 3 shows a docking study for compounds of the present invention with a homology model of Axl kinase.

The interaction between the hydrophobic slightly basic dialkylamide and the Phe228 of the DFG loop can be strengthened by introduction of more hydrophobic cycloalkyls, locking the inhibitor conformation and "pushing" the $R^d$ moiety closer to the β-sheet. Introduction of electron-withdrawing substituents on that ring can favor interaction to the LGE of AXL vs. LGK of Auroras (see FIG. 3 for docking model)

E. Methods of Making the Compounds

In one aspect, the invention relates to methods of making compounds useful as inhibitors of protein kinase, which can be useful in the treatment of disorders of uncontrolled cellular proliferation. In a further aspect, the protein kinase is Axl.

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, in addition to other standard manipulations known in the literature or to one skilled in the art. The following examples are provided so that the invention might be more fully understood, are illustrative only, and should not be construed as limiting.

In one aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

1. Route I

In one aspect, substituted 2-halo-4-phenylpyrimidine analogs can be prepared as shown below.

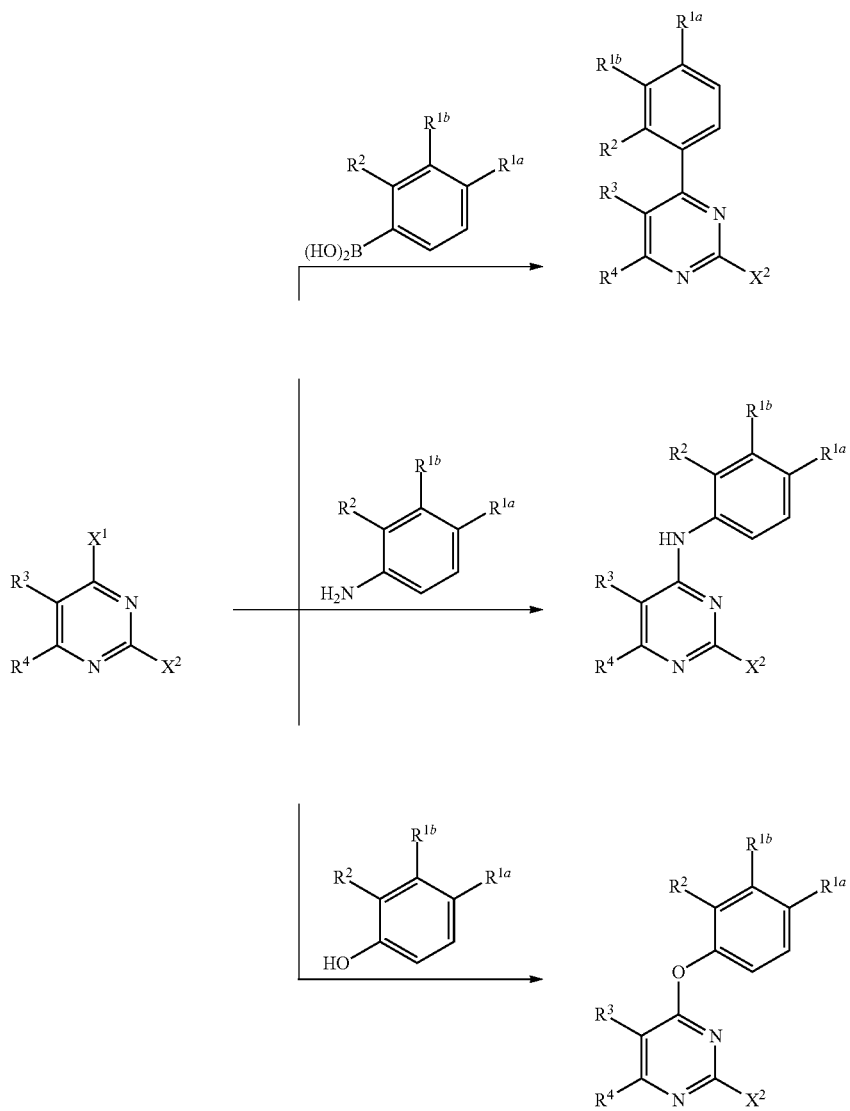

Compounds are represented in generic form, with substituents as noted in compound descriptions elsewhere herein. More specific examples are set forth below.

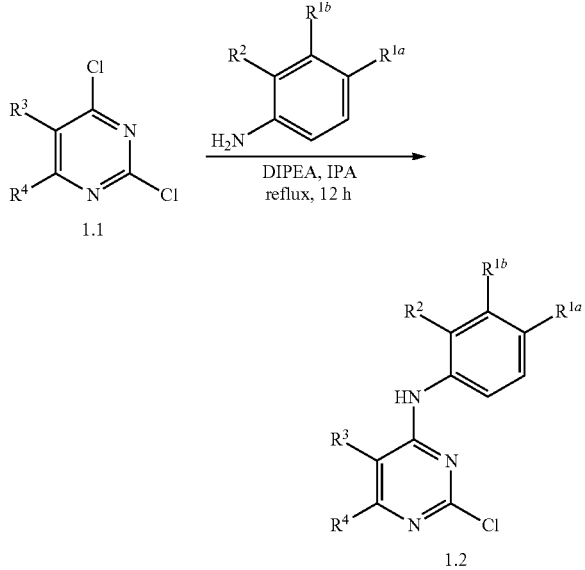

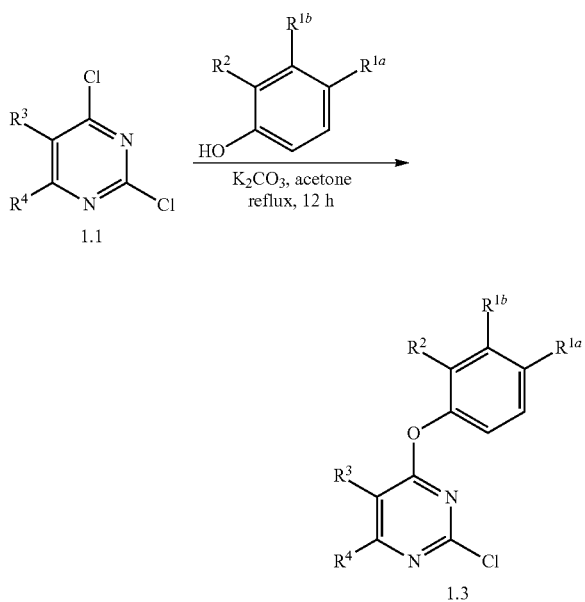

As an example, compound 1.2 can be prepared according to Route I. Beginning with compound 1.1, a nucleophilic aromatic substitution reaction with an optionally substituted aniline in the presence of a base (e.g., DIPEA or DIEA) provides compound 1.2.

As a further example, compound 1.3 can be prepared according to Route I. Beginning with compound 1.1, a nucleophilic aromatic substitution reaction with an optionally substituted phenol in the presence of a base (e.g., potassium carbonate) provides compound 1.3.

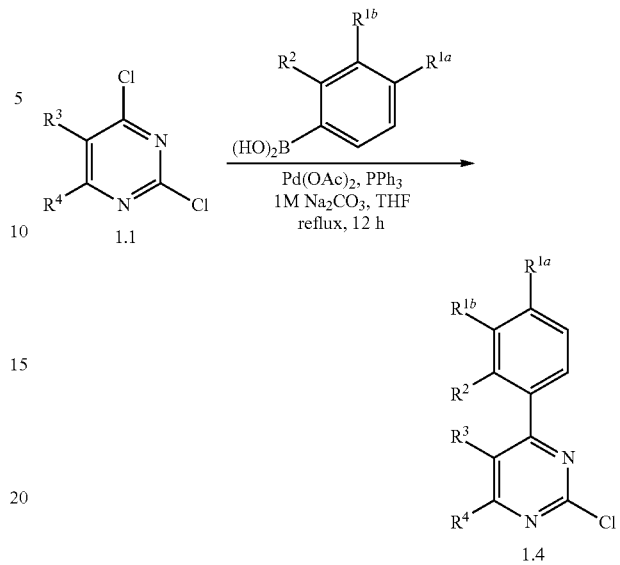

As a further example, compound 1.4 can be prepared according to Route I. Beginning with compound 1.1, palladium-catalyzed cross-coupling reaction with an optionally substituted boronic acid in the presence of a base (e.g., sodium carbonate) provides compound 1.4.

Thus, in one aspect, the invention relates to a method comprising the steps of: providing a first compound having a structure represented by a formula:

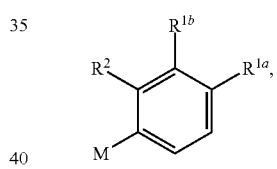

wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-$C_6$ cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein M is selected from:

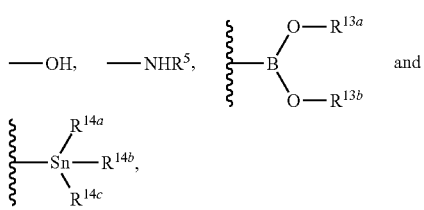

wherein each of $R^{13a}$ and $R^{13b}$ is independently selected from hydrogen, and C1-C6 alkyl; or $R^{13a}$ and $R^{13b}$ are covalently bonded and, together with the intermediate atoms, comprise an optionally substituted heterocyclic ring; and wherein each of $R^{14a}$, $R^{14b}$, and $R^{14c}$ is independently C1-C6 alkyl; and coupling with a second compound having a structure represented by a formula:

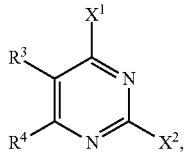

wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; wherein $X^1$ is halide or pseudohalide; wherein $X^2$ is halide, pseudohalide, or a group having a structure represented by the formula:

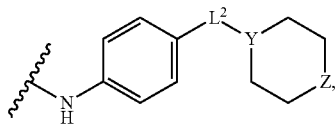

wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein coupling is performed for a time and at a temperature sufficient to provide a product having a structure represented by a formula:

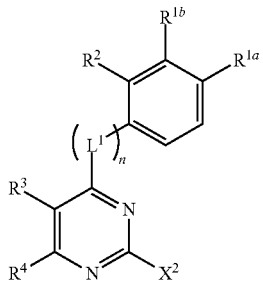

wherein $L^1$ is selected from O and $NR^5$, wherein n is 0 or 1; wherein $R^5$ is selected from is selected from hydrogen and C1-C6 alkyl.

Thus, in various aspects, the invention relates to a method comprising the steps of: providing a first compound having a structure represented by a formula:

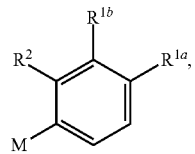

wherein each of $R^{1a}$ and $R^{1b}$ is independently selected from hydrogen, halogen, OH, CN, $SO_2CH_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein M is selected from:

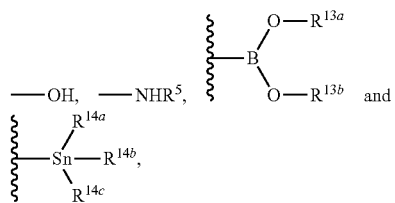

wherein each of $R^{13a}$ and $R^{13b}$ is independently selected from hydrogen, and C1-C6 alkyl; or $R^{13a}$ and $R^{13b}$ are covalently bonded and, together with the intermediate atoms, comprise an optionally substituted heterocyclic ring; and wherein each of $R^{14a}$, $R^{14b}$, and $R^{14c}$ is independently C1-C6 alkyl; and coupling with a second compound having a structure represented by a formula:

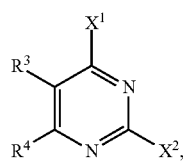

wherein $R^3$ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; wherein $X^1$ is halide or pseudohalide; wherein $X^2$ is halide, pseudohalide, or a group having a structure represented by the formula:

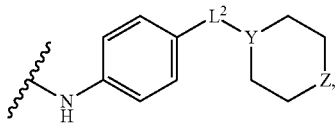

wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein coupling is performed for a time and at a temperature sufficient to provide a product having a structure represented by a formula:

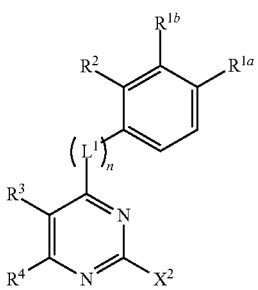

wherein $L^1$ is selected from O and $NR^5$, wherein n is 0 or 1; wherein $R^5$ is selected from is selected from hydrogen and C1-C6 alkyl.

In a further aspect, M is selected from:

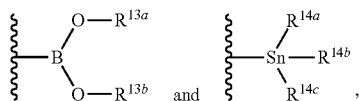

wherein coupling is performed in the presence of a palladium (0) catalyst.

In a further aspect, $X^2$ is halide or pseudohalide, the method further comprising the step of reacting the product with a third compound having a structure represented by a formula:

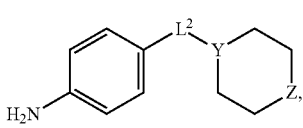

in the presence of a palladium(0) catalyst for a time and at a temperature sufficient to provide a product having a structure represented by a formula:

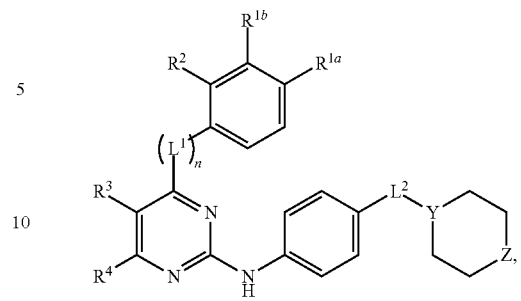

In a further aspect, $R^2$ is hydrogen, the method further comprising the step of halosulfonation to provide a compound having a structure represented by a formula:

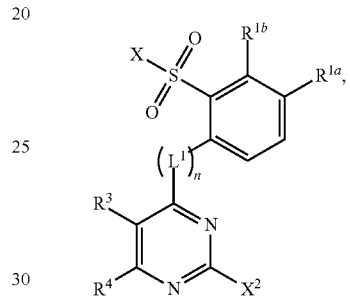

wherein X is halogen.

In a further aspect, $X^2$ is halide or pseudohalide.

In a further aspect, $X^2$ is a group having a structure represented by the formula:

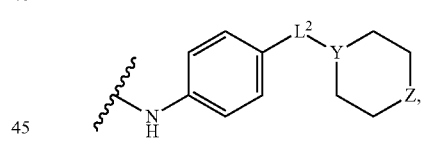

wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$.

In a further aspect, the method further comprises the step of reacting the halosulfonation product with an amine having a structure represented by a formula:

wherein $R^{10}$ is selected from hydrogen, C1-C6 alkyl, and C3-C6 cycloalkyl; and wherein $R^{11}$ is selected from hydrogen and C1-C6 alkyl; or wherein $R^{10}$ and $R^{11}$ are covalently bonded and, together with the intermediate nitrogen, comprise an optionally substituted 3-7 membered heterocycloalkyl ring; thereby providing a product having a structure represented by a formula:

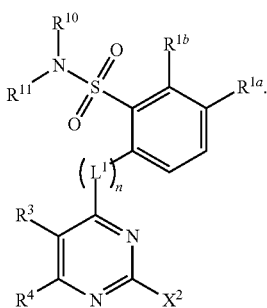

In a further aspect, $X^2$ is a group having a structure represented by the formula:

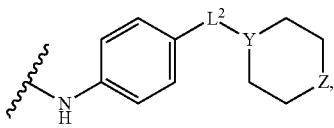

wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$.

In a further aspect, $X^2$ is halide or pseudohalide, the method further comprising the step of reacting the product with an amine having a structure represented by a formula:

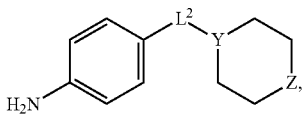

in the presence of a palladium(0) catalyst for a time and at a temperature sufficient to provide a product having a structure represented by a formula:

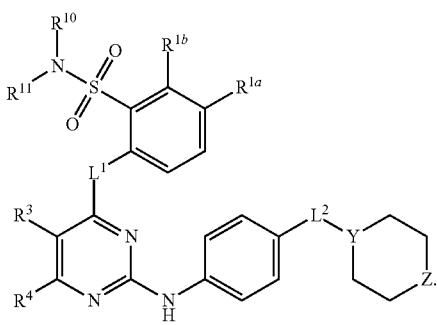

2. Route II

In one aspect, substituted 2-(2-halopyrimidin-4-yl)-benzenesulfonamide analogs can be prepared as shown below.

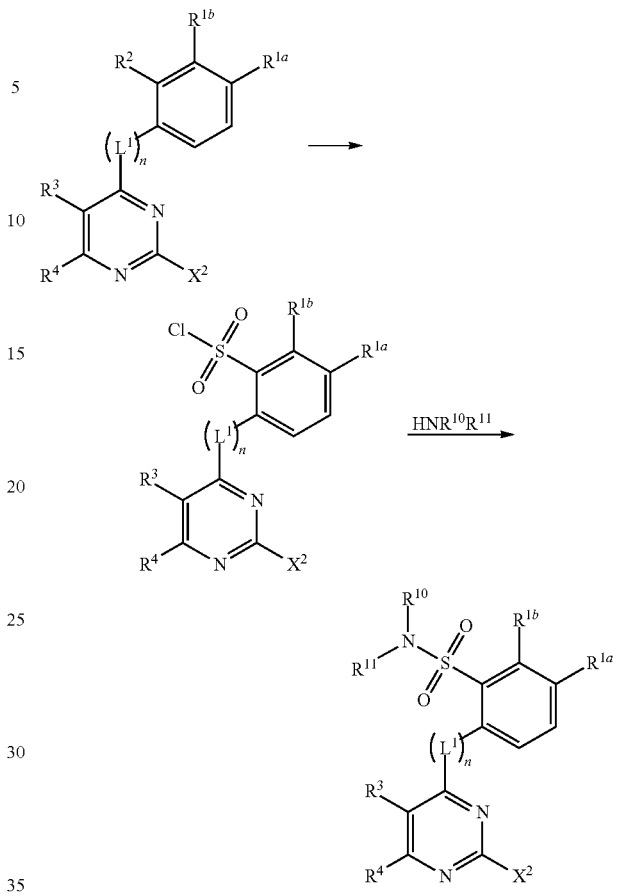

Compounds are represented in generic form, with substituents as noted in compound descriptions elsewhere herein. More specific examples are set forth below.

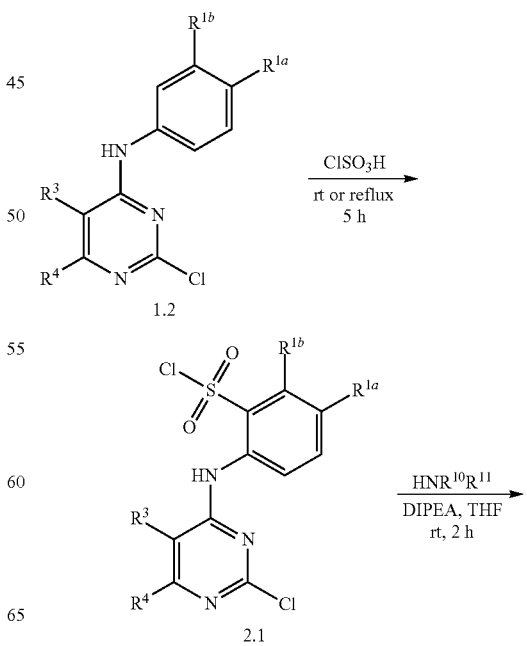

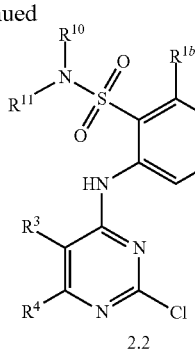

2.2

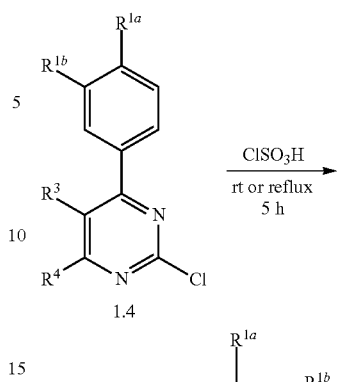

1.4

As an example, compound 2.2 can be prepared according to Route II. Beginning with compound 1.2, halosulfonation (e.g., chlorosulfonation) provides compound 2.1. Subsequent reaction with an amine yields compound 2.2.

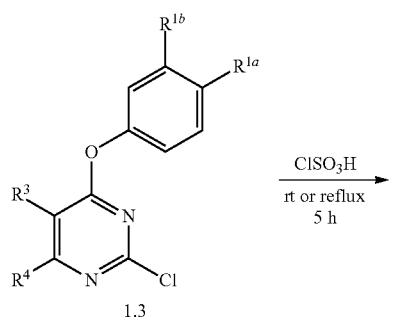

1.3

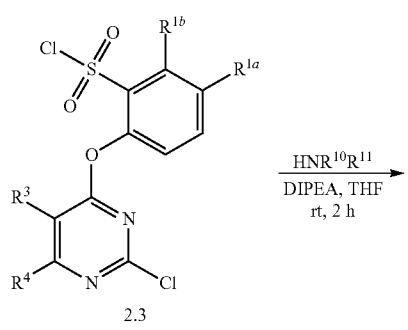

2.3

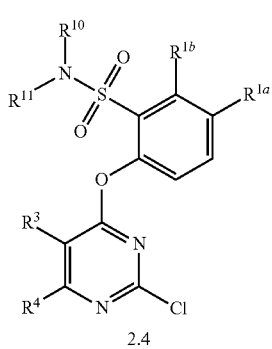

2.4

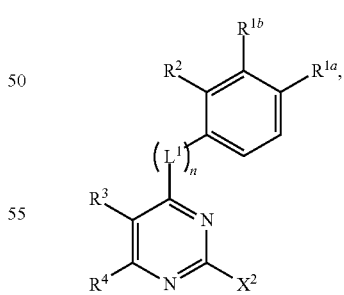

2.5

2.6

As a further example, compound 2.6 can be prepared according to Route II. Beginning with compound 1.4, halosulfonation (e.g., chlorosulfonation) provides compound 2.5. Subsequent reaction with an amine yields compound 2.6.

Thus, in one aspect, the invention relates to a method comprising the steps of: providing a compound having a structure represented by a formula:

As a further example, compound 2.4 can be prepared according to Route II. Beginning with compound 1.3, halosulfonation (e.g., chlorosulfonation) provides compound 2.3. Subsequent reaction with an amine yields compound 2.4.

wherein $L^1$ is selected from O and $NR^5$, wherein n is 0 or 1; wherein $R^5$ is selected from is selected from hydrogen and C1-C6 alkyl; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is hydrogen; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; and wherein $X^2$ is halide, pseudohalide, or a group having a structure represented by the formula:

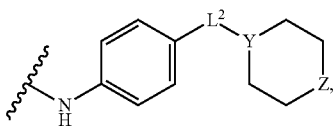

wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; halosulfonation to provide a compound having a structure represented by a formula:

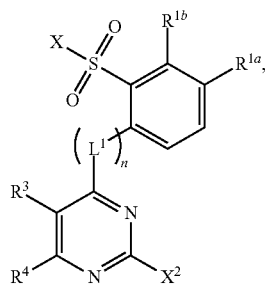

wherein X is halogen.

Thus, in various aspects, the invention relates to a method comprising the steps of: providing a compound having a structure represented by a formula:

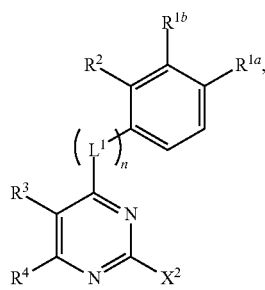

wherein $L^1$ is selected from O and $NR^5$, wherein n is 0 or 1; wherein $R^5$ is selected from is selected from hydrogen and C1-C6 alkyl; wherein each of $R^{1a}$ and $R^{1b}$ is independently selected from hydrogen, halogen, OH, CN, $SO_2CH_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is hydrogen; wherein $R^3$ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; and wherein $X^2$ is halide, pseudohalide, or a group having a structure represented by the formula:

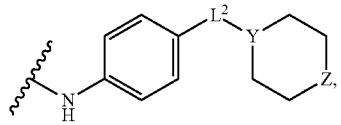

wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; halosulfonation to provide a compound having a structure represented by a formula:

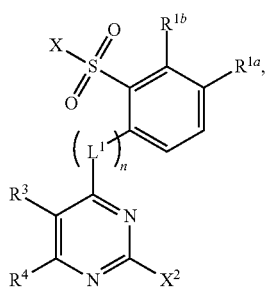

wherein X is halogen.

In a further aspect, $X^2$ is halide or pseudohalide. In a further aspect, $X^2$ is a group having a structure represented by the formula:

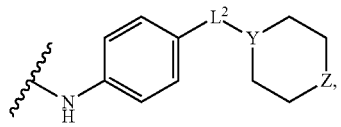

wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$.

In a further aspect, the method further comprises the step of reacting the halosulfonation product with an amine having a structure represented by a formula:

HNR$^{10}$R$^{11}$, wherein R$^{10}$ is selected from hydrogen, C1-C6 alkyl, and C3-C6 cycloalkyl; and wherein R$^{11}$ is selected from hydrogen and C1-C6 alkyl; or wherein R$^{10}$ and R$^{11}$ are covalently bonded and, together with the intermediate nitrogen, comprise an optionally substituted 3-7 membered heterocycloalkyl ring; thereby providing a product having a structure represented by a formula:

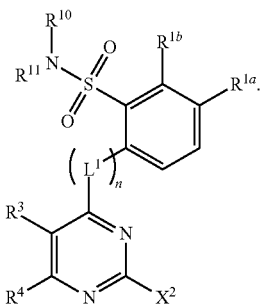

In a further aspect, X$^2$ is a group having a structure represented by the formula:

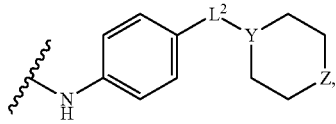

wherein L$^2$ is selected from CH$_2$ and NCH$_3$, provided that L$^2$ is CH$_2$ when Y is N; wherein Y is selected from CH or N; wherein Z is selected from O, NR$^6$ and CH$_2$; wherein R$^6$ is selected from hydrogen and CH$_3$.

In a further aspect, X$^2$ is halide or pseudohalide, the method further comprising the step of reacting the product with an amine having a structure represented by a formula:

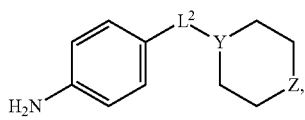

in the presence of a palladium(0) catalyst for a time and at a temperature sufficient to provide a product having a structure represented by a formula:

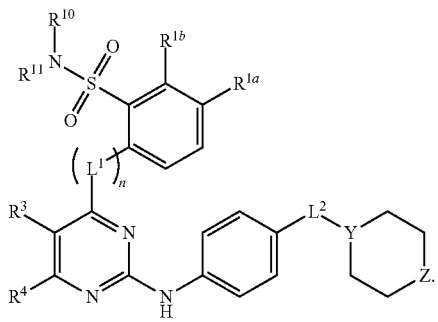

In a further aspect, the invention relates to a method comprising the steps of: providing a compound having a structure represented by a formula:

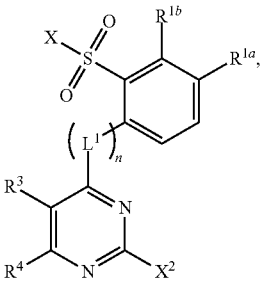

wherein L$^1$ is selected from O and NR$^5$, wherein n is 0 or 1; wherein R$^5$ is selected from is selected from hydrogen and C1-C6 alkyl; wherein each of R$^{1a}$ and R$^{1b}$ is independently selected from hydrogen, halogen, OH, CN, SO$_2$CH$_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R$^7$; wherein R$^7$ is selected from hydrogen and C1-C6 alkyl; wherein R$^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; wherein R$^4$ is selected from hydrogen, halogen, Ar$^1$, C1-C6 alkyl, C3-C6 cycloalkyl, and C3-C6 heterocycloalkyl; wherein Ar$^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino; wherein R$^{12}$ is selected from C1-C6 alkyl and C3-C6 cycloalkyl; and wherein X$^2$ is halide, pseudohalide, or a group having a structure represented by the formula:

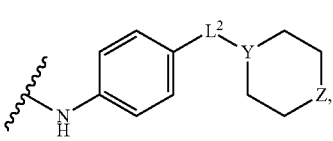

wherein L$^2$ is selected from CH$_2$ and NCH$_3$, provided that L$^2$ is CH$_2$ when Y is N; wherein Y is selected from CH or N; wherein Z is selected from O, NR$^6$ and CH$_2$; wherein R$^6$ is selected from hydrogen and CH$_3$; reacting the compound with an amine having a structure represented by a formula:

HNR$^{10}$R$^{11}$, wherein R$^{10}$ is selected from hydrogen, C1-C6 alkyl, and C3-C6 cycloalkyl; and wherein R$^{11}$ is selected from hydrogen and C1-C6 alkyl; or wherein R$^{10}$ and R$^{11}$ are covalently bonded and, together with the intermediate nitrogen, comprise an optionally substituted 3-7 membered heterocycloalkyl ring; thereby providing a product having a structure represented by a formula:

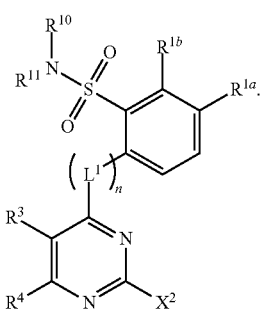

In a further aspect, the invention relates to a method comprising the steps of: providing a compound having a structure represented by a formula:

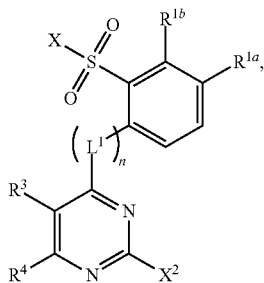

wherein $L^1$ is selected from O and $NR^5$, wherein n is 0 or 1; wherein $R^5$ is selected from is selected from hydrogen and C1-C6 alkyl; wherein each of $R^{1a}$ and $R^{1b}$ is independently selected from hydrogen, halogen, OH, CN, $SO_2CH_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^3$ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; and wherein $X^2$ is halide, pseudohalide, or a group having a structure represented by the formula:

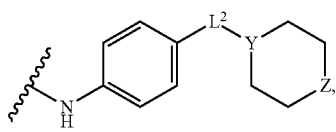

wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; reacting the compound with an amine having a structure represented by a formula:

$$HNR^{10}R^{11},$$

wherein $R^{10}$ is selected from hydrogen, C1-C6 alkyl, and C3-C6 cycloalkyl; and wherein $R^{11}$ is selected from hydrogen and C1-C6 alkyl; or wherein $R^{10}$ and $R^{11}$ are covalently bonded and, together with the intermediate nitrogen, comprise an optionally substituted 3-7 membered heterocycloalkyl ring; thereby providing a product having a structure represented by a formula:

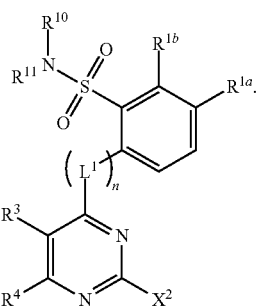

In a further aspect, $X^2$ is a group having a structure represented by the formula:

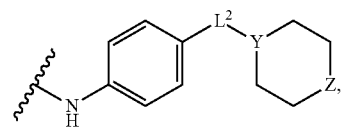

wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$.

In a further aspect, $X^2$ is halide or pseudohalide, the method further comprising the step of reacting the halosulfonation product with an amine having a structure represented by a formula:

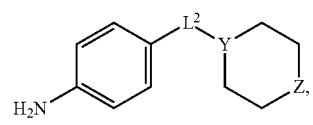

in the presence of a palladium(0) catalyst for a time and at a temperature sufficient to provide a product having a structure represented by a formula:

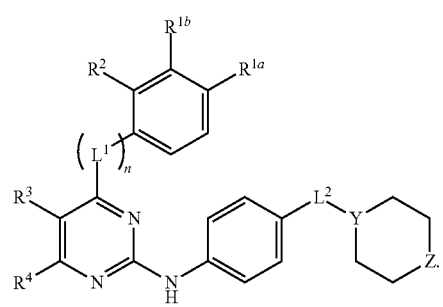

3. Route III

In one aspect, substituted N-phenylpyrimidin-2-amine analogs can be prepared as shown below.

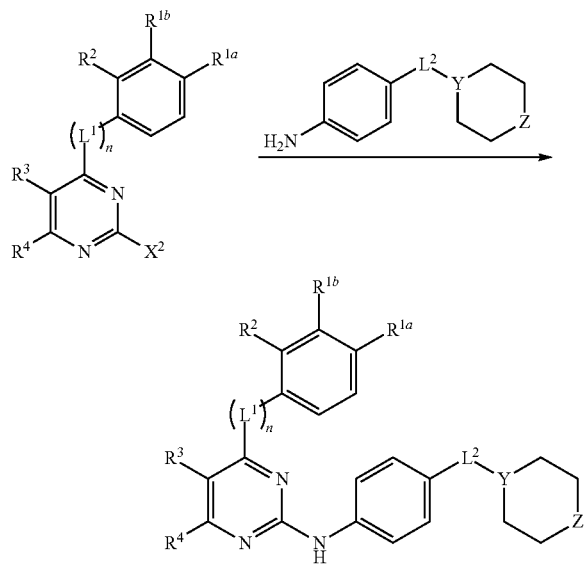

Compounds are represented in generic form, with substituents as noted in compound descriptions elsewhere herein. More specific examples are set forth below.

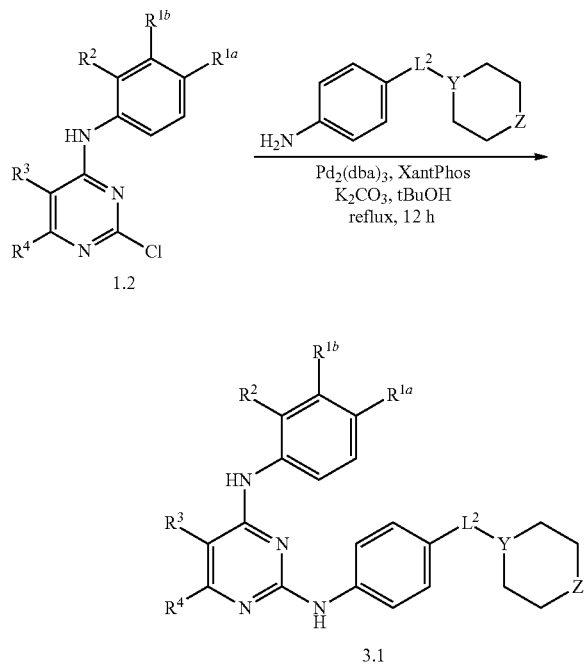

As an example, compound 3.1 can be prepared according to Route III. Beginning with compound 1.2, palladium-catalyzed aminolysis with a substituted aniline in the presence of a base (e.g., potassium carbonate) provides compound 3.1.

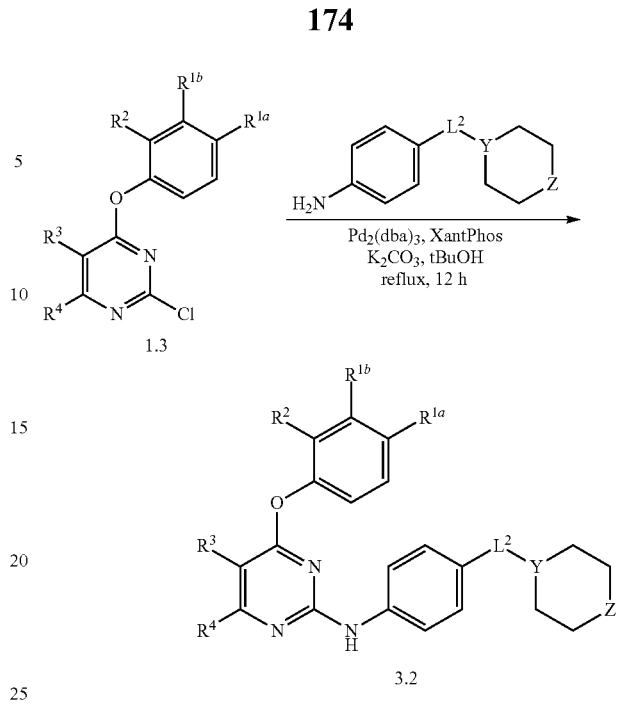

As a further example, compound 3.2 can be prepared according to Route III. Beginning with compound 1.3, palladium-catalyzed aminolysis with a substituted aniline in the presence of a base (e.g., potassium carbonate) provides compound 3.2.

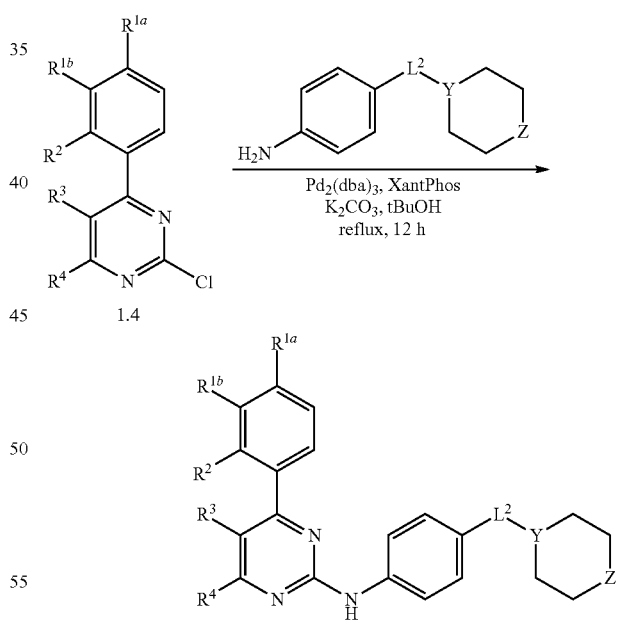

As a further example, compound 3.3 can be prepared according to Route III. Beginning with compound 1.4, palladium-catalyzed aminolysis with a substituted aniline in the presence of a base (e.g., potassium carbonate) provides compound 3.3.

Thus, in one aspect, the invention relates to a method comprising the steps of: providing a first compound having a structure represented by a formula:

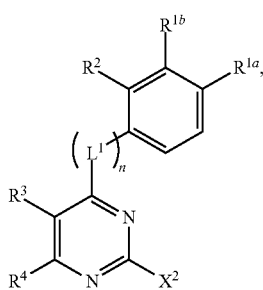

wherein $L^1$ is selected from O and $NR^5$, wherein n is 0 or 1; wherein $R^5$ is selected from is selected from hydrogen and C1-C6 alkyl; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; and wherein $X^2$ is halide or pseudohalide; reacting the compound with an amine having a structure represented by a formula:

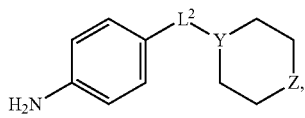

in the presence of a palladium(0) catalyst for a time and at a temperature sufficient to provide a product having a structure represented by a formula:

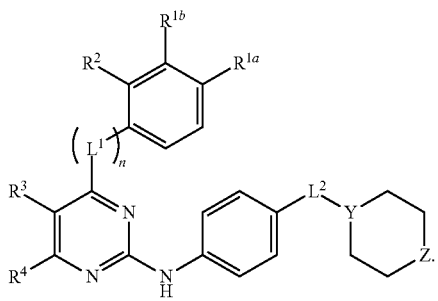

Thus, in various aspects, the invention relates to a method comprising the steps of: providing a first compound having a structure represented by a formula:

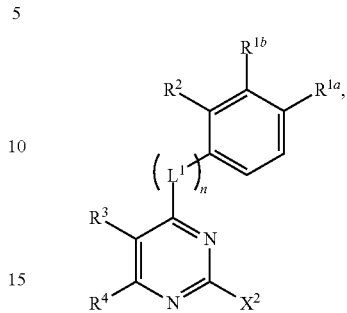

wherein $L^1$ is selected from O and $NR^5$, wherein n is 0 or 1; wherein $R^5$ is selected from is selected from hydrogen and C1-C6 alkyl; wherein each of $R^{1a}$ and $R^{1b}$ is independently selected from hydrogen, halogen, OH, CN, $SO_2CH_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; and wherein $X^2$ is halide or pseudohalide; reacting the compound with an amine having a structure represented by a formula:

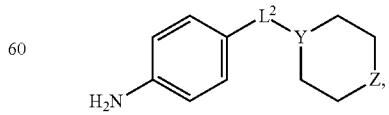

in the presence of a palladium(0) catalyst for a time and at a temperature sufficient to provide a product having a structure represented by a formula:

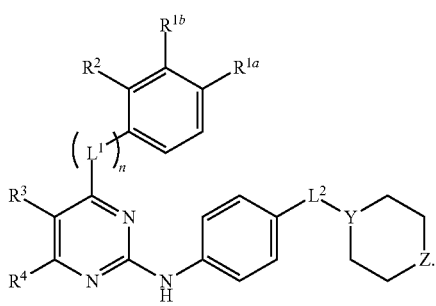

In a further aspect, the compound produced exhibits inhibition of the PI3K/Akt pathway. In a yet further aspect, the compound produced exhibits inhibition Axl. In a still further aspect, the compound produced exhibits inhibition of cell viability.

In a further aspect, the compound produced exhibits inhibition of a protein kinase. In a still further aspect, the compound produced exhibits inhibition of a protein kinase selected from c-abl oncogene 1 kinase, c-abl oncogene 1 kinase (T315I form), ALK tyrosine kinase receptor, aurora kinase A, AXL receptor tyrosine kinase, cyclin-dependent kinase 1, cyclin-dependent kinase 2, serine/threonine-protein kinase Chk1, macrophage colony-stimulating factor 1 receptor kinase, ephrin type-A receptor 1 kinase, tyrosine-protein kinase Fer, tyrosine-protein kinase Fes/Fps, fibroblast growth factor receptor 1, tyrosine-protein kinase Fgr, insulin-like growth factor 1 receptor, macrophage-stimulating protein receptor kinase, proto-oncogene tyrosine-protein kinase receptor Ret, proto-oncogene tyrosine-protein kinase ROS, proto-oncogene tyrosine-protein kinase Src, proto-oncogene tyrosine-protein kinase Yes, PTK2B protein tyrosine kinase 2 beta, serine/threonine-protein kinase MST4, serine/threonine-protein kinase PAK 4, yyrosine-protein kinase JAK1, tyrosine-protein kinase JAK2, tyrosine-protein kinase JAK3, tyrosine-protein kinase Lck, tyrosine-protein kinase Lyn, tyrosine-protein kinase Mer, tyrosine-protein kinase SYK, vascular endothelial growth factor receptor 2, and vascular endothelial growth factor receptor 3. In a yet further aspect, the compound exhibits inhibition of receptor tyrosine kinase Axl ("Axl").

In a further aspect, the compound produced exhibits inhibition with an $IC_{50}$ of less than about $1.0 \times 10^{-4}$ M. In a still further aspect, the compound produced exhibits inhibition with an $IC_{50}$ of less than about $1.0 \times 10^{-5}$ M. In a yet further aspect, the compound produced exhibits inhibition with an $IC_{50}$ of less than about $1.0 \times 10^{-6}$ M. In an even further aspect, the compound produced exhibits inhibition with an $IC_{50}$ of less than about $1.0 \times 10^{-7}$ M. In a still further aspect, the compound produced exhibits inhibition with an $IC_{50}$ of less than about $1.0 \times 10^{-8}$ M. In a yet further aspect, the compound produced exhibits inhibition with an $IC_{50}$ of less than about $1.0 \times 10^{-9}$ M.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

Table I below lists specific compounds as well as experimentally determined Axl kinase activity determined in the activity assay as described below in the examples. The compounds in Table I were synthesized with methods identical or analogous to those shown herein. The requisite starting materials were commercially available, described in the literature, or readily synthesized by one skilled in the art of organic synthesis.

TABLE I

| No. | Structure | $IC_{50}$ (μM) |
|---|---|---|
| 1 | 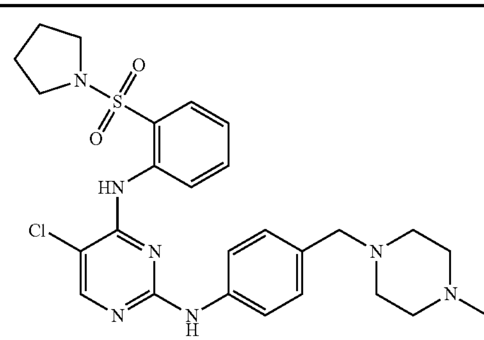 | 0.020 |
| 2 | 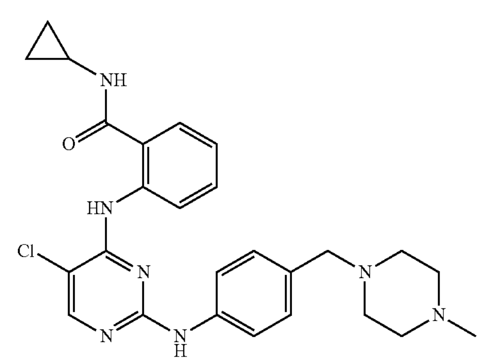 [SMILES: CN1CCN(Cc2ccc(Nc3ncc(Cl)c(Nc4ccccc4C(=O)NC4CC4)n3)cc2)CC1] | 0.032 |

TABLE I-continued
| No. | Structure | IC$_{50}$ (µM) |
|---|---|---|
| 3 | 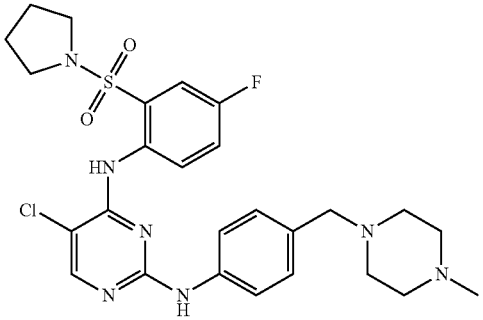 [SMILES: CN1CCN(Cc2ccc(Nc3ncc(Cl)c(Nc4ccc(F)cc4S(=O)(=O)N4CCCC4)n3)cc2)CC1] | 0.037 |
| 4 | 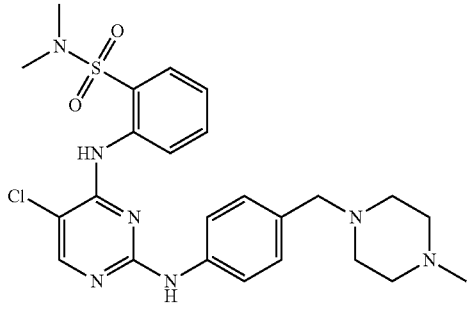 [SMILES: CN1CCN(Cc2ccc(Nc3ncc(Cl)c(Nc4ccccc4S(=O)(=O)N(C)C)n3)cc2)CC1] | 0.053 |
| 5 | 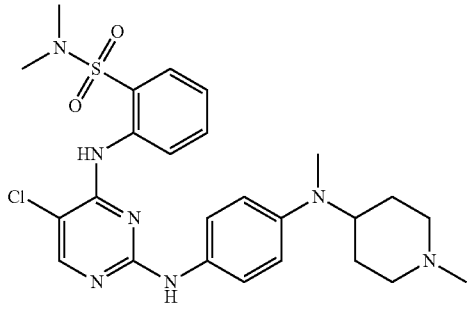 [SMILES: CN1CCC(N(C)c2ccc(Nc3ncc(Cl)c(Nc4ccccc4S(=O)(=O)N(C)C)n3)cc2)CC1] | 0.056 |
| 6 | 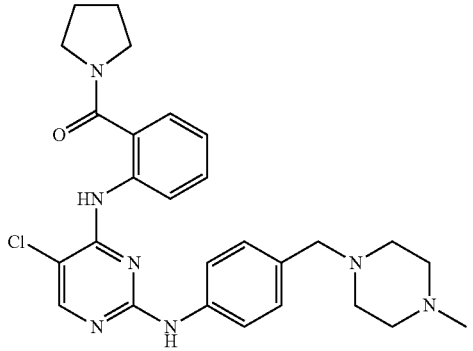 [SMILES: CN1CCN(Cc2ccc(Nc3ncc(Cl)c(Nc4ccccc4C(=O)N4CCCC4)n3)cc2)CC1] | 0.061 |

TABLE I-continued

| No. | Structure | IC$_{50}$ (μM) |
|---|---|---|
| 7 | 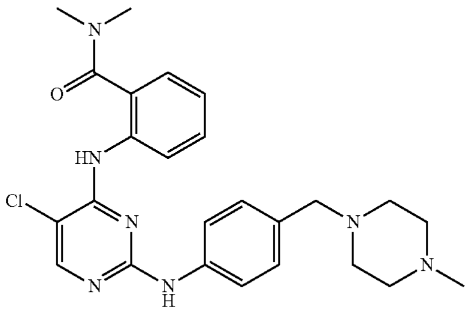 [SMILES: CN1CCN(Cc2ccc(Nc3ncc(Cl)c(Nc4ccccc4C(=O)N(C)C)n3)cc2)CC1] | 0.088 |
| 8 | 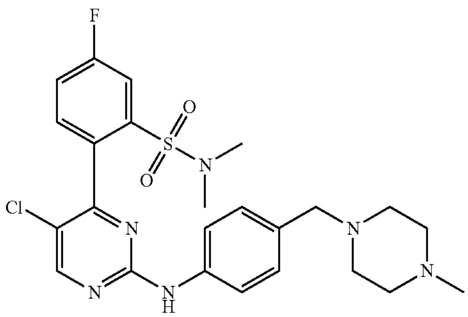 [SMILES: CN1CCN(Cc2ccc(Nc3ncc(Cl)c(-c4ccc(F)cc4S(=O)(=O)N(C)C)n3)cc2)CC1] | 0.099 |
| 9 | 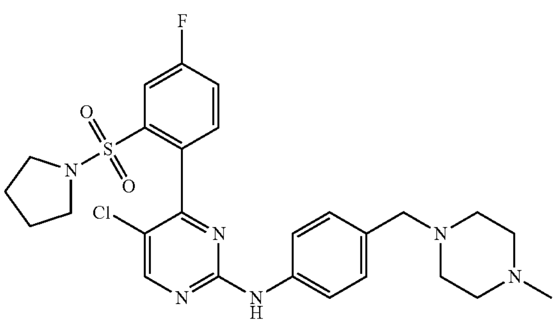 [SMILES: CN1CCN(Cc2ccc(Nc3ncc(Cl)c(-c4ccc(F)cc4S(=O)(=O)N4CCCC4)n3)cc2)CC1] | 0.119 |
| 10 | 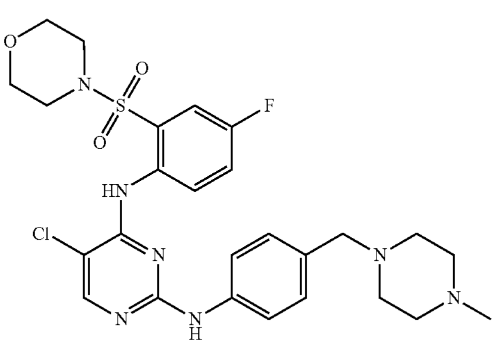 [SMILES: CN1CCN(Cc2ccc(Nc3ncc(Cl)c(Nc4ccc(F)cc4S(=O)(=O)N4CCOCC4)n3)cc2)CC1] | 0.240 |

TABLE I-continued

| No. | Structure | IC$_{50}$ (µM) |
|---|---|---|
| 11 | 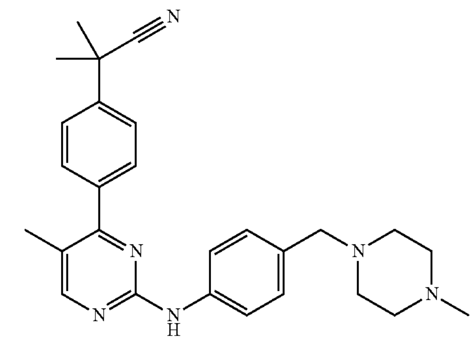 | 0.289 |
| 12 | 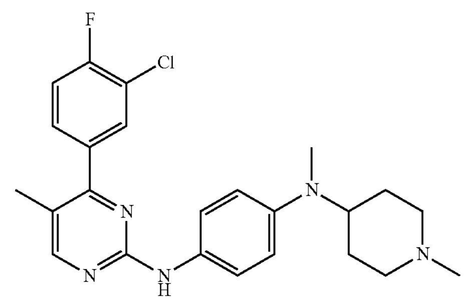 | 0.416 |
| 13 | 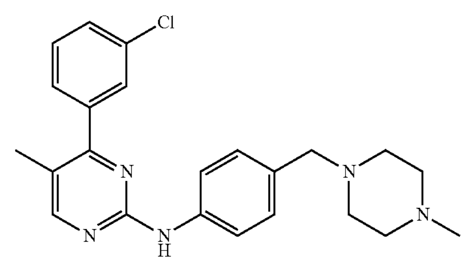 | 0.445 |
| 14 | 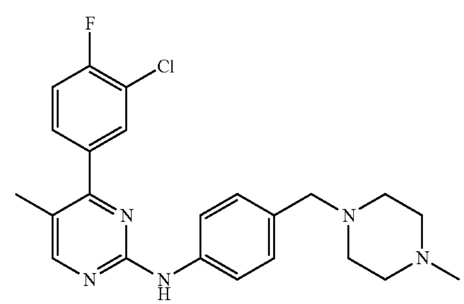 | 0.730 |
| 15 | 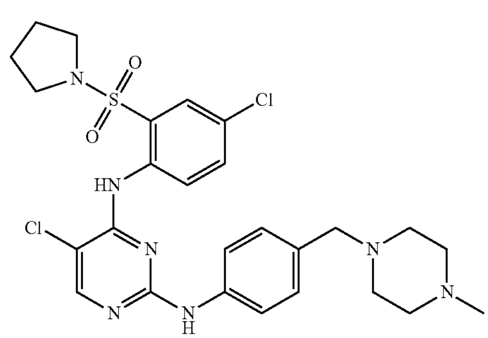 | 1.08 |

TABLE I-continued

| No. | Structure | IC$_{50}$ (μM) |
|---|---|---|
| 16 | 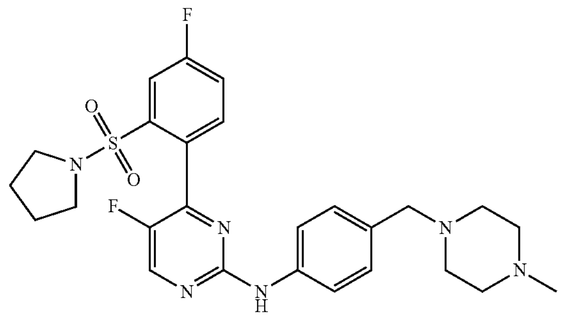 | 1.14 |
| 17 | 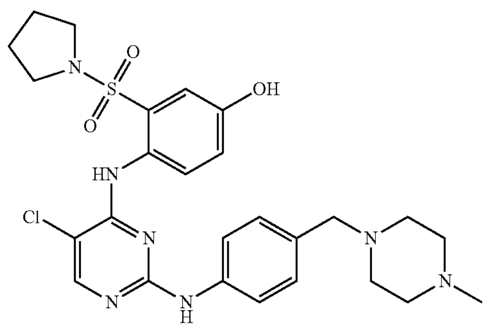 [SMILES: CN1CCN(Cc2ccc(Nc3ncc(Cl)c(Nc4ccc(O)cc4S(=O)(=O)N4CCCC4)n3)cc2)CC1] | 1.31 |
| 18 | 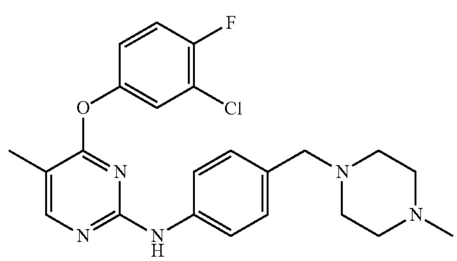 | 1.40 |
| 19 | 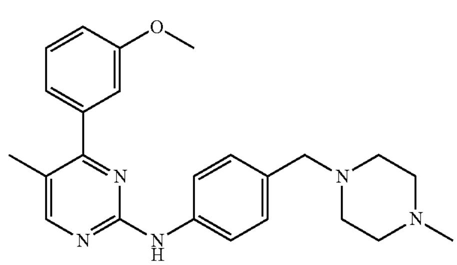 | 1.61 |
| 20 | 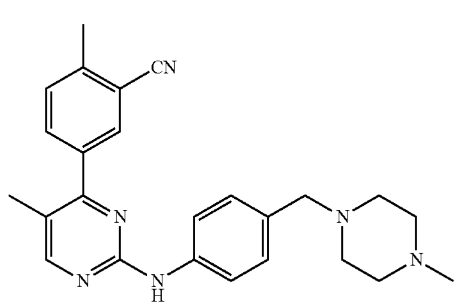 | 1.83 |

TABLE I-continued

| No. | Structure | IC$_{50}$ (μM) |
|---|---|---|
| 21 | 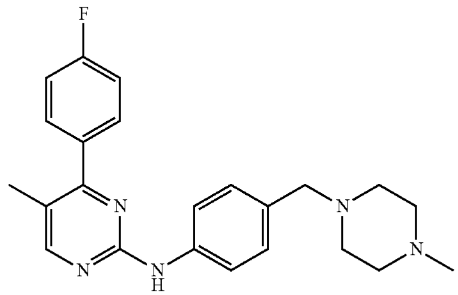 | 1.86 |
| 22 | 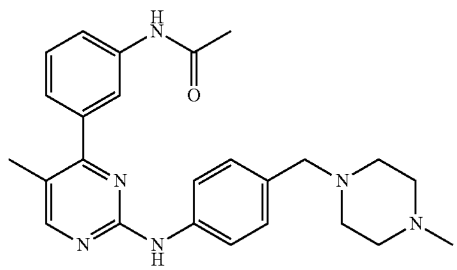 | 2.30 |
| 23 | 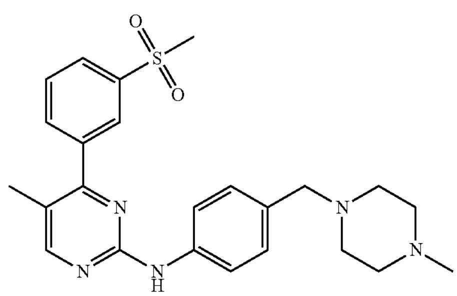 | 2.91 |
| 24 | 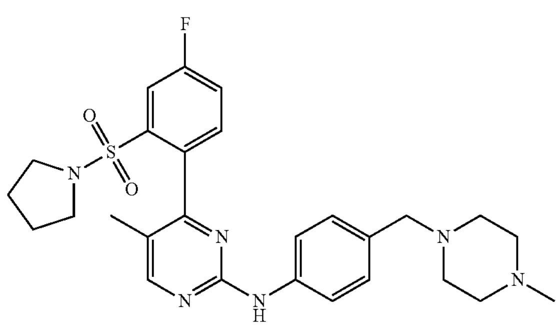 [SMILES: Cc1cnc(Nc2ccc(CN3CCN(C)CC3)cc2)nc1-c1ccc(F)cc1S(=O)(=O)N1CCCC1] | 2.93 |
| 25 | 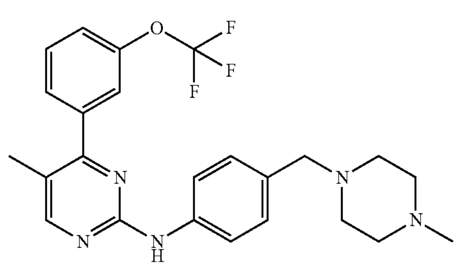 | 3.30 |

TABLE I-continued

| No. | Structure | IC$_{50}$ (μM) |
|---|---|---|
| 26 | 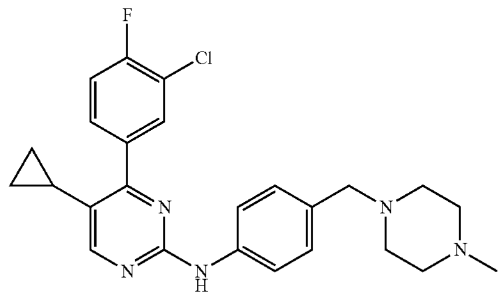 [SMILES: CN1CCN(Cc2ccc(Nc3ncc(C4CC4)c(-c4ccc(F)c(Cl)c4)n3)cc2)CC1] | 3.35 |
| 27 | 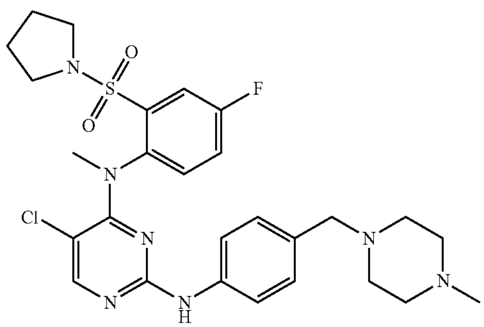 [SMILES: CN1CCN(Cc2ccc(Nc3ncc(Cl)c(N(C)c4ccc(F)cc4S(=O)(=O)N4CCCC4)n3)cc2)CC1] | 3.90 |
| 28 | 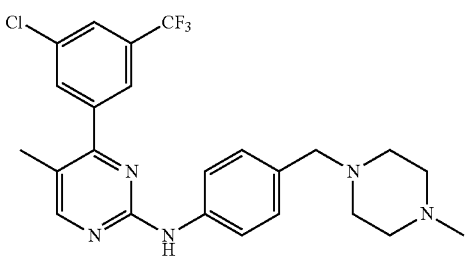 | 5.14 |
| 29 | 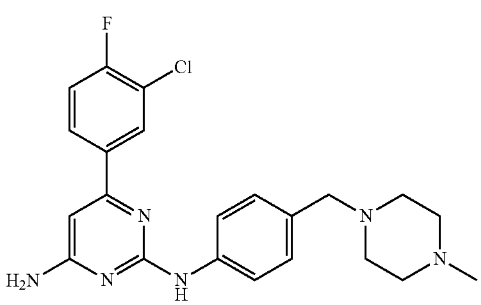 [SMILES: CN1CCN(Cc2ccc(Nc3nc(N)cc(-c4ccc(F)c(Cl)c4)n3)cc2)CC1] | 57.2 |
| 30 | 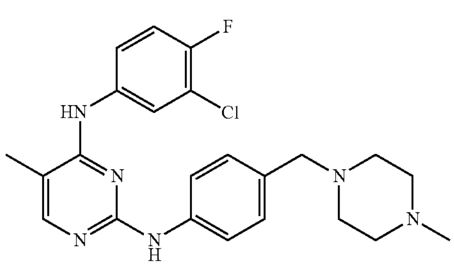 | 62.7 |

TABLE I-continued

| No. | Structure | IC$_{50}$ (μM) |
|---|---|---|
| 31 | 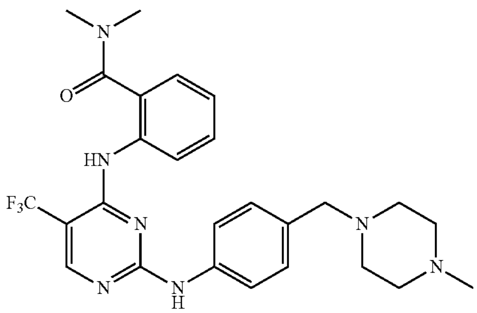 [SMILES: CN1CCN(Cc2ccc(Nc3ncc(C(F)(F)F)c(Nc4ccccc4C(=O)N(C)C)n3)cc2)CC1] | >100 um |

F. Pharmaceutical Compositions

In one aspect, the invention relates to pharmaceutical compositions comprising a pharmaceutically acceptable carrier and an effective amount of a compound represented by a formula:

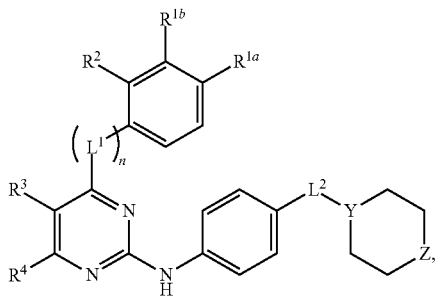

wherein L$^1$ is selected from O and NR$^5$, wherein n is 0 or 1; wherein R$^5$ is selected from is selected from hydrogen and C1-C6 alkyl; wherein L$^2$ is selected from CH$_2$ and NCH$_3$, provided that L$^2$ is CH$_2$ when Y is N; wherein Y is selected from CH or N; wherein Z is selected from O, NR$^6$ and CH$_2$; wherein R$^6$ is selected from hydrogen and CH$_3$; wherein each of R$^{1a}$ and R$^{1b}$ is independently selected from hydrogen, halogen, OH, CN, SO$_2$CH$_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R$^7$; wherein R$^7$ is selected from hydrogen and C1-C6 alkyl; wherein R$^2$ is selected from hydrogen, C1-C6 alkyl, SO$_2$R$^8$, and (C=O)R$^8$; wherein R$^8$ is selected from hydrogen, C1-C6 alkyl, C3-C6 cycloalkyl, C3-C6 heterocycloalkyl, and NR$^{10}$R$^{11}$; wherein R$^{10}$ is selected from hydrogen, C1-C6 alkyl, and C3-C6 cycloalkyl; and wherein R$^{11}$, when present, is selected from hydrogen and C1-C6 alkyl; or R$^{10}$ and R$^{11}$ are covalently bonded and, together with the intermediate nitrogen, comprise an optionally substituted 3-7 membered heterocycloalkyl ring; wherein R$^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein R$^4$ is selected from hydrogen, halogen, Ar$^1$, C1-C6 alkyl, C3-C6 cycloalkyl, and C3-C6 heterocycloalkyl; wherein Ar$^1$ is either phenyl substituted with 0-3 substituents independently selected from cyano, C1-C6 alkyl, C1-C6 haloalkoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino; wherein R$^{12}$ is selected from C1-C6 alkyl and C3-C6 cycloalkyl; or a pharmaceutically acceptable salt, hydrate, solvate, or polymorph thereof.

In various aspects, the invention relates to pharmaceutical compositions comprising a pharmaceutically acceptable carrier and an effective amount of a compound represented by a formula:

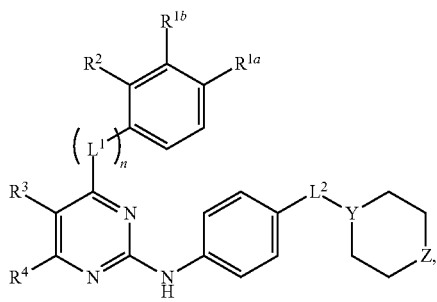

wherein L$^1$ is selected from O and NR$^5$, wherein n is 0 or 1; wherein R$^5$ is selected from is selected from hydrogen and C1-C6 alkyl; wherein L$^2$ is selected from CH$_2$ and NCH$_3$, provided that L$^2$ is CH$_2$ when Y is N; wherein Y is selected from CH or N; wherein Z is selected from O, NR$^6$ and CH$_2$; wherein R$^6$ is selected from hydrogen and CH$_3$; wherein each of R$^{1a}$ and R$^{1b}$ is independently selected from hydrogen, halogen, OH, CN, SO$_2$CH$_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R$^7$; wherein R$^7$ is selected from hydrogen and C1-C6 alkyl; wherein R$^2$ is selected from hydrogen, C1-C6 alkyl, SO$_2$R$^8$, and (C=O)R$^8$; wherein R$^8$ is selected from hydrogen, C1-C6 alkyl, C3-C6 cycloalkyl, C3-C6 heterocycloalkyl, and NR$^{10}$R$^{11}$; wherein R$^{10}$ is selected from hydrogen, C1-C6 alkyl, and C3-C6 cycloalkyl; and wherein R$^{11}$, when present, is selected from hydrogen and C1-C6 alkyl; or R$^{10}$ and R$^{11}$ are covalently bonded and, together with the intermediate nitrogen, comprise an optionally substituted 3-7 membered heterocycloalkyl ring; wherein R$^3$ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof.

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier. In a still further aspect, the effective amount is a therapeutically effective amount. In a yet still further aspect, the effective amount is a prophylactically effective amount.

In a further aspect, the pharmaceutical composition exhibits inhibition of the PI3K/Akt pathway. In a still further aspect, the inhibition of PI3K/Akt pathway is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a still further aspect, the pharmaceutical composition exhibits inhibition of the MAPK pathway. In a still further aspect, the inhibition of MAPK pathway is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the pharmaceutical composition exhibits inhibition of the phosphorylation of Akt. In a still further aspect, the inhibition of Akt phosphorylation is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the pharmaceutical composition exhibits inhibition of a protein kinase. In a still further aspect, the protein kinase is selected from the protein kinase that is inhibited is selected from c-abl oncogene 1 kinase, c-abl oncogene 1 kinase (T315I form), ALK tyrosine kinase receptor, aurora kinase A, AXL receptor tyrosine kinase, cyclin-dependent kinase 1, cyclin-dependent kinase 2, serine/threonine-protein kinase Chk1, macrophage colony-stimulating factor 1 receptor kinase, ephrin type-A receptor 1 kinase, tyrosine-protein kinase Fer, tyrosine-protein kinase Fes/Fps, fibroblast growth factor receptor 1, tyrosine-protein kinase Fgr, insulin-like growth factor 1 receptor, macrophage-stimulating protein receptor kinase, proto-oncogene tyrosine-protein kinase receptor Ret, proto-oncogene tyrosine-protein kinase ROS, proto-oncogene tyrosine-protein kinase Src, proto-oncogene tyrosine-protein kinase Yes, PTK2B protein tyrosine kinase 2 beta, serine/threonine-protein kinase MST4, serine/threonine-protein kinase PAK 4, yyrosine-protein kinase JAK1, tyrosine-protein kinase JAK2, tyrosine-protein kinase JAK3, tyrosine-protein kinase Lck, tyrosine-protein kinase Lyn, tyrosine-protein kinase Mer, tyrosine-protein kinase SYK, vascular endothelial growth factor receptor 2, and vascular endothelial growth factor receptor 3. In a still further aspect, the protein kinase that is inhibited is AXL receptor tyrosine kinase.

In a still further aspect, the inhibition of the protein kinase is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the pharmaceutical composition exhibits inhibition of cell viability. In a still further aspect, inhibition of cell viability is determined in a cell line selected from K562, MCF-7, PL-45, PANC-1, PSN-1, HepG2, and A549 cells. In a yet further aspect, the inhibition of cell viability is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the pharmaceutical composition is administered to a mammal. In a yet further aspect, the mammal is a human. In a still further aspect, the pharmaceutical composition is administered following identification of a mammal in need of treatment of a disorder of uncontrolled cellular proliferation. In a still further aspect, the mammal has been diagnosed with a need for treatment of a disorder of uncontrolled cellular proliferation prior to the administering step.

In a further aspect, the pharmaceutical composition is administered to treat a disorder of uncontrolled cellular proliferation. In a yet further aspect, the disorder of uncontrolled cellular proliferation is associated with a protein kinase dysfunction. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a still further aspect, the cancer is selected from cancers of the brain, genitourinary tract, endocrine system, gastrointestinal tract, colon, rectum, breast, kidney, lymphatic system, stomachydrogen, lung, pancreas, and skin. In a yet further aspect, the cancer is selected from cancers of the pancreas, lung, breast, brain, skin, and blood. In a still further aspect, the cancer is pancreatic cancer.

In a further aspect, the cancer is a cancer of the brain. In a still further aspect, the cancer is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor cell.

In a further aspect, the cancer is a glioma. In a still further aspect, the glioma is glioblastoma multiforme. In a yet further aspect, the glioma is selected from is selected from a ependymoma, astrocytoma, oligodendroglioma, and oligoastrocytoma. In a yet further aspect, the glioma is selected from a juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, paraganglioma, and ganglioglioma cell.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment conditions which require negative allosteric modulation of metabotropic glutamate receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the from of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for modulating glutamate receptor activity (e.g., treatment of one or more neurological and/or psychiatric disorder associated with glutamate dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one product of a disclosed method with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

G. Methods of Using the Compounds and Compositions

The TAM receptor tyrosine kinase subfamily comprises Axl (also known as UFO, ARK, and Tyrol; nucleotide accession numbers NM__021913 and NM__001699; protein accession numbers NP__068713 and NP__001690), Mer (Stk, Nyk) and Tyro3 (Rse/Dtk/Sky). The TAM receptor tyrosine kinase subfamily is characterised by a common protein domain structure comprising a C-terminal extracellular ligand-binding domain and N-terminal cytoplasmic region containing the catalytic domain. The members all possess the combination of two extracellular N-terminal immunoglobulin type domains and two fibronectin III domains, a single span transmembrane region followed by C-terminal kinase domain (e.g. see Hafizi, S., et al., Cytokine Growth Factor Rev., 2006, 17:295-304). All members of this kinase subfamily bind and are stimulated to varying degrees by the same ligand, Gas6 (growth arrest specific-6), an approximately 76 kDa secreted protein with significant homology to the coagulation cascade regulator, Protein S.

Gas6 acts as a ligand to all of the TAM receptor tyrosine kinase subfamily, but exhibits differing affinities for the receptors and activates the three proteins to varying degrees. Gas6 is a member of the vitamin K-dependent family of proteins and shows a 43% sequence identity and the same domain organisation to protein S, a serum protein which has been shown to be a negative regulator of blood coagulation (e.g. see Hafizi, S., et al., FEBS J., 2006, 273: 5231-5244). Gas6 is upregulated in growth arrested cells (e.g. see Manfioletti, G., Mol. Cell. Biol., 1993, 13: 4976-4985) which indicates a function in protection of the cell against cellular stresses. It has since been shown that Gas6 can cross link Axl monomers and promote cellular survival, proliferation and migration (e.g. see Bellosta, P., et al., Oncogene, 1997, 15:2387-2397; Sainaghi, P. P., et al., 2005, J. Cell Physiol., 2005, 204:36-44; Fridell, Y. W., et al., J. Biol. Chem., 1998, 273:7123-7126).

In addition to binding to ligands, the Axl extracellular domain has been shown to undergo homophilic interactions that mediate cell aggregation, suggesting that one important function of Axl may be to mediate cell-cell adhesion. This homophilic binding of the Axl extracellular domain can result in cellular aggregation and this event is independent of the intracellular kinase activity (e.g. see Bellosta, P., et al., Mol. Cell. Biol., 1995, 15:614-625.).

The Axl intracellular kinase domain (ICD) is responsible for the oncogenic transforming ability of Axl RTK. The Gas6/Axl signal trangduction pathway operates, although not exclusively, through activation of the phosphatidylinositol 3-kinase (PI3K) pathway (e.g. see Shankar, S. L., et al., J. Neurosci., 2006, 26:5638-5648.). The PI3K/Akt signaling network is crucial to widely divergent physiological processes that include cell cycle progression, differentiation, transcription, translation and apoptosis (e.g. see Hanada, M., Biochim. Biophys. Acta, 2004, 1697:3-16.). Activation of PI3K/Akt signaling results in disturbance of control of cell proliferation and apoptosis, ensuing in competitive growth advantage for tumor cells. Activation of Akt is associated with phosphorylation of Ser 473 (e.g. see Alessi, D. R., EMBO J., 1996, 15:6541-6551) and monitoring changes in levels of total and phosphorylated Akt within the cell enables an assessment of the efficacy of drugs which act upstream of Akt. The intracellular domain of Axl kinase has been shown to associate with many proteins, e.g. p55gamma, p85alpha and beta subunits of PI3K, phospholipaseC-gamma, Grb2, c-Src, Lck, SOCS-1, Nck2, RanBMP, C1-TEN and Axl ICD itself (Hafizi, S., et al., Cytokine Growth Factor Rev., 2006, 17:295-304; Hafizi, S., et al., Biochem. Biophys. Res. Commun., 2002. 299:793-800; Braunger, J., et al., Oncogene, 1997, 14:2619-2631).

Axl is predominantly expressed in the vasculature in both endothelial cells (ECs) and vascular smooth muscle cells (VSMCs) and in cells of the myeloid lineage and is also detected in breast epithelial cells, chondrocytes, Sertoli cells and neurons. Axl is ubiquitously expressed at low levels and is detectable in a variety of organs (e.g. see Rescigno, J., et al., Oncogene, 1991, 6:1909-1913). Expression patterns of the other two family members (Mer and Tyro3) differ from that of Axl. Expression of Tyro3 is predominantly in the brain and the CNS (e.g. see Mark, M. R., et al., J. Biol. Chem., 1994, 269:10720-10728), and expression of Mer is almost exclusively in the monocyte cell lineage (Graham, D. K., et al., Cell Growth Differ., 1994, 5: 647-657). Several functions are attributed to Axl signaling in cell culture, including, but not limited to, protection from apoptosis induced by serum starvation, TNF-α or the viral protein E1A, as well as migration and cell differentiation. However, Axl-/- mice exhibit no overt developmental phenotype and the physiological function of Axl in vivo is not clearly established in the literature.

The overexpression of Axl and/or its ligand has also been reported in a wide variety of solid tumor types including, but not limited to, breast, renal, endometrial, ovarian, thyroid, non-small cell lung carcinoma, and uveal melanoma as well as in myeloid leukemias. Furthermore, it possesses transforming activity in NIH3T3 and 32D cells. It has been demonstrated that loss of Axl expression in tumor cells blocks the growth of solid human neoplasms in an in vivo MDA-MB-231 breast carcinoma xenograft model. Overexpression of Axl has been demonstrated in numerous cancer cell lines, e.g., colon, gastric, breast, lung, AML, thyroid, ocular, prostate, ocular melanoma, ovarian, renal, and SCC (e.g. see Sainaghi, P. P., et al., J. Cell Physiol., 2005, 204:36-44; Sawaby, T., et al., Mol. Carcinog., 2007, 46:155-164; Vajkoczy, P., et al., Proc. Nat. Acad. Sci. USA, 2006, 103: 5799-5804; Shieh, Y. S., et al., Neoplasia, 2005, 7:1058-1064). This expression has been linked to the development of an oncogenic cellular phenotype (e.g. see Shieh, Y. S., et al., Neoplasia, 2005, 7:1058-1064). Overexpression of Axl has been linked to stage of disease and prognosis (Sawaby, T., et al., Mol. Carcinog., 2007, 46:155-164; Vajkoczy, P., et al., Proc. Nat. Acad. Sci. USA, 2006, 103:5799-5804; Shieh, Y. S., et al., Neoplasia, 2005, 7:1058-1064; Sun, W. S., et al., Mol. Hum. Reprod., 2003, 9:701-707; Green, J., Br. J. Cancer, 2006, 94:1446-1451). Taken together, these data suggest Axl signaling can independently regulate angiogenesis and tumor growth and thus represents a novel target class for tumor therapeutic development Angiogenesis (the formation of new blood vessels) is limited to functions such as wound healing and the female reproductive cycle in healthy adults. This physiological process has been co-opted by tumors, thus securing an adequate blood supply that feeds tumor growth and facilitates metastasis. Deregulated angiogenesis is also a feature of many other diseases (for example, psoriasis, rheumatoid arthritis, endometriosis and blindness due to age-related macular degeneration (AMD), retinopathy of prematurity and diabetes) and often contributes to the progression or pathology of the condition.

The expression of Axl and Gas6 proteins is upregulated in a variety of other disease states including endometriosis, vascular injury and kidney disease and Axl signaling is functionally implicated in the latter two indications. Axl-Gas6 signaling amplifies platelet responses and is implicated in thrombus formation.

The disclosed compounds can be used as single agents or in combination with one or more other drugs in the treatment, prevention, control, amelioration or reduction of risk of the aforementioned diseases, disorders and conditions for which compounds of formula I or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders of uncontrolled cellular proliferation. In one aspect, the disorder of uncontrolled cellular proliferation is associated with a dysfunction in the PI3K/Akt signaling pathway. In a further aspect, the disorder of uncontrolled cellular proliferation is associated with a protein kinase dysfunction. In a further aspect, the protein kinase dysfunction is disregulation of Axl.

Examples of disorders associated with a dysfunction in the PI3K/Akt pathway include cancers such as leukemias, lymphomas, and solid tumors. In one aspect, the cancer can be a cancer selected from cancers of the brain, genitourinary tract, gastrointestinal tract, colon, rectum, breast, kidney, lymphatic system, stomach, lung, pancreas, and skin. In a further aspect, the cancer is selected from. prostate cancer, glioblastoma multiforme, endometrial cancer, breast cancer, and colon cancer.

In one aspect, the compounds disclosed herein are useful for treating disorders including solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis and cataracts.

In one aspect, the compounds and compositions of the invention have utility in a broad range of diseases and conditions mediated by protein kinases, including diseases and conditions mediated by Axl kinase. Such diseases may include by way of example and not limitation, cancers such as lung cancer, NSCLC (non small cell lung cancer), oat-cell cancer, bone cancer, pancreatic cancer, skin cancer, dermatofibrosarcoma protuberans, cancer of the head and neck, cutaneous or intraocular melanoma, uterine cancer, ovarian cancer, colo-rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, hepatocellular cancer, cancer of the esophagus, cancer of the small intestine, cancer of the endocrine system (e.g., cancer of the thyroid, pancreas, parathyroid or adrenal glands), sarcomas of soft tissues, cancer of the urethra, cancer of the penis, prostate cancer (particularly hormone-refractory), chronic or acute leukemia, solid tumors of childhood, hypereosinophilia, lymphocytic lymphomas, cancer of the bladder, cancer of the kidney or ureter (e.g., renal cell carcinoma, carcinoma of the renal pelvis), pediatric malignancy, neoplasms of the central nervous system (e.g., primary CNS lymphoma, spinal axis tumors, medulloblastoma, brain stem gliomas or pituitary adenomas), Barrett's esophagus (pre-malignant syndrome), neoplastic cutaneous disease, psoriasis, mycoses fungoides, and benign prostatic hypertrophy, diabetes related diseases such as diabetic retinopathy, retinal ischemia, and retinal neovascularization, hepatic cirrhosis, angiogenesis, cardiovascular disease such as atherosclerosis, immunological disease such as autoimmune disease and renal disease.

In a further aspect, the compounds disclosed herein are useful in treating, inhibiting, and/or preventing diseases that are characterized by caused by and/or associated with apoptosis induced by serum starvation, TNF-α or the viral protein E1A, as well as migration and cell differentiation. Such diseases include, by way of example and not limitation, solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis and cataracts.

a. Treatment of a Disorder of Uncontrolled Cellular Proliferation

In one aspect, the invention relates to a method for the treatment of a disorder of uncontrolled cellular proliferation disorder in a mammal, the method comprising the step of administering to the mammal an effective amount of least one compound having a structure represented by a formula:

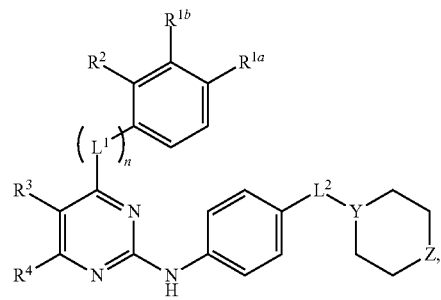

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof.

In various aspects, the invention relates to a method for the treatment of a disorder of uncontrolled cellular proliferation disorder in a mammal, the method comprising the step of administering to the mammal an effective amount of least one compound having a structure represented by a formula:

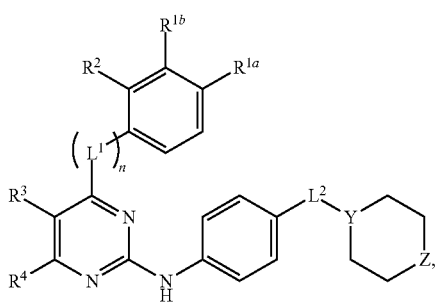

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof.

In a further aspect, the compound administered is a disclosed compound or a product of a disclosed method of making a compound. In a still further aspect, the effective amount is a therapeutically effective amount. In a yet still further aspect, the effective amount is a prophylactically effective amount.

In a further aspect, the compound administered exhibits inhibition of the PI3K/Akt pathway. In a still further aspect, the inhibition of PI3K/Akt pathway is with an $IC_{50}$ of less than about $1.0\times10^{-4}$ M, an $IC_{50}$ of less than about $1.0\times10^{-5}$ M, an $IC_{50}$ of less than about $1.0\times10^{-6}$ M, an $IC_{50}$ of less than about $1.0\times10^{-7}$ M, an $IC_{50}$ of less than about $1.0\times10^{-8}$ M, or an $IC_{50}$ of less than about $1.0\times10^{-9}$ M.

In a still further aspect, the compound administered exhibits inhibition of the MAPK pathway. In a still further aspect, the inhibition of MAPK pathway is with an $IC_{50}$ of less than about $1.0\times10^{-4}$ M, an $IC_{50}$ of less than about $1.0\times10^{-5}$ M, an $IC_{50}$ of less than about $1.0\times10^{-6}$ M, an $IC_{50}$ of less than about $1.0\times10^{-7}$ M, an $IC_{50}$ of less than about $1.0\times10^{-8}$ M, or an $IC_{50}$ of less than about $1.0\times10^{-9}$ M.

In a further aspect, the compound administered exhibits inhibition of the phosphorylation of Akt. In a still further aspect, the inhibition of Akt phosphorylation is with an $IC_{50}$ of less than about $1.0\times10^{-4}$ M, an $IC_{50}$ of less than about $1.0\times10^{-5}$ M, an $IC_{50}$ of less than about $1.0\times10^{-6}$ M, an $IC_{50}$ of less than about $1.0\times10^{-7}$ M, an $IC_{50}$ of less than about $1.0\times10^{-8}$ M, or an $IC_{50}$ of less than about $1.0\times10^{-9}$ M.

In a further aspect, the compound administered exhibits inhibition of a protein kinase. In a yet further aspect, the protein kinase that is inhibited is selected from c-abl oncogene 1 kinase, c-abl oncogene 1 kinase (T315I form), ALK tyrosine kinase receptor, aurora kinase A, AXL receptor tyrosine kinase, cyclin-dependent kinase 1, cyclin-dependent kinase 2, serine/threonine-protein kinase Chk1, macrophage colony-stimulating factor 1 receptor kinase, ephrin type-A receptor 1 kinase, tyrosine-protein kinase Fer, tyrosine-protein kinase Fes/Fps, fibroblast growth factor receptor 1, tyrosine-protein kinase Fgr, insulin-like growth factor 1 receptor, macrophage-stimulating protein receptor kinase, proto-oncogene tyrosine-protein kinase receptor Ret, proto-oncogene tyrosine-protein kinase ROS, proto-oncogene tyrosine-protein kinase Src, proto-oncogene tyrosine-protein kinase Yes, PTK2B protein tyrosine kinase 2 beta, serine/threonine-protein kinase MST4, serine/threonine-protein kinase PAK 4, yyrosine-protein kinase JAK1, tyrosine-protein kinase JAK2, tyrosine-protein kinase JAK3, tyrosine-protein kinase Lck, tyrosine-protein kinase Lyn, tyrosine-protein kinase Mer, tyrosine-protein kinase SYK, vascular endothelial growth factor receptor 2, and vascular endothelial growth factor receptor 3. In a still further aspect, the protein kinase that is inhibited is AXL receptor tyrosine kinase.

In a further aspect, the inhibition of the protein kinase is with an $IC_{50}$ of less than about $1.0\times10^{-4}$ M, an $IC_{50}$ of less than about $1.0\times10^{-5}$ M, an $IC_{50}$ of less than about $1.0\times10^{-6}$ M, an $IC_{50}$ of less than about $1.0\times10^{-7}$ M, an $IC_{50}$ of less than about $1.0\times10^{-8}$ M, or an $IC_{50}$ of less than about $1.0\times10^{-9}$ M.

In a further aspect, the compound administered exhibits inhibition of cell viability. In a still further aspect, inhibition of cell viability is determined in a cell line selected from K562, MCF-7, PL-45, PANC-1, PSN-1, HepG2, and A549 cells. In a yet further aspect, the inhibition of cell viability is with an $IC_{50}$ of less than about $1.0\times10^{-4}$ M, an $IC_{50}$ of less than about $1.0\times10^{-5}$ M, an $IC_{50}$ of less than about $1.0\times10^{-6}$ M, an $IC_{50}$ of less than about $1.0\times10^{-7}$ M, an $IC_{50}$ of less than about $1.0\times10^{-8}$ M, or an $IC_{50}$ of less than about $1.0\times10^{-9}$ M.

In a further aspect, the mammal is human. In a yet further aspect, the method further comprises the step of identifying a mammal in need of treatment of a disorder of uncontrolled cellular proliferation. In a still further aspect, the mammal has been diagnosed with a need for treatment of a disorder of uncontrolled cellular proliferation prior to the administering step.

In a further aspect, the disorder of uncontrolled cellular proliferation is associated with a protein kinase dysfunction. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a further aspect, the cancer is selected from is selected from cancers of the brain, genitourinary tract, endocrine system, gastrointestinal tract, colon, rectum, breast, kidney, lymphatic system, stomachydrogen, lung, pancreas, and skin. In a yet further aspect, the cancer is selected from cancers of the pancreas, lung, breast, brain, skin, and blood. In a still further aspect, the cancer is pancreatic cancer.

In a further aspect, the cancer is a cancer of the brain. In a still further aspect, the cancer is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor cell.

In a further aspect, the cancer is a glioma. In a still further aspect, the glioma is glioblastoma multiforme. In a yet further aspect, the glioma is selected from is selected from a ependymoma, astrocytoma, oligodendroglioma, and oligoastrocytoma. In a yet further aspect, the glioma is selected from a juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, paraganglioma, and ganglioglioma cell.

b. Decreasing Kinase Activity

In one aspect, the invention relates to a method for decreasing kinase activity in a mammal, the method comprising the step of administering to the mammal a therapeutically effective amount of at least one compound having a structure represented by a formula:

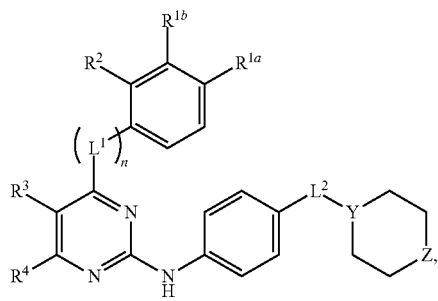

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof.

In various aspects, the invention relates to a method for decreasing kinase activity in a mammal, the method comprising the step of administering to the mammal a therapeutically effective amount of at least one compound having a structure represented by a formula:

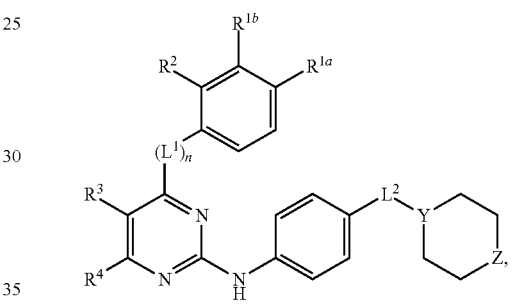

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof.

In a further aspect, the compound administered is a disclosed compound or a product of a disclosed method of making a compound. In a still further aspect, the effective amount is a therapeutically effective amount. In a yet still further aspect, the effective amount is a prophylactically effective amount.

In a further aspect, the decreasing kinase activity is inhibition of the PI3K/Akt pathway. In a still further aspect, the inhibition of PI3K/Akt pathway is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a still further aspect, the decreasing kinase activity is inhibition of the MAPK pathway. In a still further aspect, the inhibition of MAPK pathway is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the decreasing kinase activity is inhibition of the phosphorylation of Akt. In a still further aspect, the inhibition of Akt phosphorylation is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the decreasing kinase activity is inhibition of a protein kinase selected from selected from c-abl oncogene 1 kinase, c-abl oncogene 1 kinase (T315I form), ALK tyrosine kinase receptor, aurora kinase A, AXL receptor tyrosine kinase, cyclin-dependent kinase 1, cyclin-dependent kinase 2, serine/threonine-protein kinase Chk1, macrophage colony-stimulating factor 1 receptor kinase, ephrin type-A receptor 1 kinase, tyrosine-protein kinase Fer, tyrosine-protein kinase Fes/Fps, fibroblast growth factor receptor 1, tyrosine-protein kinase Fgr, insulin-like growth factor 1 receptor, macrophage-stimulating protein receptor kinase, proto-oncogene tyrosine-protein kinase receptor Ret, proto-oncogene tyrosine-protein kinase ROS, proto-oncogene tyrosine-protein kinase Src, proto-oncogene tyrosine-protein kinase Yes, PTK2B protein tyrosine kinase 2 beta, serine/threonine-protein kinase MST4, serine/threonine-protein kinase PAK 4, yyrosine-protein kinase JAK1, tyrosine-protein kinase JAK2, tyrosine-protein kinase JAK3, tyrosine-protein kinase Lck, tyrosine-protein kinase Lyn, tyrosine-protein kinase Mer, tyrosine-protein kinase SYK, vascular endothelial growth factor receptor 2, and vascular endothelial growth factor receptor 3. In a still further aspect, the protein kinase that is inhibited is AXL receptor tyrosine kinase.

In a still further aspect, the inhibition of the protein kinase is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the decreasing kinase activity inhibits cell viability In a still further aspect, inhibition of cell viability is determined in a cell line selected from K562, MCF-7, PL-45, PANC-1, PSN-1, HepG2, and A549 cells. In a yet further aspect, the inhibition of cell viability is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the mammal is a human. In a yet further aspect, the method further comprises the step of identifying a mammal in need of decreasing kinase activity. In a still further aspect, the mammal has been diagnosed with a need for decreasing kinase activity prior to the administering step.

In a further aspect, the need for decreasing kinase activity is associated with treatment of a disorder of uncontrolled cellular proliferation. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a still further aspect, the cancer is selected from is selected from cancers of the brain, genitourinary tract, endocrine system, gastrointestinal tract, colon, rectum, breast, kidney, lymphatic system, stomachydrogen, lung, pancreas, and skin. In a yet further aspect, the cancer is selected from cancers of the pancreas, lung, breast, brain, skin, and blood. In a still further aspect, the cancer is pancreatic cancer.

In a further aspect, the cancer is a cancer of the brain. In a still further aspect, the cancer is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor cell.

In a further aspect, the cancer is a glioma. In a still further aspect, the glioma is glioblastoma multiforme. In a yet further aspect, the glioma is selected from is selected from a ependymoma, astrocytoma, oligodendroglioma, and oligoastrocytoma. In a yet further aspect, the glioma is selected from a juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, paraganglioma, and ganglioglioma cell.

c. Decreasing Kinase Activity in Cells

In one aspect, the invention relates to a method for decreasing kinase activity in at least one cell, the method comprising the step of contacting the at least one cell with an effective amount of least one compound having a structure represented by a formula:

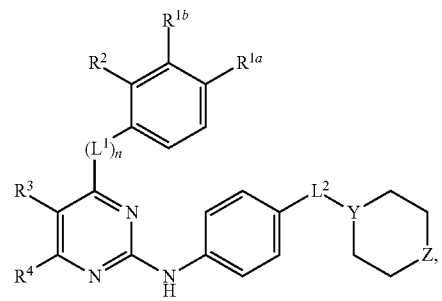

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, NR$^6$ and CH$_2$; wherein R$^6$ is selected from hydrogen and CH$_3$; wherein each of R$^{1a}$ and R$^{1b}$ is independently selected from hydrogen, halogen, OH, CN, SO$_2$CH$_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R$^7$; wherein R$^7$ is selected from hydrogen and C1-C6 alkyl; wherein R$^2$ is selected from hydrogen, C1-C6 alkyl, SO$_2$R$^8$, and (C=O)R$^8$; wherein R$^8$ is selected from hydrogen, C1-C6 alkyl, C3-C6 cycloalkyl, C3-C6 heterocycloalkyl, and NR$^{10}$R$^{11}$; wherein R$^{10}$ is selected from hydrogen, C1-C6 alkyl, and C3-C$_6$ cycloalkyl; and wherein R$^{11}$, when present, is selected from hydrogen and C1-C6 alkyl; or R$^{10}$ and R$^{11}$ are covalently bonded and, together with the intermediate nitrogen, comprise an optionally substituted 3-7 membered heterocycloalkyl ring; wherein R$^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein R$^4$ is selected from hydrogen, halogen, Ar$^1$, C1-C6 alkyl, C3-C6 cycloalkyl, and C3-C6 heterocycloalkyl; wherein Ar$^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino; wherein R$^{12}$ is selected from C1-C6 alkyl and C3-C6 cycloalkyl; or a pharmaceutically acceptable salt, hydrate, solvate, or polymorph thereof.

In various aspects, the invention relates to a method for decreasing kinase activity in at least one cell, the method comprising the step of contacting the at least one cell with an effective amount of least one compound having a structure represented by a formula:

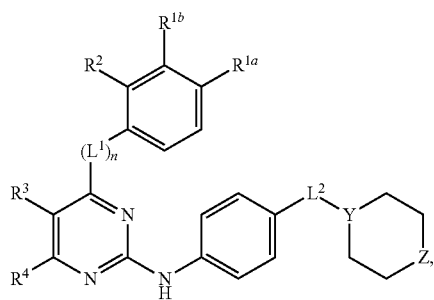

wherein L$^1$ is selected from O and NR$^5$, wherein n is 0 or 1; wherein R$^5$ is selected from is selected from hydrogen and C1-C6 alkyl; wherein L$^2$ is selected from CH$_2$ and NCH$_3$, provided that L$^2$ is CH$_2$ when Y is N; wherein Y is selected from CH or N; wherein Z is selected from O, NR$^6$ and CH$_2$; wherein R$^6$ is selected from hydrogen and CH$_3$; wherein each of R$^{1a}$ and R$^{1b}$ is independently selected from hydrogen, halogen, OH, CN, SO$_2$CH$_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R$^7$; wherein R$^7$ is selected from hydrogen and C1-C6 alkyl; wherein R$^2$ is selected from hydrogen, C1-C6 alkyl, SO$_2$R$^8$, and (C=O)R$^8$; wherein R$^8$ is selected from hydrogen, C1-C6 alkyl, C3-C6 cycloalkyl, C3-C6 heterocycloalkyl, and NR$^{10}$R$^{11}$; wherein R$^{10}$ is selected from hydrogen, C1-C6 alkyl, and C3-C6 cycloalkyl; and wherein R$^{11}$, when present, is selected from hydrogen and C1-C6 alkyl; or R$^{10}$ and R$^{11}$ are covalently bonded and, together with the intermediate nitrogen, comprise an optionally substituted 3-7 membered heterocycloalkyl ring; wherein R$^3$ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein R$^4$ is selected from hydrogen, halogen, Ar$^1$, C1-C6 alkyl, C3-C6 cycloalkyl, and C3-C6 heterocycloalkyl; wherein Ar$^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino; wherein R$^{12}$ is selected from C1-C6 alkyl and C3-C6 cycloalkyl; or a pharmaceutically acceptable salt, hydrate, solvate, or polymorph thereof.

In a further aspect, the compound is a disclosed compound or a product of a disclosed method of making a compound. In a still further aspect, the effective amount is a therapeutically effective amount. In a yet still further aspect, the effective amount is a prophylactically effective amount.

In a further aspect, the decreasing kinase activity is inhibition of the PI3K/Akt pathway. In a still further aspect, the inhibition of PI3K/Akt pathway is with an IC$_{50}$ of less than about $1.0\times10^{-4}$ M, an IC$_{50}$ of less than about $1.0\times10^{-5}$ M, an IC$_{50}$ of less than about $1.0\times10^{-6}$ M, an IC$_{50}$ of less than about $1.0\times10^{-7}$ M, an IC$_{50}$ of less than about $1.0\times10^{-8}$ M, or an IC$_{50}$ of less than about $1.0\times10^{-9}$ M.

In a still further aspect, the decreasing kinase activity is inhibition of the MAPK pathway. In a still further aspect, the inhibition of MAPK pathway is with an IC$_{50}$ of less than about $1.0\times10^{-4}$ M, an IC$_{50}$ of less than about $1.0\times10^{-5}$ M, an IC$_{50}$ of less than about $1.0\times10^{-6}$ M, an IC$_{50}$ of less than about $1.0\times10^{-7}$ M, an IC$_{50}$ of less than about $1.0\times10^{-8}$ M, or an IC$_{50}$ of less than about $1.0\times10^{-9}$ M.

In a further aspect, the decreasing kinase activity is inhibition of the phosphorylation of Akt. In a still further aspect, the inhibition of Akt phosphorylation is with an IC$_{50}$ of less than about $1.0\times10^{-4}$ M, an IC$_{50}$ of less than about $1.0\times10^{-5}$ M, an IC$_{50}$ of less than about $1.0\times10^{-6}$ M, an IC$_{50}$ of less than about $1.0\times10^{-7}$ M, an IC$_{50}$ of less than about $1.0\times10^{-8}$ M, or an IC$_{50}$ of less than about $1.0\times10^{-9}$ M.

In a further aspect, the decreasing kinase activity is inhibition of a protein kinase is selected from c-abl oncogene 1 kinase, c-abl oncogene 1 kinase (T315I form), ALK tyrosine kinase receptor, aurora kinase A, AXL receptor tyrosine kinase, cyclin-dependent kinase 1, cyclin-dependent kinase 2, serine/threonine-protein kinase Chk1, macrophage colony-stimulating factor 1 receptor kinase, ephrin type-A receptor 1 kinase, tyrosine-protein kinase Fer, tyrosine-protein kinase Fes/Fps, fibroblast growth factor receptor 1, tyrosine-protein kinase Fgr, insulin-like growth factor 1 receptor, macrophage-stimulating protein receptor kinase, proto-oncogene tyrosine-protein kinase receptor Ret, proto-oncogene tyrosine-protein kinase ROS, proto-oncogene tyrosine-protein kinase Src, proto-oncogene tyrosine-protein kinase Yes, PTK2B protein tyrosine kinase 2 beta, serine/threonine-protein kinase MST4, serine/threonine-protein kinase PAK 4, yyrosine-protein kinase JAK1, tyrosine-protein kinase JAK2, tyrosine-protein kinase JAK3, tyrosine-protein kinase Lck, tyrosine-protein kinase Lyn, tyrosine-protein kinase Mer, tyrosine-protein kinase SYK, vascular endothelial growth factor receptor 2, and vascular endothelial growth factor receptor 3. In a still further aspect, the protein kinase that is inhibited is AXL receptor tyrosine kinase.

In a further aspect, the inhibition of the protein kinase is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the decreasing kinase activity inhibits cell viability. In a still further aspect, inhibition of cell viability is determined in a cell line selected from K562, MCF-7, PL-45, PANC-1, PSN-1, HepG2, and A549 cells. In a yet further aspect, the inhibition of cell viability is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the cell is mammalian. In a still further aspect, the cell is human. In a yet further aspect, contacting is via administration to a mammal. In an even further aspect, contacting is via administration to a human.

In a further aspect, the method further comprises the step of identifying a mammal in need of decreasing kinase activity in a cell. In a still further aspect, the mammal has been diagnosed with a need for decreasing kinase activity prior to the administering step.

In a further aspect, the need for decreasing kinase activity in a cell is associated with a disorder of uncontrolled cellular. In a still further aspect, the disorder of uncontrolled cellular proliferation is a cancer. In a yet further aspect, the cancer is a leukemia. In an even further aspect, the cancer is a lymphoma. In a still further aspect, the cancer is a solid tumor. In a further aspect, the cancer is selected from is selected from cancers of the brain, genitourinary tract, endocrine system, gastrointestinal tract, colon, rectum, breast, kidney, lymphatic system, stomachydrogen, lung, pancreas, and skin. In a yet further aspect, the cancer is selected from cancers of the pancreas, lung, breast, brain, skin, and blood. In a still further aspect, the cancer is pancreatic cancer.

In a further aspect, the cancer is a cancer of the brain. In a still further aspect, the cancer is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor cell.

In a further aspect, the cancer is a glioma. In a still further aspect, the glioma is glioblastoma multiforme. In a yet further aspect, the glioma is selected from is selected from a ependymoma, astrocytoma, oligodendroglioma, and oligoastrocytoma. In a yet further aspect, the glioma is selected from a juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, paraganglioma, and ganglioglioma cell.

2. Manufacture of a Medicament

In one aspect, the invention relates to a method for the manufacture of a medicament for inhibition of the PI3K/Akt pathway in a mammal comprising combining a therapeutically effective amount of a disclosed compound or product of a disclosed method with a pharmaceutically acceptable carrier or diluent.

In a further aspect, the invention relates to a method for the manufacture of a medicament for inhibition of Axl in a mammal comprising combining a therapeutically effective amount of a disclosed compound or product of a disclosed method with a pharmaceutically acceptable carrier or diluent.

3. Use of Compounds

In one aspect, the invention relates to a use of a compound for decreasing kinase activity in a mammal, the compound having a structure represented by a formula:

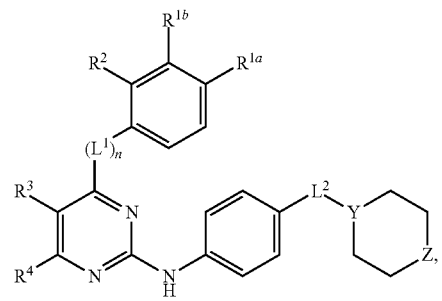

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein R$^{12}$ is selected from C1-C6 alkyl and C3-C6 cycloalkyl; or a pharmaceutically acceptable salt, hydrate, solvate, or polymorph thereof.

In various aspects, the invention relates to a use of a compound for decreasing kinase activity in a mammal, the compound having a structure represented by a formula:

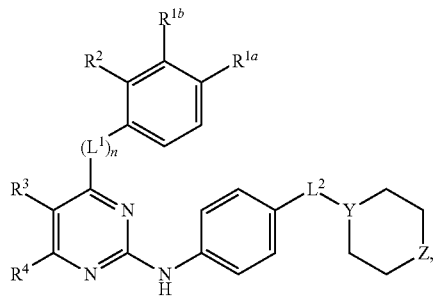

wherein L$^1$ is selected from O and NR$^5$, wherein n is 0 or 1; wherein R$^5$ is selected from is selected from hydrogen and C1-C6 alkyl; wherein L$^2$ is selected from CH$_2$ and NCH$_3$, provided that L$^2$ is CH$_2$ when Y is N; wherein Y is selected from CH or N; wherein Z is selected from O, NR$^6$ and CH$_2$; wherein R$^6$ is selected from hydrogen and CH$_3$; wherein each of R$^{1a}$ and R$^{1b}$ is independently selected from hydrogen, halogen, OH, CN, SO$_2$CH$_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)R$^7$; wherein R$^7$ is selected from hydrogen and C1-C6 alkyl; wherein R$^2$ is selected from hydrogen, C1-C6 alkyl, SO$_2$R$^8$, and (C=O)R$^8$; wherein R$^8$ is selected from hydrogen, C1-C6 alkyl, C3-C6 cycloalkyl, C3-C6 heterocycloalkyl, and NR$^{10}$R$^{11}$; wherein R$^{10}$ is selected from hydrogen, C1-C6 alkyl, and C3-C6 cycloalkyl; and wherein R$^{11}$, when present, is selected from hydrogen and C1-C6 alkyl; or R$^{10}$ and R$^{11}$ are covalently bonded and, together with the intermediate nitrogen, comprise an optionally substituted 3-7 membered heterocycloalkyl ring; wherein R$^3$ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein R$^4$ is selected from hydrogen, halogen, Ar$^1$, C1-C6 alkyl, C3-C6 cycloalkyl, and C3-C6 heterocycloalkyl; wherein Ar$^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, SO$_2$R$^{12}$, C1-C3 alkyl, C1-C3 alkylamine, and C1-C3 dialkylamino; wherein R$^{12}$ is selected from C1-C6 alkyl and C3-C6 cycloalkyl; or a pharmaceutically acceptable salt, hydrate, solvate, or polymorph thereof.

In a further aspect, the compound is a disclosed compound or a product of a disclosed method of making a compound.

In a further aspect, decreasing kinase activity is inhibition of the PI3K/Akt pathway. In a still further aspect, the inhibition of PI3K/Akt pathway is with an IC$_{50}$ of less than about $1.0 \times 10^{-4}$ M, an IC$_{50}$ of less than about $1.0 \times 10^{-5}$ M, an IC$_{50}$ of less than about $1.0 \times 10^{-6}$ M, an IC$_{50}$ of less than about $1.0 \times 10^{-7}$ M, an IC$_{50}$ of less than about $1.0 \times 10^{-8}$ M, or an IC$_{50}$ of less than about $1.0 \times 10^{-9}$ M.

In a still further aspect, the decreasing kinase activity is inhibition of the MAPK pathway. In a still further aspect, the inhibition of MAPK pathway is with an IC$_{50}$ of less than about $1.0 \times 10^{-4}$ M, an IC$_{50}$ of less than about $1.0 \times 10^{-5}$ M, an IC$_{50}$ of less than about $1.0 \times 10^{-6}$ M, an IC$_{50}$ of less than about $1.0 \times 10^{-7}$ M, an IC$_{50}$ of less than about $1.0 \times 10^{-8}$ M, or an IC$_{50}$ of less than about $1.0 \times 10^{-9}$ M.

In a further aspect, the decreasing kinase activity is inhibition of the phosphorylation of Akt. In a still further aspect, the inhibition of Akt phosphorylation is with an IC$_{50}$ of less than about $1.0 \times 10^{-4}$ M, an IC$_{50}$ of less than about $1.0 \times 10^{-5}$ M, an IC$_{50}$ of less than about $1.0 \times 10^{-6}$ M, an IC$_{50}$ of less than about $1.0 \times 10^{-7}$ M, an IC$_{50}$ of less than about $1.0 \times 10^{-8}$ M, or an IC$_{50}$ of less than about $1.0 \times 10^{-9}$ M.

In a further aspect, the decreasing kinase activity is inhibition of a protein kinase is selected from selected from c-abl oncogene 1 kinase, c-abl oncogene 1 kinase (T315I form), ALK tyrosine kinase receptor, aurora kinase A, AXL receptor tyrosine kinase, cyclin-dependent kinase 1, cyclin-dependent kinase 2, serine/threonine-protein kinase Chk1, macrophage colony-stimulating factor 1 receptor kinase, ephrin type-A receptor 1 kinase, tyrosine-protein kinase Fer, tyrosine-protein kinase Fes/Fps, fibroblast growth factor receptor 1, tyrosine-protein kinase Fgr, insulin-like growth factor 1 receptor, macrophage-stimulating protein receptor kinase, proto-oncogene tyrosine-protein kinase receptor Ret, proto-oncogene tyrosine-protein kinase ROS, proto-oncogene tyrosine-protein kinase Src, proto-oncogene tyrosine-protein kinase Yes, PTK2B protein tyrosine kinase 2 beta, serine/threonine-protein kinase MST4, serine/threonine-protein kinase PAK 4, yyrosine-protein kinase JAK1, tyrosine-protein kinase JAK2, tyrosine-protein kinase JAK3, tyrosine-protein kinase Lck, tyrosine-protein kinase Lyn, tyrosine-protein kinase Mer, tyrosine-protein kinase SYK, vascular endothelial growth factor receptor 2, and vascular endothelial growth factor receptor 3. In a still further aspect, the protein kinase that is inhibited is AXL receptor tyrosine kinase.

In a further aspect, the inhibition of the protein kinase is with an IC$_{50}$ of less than about $1.0 \times 10^{-4}$ M, an IC$_{50}$ of less than about $1.0 \times 10^{-5}$ M, an IC$_{50}$ of less than about $1.0 \times 10^{-6}$ M, an IC$_{50}$ of less than about $1.0 \times 10^{-7}$ M, an IC$_{50}$ of less than about $1.0 \times 10^{-8}$ M, or an IC$_{50}$ of less than about $1.0 \times 10^{-9}$ M.

In a further aspect, the decreasing kinase activity inhibits cell viability. In a still further aspect, inhibition of cell viability is determined in a cell line selected from AN3-CA, LNCaP, RL95-2, KG-1, MV4-11, BT-20, RKO, MCF7, BT549, U87-MG, PC3, and Kasumi cells. In a still further aspect, the inhibition of cell viability is with an IC$_{50}$ of less than about $1.0 \times 10^{-4}$ M, an IC$_{50}$ of less than about $1.0 \times 10^{-5}$ M, an IC$_{50}$ of less than about $1.0 \times 10^{-6}$ M, an IC$_{50}$ of less than about $1.0 \times 10^{-7}$ M, an IC$_{50}$ of less than about $1.0 \times 10^{-8}$ M, or an IC$_{50}$ of less than about $1.0 \times 10^{-9}$ M.

In a further aspect, the decreasing kinase activity treats a disorder of uncontrolled cellular proliferation in a mammal. In a still further aspect, the mammal is a human. In a yet further aspect, the disorder of uncontrolled cellular proliferation is associated with a protein kinase dysfunction. In an even further aspect, the disorder of uncontrolled cellular proliferation is a cancer.

In a further aspect, the cancer is a leukemia. In an even further aspect, the cancer is a lymphoma. In a yet further aspect, the cancer is a solid tumor. In a still further aspect, the cancer is selected from cancers of the brain, genitourinary tract, endocrine system, gastrointestinal tract, colon, rectum, breast, kidney, lymphatic system, stomachydrogen, lung, pancreas, and skin. In a yet further aspect, the cancer is selected from cancers of the pancreas, lung, breast, brain, skin, and blood. In a still further aspect, the cancer is pancreatic cancer.

In a further aspect, the cancer is a cancer of the brain. In a still further aspect, the cancer is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor cell.

In a further aspect, the cancer is a glioma. In a still further aspect, the glioma is glioblastoma multiforme. In a yet further aspect, the glioma is selected from is selected from a ependymoma, astrocytoma, oligodendroglioma, and oligoastrocytoma. In a yet further aspect, the glioma is selected from a juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, paraganglioma, and ganglioglioma cell.

4. Kits

In one aspect, the invention relates to a kit comprising at least one compound having a structure represented by a formula:

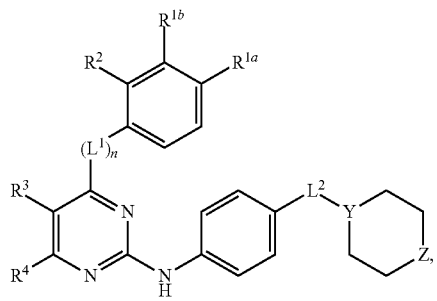

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)$R^7$; wherein $R^7$ is selected from hydrogen and C1-C6 alkyl; wherein $R^2$ is selected from hydrogen, C1-C6 alkyl, $SO_2R^8$, and (C=O)$R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof; and one or more of: (a) at least one agent known to increase kinase activity; (b) at least one agent known to decrease kinase activity; (c) at least one agent known to treat a disorder of uncontrolled cellular proliferation; or (d) instructions for treating a disorder associated with uncontrolled cellular proliferation.

In various aspects, the invention relates to a kit comprising at least one compound having a structure represented by a formula:

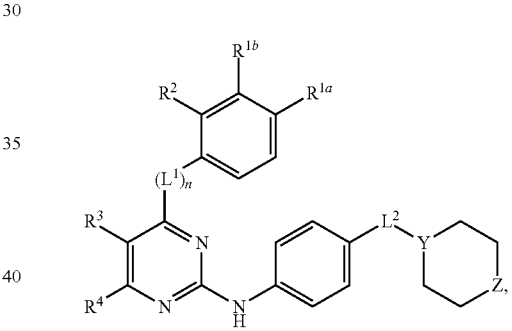

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and NH(C=O)$R^7$; wherein $R^7$ is selected from hydrogen and C1-C6 alkyl; wherein $R^2$ is selected from hydrogen, C1-C6 alkyl, $SO_2R^8$, and (C=O)$R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 cyanoalkyl, C1-C6 hydroxyalkyl, C1-C6 haloalkyl, C1-C6 polyalkyl, C3-C6 cycloalkyl, $C_3$-$C_6$ haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof.

In a further aspect, the compound is a disclosed compound or a product of a disclosed method of making a compound.

In a further aspect, the compound exhibits inhibition of the PI3K/Akt pathway. In a still further aspect, the inhibition of PI3K/Akt pathway is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a still further aspect, the compound exhibits inhibition of the MAPK pathway. In a still further aspect, the inhibition of MAPK pathway is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the compound exhibits inhibition of the phosphorylation of Akt. In a still further aspect, the inhibition of Akt phosphorylation is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the compound exhibits inhibition of a protein kinase. In a still further aspect, the protein kinase that is inhibited is selected from c-abl oncogene 1 kinase, c-abl oncogene 1 kinase (T315I form), ALK tyrosine kinase receptor, aurora kinase A, AXL receptor tyrosine kinase, cyclin-dependent kinase 1, cyclin-dependent kinase 2, serine/threonine-protein kinase Chk1, macrophage colony-stimulating factor 1 receptor kinase, ephrin type-A receptor 1 kinase, tyrosine-protein kinase Fer, tyrosine-protein kinase Fes/Fps, fibroblast growth factor receptor 1, tyrosine-protein kinase Fgr, insulin-like growth factor 1 receptor, macrophage-stimulating protein receptor kinase, proto-oncogene tyrosine-protein kinase receptor Ret, proto-oncogene tyrosine-protein kinase ROS, proto-oncogene tyrosine-protein kinase Src, proto-oncogene tyrosine-protein kinase Yes, PTK2B protein tyrosine kinase 2 beta, serine/threonine-protein kinase MST4, serine/threonine-protein kinase PAK 4, yyrosine-protein kinase JAK1, tyrosine-protein kinase JAK2, tyrosine-protein kinase JAK3, tyrosine-protein kinase Lck, tyrosine-protein kinase Lyn, tyrosine-protein kinase Mer, tyrosine-protein kinase SYK, vascular endothelial growth factor receptor 2, and vascular endothelial growth factor receptor 3. In a still further aspect, the protein kinase that is inhibited is AXL receptor tyrosine kinase.

In a still further aspect, the inhibition of the protein kinase is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

In a further aspect, the compound exhibits inhibition of cell viability. In a still further aspect, inhibition of cell viability is determined in a cell line selected from K562, MCF-7, PL-45, PANC-1, PSN-1, HepG2, and A549 cells. In a yet further aspect, the inhibition of cell viability is with an $IC_{50}$ of less than about $1.0 \times 10^{-4}$ M, an $IC_{50}$ of less than about $1.0 \times 10^{-5}$ M, an $IC_{50}$ of less than about $1.0 \times 10^{-6}$ M, an $IC_{50}$ of less than about $1.0 \times 10^{-7}$ M, an $IC_{50}$ of less than about $1.0 \times 10^{-8}$ M, or an $IC_{50}$ of less than about $1.0 \times 10^{-9}$ M.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient. In a further aspect, the at least one compound or the at least one product and the at least one agent are co-formulated. In a still further aspect, the at least one compound or the at least one product and the at least one agent are co-packaged.

In a further aspect, the at least one agent is selected from gemcitabine, cisplatin, paclitaxel or docetaxel, temazolide, and doxorubicin. In a still further aspecgt, the at least one agent is selected from a BRAF inhibitor and a EGFR inhibitor.

In a further aspect, the at least one agent is a hormone therapy agent. In a still further aspect, the hormone therapy agent is selected from one or more of the group consisting of leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, or a pharmaceutically acceptable salt, hydrate, solvate, or polymorph thereof.

In a further aspect, the at least one agent is a chemotherapeutic agent. In a still further aspect, the chemotherapeutic agent is selected from one or more of the group consisting of an alkylating agent, an antimetabolite agent, an antineoplastic antibiotic agent, a mitotic inhibitor agent, a mTor inhibitor agent or other chemotherapeutic agent.

In a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt, hydrate, solvate, or polymorph thereof.

In a further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt, hydrate, solvate, or polymorph thereof.

In a further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof.

In a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt, hydrate, solvate, or polymorph thereof. In an even further aspect, the mTor inhibitor agent is selected from one or more of the group consisting of everolimus, siroliumus, and temsirolimus, or a pharmaceutically acceptable salt, hydrate, solvate, or polymorph thereof.

In a further aspect, the instructions for treating a disorder further comprise providing the compound in connection with surgery. In a yet further aspect, the instructions provide that the surgery is performed prior to the administering of at least one compound. In a still further aspect, the instructions provide that the surgery is performed after the administering of at least one compound. In an even further aspect, the instructions provide that the administering of at least one compound is to effect presurgical debulking of a tumor. In a still further aspect, the instructions provide that surgery is performed at about the same time as the administering of at least one compound.

In a further aspect, the instructions for treating a disorder further comprise providing the compound in connection with radiotherapy. In a still further aspect, the instructions provide that radiotherapy is performed prior to the administering of at least one compound. In a yet further aspect, the instructions provide that radiotherapy is performed after the step of the administering of at least one compound. In an even further aspect, the instructions provide that radiotherapy is performed at about the same time as the step of the administering of at least one compound.

In a further aspect, the instructions further comprise providing the compound in connection with at least one agent that is a chemotherapeutic agent. In a yet further aspect, the instructions further comprise providing the compound in connection with at least one agent selected from a BRAF inhibitor and a EGFR inhibitor. In a yet further aspect, the instructions further comprise providing the compound in connection with at least one agent selected from a the hormone therapy agent, an alkylating agent, an antimetabolite agent, an antineoplastic antibiotic agent, a mitotic inhibitor agent, a mTor inhibitor agent or other chemotherapeutic agent. In an even further aspect, the instructions further comprise providing the compound in connection with at least one agent selected from gemcitabine, leuprolide, tamoxifen, raloxifene, megestrol, fulvestrant, triptorelin, medroxyprogesterone, letrozole, anastrozole, exemestane, bicalutamide, goserelin, histrelin, fluoxymesterone, estramustine, flutamide, toremifene, degarelix, nilutamide, abarelix, and testolactone, doxorubicin, mitoxantrone, bleomycin, daunorubicin, dactinomycin, epirubicin, idarubicin, plicamycin, mitomycin, pentostatin, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, irinotecan, topotecan, rubitecan, cabazitaxel, docetaxel, paclitaxel, etopside, vincristine, ixabepilone, vinorelbine, vinblastine, teniposide, everolimus, siroliumus, and temsirolimus, or a pharmaceutically acceptable salt, hydrate, solvate, or polymorph thereof.

In a further aspect, the instructions for treating a disorder further comprise instructions for administering the compound to a mammal. In a still further aspect, the mammal is a human. In a further aspect, the instructions for treating a disorder further comprise instructions for administering the compound for treatment of a disorder of uncontrolled cellular proliferation. In a still further aspect, the instructions for treating a disorder further comprise instructions for administering the compound for treatment of a kinase dysfunction. In a still further aspect, the disorder of uncontrolled cellular proliferation is a cancer. In a yet further aspect, the cancer is a leukemia. In an even further aspect, the cancer is a lymphoma. In a yet further aspect, the cancer is a solid tumor. In a still further aspect, the cancer is selected from is selected from cancers of the brain, genitourinary tract, endocrine system, gastrointestinal tract, colon, rectum, breast, kidney, lymphatic system, stomachydrogen, lung, pancreas, and skin. In a yet further aspect, the cancer is selected from cancers of the pancreas, lung, breast, brain, skin, and blood. In a still further aspect, the cancer is pancreatic cancer.

In a further aspect, the cancer is a cancer of the brain. In a still further aspect, the cancer is selected from acoustic neuroma, glioma, meningioma, pituitary adenoma, schwannoma, CNS lymphoma, primitive neuroectodermal tumor, craniopharyngioma, chordoma, medulloblastoma, cerebral neuroblastoma, central neurocytoma, pineocytoma, pineoblastoma, atypical teratoid rhabdoid tumor, chondrosarcoma, chondroma, choroid plexus carcinoma, choroid plexus papilloma, craniopharyngioma, dysembryoplastic neuroepithelial tumor, gangliocytoma, germinoma, hemangioblastoma, hemangiopercytoma, and metastatic brain tumor cell.

In a further aspect, the cancer is a glioma. In a still further aspect, the glioma is glioblastoma multiforme. In a yet further aspect, the glioma is selected from is selected from a ependymoma, astrocytoma, oligodendroglioma, and oligoastrocytoma. In a yet further aspect, the glioma is selected from a juvenile pilocytic astrocytoma, subependymal giant cell astrocytoma, ganglioglioma, subependymoma, pleomorphic xanthoastrocytom, anaplastic astrocytoma, glioblastoma multiforme, brain stem glioma, oligodendroglioma, ependymoma, oligoastrocytoma, cerebellar astrocytoma, desmoplastic infantile astrocytoma, subependymal giant cell astrocytoma, diffuse astrocytoma, mixed glioma, optic glioma, gliomatosis cerebri, paraganglioma, and ganglioglioma cell.

It is contemplated that the disclosed kits can be used in connection with the disclosed methods of making, the disclosed methods of using, and/or the disclosed compositions.

5. Non-Medical Uses

Also provided are the uses of the disclosed compounds and products as pharmacological tools in the development and standardization of in vitro and in vivo test systems for the evaluation of the effects of inhibitors of Axl activity in laboratory animals such as cats, dogs, rabbits, monkeys, rats and mice, as part of the search for new therapeutic agents that inhibit Axl.

In a further aspect, the invention relates to the use of a disclosed compound or a disclosed product as pharmacological tools in the development and standardization of in vitro and in vivo test systems for the evaluation of the effects of inhibitors of the PI3K/Akt pathway in laboratory animals such as cats, dogs, rabbits, monkeys, rats and mice, as part of the search for new therapeutic agents that inhibit the PI3/Akt pathway.

H. Experimental

The following examples are put forth so as to provide those of ordinary skill in the art with a complete disclosure and description of how the compounds, compositions, articles, devices and/or methods claimed herein are made and evaluated, and are not intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein.

The following exemplary compounds of the invention were synthesized. The Examples are provided herein to illustrate the invention, and should not be construed as limiting the invention in any way. The Examples are typically depicted in free base form, according to the IUPAC naming convention. However, some of the Examples were obtained or isolated in salt form.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Methods

All routine reagents and solvents were purchased from Sigma Aldrich and used as received. They were of reagent grade, purity ≥99%. Specialty chemicals and building blocks obtained from several suppliers were of the highest offered purity (always ≥95%).

NMR spectroscopy was performed on a Mercury 400 MHz operating at 400 MHz, equipped with a 5 mm broadband probe and using standard pulse sequences. Chemical shifts (δ) are reported in parts-per-million (ppm) relative to the residual solvent signals. Coupling constants (J-values) are expressed in Hz.

Mass spectrometry was performed on a Waters Quattro-II triple quadrupole mass spectrometer. All samples were analyzed by positive ESI-MS and the mass-to-charge ratio (m/z) of the protonated molecular ion is reported.

Microwave-assisted reactions were performed on a Biotage Initiator 2.5 at various powers.

Hydrogenation reactions were performed on a standard Parr hydrogenation apparatus.

Reactions were monitored by TLC on Baker flexible-backed plates coated with 200 μm of silica gel containing a fluorescent indicator. Preparative TLC was performed on 20 cm×20 cm Analtech Uniplates coated with a 1000 or 2000 μm silica gel layer containing a fluorescent (UV 254) indicator. Elution mixtures are reported as v:v. Spot visualization was achieved using UV light.

Flash chromatography was performed on a Teledyne Isco CombiFlash RF 200 using appropriately sized Redisep Rf Gold or Standard normal-phase silica or reversed-phase C-18 columns. Crude compounds were adsorbed on silica gel, 70-230 mesh 40 Å (for normal phase) or celite 503 (for reversed-phase) and loaded into solid cartridges. Elution mixtures are reported as v:v.

2. General Suzuki Cross—Coupling Procedure (Synthesis Procedure A)

The desired substituted aryl chloride analog (1.0 equiv), substituted arylboronic acid analog (1.05 equiv) and triphenylphosphine (0.04 equiv) were dissolved in a mixture of THF (final concentration of limiting reagent 0.1 mM) and 1 M aqueous sodium carbonate (2.0 equiv) after which palladium (II) acetate (0.02 equiv) was added and the solution was heated at reflux for 12 h. Following cooling, the solvent was removed in vacuo, and the residue was dissolved in ethyl acetate and poured in water. The organic phase was separated, and the aqueous phase was extracted with ethyl acetate. The combined organic phases were washed with water and brine., dried over $Na_2SO_4$, and concentrated. The crude material was purified by flash chromatography. An exemplary generalized reaction scheme is given below, with the substituent positions as defined elsewhere in the specification.

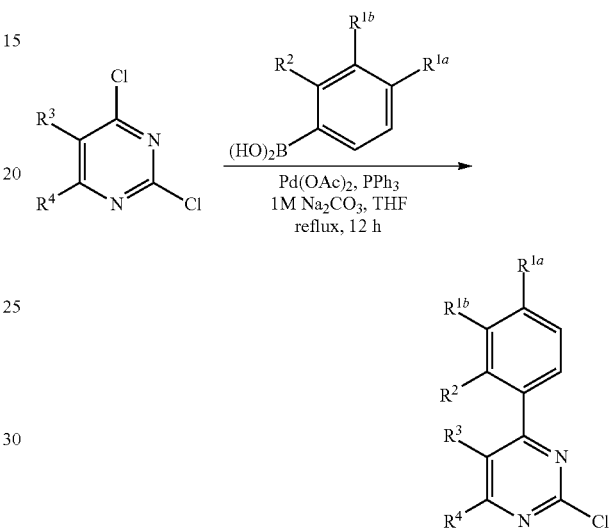

3. General Buchwald-Hartwig Amination Procedure (Synthesis Procedure B)

The desired substituted aryl chloride analog (1.0 equiv), substituted aniline analog (1.05 equiv) and potassium carbonate (1.5 equiv) were dissolved in t-butanol (concentration of limiting reagent 0.05-0.1 mM). The resulting mixture was thoroughly degassed after which $Pd_2(dba)_3$ (0.05 equiv) and XantPhos (0.05 equiv) were added, and the solution was heated at reflux for 12 h. Following cooling, the reaction mixture was diluted with ethyl acetate and poured in water. The organic phase was separated, and the aqueous phase was extracted with ethyl acetate. The combined organic phases were washed with water and brine, dried over $Na_2SO_4$, and concentrated. The crude material was purified by flash chromatography. An exemplary generalized reaction scheme is given below, with the substituent positions as defined elsewhere in the specification.

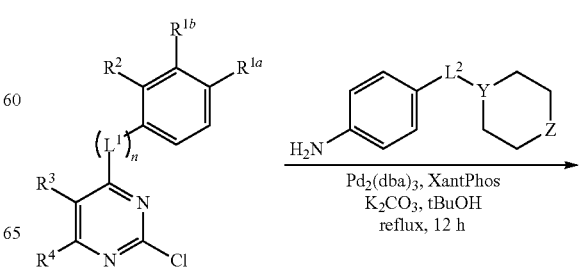

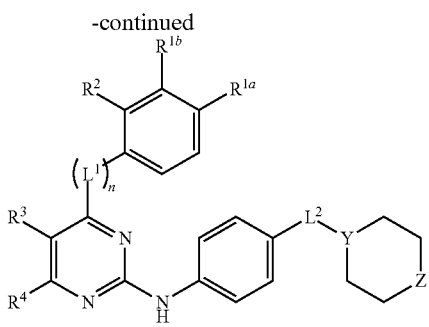

4. General Procedure for the Amination of 4-Chloropyrimidines (Synthesis Procedure C)

The desired substituted 4-chloropyrimidine analog (1.00 equiv) and DIPEA (1.20 equiv) were dissolved in isopropyl alcohol (concentration of limiting reagent 0.05-0.1 mM). The desired substituted aniline analog (1.05 equiv) was added and the resulting mixture was heated at reflux for 12 h. Following cooling, the solvent was removed in vacuo, and the residue was dissolved in ethyl acetate and poured in water. The organic phase was separated, and the aqueous phase was extracted with ethyl acetate. The combined organic phases were washed with water and brine; dried over $Na_2SO_4$, and concentrated. The crude material was purified by flash chromatography. An exemplary generalized reaction scheme is given below, with the substituent positions as defined elsewhere in the specification.

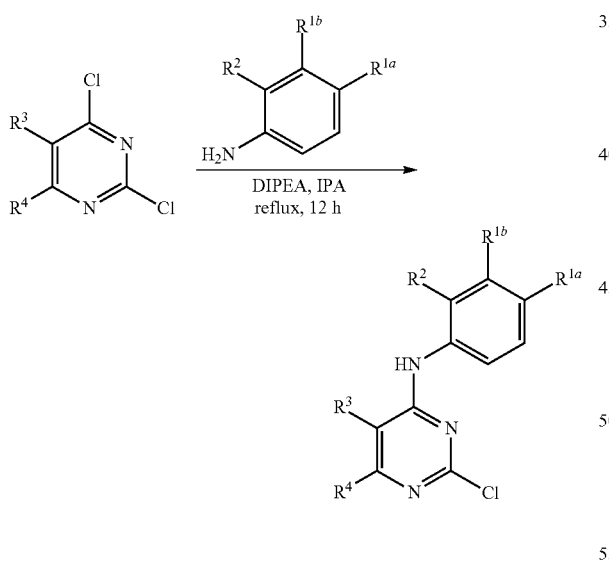

5. General Chlorosulfonation Procedure (Synthesis Procedure D)

The desired substituted aryl analog (1.0 equiv) was dissolved in chlorosulfonic acid (at least 10.0 equiv. or the smallest volume necessary to ensure complete dissolution) and the resulting mixture was stirred for 4 h (room temperature or 90° C.) after which it was carefully poured on ice. The resulting solution was extracted twice with ethyl acetate. The combined organic phases were washed with water and brine, dried over $Na_2SO_4$, and concentrated. The crude material was purified by flash chromatography. Exemplary generalized reaction schemes are given below, with the substituent positions as defined elsewhere in the specification.

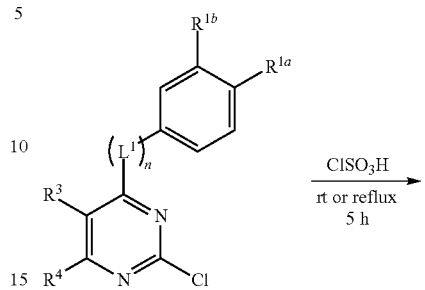

6. General Sulfonamide Synthesis (Synthesis Procedure E)

The desired substituted sulfonyl chloride analog (1.00 equiv) and DIPEA (2.50 equiv) were dissolved in THF (concentration of limiting reagent 0.05-0.1 mM). The desired amine (1.05 equiv) was added and the resulting mixture was stirred at room temperature for 2 h. Following removal of the solvent, the crude material was purified by flash chromatography. Exemplary generalized reaction schemes are given below, with the substituent positions as defined elsewhere in the specification.

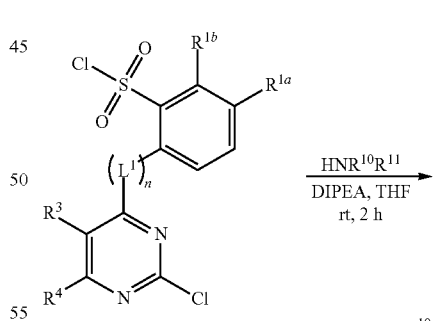

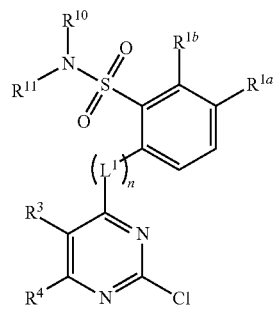

7. Preparation of 4-(3-chloro-4-fluorophenyl)-5-methyl-N-(4-((4-methylpiperazin-1-yl)methyl)phenyl)pyrimidin-2-amine

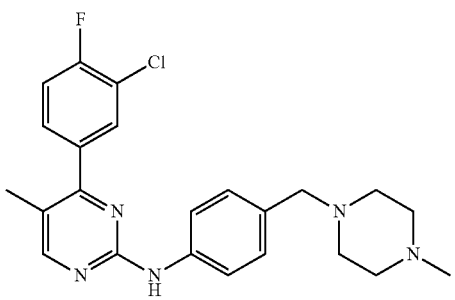

The title compound was prepared according to synthesis procedure B described above from 2-chloro-4-(3-chloro-4-fluorophenyl)-5-methylpyrimidine and 4-((4-methylpiperazin-1-yl)methyl)aniline in 84% yield (yellow solid) after purification by flash chromatography (CH$_2$Cl$_2$/CH$_3$OH 99:1 gradually increasing to 95:5). $^1$H NMR (400 MHz, CDCl$_3$): δ 8.30 (s, 1H), 7.70 (m, 1H), 7.56 (d, 2H, J=8.6 Hz), 7.51 (m, 1H), 7.25 (d, 2H, J: not calculated due to overlapping peaks), 7.05 (s, 1H), 3.46 (s, 2H), 2.46 (bs, 8H), 2.28 (s, 3H), 2.25 (s, 3H); MS (ESI): 426.3 [M+H]$^+$, 213.7 [M+2H]$^{2+}$.

8. Preparation of 4-(4-fluorophenyl)-5-methyl-N-(4-((4-methylpiperazin-1-yl)methyl)phenyl)pyrimidin-2-amine

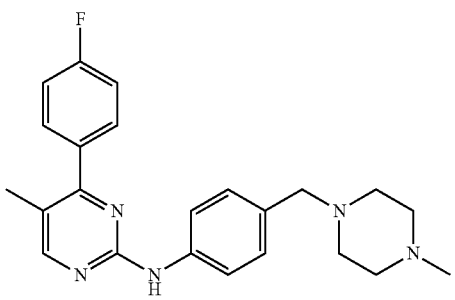

The title compound was prepared according to procedure B from 2-chloro-4-(4-fluorophenyl)-5-methylpyrimidine and 4-((4-methylpiperazin-1-yl)methyl)aniline in 79% yield (yellow solid) after purification by flash chromatography (CH$_2$Cl$_2$/CH$_3$OH 99:1 gradually increasing to 95:5). $^1$H NMR (400 MHz, CDCl$_3$): δ 8.28 (s, 1H), 7.63 (m, 2H), 7.55 (d, 2H, J=8.5 Hz), 7.22 (t, 2H, J=8.7 Hz), 7.14 (t, 2H, J=8.7 Hz), 3.44 (s, 2H), 2.42 (bs, 8H), 2.25 (s, 3H), 2.24 (s, 3H); MS (ESI): 392.0 [M+H]$^+$, 196 [M+H]$^{2+}$.

9. Preparation of 4-(3-chloro-4-fluorophenoxy)-5-methyl-N-(4-((4-methylpiperazin-1-yl)methyl)phenyl)pyrimidin-2-amine

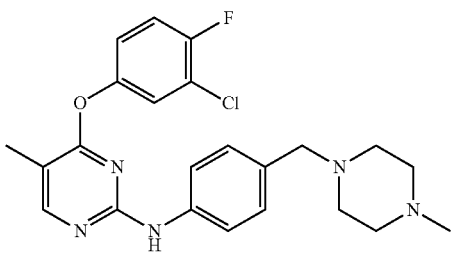

The title compound was prepared according to synthesis procedure B described above from 2-chloro-4-(3-chloro-4-fluorophenoxy)-5-methylpyrimidine and 4-((4-methylpiperazin-1-yl)methyl)aniline in 59% yield (yellow solid) after flash chromatography (CH$_2$Cl$_2$/CH$_3$OH 99:1 gradually increasing to 95:5). $^1$H NMR (400 MHz, CDCl$_3$): δ H 8.10 (s, 1H), 7.43 (t, 1H, J=8.4 Hz), 7.23 (d, 2H), 7.09 (d, 2H, J=8.2 Hz), 7.04 (dd, 1H, J=9.6, 2.4 Hz), 6.94 (m, 1H), 3.42 (s, 2H), 2.46 (bs, 8H) 2.27 (s, 3H), 2.18 (s, 3H); MS (ESI): 442.3 [M+H]$^+$, 221.7 [M+2H]$^{2+}$.

10. Preparation of 6-(3-chloro-4-fluorophenyl)-N$^2$-(4-((4-methylpiperazin-1-yl)methyl)phenyl)pyrimidine-2,4-diamine

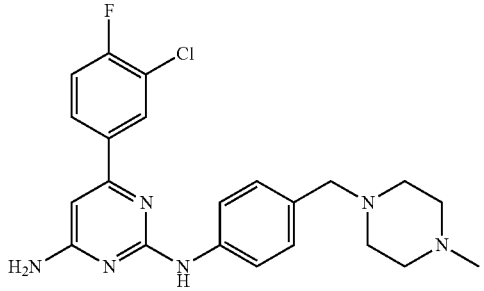 [SMILES: CN1CCN(Cc2ccc(Nc3nc(N)cc(-c4ccc(F)c(Cl)c4)n3)cc2)CC1]

The title compound was prepared according to synthesis procedure B described above from 2-chloro-6-(3-chloro-4-fluorophenyl)pyrimidin-4-amine and 4-((4-methylpiperazin-1-yl)methyl)aniline in 84% yield (yellow solid) after flash chromatography (CH$_2$Cl$_2$/CH$_3$OH 99:1 gradually increasing to 95:5). MS (ESI): 214.2 [M+2H]$^{2+}$.

11. Preparation of N$^4$-(3-chloro-4-fluorophenyl)-5-methyl-N$^2$-(4-((4-methylpiperazin-1-yl)methyl)phenyl)pyrimidine-2,4-diamine

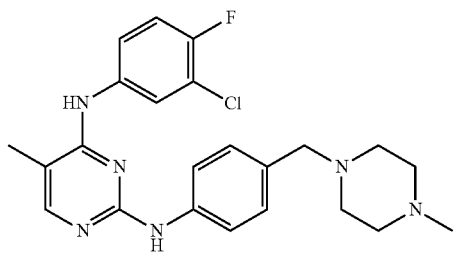

The title compound was prepared according to synthesis procedure B described above from 2-chloro-N-(3-chloro-4-fluorophenyl)-5-methylpyrimidin-4-amine and 4-((4-methylpiperazin-1-yl)methyl)aniline in 78% yield (yellow solid) after flash chromatography (CH$_2$Cl$_2$/CH$_3$OH 99:1 gradually increasing to 95:5). MS (ESI): 440.4 [M+H]$^+$.

12. Preparation of 5-methyl-N-(4-((4-methylpiperazin-1-yl)methyl)phenyl)-4-(3-(methylsulfonyl)phenyl)pyrimidin-2-amine

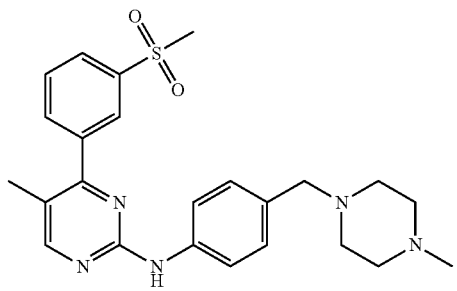

The title compound was prepared according to synthesis procedure B described above from 2-chloro-5-methyl-4-(3-(methylsulfonyl)phenyl)pyrimidine and 4-((4-methylpiperazin-1-yl)methyl)aniline in 63% yield (yellow solid) after flash chromatography (CH$_2$Cl$_2$/CH$_3$OH 99:1 gradually increasing to 95:5). $^1$H NMR (400 MHz, CDCl$_3$): δ 8.35 (s, 1H), 8.23 (s, 1H), 8.03 (d, 1H, J=7.8 Hz), 7.93 (d, 1H, J=7.8 Hz), 7.70 (t, 1H, J=7.8 Hz), 7.56 (d, 2H, J=8.2 Hz), 7.26 (d, 2H, J: not calculated due to overlapping peaks), 3.45 (s, 2H), 3.09 (s, 3H), 2.43 (bs, 8H), 2.26 (s, 6H). MS (ESI): 452.3 [M+H]$^+$, 226.8 [M+2H]$^{2+}$.

13. Preparation of 4-(3-chlorophenyl)-5-methyl-N-(4-((4-methylpiperazin-1-yl)methyl)phenyl)pyrimidin-2-amine

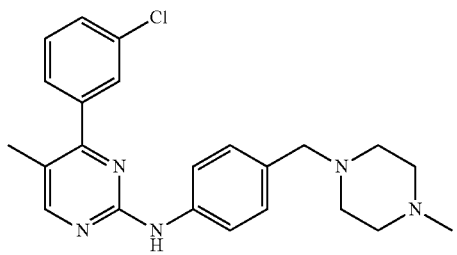

The title compound was prepared according to synthesis procedure B described above from 2-chloro-4-(3-chlorophenyl)-5-methylpyrimidine and 4-((4-methylpiperazin-1-yl)methyl)aniline in 77% yield (yellow solid) after flash chromatography (CH$_2$Cl$_2$/CH$_3$OH 99:1 gradually increasing to 95:5). $^1$H NMR (400 MHz, CDCl$_3$): δ 8.31 (s, 1H), 7.61 (s, 1H), 7.56 (d, 2H, J=8.2 Hz), 7.48 (m, 1H), 7.40 (m, 2H), 7.25 (d, 2H, J: not calculated due to overlapping peaks), 3.45 (s, 2H), 2.45 (bs, 8H), 2.27 (s, 3H), 2.24 (s, 3H); MS (ESI): 408.4 [M+H]$^+$, 204.7 [M+2H]$^{2+}$.

14. Preparation of 2-methyl-5-(5-methyl-2-((4-((4-methylpiperazin-1-yl)methyl)phenyl)amino)pyrimidin-4-yl)benzonitrile

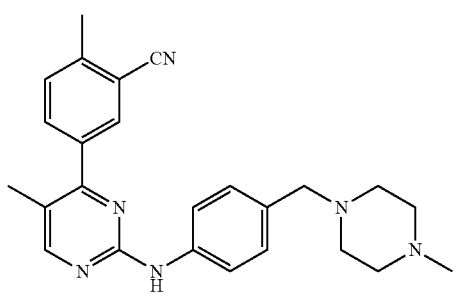

The title compound was prepared according to synthesis procedure B described above from 5-(2-chloro-5-methylpyrimidin-4-yl)-2-methylbenzonitrile and 4-((4-methylpiperazin-1-yl)methyl)aniline in 93% yield (yellow solid). After flash chromatography (CH$_2$Cl$_2$/CH$_3$OH 99:1 gradually increasing to 95:5). $^1$H NMR (400 MHz, CDCl$_3$): δ 8.31 (s, 1H), 7.88 (d, 1H, J=1.7 Hz), 7.76 (dd, 1H, J=8.0, 1.9 Hz), 7.55 (d, 2H, J=8.6 Hz), 7.43 (d, 1H, J=7.9 Hz), 7.25 (d, 2H, J: not calculated due to overlapping peaks), 3.45 (s, 2H), 2.62 (s, 3H), 2.45 (bs, 8H), 2.26 (s, 3H), 2.25 (s, 3H); MS (ESI): 413.5 [M+H]$^+$, 207.4 [M+2H]$^{2+}$.

15. Preparation of N-(3-(5-methyl-2-((4-((4-methylpiperazin-1-yl)methyl)phenyl)amino)pyrimidin-4-yl)phenyl)acetamide

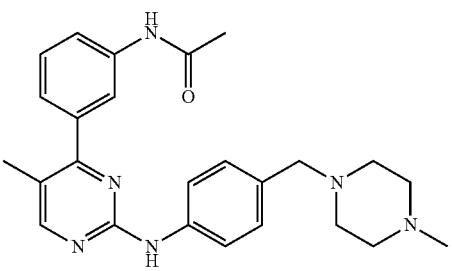

The title compound was prepared according to synthesis procedure B described above from N-(3-(2-chloro-5-methylpyrimidin-4-yl)phenyl)acetamide and 4-((4-methylpiperazin-1-yl)methyl)aniline in 82% yield (yellow solid) after flash chromatography (CH$_2$Cl$_2$/CH$_3$OH 99:1 gradually increasing to 95:5). $^1$H NMR (400 MHz, CDCl$_3$): δ 8.29 (s, 1H), 7.79 (s, 1H), 7.57 (d, 3H, J=8.2 Hz), 7.42 (t, 1H, J=7.9 Hz), 7.35 (d, 1H, J=7.5 Hz), 7.22 (m, 2H), 3.44 (s, 2H), 2.42 (bs, 8H), 2.26 (s, 3H), 2.19 (s, 3H); (ESI): 431.3 [M+H]$^+$, 216.3 [M+2H]$^{2\pm}$.

16. Preparation of 5-methyl-N-(4-((4-methylpiperazin-1-yl)methyl)phenyl)-4-(3-(trifluoromethoxy)phenyl)pyrimidin-2-amine

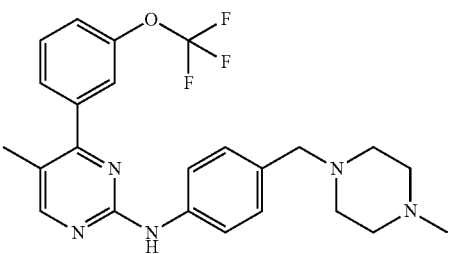

The title compound was prepared according to synthesis procedure B described above from 2-chloro-5-methyl-4-(3-(trifluoromethoxy)phenyl)pyrimidine and 4-((4-methylpiperazin-1-yl)methyl)aniline in 79% yield (yellow solid) after flash chromatography (CH$_2$Cl$_2$/CH$_3$OH 99:1 gradually increasing to 95:5). $^1$H NMR (400 MHz, CDCl$_3$): δ 8.32 (s, 1H), 7.57 (d, 3H, J=8.5 Hz), 7.52 (s, 1H), 7.50 (t, 1H, J=7.9 Hz), 7.29 (d, 1H, J=7.9 Hz), 7.25 (d, 2H, J: not calculated due to overlapping peaks), 3.45 (s, 2H), 2.47 (bs, 8H), 2.28 (s, 3H), 2.26 (s, 3H); MS (ESI): 458.3 [M+H]$^+$, 229.7 [M+2H]$^{2+}$.

17. Preparation of 4-(3-chloro-4-fluorophenyl)-5-CYCLOPROPYL-N-(4-((4-methylpiperazin-1-yl)methyl)phenyl)pyrimidin-2-amine

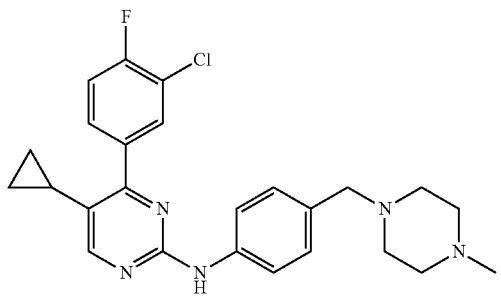 [SMILES: CN1CCN(Cc2ccc(Nc3ncc(C4CC4)c(-c4ccc(F)c(Cl)c4)n3)cc2)CC1]

The title compound was prepared according to synthesis procedure B described above from 2-chloro-4-(3-chloro-4-fluorophenyl)-5-cyclopropylpyrimidine and 4-((4-methylpiperazin-1-yl)methyl)aniline in 51% yield (yellow solid) after flash chromatography (CH$_2$Cl$_2$/CH$_3$OH 99:1 gradually increasing to 95:5). $^1$H NMR (400 MHz, CDCl$_3$): δ 8.22 (s, 1H), 7.90 (dd, 1H, J=7.0, 2.0 Hz), 7.72 (m, 1H), 7.55 (d, 2H, J=8.6 Hz), 7.22 (d, 1H, J=8.6 Hz), 7.09 (d, 2H, J=8.6 Hz), 3.45 (s, 2H), 2.43 (bs, 8H), 2.26 (s, 3H), 1.86 (m, 1H), 0.92 (m, 2H), 0.63 (m, 2H); MS (ESI): 452.3 [M+H]$^+$, 226.9 [M+2H]$^{2+}$.

18. Preparation of 2-methyl-2-(4-(5-methyl-2-((4-((4-methylpiperazin-1-yl)methyl)phenyl)amino)pyrimidin-4-yl)phenyl)propanenitrile

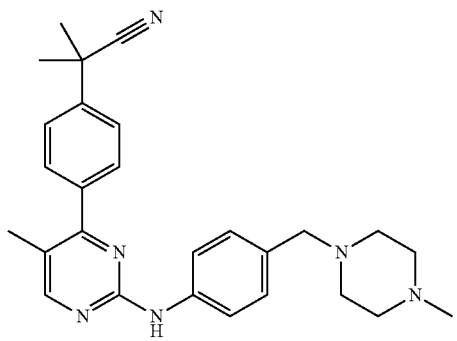

The title compound was prepared according to synthesis procedure B described above from 2-(4-(2-chloro-5-methylpyrimidin-4-yl)phenyl)-2-methylpropanenitrile and 44(4-methylpiperazin-1-yl)methyl)-aniline in 39% yield (yellow solid) after flash chromatography (CH$_2$Cl$_2$/CH$_3$OH 99:1 gradually increasing to 95:5). $^1$H NMR (400 MHz, CDCl$_3$): δ 8.30 (s, 1H), 7.66 (d, 2H, J=8.6 Hz), 7.58 (d, 2H, J=4.7 Hz), 7.56 (d, 2H, J=4.7 Hz), 7.25 (d, 2H, J: not calculated due to overlapping peaks), 3.44 (s, 2H), 2.42 (bs, 8H), 2.26 (s, 6H), 1.76 (s, 6H); MS (ESI): 441.4 [M+H]$^+$, 221.4 [M+2H]$^{2+}$.

19. Preparation of 4-(3-chloro-5-(trifluoromethyl)phenyl)-5-methyl-N-(4-((4-methylpiperazin-1-yl)methyl)phenyl)pyrimidin-2-amine

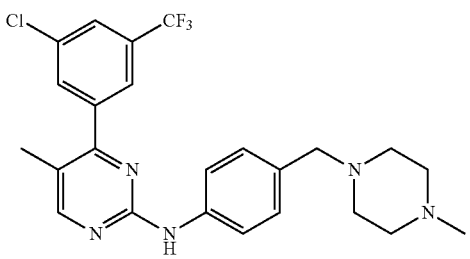

The title compound was prepared according to synthesis procedure B described above from 2-chloro-4-(3-chloro-5-(trifluoromethyl)phenyl)-5-methylpyrimidine and 4-((4-methylpiperazin-1-yl)methyl)aniline in 76% yield (yellow solid) after flash chromatography (CH$_2$Cl$_2$/CH$_3$OH 99:1 gradually increasing to 95:5). $^1$H NMR (400 MHz, CDCl$_3$): δ 8.35 (s, 1H), 7.79 (d, 2H, J=7.8 Hz), 7.69 (s, 1H), 7.55 (d, 2H, J=8.2 Hz), 7.26 (d, 2H, J=8.6 Hz), 3.47 (s, 2H), 2.50 (bs, 8H), 2.31 (s, 3H), 2.25 (s, 3H); MS (ESI): 476.3 [M+H]$^+$, 238.7 [M+2H]$^{2+}$.

20. Preparation of 4-(3-methoxyphenyl)-5-methyl-N-(4-((4-methylpiperazin-1-yl)methyl)phenyl)pyrimidin-2-amine

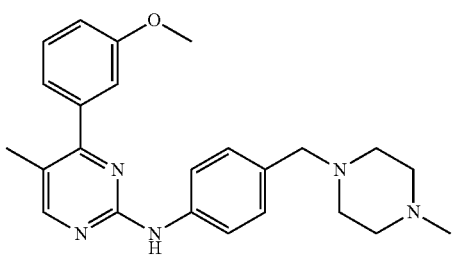

The title compound was prepared according to synthesis procedure B described above from 2-chloro-4-(3-methoxyphenyl)-5-methylpyrimidine and 4-((4-methylpiperazin-1-yl)methyl)aniline in 20% yield (yellow solid) after flash chromatography (CH$_2$Cl$_2$/CH$_3$OH 99:1 gradually increasing to 95:5). $^1$H NMR (400 MHz, CDCl$_3$): δ 8.29 (s, 1H), 7.59 (d, 2H, J=8.2 Hz), 7.37 (t, 1H, J=8.0 Hz), 7.24 (d, 2H, J: not calculated due to overlapping peaks), 7.16 (m, 2H), 6.98 (d, 1H, J=8.2 Hz), 3.85 (s, 3H), 3.49 (s, 2H), 2.57 (bs, 8H), 2.36 (s, 3H), 2.24 (s, 3H); MS (ESI): 404.4 [M+H]$^+$, 202.9 [M+2H]$^{2+}$.

21. Preparation of N¹-(4-(3-chloro-4-fluorophenyl)-5-methylpyrimidin-2-yl)-N⁴-methyl-N⁴-(1-methylpiperidin-4-yl)benzene-1,4-diamine

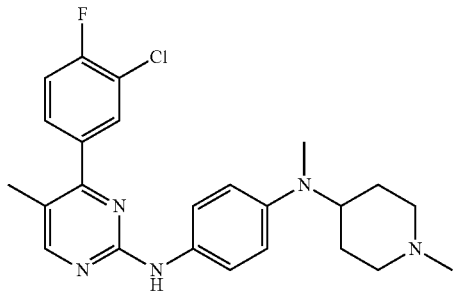

The title compound was prepared according to synthesis procedure B described above from 2-chloro-4-(3-chloro-4-fluorophenyl)-5-methylpyrimidine and N¹-methyl-N¹-(1-methylpiperidin-4-yl)benzene-1,4-diamine in 25% yield (yellow solid) after flash chromatography (CH$_2$Cl$_2$/CH$_3$OH 99:1 gradually increasing to 95:5). ¹H NMR (400 MHz, CDCl$_3$): δ 8.24 (s, 1H), 7.69 (dd, 1H, J=7.2, 1.7 Hz), 7.49 (m, 1H), 7.41 (d, 2H, J=8.9 Hz), 7.20 (d, 1H, 8.5 Hz), 6.79 (d, 2H, J=8.5 Hz), 3.49 (m, 1H), 3.00 (d, 2H, J=10.6 Hz), 2.74 (s, 3H), 2.34 (s, 3H), 2.21 (s, 3H), 2.11 (m, 2H), 1.89 (m, 2H), 1.72 (d, 2H, J=11.6 Hz); MS (ESI): 440.3 [M+H]⁺, 220.8 [M+2H]²⁺.

22. Preparation of 2-((5-chloro-2-((4-((4-methylpiperazin-1-yl)methyl)phenyl)amino)pyrimidin-4-yl)amino)-N,N-dimethylbenzenesulfonamide

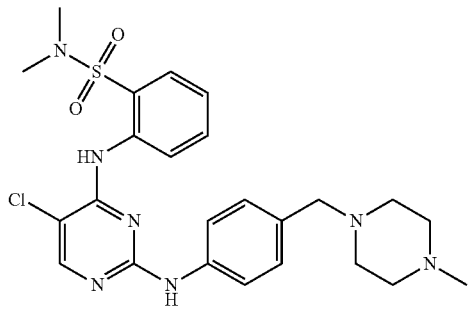 [SMILES: CN1CCN(Cc2ccc(Nc3ncc(Cl)c(Nc4ccccc4S(=O)(=O)N(C)C)n3)cc2)CC1]

The title compound was prepared according to synthesis procedure B described above from 2-((2,5-dichloropyrimidin-4-yl)amino)-N,N-dimethylbenzenesulfonamide and 4-((4-methylpiperazin-1-yl)methyl)aniline in 62% yield (yellow solid) after flash chromatography (CH$_2$Cl$_2$/CH$_3$OH 99:1 gradually increasing to 95:5). ¹H NMR (400 MHz, CDCl$_3$): δ 8.53 (d, 1H, J=8.2 Hz), 8.11 (s, 1H), 7.84 (dd, 1H, J=8.2, 1.3 Hz), 7.54 (m, 1H), 7.45 (d, 2H, J=8.2 Hz), 7.22 (m, 3H), 3.47 (s, 2H), 2.72 (s, 6H), 2.48 (bs, 8H), 2.29 (s, 3H); MS (ESI): 516.3 [M+H]⁺, 258.8 [M+2H]²⁺.

23. Preparation of 2-((5-chloro-2-((4-(methyl(1-methylpiperidin-4-yl)amino)phenyl)amino)pyrimidin-4-yl)amino)-N,N-dimethylbenzenesulfonamide

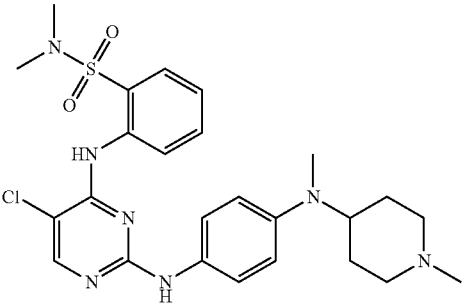 [SMILES: CN1CCC(N(C)c2ccc(Nc3ncc(Cl)c(Nc4ccccc4S(=O)(=O)N(C)C)n3)cc2)CC1]

The title compound was prepared according to synthesis procedure B described above from 2-((2,5-dichloropyrimidin-4-yl)amino)-N,N-dimethylbenzenesulfonamide and N¹-methyl-N¹-(1-methylpiperidin-4-yl)benzene-1,4-diamine in 34% yield (yellow solid) after flash chromatography (CH$_2$Cl$_2$/CH$_3$OH 99:1 gradually increasing to 95:5). ¹H NMR (400 MHz, CDCl$_3$): δ 9.45 (s, 1H), 8.60 (d, 1H, J=8.2 Hz), 8.06 (s, 1H), 8.18 (d, 1H, J=8.0 Hz), 7.47 (t, 1H, J=7.7 Hz), 7.31 (d, 2H, J=8.9 Hz), 7.16 (t, 1H, J=7.5 Hz), 6.77 (d, 2H, J=8.9 Hz), 3.51 (tt, 1H, J=11.3, 3.8 Hz), 3.00 (d, 2H, J=10.6 Hz), 2.76 (s, 3H), 2.72 (s, 3H), 2.34 (s, 3H), 2.11 (t, 2H, J=10.2 Hz), 1.90 (q, 2H, J=11.3 Hz), 1.73 (d, 2H, J=12.0 Hz); MS (ESI): 530.3 [M+H]⁺.

24. Preparation of N,N-dimethyl-2-((2-((4-((4-methylpiperazin-1-yl)methyl)phenyl)amino)-5-(trifluoromethyl)pyrimidin-4-yl)amino)benzamide

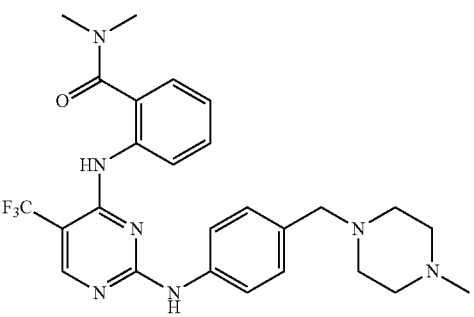 [SMILES: CN1CCN(Cc2ccc(Nc3ncc(C(F)(F)F)c(Nc4ccccc4C(=O)N(C)C)n3)cc2)CC1]

The title compound was prepared according to synthesis procedure B described above from 2-((2-chloro-5-(trifluoromethyl)pyrimidin-4-yl)amino)-N,N-dimethylbenzamide and 4-((4-methylpiperazin-1-yl)methyl)aniline in 12% yield (pale yellow oil that solidifies on standing) after flash chromatography eluent (CH$_2$Cl$_2$/CH$_3$OH 99:1 gradually increasing to 95:5). ¹H NMR (400 MHz, CDCl$_3$): δ 8.46 (s, 1H), 8.28 (s, 1H), 8.15 (d, 1H, J=8.2 Hz), 7.44 (d, 2H, J=8.5 Hz), 7.30 (d, 2H, J=8.2 Hz), 7.21 (t, 1H, J=7.5 Hz), 7.02 (t, 1H, J=7.4 Hz), 6.81 (s, 1H), 3.50 (s, 2H), 3.09 (s, 3H), 2.96 (s, 3H), 2.49 (bs, 8H), 2.30 (s, 3H); MS (ESI): 514.2 [M+H]⁺.

25. Preparation of 2-((5-chloro-2-((4-((4-methylpiperazin-1-yl)methyl)phenyl)amino)pyrimidin-4-yl)amino)-N,N-dimethylbenzamide

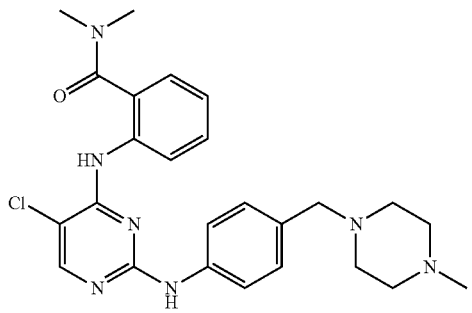 [SMILES: CN1CCN(Cc2ccc(Nc3ncc(Cl)c(Nc4ccccc4C(=O)N(C)C)n3)cc2)CC1]

The title compound was prepared according to synthesis procedure B described above from 2-((2,5-dichloropyrimidin-4-yl)amino)-N,N-dimethylbenzamide and 4-((4-methylpiperazin-1-yl)methyl)aniline in 32% yield (yellow solid) after flash chromatography (CH$_2$Cl$_2$/CH$_3$OH 99:1 gradually increasing to 95:5). $^1$H NMR (400 MHz, CDCl$_3$): δ 9.07 (s, 1H), 8.35 (d, 1H J=8.2 Hz), 8.05 (s, 1H), 7.46 (s, 2H, J=8.2 Hz), 7.38 (t, 1H, J=7.8 Hz), 7.29 (d, 1H, J=7.5 Hz), 7.21 (d, 2H, J=8.2 Hz), 7.10 (t, 1H, J=7.5 Hz), 7.01 (s, 1H), 3.45 (s, 2H), 3.11 (s, 3H), 3.04 (s, 3H), 2.43 (bs, 8H), 2.27 (s, 3H); MS (ESI): 480.1 [M+H]$^+$.

26. Preparation of (2-((5-chloro-2-((4-((4-methylpiperazin-1-yl)methyl)phenyl)amino)pyrimidin-4-yl)amino)phenyl)(pyrrolidin-1-yl)methanone

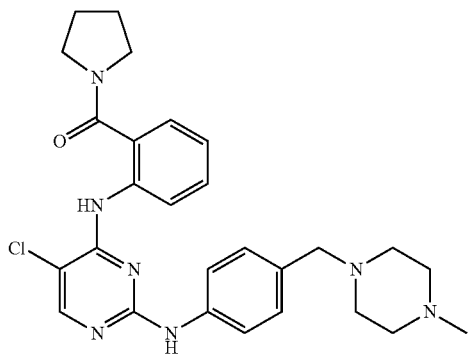 [SMILES: CN1CCN(Cc2ccc(Nc3ncc(Cl)c(Nc4ccccc4C(=O)N4CCCC4)n3)cc2)CC1]

The title compound was prepared according to synthesis procedure B described above from (2-((2,5-dichloropyrimidin-4-yl)amino)phenyl)(pyrrolidin-1-yl)methanone and 4-((4-methylpiperazin-1-yl)methyl)aniline in 73% yield (yellow solid) after flash chromatography (CH$_2$Cl$_2$/CH$_3$OH 99:1 gradually increasing to 95:5). $^1$H NMR (400 MHz, CDCl$_3$): δ 9.68 (s, 1H), 8.40 (d, 1H, J=8.2 Hz), 8.04 (s, 1H), 7.46 (d, 2H, J=8.2 Hz), 7.39-7.34 (m, 2H), 7.21 (d, 2H, J=8.2 Hz), 7.06 (t, 1H, J=7.5 Hz), 3.65 (t, 2H, J=7.0 Hz), 3.48 (t, 2H, J=6.3 Hz), 3.44 (s, 2H), 2.44 (bs, 8H), 2.26 (s, 3H), 1.95 (m, 2H), 1.83 (m, 2H); MS (ESI): 506.1 [M+H]$^+$.

27. Preparation of 2-((5-chloro-2-((4-((4-methylpiperazin-1-yl)methyl)phenyl)amino)pyrimidin-4-yl)amino)-N-CYCLOPROPYLBENZAMIDE

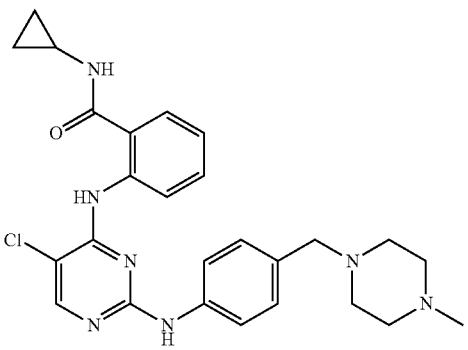 [SMILES: CN1CCN(Cc2ccc(Nc3ncc(Cl)c(Nc4ccccc4C(=O)NC4CC4)n3)cc2)CC1]

The title compound was prepared according to synthesis procedure B described above from N-cyclopropyl-2((2,5-dichloropyrimidin-4-yl)amino)benzamide and 4-((4-methylpiperazin-1-yl)methyl)aniline in 38% yield (yellow solid) after flash chromatography (CH$_2$Cl$_2$/CH$_3$OH 99:1 gradually increasing to 95:5). $^1$H NMR (400 MHz, CDCl$_3$): δ 8.64 (d, 1H, J=8.5 Hz), 8.11 (s, 1H), 7.50 (d, 2H, J=8.2 Hz), 7.44 (m, 2H), 7.25 (d, 2H, J=8.2 Hz), 7.07 (t, 1H, J=7.5 Hz), 6.38 (bs, 1H), 3.50 (s, 2H), 2.93 (q, 1H, J=3.4 Hz), 2.55 (bs, 8H), 2.35 (s, 3H), 0.92 (m, 2H), 0.65 (m, 2H); MS (ESI): 492.1 [M+H]$^+$.

28. Preparation of 5-chloro-N$^4$-(4-fluoro-2-(morpholinosulfonyl)phenyl)-N$^2$-(4-((4-methylpiperazin-1-yl)methyl)phenyl)pyrimidine-2,4-diamine

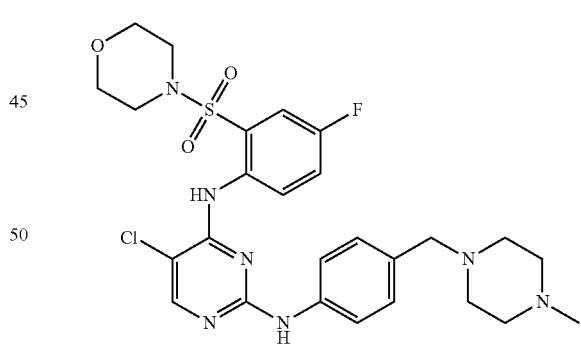

The title compound was: prepared according to synthesis procedure B described above from 2,5-dichloro-N-(4-fluoro-2-(morpholinosulfonyl)phenyl)pyrimidin-4-amine and 4-((4-methylpiperazin-1-yl)methyl)aniline in 62% yield (yellow solid) after flash chromatography (CH$_2$Cl$_2$/CH$_3$OH 99:1 gradually increasing to 95:5). $^1$H NMR (400 MHz, CDCl$_3$): δ 9.12 (s, 1H), 8.49 (dd, 1H, J=4.8, 9.2 Hz), 8.10 (s, 1H), 7.54 (dd, 1H, J=3.1, 7.9 Hz), 7.40 (d, 2H, J=8.2 Hz), 7.27-7.20 (m, 3H), 3.64 (m, 4H), 3.47 (s, 2H), 3.06 (m, 4H), 2.47 (bs, 8H), 2.28 (s, 3H); MS (ESI): 576.2 [M+H]$^+$.

29. Preparation of 5-CHLORO-N⁴-(4-fluoro-2-(pyrrolidin-1-ylsulfonyl)phenyl)-N²-(4-((4-methylpiperazin-1-yl)methyl)phenyl)pyrimidine-2,4-diamine

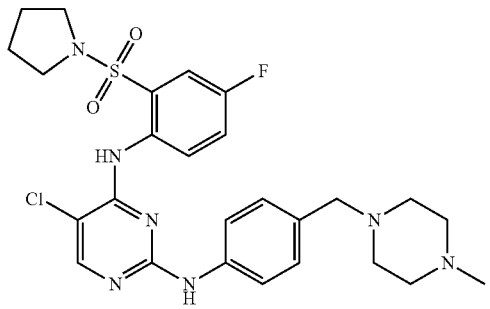 [SMILES: CN1CCN(Cc2ccc(Nc3ncc(Cl)c(Nc4ccc(F)cc4S(=O)(=O)N4CCCC4)n3)cc2)CC1]

The title compound was prepared according to synthesis procedure B described above from 2,5-dichloro-N-(4-fluoro-2-(pyrrolidin-1-ylsulfonyl)phenyl)pyrimidin-4-amine and 4-((4-methylpiperazin-1-yl)methyl)aniline in 78% yield (yellow solid) after flash chromatography (CH$_2$Cl$_2$/CH$_3$OH 99:1 gradually increasing to 95:5). $^1$H NMR (400 MHz, CDCl$_3$): δ 9.30 (s, 1H), 8.49 (dd, 1H, J=9.2, 4.8 Hz), 7.60 (dd, 1H, J=8.0, 2.9 Hz), 7.41 (d, 2H, J=8.2 Hz), 7.23 (d, 2H, J=8.2 Hz), 7.19 (m, 1H), 3.48 (s, 2H), 3.23 (m, 4H), 2.50 (bs, 8H), 2.31 (s, 3H), 1.78 (m, 4H); MS (ESI): 560.3 [M+H]$^+$.

30. Preparation of 5-chloro-N²-(4-((4-methylpiperazin-1-yl)methyl)phenyl)-N⁴-(2-(pyrrolidin-1-ylsulfonyl)phenyl)pyrimidine-2,4-diamine

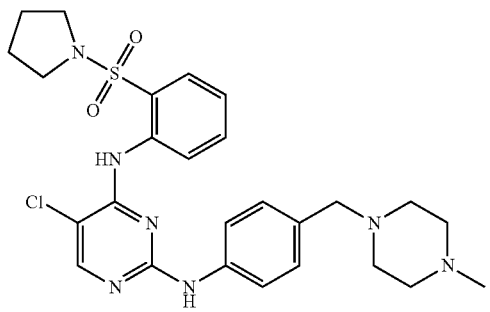 [SMILES: CN1CCN(Cc2ccc(Nc3ncc(Cl)c(Nc4ccccc4S(=O)(=O)N4CCCC4)n3)cc2)CC1]

The title compound was prepared according to synthesis procedure B described above from 2,5-dichloro-N-(2-(pyrrolidin-1-ylsulfonyl)phenyl)pyrimidin-4-amine and 4-((4-methylpiperazin-1-yl)methyl)aniline in 50% yield (yellow solid) after flash chromatography eluent (CH$_2$Cl$_2$/CH$_3$OH 99:1 gradually increasing to 95:5). $^1$H NMR (400 MHz, CDCl$_3$): δ 9.58 (s, 1H), 8.61 (d, 1H, J=8.2 Hz), 8.18 (s, 1H), 7.96 (d, 1H, J=7.9 Hz), 7.58 (t, 1H, J=7.7 Hz), 7.51 (d, 2H, J=8.2 Hz), 7.30 (d, 2H, J=8.2 Hz), 7.26 (m, 1H), 3.53 (s, 2H), 3.30 (m, 4H), 2.53 (bs, 8H), 2.34 (s, 3H), 1.84 (m, 4H); MS (ESI): 542.20 [M+H]$^+$.

31. Preparation of 5-chloro-4-(4-fluoro-2-(pyrrolidin-1-yl)sulfonyl)phenyl)-N-(4-((4-methylpiperazin-1-yl)methyl)phenyl)pyrimidin-2-amine

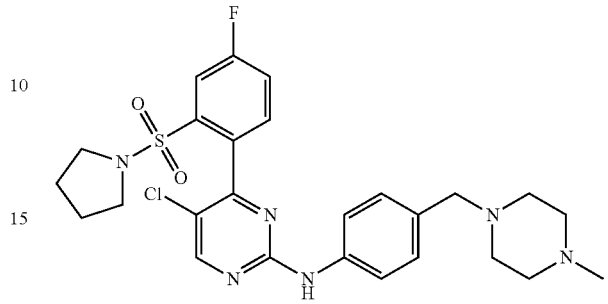

The title compound was prepared according to synthesis procedure B described above from 2,5-dichloro-4-(4-fluoro-2-(pyrrolidin-1-ylsulfonyl)phenyl)pyrimidine and 4-((4-methylpiperazin-1-yl)methyl)aniline in 96% yield (yellow solid) after flash chromatography (CH$_2$Cl$_2$/CH$_3$OH 99:1 gradually increasing to 95:5). $^1$H NMR (400 MHz, CDCl$_3$): δ 9.48 (s, 1H), 8.55 (d, 1H, J=8.9 Hz), 8.11 (s, 1H), 7.85 (d, 1H, J=2.4 Hz), 7.42 (1H), 7.41 (d, 2H, J=8.2 Hz), 7.25 (d, 2H, J=8.2 Hz), 3.48 (s, 2H), 3.24 (m, 4H), 2.49 (bs, 8H), 2.29 (s, 3H), 1.79 (m, 4H); MS (ESI): 545.2 [M+H]$^+$.

32. Preparation of 5-chloro-N⁴-(4-chloro-2-(pyrrolidin-1-yl)sulfonyl)phenyl)-N²-(4-((4-methylpiperazin-1-yl)methyl)phenyl)pyrimidine-2,4-diamine

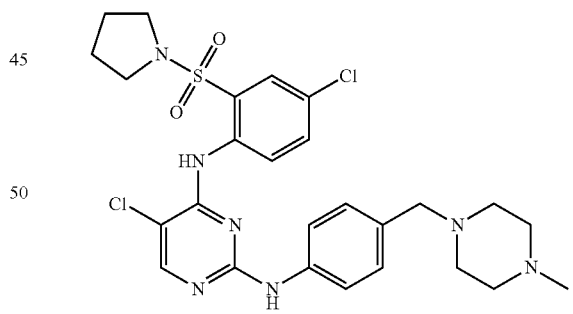

The title compound was prepared according to synthesis procedure B described above from 2,5-dichloro-N-(4-chloro-2-(pyrrolidin-1-ylsulfonyl)phenyl)pyrimidin-4-amine and 4((4-methylpiperazin-1-yl)methyl)-aniline in 26% yield (yellow solid) after flash chromatography (CH$_2$Cl$_2$/CH$_3$OH 99:1 gradually increasing to 95:5). $^1$H NMR (400 MHz, CDCl$_3$): δ 8.46 (dd, 1H, J=6.5, 2.1 Hz), 8.42 (s, 1H), 8.10 (m, 1H), 7.52 (d, 2H, J=8.2 Hz), 7.31 (t, 1H, J=9.2 Hz), 7.26 (d, 2H, J=8.2 Hz), 3.45 (s, 2H), 3.39 (m, 4H), 2.46 (bs, 8H), 2.27 (s, 3H), 1.85 (m, 4H); MS (ESI): 576.2 [M+H]$^+$.

33. Preparation of 4-((5-chloro-2-((4-((4-methylpiperazin-1-yl)methyl)phenyl)amino)pyrimidin-4-yl)amino)-3-(pyrrolidin-1-ylsulfonyl)phenol

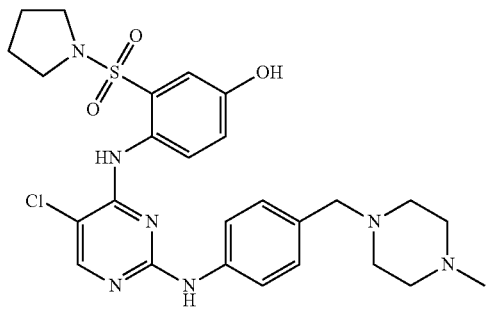 [SMILES: CN1CCN(Cc2ccc(Nc3ncc(Cl)c(Nc4ccc(O)cc4S(=O)(=O)N4CCCC4)n3)cc2)CC1]

The title compound was prepared according to synthesis procedure B described above from 4-((2,5-dichloropyrimidin-4-yl)amino)-3-(pyrrolidin-1-ylsulfonyl)phenol and 4-((4-methylpiperazin-1-yl)methyl)aniline in 27% yield (yellow solid) after flash chromatography (CH$_2$Cl$_2$/CH$_3$OH 99:1 gradually increasing to 95:5). $^1$H NMR (400 MHz, CDCl$_3$): δ 8.08 (s, 1H), 7.87 (d, 1H, J=8.4 Hz), 7.67 (s, 1H), 7.44 (d, 2H, J=8.1 Hz), 7.26 (1H), 7.23 (d, 2H, J=8.4 Hz), 7.10 (d, 1H, J=8.8 Hz), 3.53 (s, 2H), 3.33 (m, 4H), 2.63 (bs, 8H), 2.43 (s, 3H), 1.83 (m, 4H); MS (ESI): 558.1 [M+H]$^+$.

34. Preparation of 5-chloro-N$^4$-(4-fluoro-2-(pyrrolidin-1-yl)sulfonyl)phenyl)-N$^4$-methyl-N$^2$-(4-((4-methylpiperazin-1-yl)methyl)phenyl)pyrimidine-2,4-diamine

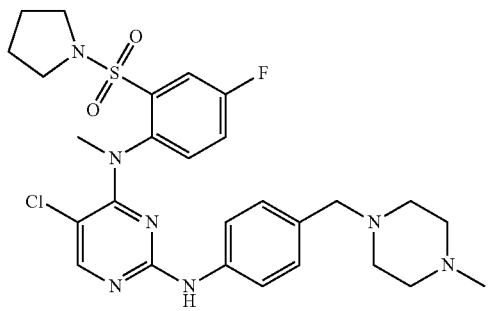 [SMILES: CN1CCN(Cc2ccc(Nc3ncc(Cl)c(N(C)c4ccc(F)cc4S(=O)(=O)N4CCCC4)n3)cc2)CC1]

The title compound was prepared according to synthesis procedure B described above from 2,5-dichloro-N-(4-fluoro-2-(pyrrolidin-1-ylsulfonyl)phenyl)-N-methylpyrimidin-4-amine and 4-((4-methylpiperazin-1-yl)methyl)aniline in 39% yield (yellow solid) after flash chromatography (CH$_2$Cl$_2$/CH$_3$OH 99:1 gradually increasing to 95:5). $^1$H NMR (400 MHz, CDCl$_3$): δ 7.92 (s, 1H), 7.58 (m, 1H), 7.45 (d, 2H, J=8.5 Hz), 7.25 (m, 1H), 7.21 (d, 2H, J=8.4 Hz), 7.13 (t, 1H, J=9.0 Hz), 7.10 (s, 1H), 3.43 (s, 3H), 3.41 (s, 2H), 3.31 (m, 4H), 2.38 (bs, 8H), 2.22 (s, 0.79 (m, 4H); MS (ESI): 574.2 [M+H]$^+$.

35. Preparation of 5-fluoro-4-(4-fluoro-2-(pyrrolidin-1-yl)sulfonyl)phenyl)-N-(4-((4-methylpiperazin-1-yl)methyl)phenyl)pyrimidin-2-amine

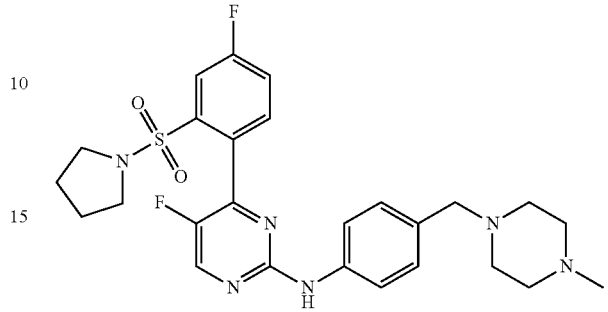

The title compound was prepared according to synthesis procedure B described above from 2-chloro-5-fluoro-4-(4-fluoro-2-(pyrrolidin-1-ylsulfonyl)phenyl)pyrimidine and 4-((4-methylpiperazin-1-yl)methyl)aniline in 60% yield (yellow solid) after flash chromatography (CH$_2$Cl$_2$/CH$_3$OH 99:1 gradually increasing to 95:5). $^1$H NMR (400 MHz, CDCl$_3$): δ 8.65 (dd, 1H, J=6.8, 2.0 Hz), 8.30 (d, 1H, J=3.3 Hz), 8.24 (m, 1H), 7.50 (d, 2H, J=8.4 Hz), 7.30-7.19 (m, 4H), 3.43 (s, 2H), 3.34 (m, 4H), 2.46 (bs, 8H), 2.26 (s, 1H), 1.79 (m, 4H); MS (ESI): 529.2 [M+H]$^+$.

36. Preparation of 4-(4-fluoro-2-(pyrrolidin-1-yl)sulfonyl)phenyl)-5-methyl-N-(4-((4-methylpiperazin-1-yl)methyl)phenyl)pyrimidin-2-amine

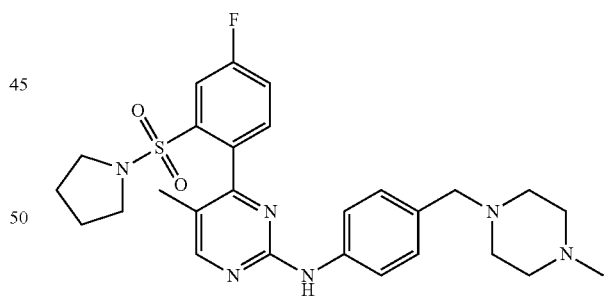

The title compound was prepared according to synthesis procedure B described above from 2-chloro-4-(4-fluoro-2-(pyrrolidin-1-ylsulfonyl)phenyl)-5-methylpyrimidine and 4-((4-methylpiperazin-1-yl)methyl)-aniline in 60% yield (yellow solid) after flash chromatography (CH$_2$Cl$_2$/CH$_3$OH 99:1 gradually increasing to 95:5). $^1$H NMR (400 MHz, CDCl$_3$): δ 8.32 (s, 1H), 8.21 (dd, 1H, J=6.6, 2.2 Hz), 7.87 (m, 1H), 7.55 (d, 2H, J=8.5 Hz), 7.32 (t, 1H, J=9.0 Hz), 7.25 (d, 2H, J: not calculated due to overlapping peaks), 7.10 (bs, 1H), 3.45 (s, 2H), 3.39 (m, 4H), 2.46 (bs, 8H), 2.27 (s, 3H), 1.86 (m, 4H); MS (ESI): 525.2 [M+H]$^+$.

37. Preparation of 2-(5-chloro-2-((4-((4-methylpiperazin-1-yl)methyl)phenyl)amino)pyrimidin-4-yl)-5-fluoro-N,N-dimethylbenzenesulfonamide

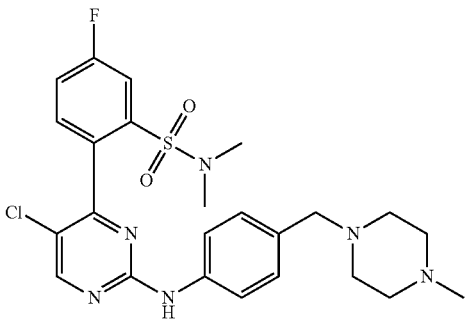 [SMILES: CN1CCN(Cc2ccc(Nc3ncc(Cl)c(-c4ccc(F)cc4S(=O)(=O)N(C)C)n3)cc2)CC1]

The title compound was prepared according to synthesis procedure B described above from 2-(2,5-dichloropyrimidin-4-yl)-5-fluoro-N,N-dimethylbenzenesulfonamide and 4-((4-methylpiperazin-1-yl)methyl)aniline in 44% yield (yellow solid) after flash chromatography ($CH_2Cl_2/CH_3OH$ 99:1 gradually increasing to 95:5). $^1$H NMR (400 MHz, $CDCl_3$): δ 8.39 (m, 2H), 8.08 (m, 1H), 7.48 (d, 2H, J=8.4 Hz), 7.30-7.20 (m, 4H), 3.41 (s, 2H), 2.82 (s, 6H), 2.40 (bs, 8H), 2.22 (s, 3H); MS (ESI): 519.2 $[M+H]^+$.

38. Cell Culture

All cell lines were cultured in media as recommended by American Type Culture Collection ("ATCC"; supplemented with 10% fetal bovine serum ("FBS") and 1% penicillin/streptomycin (100 IU/ml pencillin and 100 µg/ml streptomycin) at 37° C. and 5% $CO_2$. The cell lines used in these studies included those indicated in Table II below.

TABLE II

| Cell Line | Tissue Source | ATCC Number | Culture media |
| --- | --- | --- | --- |
| A549 | Human lung carcinoma | CCL-185 | F-12K Medium |
| HepG2 | Human hepatocellular carcinoma | HB-8065 | Eagle's Minimum Essential Medium |
| MDA-MB-231 | Breast adenocarcinoma | HTB-26 | Leibovitz's L-15 Medium |
| PL45 | Human pancreatic ductal adenocarcinoma | CRL-2558 | Dulbecco's Modified Eagle's Medium ("DMEM") |
| PANC-1 | Human pancreatic ductal epithelial carcinoma | CRL-1469 | DMEM |
| PSN-1 | Human pancreatic ductal adenocarcinoma | Not applicable | DMEM |

39. Axl Kinase Activity Assay

Test compounds were diluted to desired concentrations in kinase reaction buffer (50 mM HEPES pH 7.5, 10 mM $MgCl_2$, 1 mM EGTA, 2 mM DTT, and 0.01% v/v Tween-20) and were briefly incubated with Axl kinase (Invitrogen Corporation, Carlsbad, Calif.). The Axl kinase used was recombinant human Axl kinase (catalytic domain, amino acids 473-894) with a histidine tag. The reaction was initiated by the addition of ATP and fluorescein-labeled poly-GT substrate (poly Glu:Tyr, 4:1 polymer; Invitrogen). Concentration of the various components in the assay (10 µl reaction volume) were: 1% DMSO, 93 ng/ml Axl kinase, 20 µM ATP, and 200 nM fluorescein poly-GT substrate. Following addition of ATP and fluorescein poly-GT substrate, incubation was for 60 min at room temperature, the enzyme reaction is stopped by addition of 10 µl terbium-labeled anti-phosphotyrosine PY20 antibody in EDTA-containing buffer. Final concentration of EDTA and antibody after addition to the reaction is 10 mM and 2 nM, respectively. The terbium conjugated antibody generates a time-resolved FRET signal with the fluorescein molecule (bound to the poly-GT substrate) when the substrate is phosphorylated. After one hour incubation at room temperature, fluorescence was measured with excitation of 320 nm and dual emission of 495 and 520 urn on an EnVision microplate reader (PerkinElmer). Signal is expressed in terms of a TR-FRET ratio (fluorescence intensity at 520 nm to 495 nm). Activity data using this assay are given in Table I.

40. Mer Kinase Activity Assay

The Mer kinase assay was carried out in a manner identical to that described for Axl LanthaScreen™ assay, except that the reaction components had the following concentrations in the assay were: 1% DMSO, 53 ng/ml Mer kinase (Invitrogen), 15 µM ATP, and 200 nM fluorescein-labeled poly-GT substrate.

41. Cell Proliferation Assay

For cell proliferation assays, 45 µl containing 1000 cells per well were seeded into solid white 384-well plates in appropriate cell growth media containing 10% FBS and incubated overnight at 37° C. and 5% $CO_2$. The following day, test compounds were diluted in serum free growth media to 10× desired concentrations and 5 µl was added to each well. Combined compound and cells were incubated for 96 hours. Following incubation, 40 µl of ATP-Lite solution (PerkinElmer, Inc., Waltham, Massachussetts) was added to each well, incubated for an additional 10 minutes at room temperature and luminescence was measured on an EnVision microplate reader. Percent cell viability for test compounds was calculated by comparing treated wells to appropriate controls (e.g. vehicle treated) included on each plate.

42. GAS6-Axl Signalling Assay

Cell lines were seeded in 1 ml of the appropriate growth media with 10% FBS into 6-well plates ($8 \times 10^5$ cells/well) and incubated overnight at 37° C. and 5% $CO_2$. The following day, serum-containing growth media was replaced by serum-free media and incubated for 4 hr, and then test compounds were added to the cells at desired concentrations and incubated for an additional 2 hr. To stimulate Axl signaling, Gas6 was added to each well to a concentration of 3 µg/ml and incubated for 10 min. The cells were lysed immediately and the lysates used in a multiplex ELISA kit (Meso Scale Discovery, Gaithersburg, Md.) to quantitate the phosphorylated AKT (at position Ser473' "pAkt") or phosphorylated Axl ("pAxl").

43. $IC_{50}$ Calculation $IC_{50}$ values are determined using GraphPad Prism 5 software. The data were entered as an X-Y plot into the software as percent inhibition for each concentration of the drug. The concentration values of the drug were log transformed and the nonlinear regression was carried out using the "sigmoidal dose-response (variable slope)" option within the GraphPad software to model the data and calculate $IC_{50}$ values. The $IC_{50}$ values reported are the concentration of drug at which 50% inhibition was reached.

44. Inhibition of Kinase Activity: Determination of IC$_{50}$ for 5-chloro-N2-(4-((4-methylpiperazin-1-yl)methyl)phenyl)-N4-(2-(pyrrolidin-1-ylsulfonyl)phenyl)pyrimidine-2,4-diamine

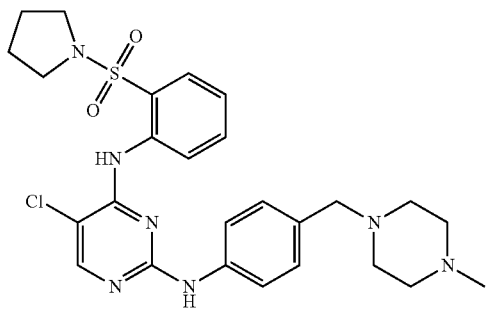 [SMILES: CN1CCN(Cc2ccc(Nc3ncc(Cl)c(Nc4ccccc4S(=O)(=O)N4CCCC4)n3)cc2)CC1]

Figure 4:
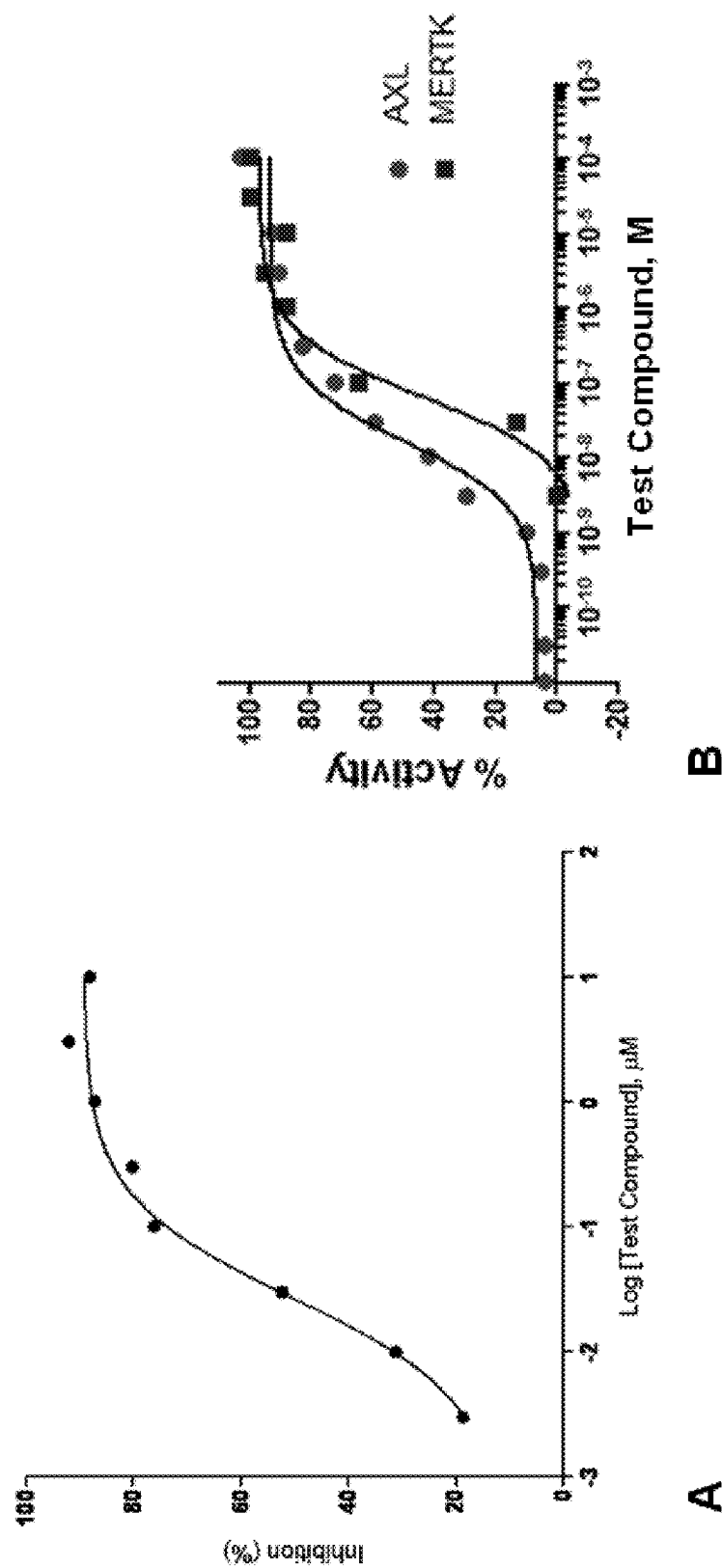
FIG. 4 shows representative data for inhibition of Axl and Mer kinases by a representative disclosed compound.

A typical example dose dependent inhibition of Axl activity and data used for IC$_{50}$ determination in the Axl activity assay is shown in FIG. 4A for the title compound shown above. The percentage inhibition of activity compared to vehicle control is given as a function of log concentration of compound (labeled as "Test Compound" in the figure) is given. In the data shown, the compounds were tested in triplicate in the TR-FRET-based binding assay as described above. IC$_{50}$ values generated from this assay was about 20 nM. Comparable IC$_{50}$ values were observed for this compound in the cell viability assay (see Table III below). A comparison of inhibition of both Axl and Mer kinases, both members of the TAM subfamily of protein kinases, is given in FIG. 4B. The activity was determined as described above for each kinase.

45. Inhibition of Kinase Activity

Figure 5:
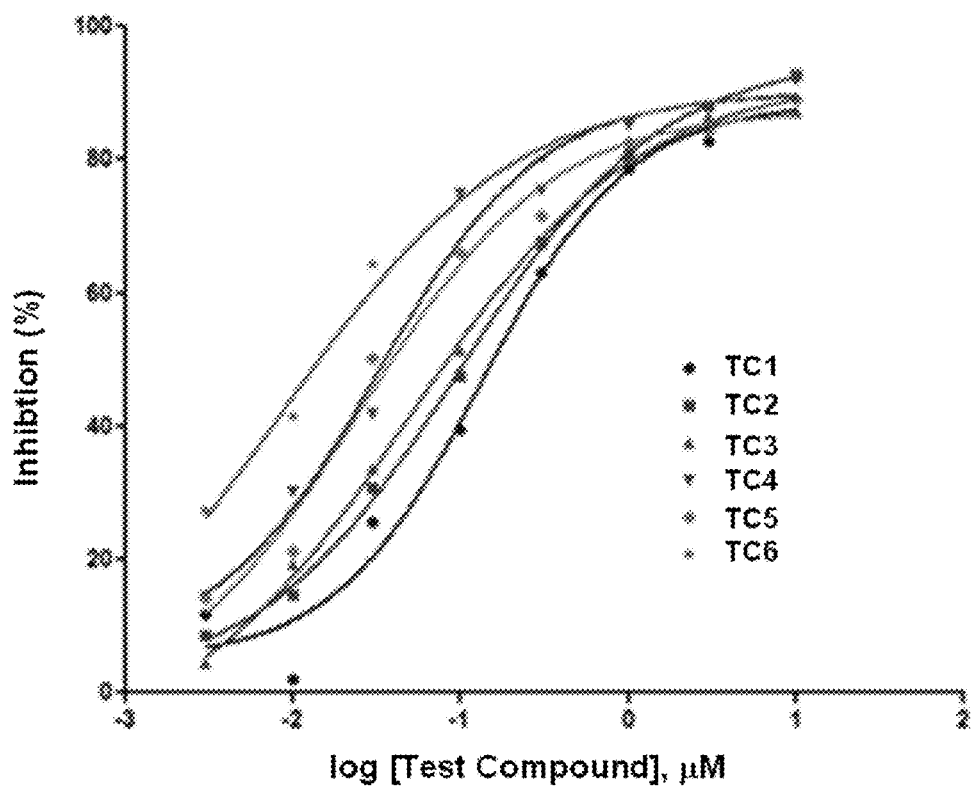
FIG. 5 shows representative data for inhibition of Axl and Mer kinases by a representative disclosed compounds.

Typical data for the concentration dependent inhibition of Axl activity are shown in FIG. 5. Activity was determined in using the Axl activity assay described above. The percentage inhibition of activity compared to vehicle control is given as a function of log concentration of compound (labeled as "Test Compound" in the figure) is given. In the data shown, the compounds were tested in triplicate in the TR-FRET-based binding assay as described above. The test compounds are labeled as TC1, TC2, etc. correspond to the compounds identified as such in Table III below.

The binding energy was calculated for the test compounds identified in Table III (TC1, TC2, etc.) are as follows (in kcal/mol): TC1, −36.21; TC2, −31.29; TC3, −29.89; TC4, −37.21; TC5, −33.23; and TC6, −31.86.

46. Axl Expression in Pancreatic Cancer Cell Lines

Figure 6:
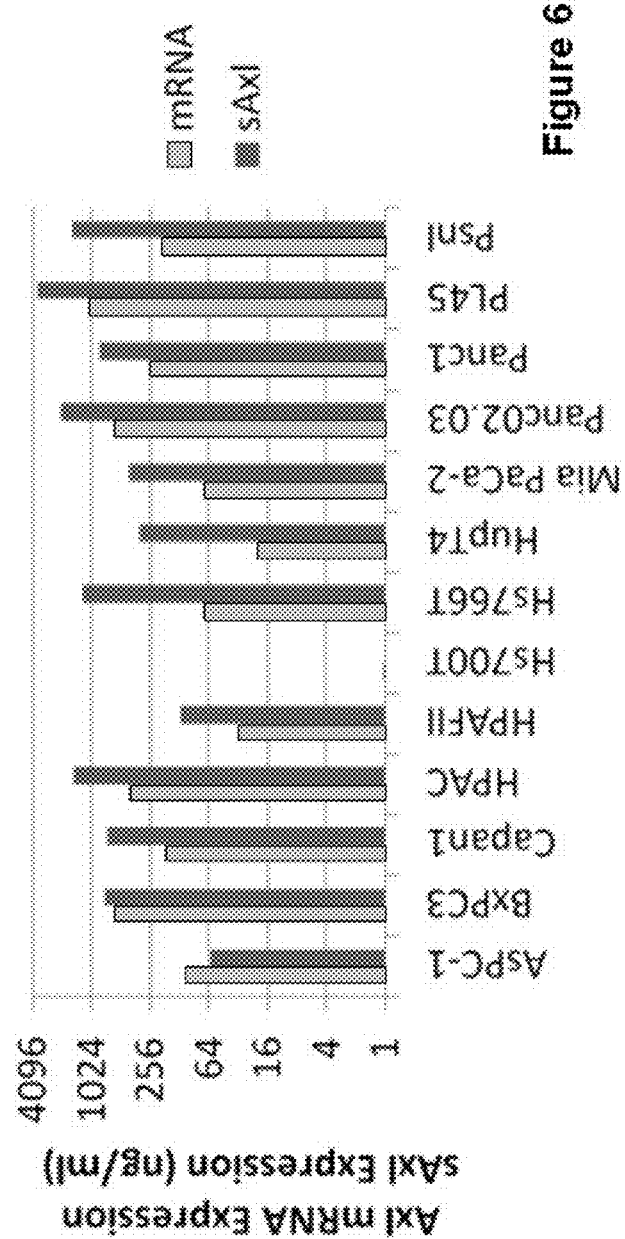
FIG. 6 shows representative data on the expression of Axl mRNA and sAxl protein in cell lines.

The expression of Axl mRNA was determined selected pancreatic cancer cell lines as shown in FIG. 6. Cells were cultured generally as described herein under conditions recommended by ATCC. RNA was isolated from pancreatic cancer cell lines, converted to cDNA by reverse transcription, and Axl expression was quantified by TaqMan real-time PCR. Axl expression in each sample was normalized to HPRT1 expression and is shown above (lighter gray bar, FIG. 6) relative to the expression in the Hs700T cell line.

For sAxl analysis, the cell culture media of each cell line was collected, centrifuged to clear any detached cells or debris, and analyzed using a sAxl ELISA (R&D Systems). Absolute sAxl levels were quantified using a standard curve and results were normalized to the percent confluency of each cell line (darker gray bar, FIG. 6).

Figure 7:
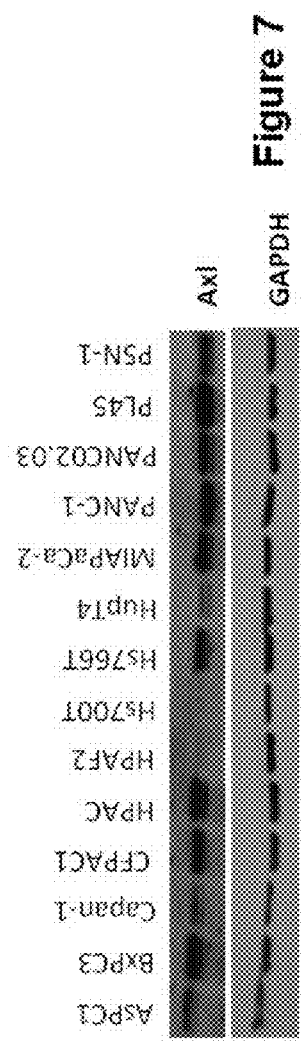
FIG. 7 shows representative on the expression of Axl protein in cell lines.

Protein lysates were generated from each cell line and analyzed by western blot (FIG. 7). The membrane was probed with an anti-Axl antibody (Novus) followed by an anti-GAPDH antibody (Cell Signaling) to use as a loading control.

47. Inhibition of AKT (S473) and Axl Phosphorylation by 2-((5-chloro-2-((4-((4-methylpiperazin-1-yl)methyl)phenyl)amino)pyrimidin-4-yl)amino)-N,N-dimethylbenzenesulfonamide

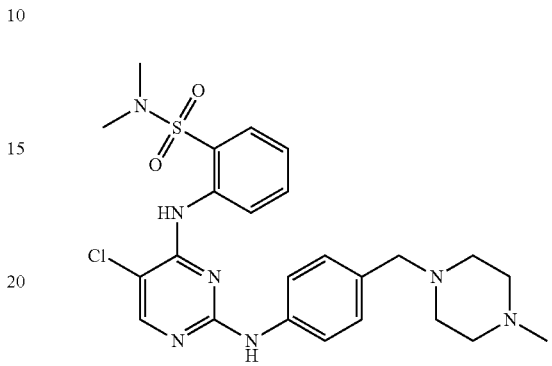

Figure 8:
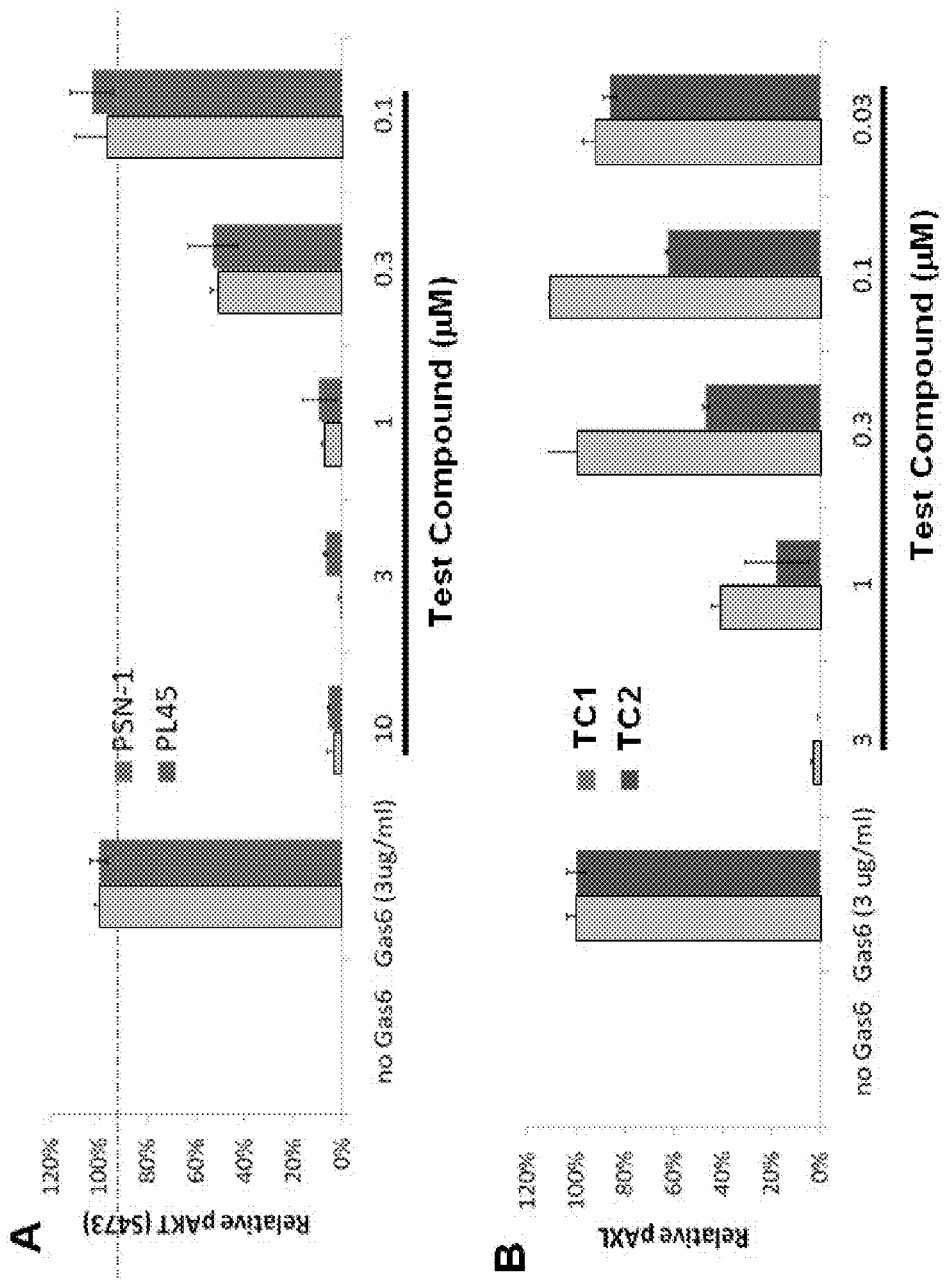
FIG. 8 shows in panel A representative data on the inhibition of phosphorylation of Akt in pancreatic cancer cell lines by representative disclosed compound, and in panel B shows representative data on the inhibition of autophosphorylation of Axl by representative disclosed compounds.

To further explore the activity of a representative compound, 2-((5-chloro-2-((4-((4-methylpiperazin-1-yl)methyl)phenyl)amino)pyrimidin-4-yl)amino)-N,N-dimethylbenzenesulfonamide, of inhibiting Axl in a cell line system, the effect of the test compound on Akt phosphorylation (at the Ser473 position) was determined. The effect on Akt phosphorylation was assessed in two cell-lines (see FIG. 8A): PSN-1 and PL45. The overall method was as described above. Briefly, the cells were treated as indicated and lysates from these treatments were analyzed for phosphorylated Akt (Ser473) as described above. The treatments are as indicated in FIG. 8A, were as follows: negative control (no test compound or Gas6 treatment), treatment with Gas6 only (no test compound), and treatment with different concentrations of test compound in the presence of Gas6. The data are shown in FIG. 8A. It can be seen that the test compound effectively inhibited phosphorylated Akt levels in a concentration dependent manner with an IC$_{50}$ of about 300 nM.

The effect of both 2-((5-chloro-2-((4-((4-methylpiperazin-1-yl)methyl)phenyl)amino)pyrimidin-4-yl)amino)-N,N-dimethylbenzenesulfonamide and 2-((5-chloro-2-((4-((4-methylpiperazin-1-yl)methyl)phenyl)amino)pyrimidin-4-yl)amino)-N,N-dimethylbenzamide (labeled as "TC1" and "TC2", respectively in FIG. 8B) on inhibition of autophosphorylation of Axl is shown in FIG. 8B.

Collectively, the data from these pharmacodynamic endpoint assays show that the test compound dramatically inhibited Akt signaling (pAKT 5473) downstream of GAS6 stimulation in pancreatic cancer cell lines, as well as autophosphorylation of Axl itself.

Figure 9:
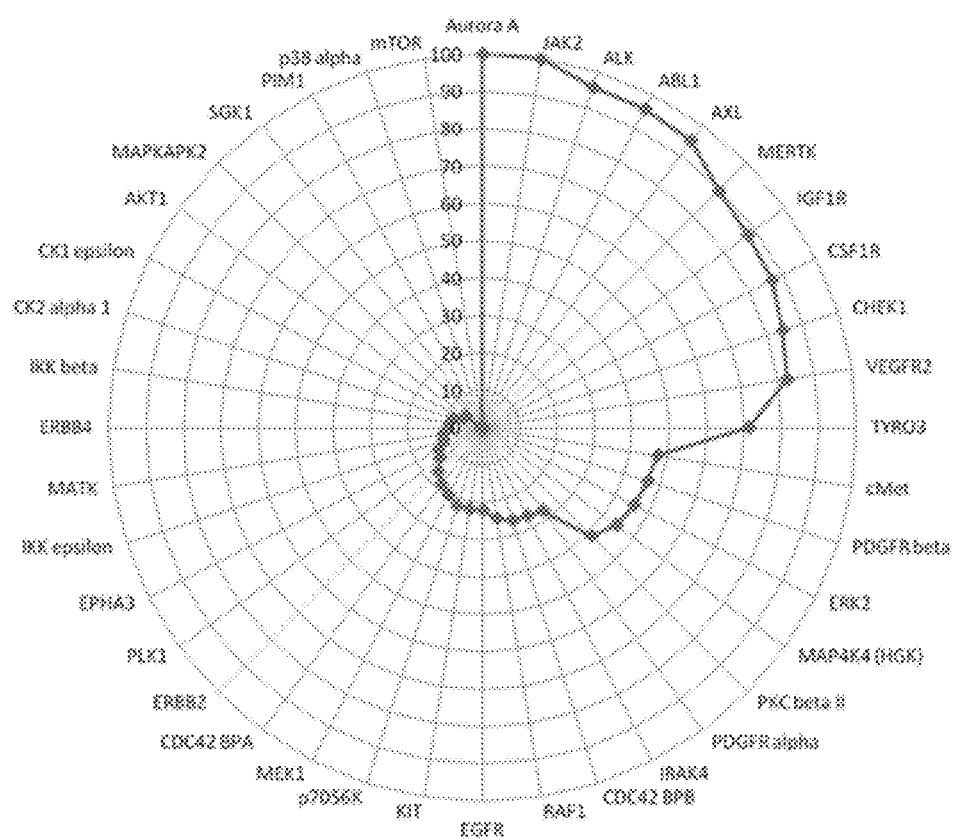
FIG. 9 shows representative data on kinase profiling for a representative disclosed compound.

48. Kinase Profiling of 2-((5-chloro-2-((4-((4-methylpiperazin-1-yl)methyl)phenyl)amino)pyrimidin-4-yl)amino)-N,N-dimethylbenzenesulfonamide The specificity of kinase inhibition was assessed with a representative compound, 2-((5-chloro-2-((4-((4-methylpiperazin-1-yl)methyl)phenyl)amino)pyrimidin-4-yl)amino)-N,N-dimethylbenzenesulfonamide, by determining the activity of this test compound against a panel of protein kinases. Kinase profiling was performed against a focus panel of kinases relevant to PDK1 signaling and other known oncogenic kinases. The panel comprised 75 distinct protein kinases, and data are shown for a subset of 39 kineases (see FIG. 9). The activity profiling as performed at 200 nM of test compound with ATP at K$_m$ apparent for each kinase, and the percent inhibition at that concentration was determined for each. The results from this screen confirmed good activity against Axl and the related members of the TAM family of kinases. In addition, significant activity was observed against the Aurora and JAK family of kinases.

Figure 10:
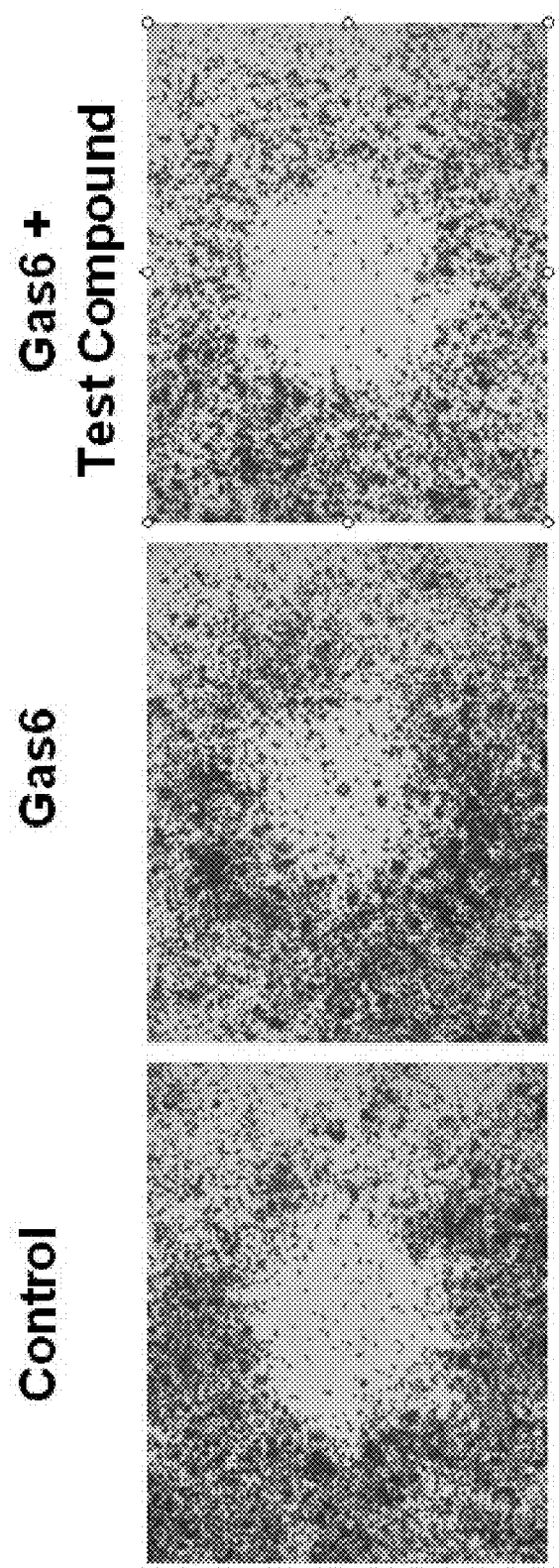
FIG. 10 shows representative data on the inhibition of cell migration by a representative disclosed compound.

49. Inhibition of Cell Migration BY 2-((5-chloro-2-((4-((4-methylpiperazin-1-yl)methyl)phenyl)amino)pyrimidin-4-yl)amino)-N,N-dimethylbenzenesulfonamide The inhibition of cell migration by of 2-((5-chloro-2-((4-((4-methylpiperazin-1-yl)methyl)phenyl)amino)pyrimidin-4-yl)amino)-N,N-dimethylbenzenesulfonamide (labeled as "Test Compound" in the figure) is shown in FIG. 10 Cells were seeded onto collagen I Platypus plates (Platyplus Technologies, LLC, Madison, Wis.). In this system, a gel prevents attachment of cells in a circle. The gel dissolves by exposure to the media, allowing cells to migrate into the open area. Cells migrated for 18 hours before fixation and staining. Assays were prepared with and without Gas6 (3 mg/ml) and Test Compound treatments as indicated in the figure. The extent of cell migration was determined by measuring the open surface in the inner circle of the well. The data show that, consistent with the known function of Axl, the test compound inhibited Gash-induced migration and invasion of pancreatic cancer cells in this in vitro system.

Figure 11:
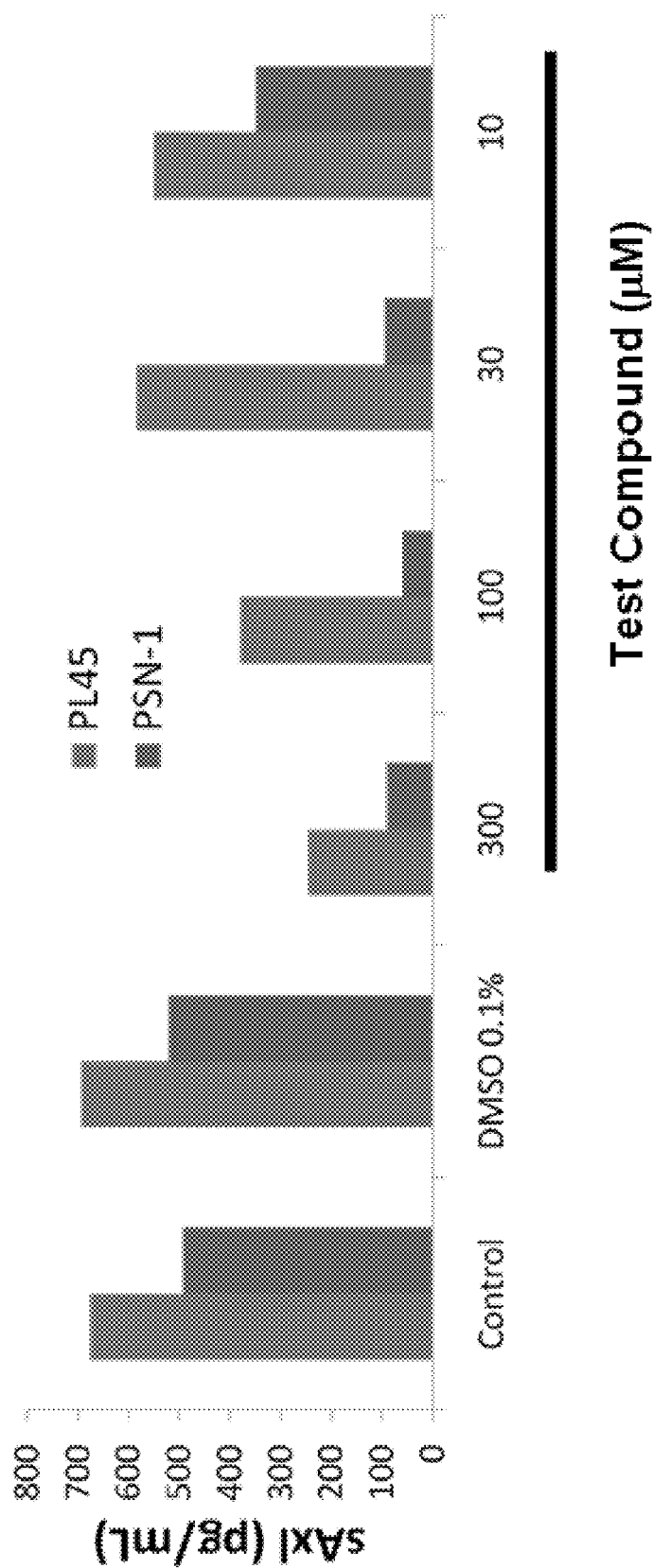
FIG. 11 shows representative data on the inhibition of release of sAxl by a representative disclosed compound.

50. Inhibition of Release of sAxl BY 2-((5-chloro-2-((4-((4-methylpiperazin-1-yl)methyl)phenyl)amino)pyrimidin-4-yl)amino)-N,N-dimethylbenzenesulfonamide The inhibition of the release of sAxl by of 2-((5-chloro-2-((4-((4-methylpiperazin-1-yl)methyl)phenyl)amino)pyrimidin-4-yl)amino)-N,N-dimethylbenzenesulfonamide (labeled as "Test Compound" in the figure) is shown in FIG. 11. Cell lines were plated and incubated overnight as described above. The inhibition on the release of sAxl was tested in the pancreatic cancer cell lines PL45 and PSN-1 as indicated in the figure. The following day the media was changed to serum-free and the cells were treated as indicated as indicated. After 24 hours, the media from the treatments were analyzed for sAxl (R&D Systems, Minneapolis, Minn.).

The proteolytic processing of the extracellular domain of the Axl receptor is a known event downstream of Axl activation and results in the release of soluble Axl (sAxl) into the cell culture media (in vitro) or into the blood stream (in vivo). The data show that sAxl levels can function as a biomarker for target inhibition. Indeed, conditioned media from pancreatic cancer cell lines treated with the test compound showed significant dose-dependent reductions in sAxl levels compared to the vehicle treated controls.

51. Inhibition of Pancreatic Cancer Cell Growth (2D and 3D Culture)

Figure 13:
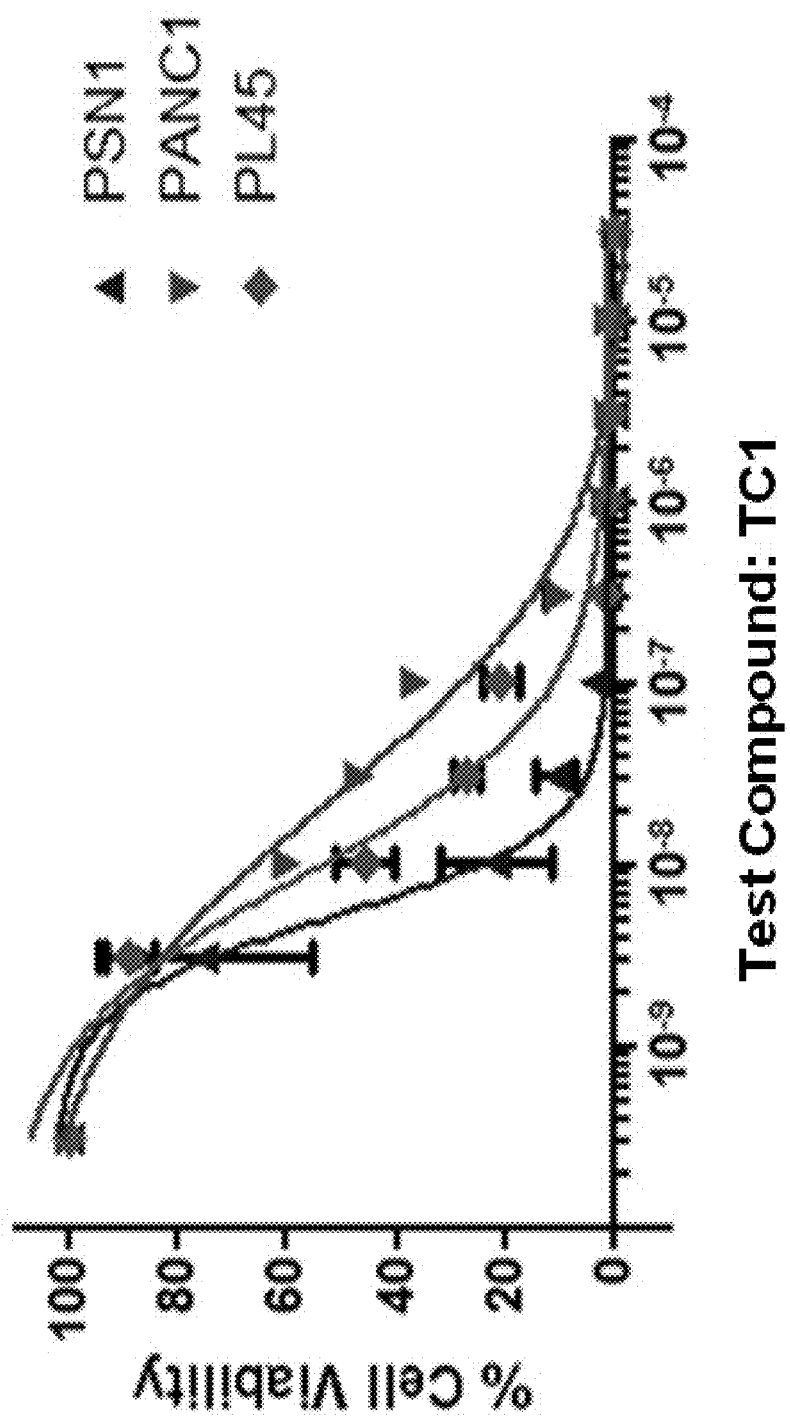
FIG. 13 shows representative data on the inhibition of cell viability in pancreatic cancer cell lines by a representative disclosed compound.

Cell viability was measured in three pancreatic cancer cell lines (PSN-1, PANC-1, and PL45). Cells were grown under conditions as described above in both standard culture (2-D) and in a 3-D culture systems (SCWAX 3-D culture system; InfiniteBio, Inc., San Jose, Calif.). Cell viability following treatment with compounds was determined using the assay system described above. The cells were treated with the indicated compounds for 96 hours. $IC_{50}$ values were calculated as described above and are given in mM. The data are given in FIG. 12. A $IC_{50}$ curve is shown for of 2-((5-chloro-2-((4-((4-methylpiperazin-1-yl)methyl)phenyl)amino)pyrimidin-4-yl)amino)-N,N-dimethylbenzenesulfonamide in FIG. 13 for several pancreatic cancer cell lines (the compound is indicated as TC1 in the figure). The test compounds were as shown in Table III below. The data show that in both 2D and 3D cell proliferation assays, the test compounds significantly inhibited pancreatic cancer cell growth at concentrations as low as 30 nM.

TABLE III

| Test compound Designation | Structure |
|---|---|
| TC1 | [structure] |
| TC2 | [structure] |

TABLE III-continued
| Test compound Designation | Structure |
|---|---|
| TC3 | 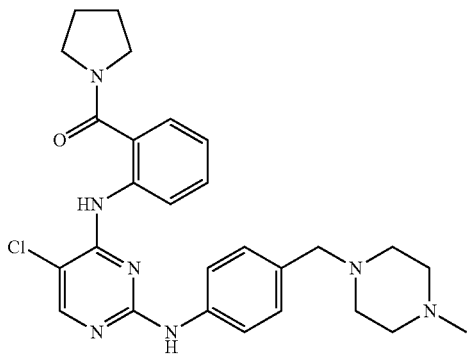 [SMILES: CN1CCN(Cc2ccc(Nc3ncc(Cl)c(Nc4ccccc4C(=O)N4CCCC4)n3)cc2)CC1] |
| TC4 | 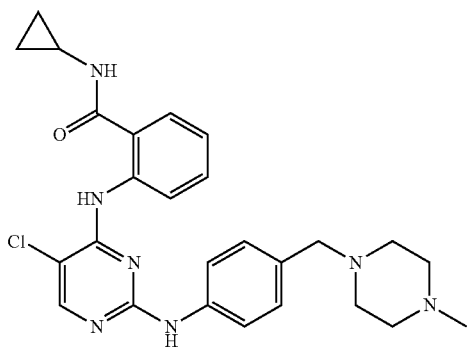 [SMILES: CN1CCN(Cc2ccc(Nc3ncc(Cl)c(Nc4ccccc4C(=O)NC4CC4)n3)cc2)CC1] |
| TC5 | 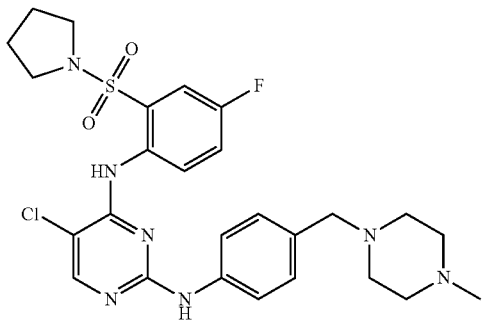 |
| TC6 | 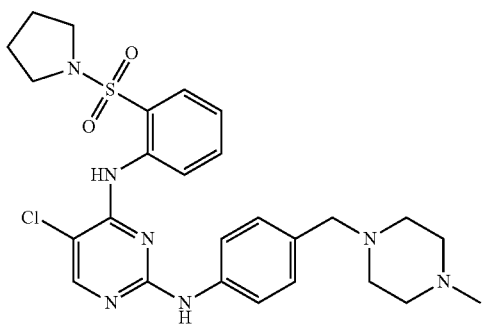 [SMILES: CN1CCN(Cc2ccc(Nc3ncc(Cl)c(Nc4ccccc4S(=O)(=O)N4CCCC4)n3)cc2)CC1] |

TABLE III-continued

| Test compound Designation | Structure |
|---|---|
| TC7 | 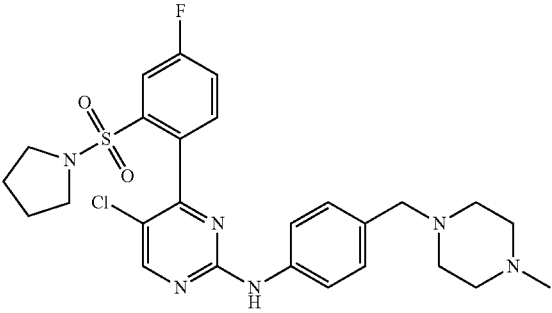 [SMILES: CN1CCN(Cc2ccc(Nc3ncc(Cl)c(-c4ccc(F)cc4S(=O)(=O)N4CCCC4)n3)cc2)CC1] |

52. Compound Activity in Cell Viability Assay

The ability of compounds to inhibit the viability of cultured cells was determined using the cell viability assay described above. Activity data for representative compounds is shown below in Table IV for the compounds was tested in the indicated cell lines (PL-45, PANC-1, PSN-1, HepG2, and A546). $IC_{50}$ values were determined as described above. If $IC_{50}$ value is indicated as "n.d.", it means that the compound was assayed in the indicated cell line. The compound number corresponds to the numbering used in Table I.

TABLE IV

| | | Cell Viability Assay ($IC_{50}$, µM) | | | | |
|---|---|---|---|---|---|---|
| No. | Structure | PL45 | PANC-1 | PSN-1 | HepG2 | A549 |
| 1 | 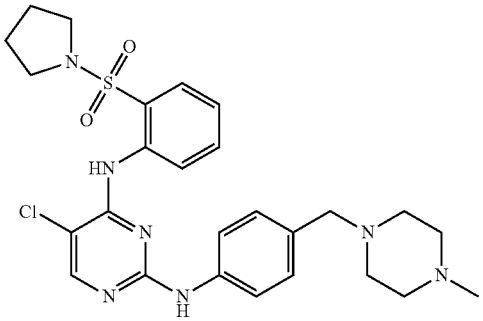 [SMILES: CN1CCN(Cc2ccc(Nc3ncc(Cl)c(Nc4ccccc4S(=O)(=O)N4CCCC4)n3)cc2)CC1] | 0.047 | 0.034 | 0.002 | 0.121 | 0.002 |
| 2 | 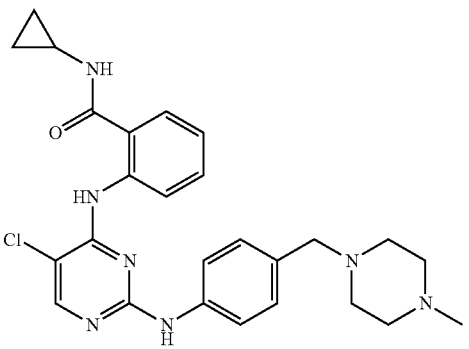 [SMILES: CN1CCN(Cc2ccc(Nc3ncc(Cl)c(Nc4ccccc4C(=O)NC4CC4)n3)cc2)CC1] | 0.003 | 0.303 | 0.064 | 0.303 | 0.003 |

TABLE IV-continued

| No. | Structure | Cell Viability Assay (IC$_{50}$, μM) | | | | |
| --- | --- | --- | --- | --- | --- | --- |
| | | PL45 | PANC-1 | PSN-1 | HepG2 | A549 |
| 3 | 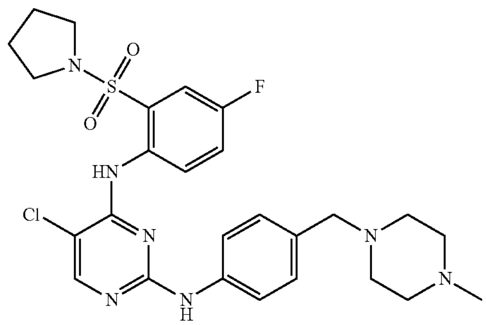 [SMILES: CN1CCN(Cc2ccc(Nc3ncc(Cl)c(Nc4ccc(F)cc4S(=O)(=O)N4CCCC4)n3)cc2)CC1] | 0.017 | 0.093 | 0.009 | 0.043 | 0.004 |
| 4 | 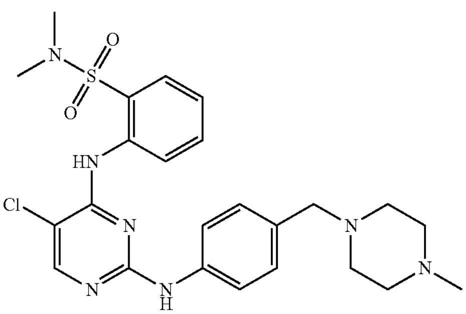 [SMILES: CN1CCN(Cc2ccc(Nc3ncc(Cl)c(Nc4ccccc4S(=O)(=O)N(C)C)n3)cc2)CC1] | 0.048 | 0.038 | 0.006 | 0.006 | 0.008 |
| 5 | 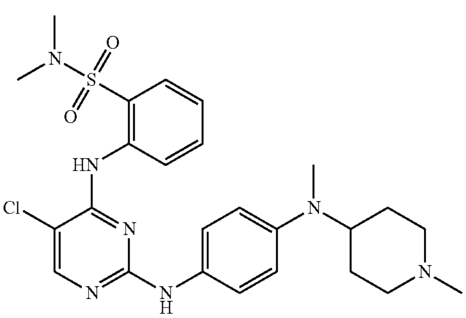 [SMILES: CN1CCC(N(C)c2ccc(Nc3ncc(Cl)c(Nc4ccccc4S(=O)(=O)N(C)C)n3)cc2)CC1] | 0.37 | 0.08 | 0.41 | n.d. | n.d. |
| 6 | 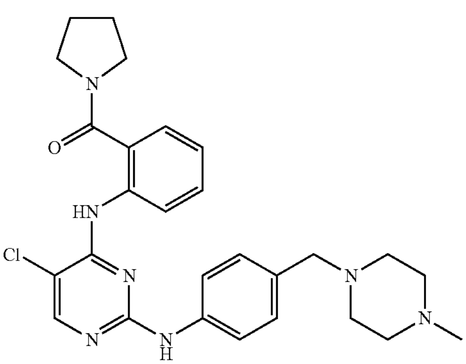 [SMILES: CN1CCN(Cc2ccc(Nc3ncc(Cl)c(Nc4ccccc4C(=O)N4CCCC4)n3)cc2)CC1] | 0.014 | 0.096 | 0.021 | 0.194 | 0.007 |

TABLE IV-continued
| | | Cell Viability Assay (IC$_{50}$, μM) | | | | |
|---|---|---|---|---|---|---|
| No. | Structure | PL45 | PANC-1 | PSN-1 | HepG2 | A549 |
| 7 | 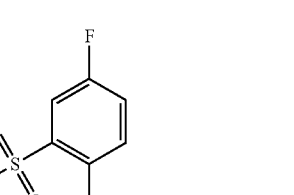 | 0.095 | 0.142 | 0.070 | 0.057 | 0.019 |
| 9 | 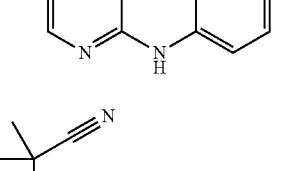 | 0.426 | 0.481 | 0.192 | 0.527 | 0.077 |
| 11 | 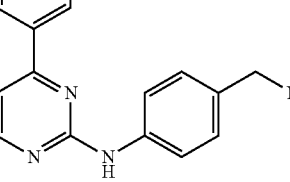 | 8.21 | 5.78 | 2.55 | n.d. | n.d. |
| 12 | 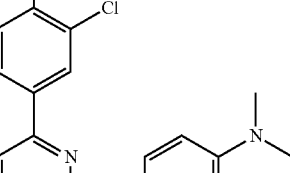 | 13.7 | 10.9 | 6.71 | n.d. | n.d. |
| 13 | 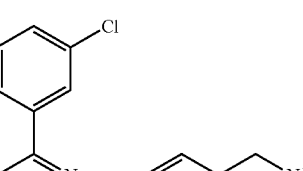 | 4.82 | 7.60 | 2.66 | n.d. | n.d. |

TABLE IV-continued

| No. | Structure | Cell Viability Assay (IC$_{50}$, µM) | | | | |
| --- | --- | --- | --- | --- | --- | --- |
| | | PL45 | PANC-1 | PSN-1 | HepG2 | A549 |
| 14 | 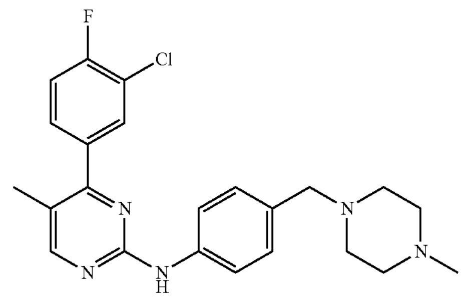 | 14.4 | 7.75 | 4.27 | n.d. | n.d. |

53. 2-((5-chloro-2-((4-((4-methylpiperazin-1-yl)methyl)phenyl)amino)pyrimidin-4-yl)amino)—N,N-dimethylbenzenesulfonamide Activity in Tumor Xenograft Animal Model The in vivo activity of the foregoing compound was assessed in a tumor xenograft model in mouse. PSN-1 cells were cultured as described above and harvested. Cells (2 to 5×10$^6$ in 100 µl culture media) were implanted subcutaneously in the right hind flank of athymic nu/nu nude mice (5 to 6 weeks old, 18-22 g). Following implantation, the tumors are allowed to grow to 100 mm$^3$ before the animals are randomized into treatment groups (vehicle and test compound). Day 1 of study corresponds to the day that the animals receive their first dose of test compound (2-((5-chloro-2-((4-((4-methylpiperazin-1-yl)methyl)phenyl)amino)pyrimidin-4-yl)amino)-N,N-dimethylbenzenesulfonamide). The vehicle for this study was 5% EtOH, 45% PEG 400, and 50% water, and animals were dosed with either vehicle or test compound dissolved in this vehicle by oral gavage. The dose level was 50 mg/kg and dosing frequency was daily (M-F) with the test compound with recovery on the weekend.

Figure 14:
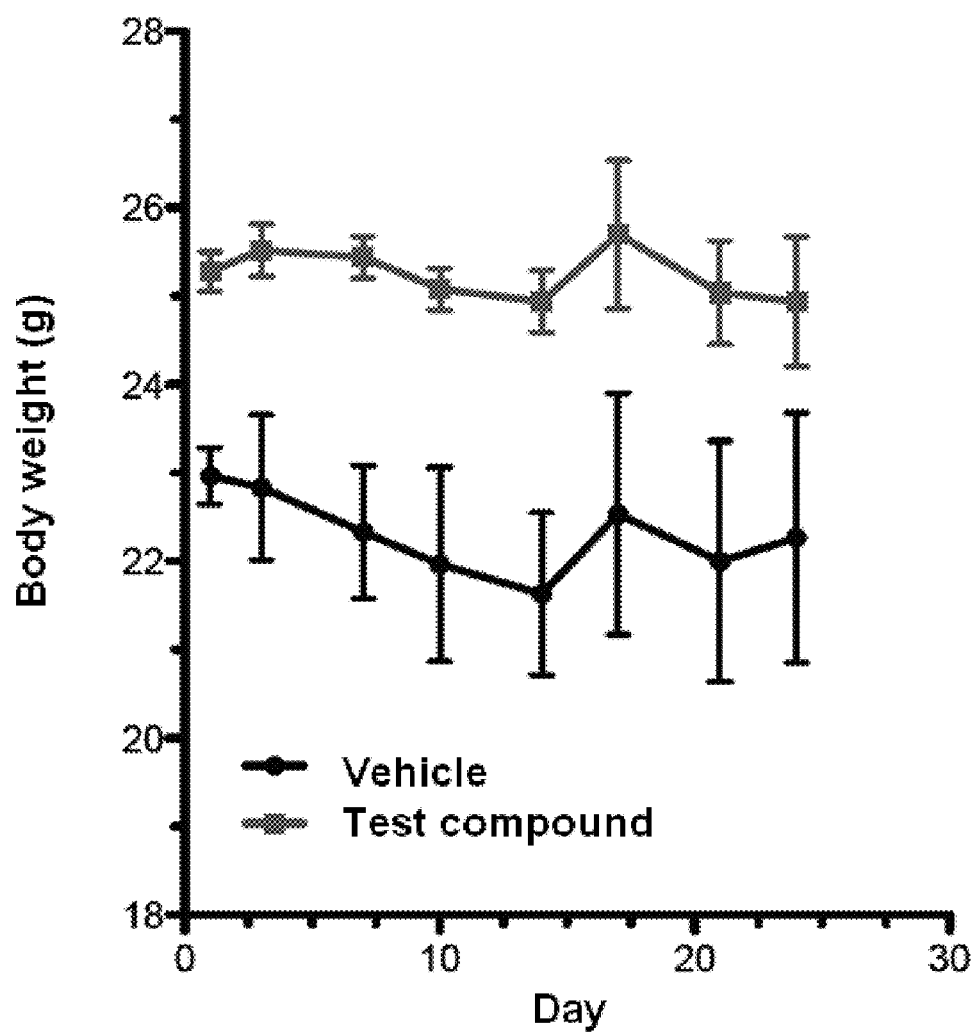
FIG. 14 shows representative data for the effect of a disclosed compound on body weight in a tumor xenograft animal model.
Figure 15:
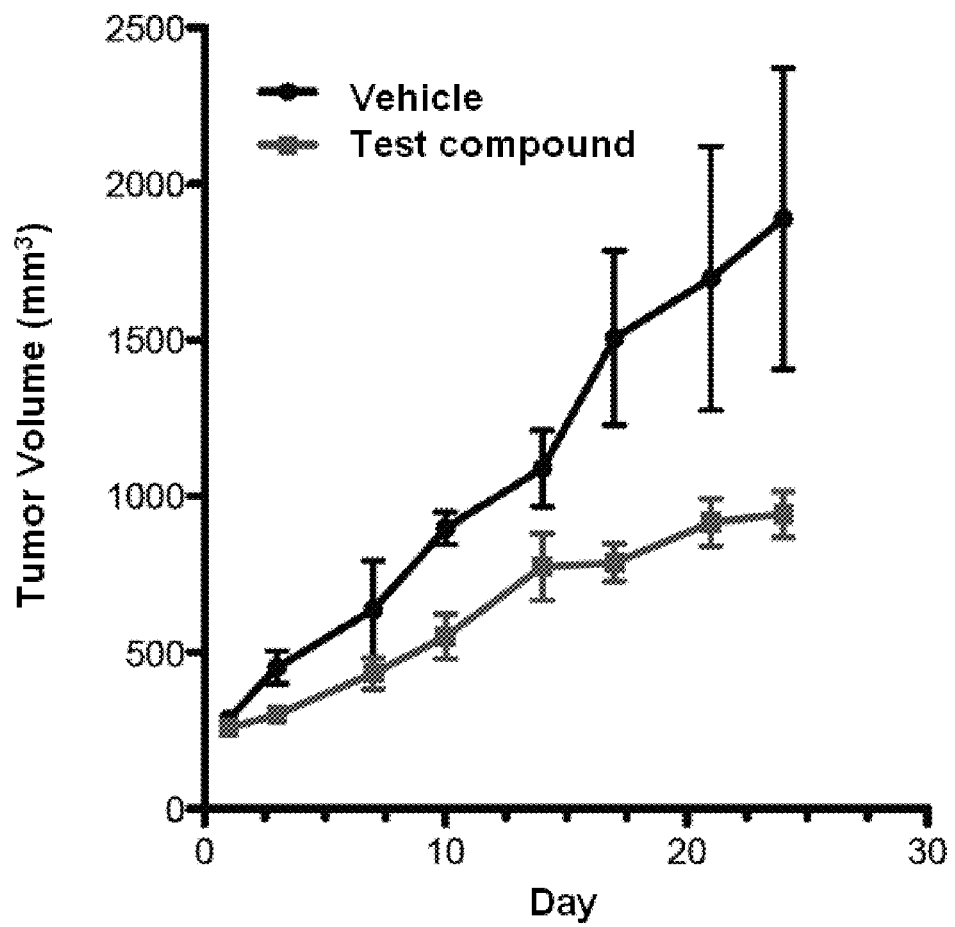
FIG. 15 shows representative data for the effect of a disclosed compound on tumor volume in a tumor xenograft animal model.

Tumor volumes and body weights were measured twice a week, and the data are provided in FIGS. 14 and 15. The data show that at the dose level used, the test compound had no apparent impact on body weight, suggesting that this dose level had no apparent significant adverse effect (FIG. 14). The test compound was efficacious in limiting tumor growth, achieving about a 50% reduction in tumor volume at this dose level during this dosing period (FIG. 15).

Figure 16:
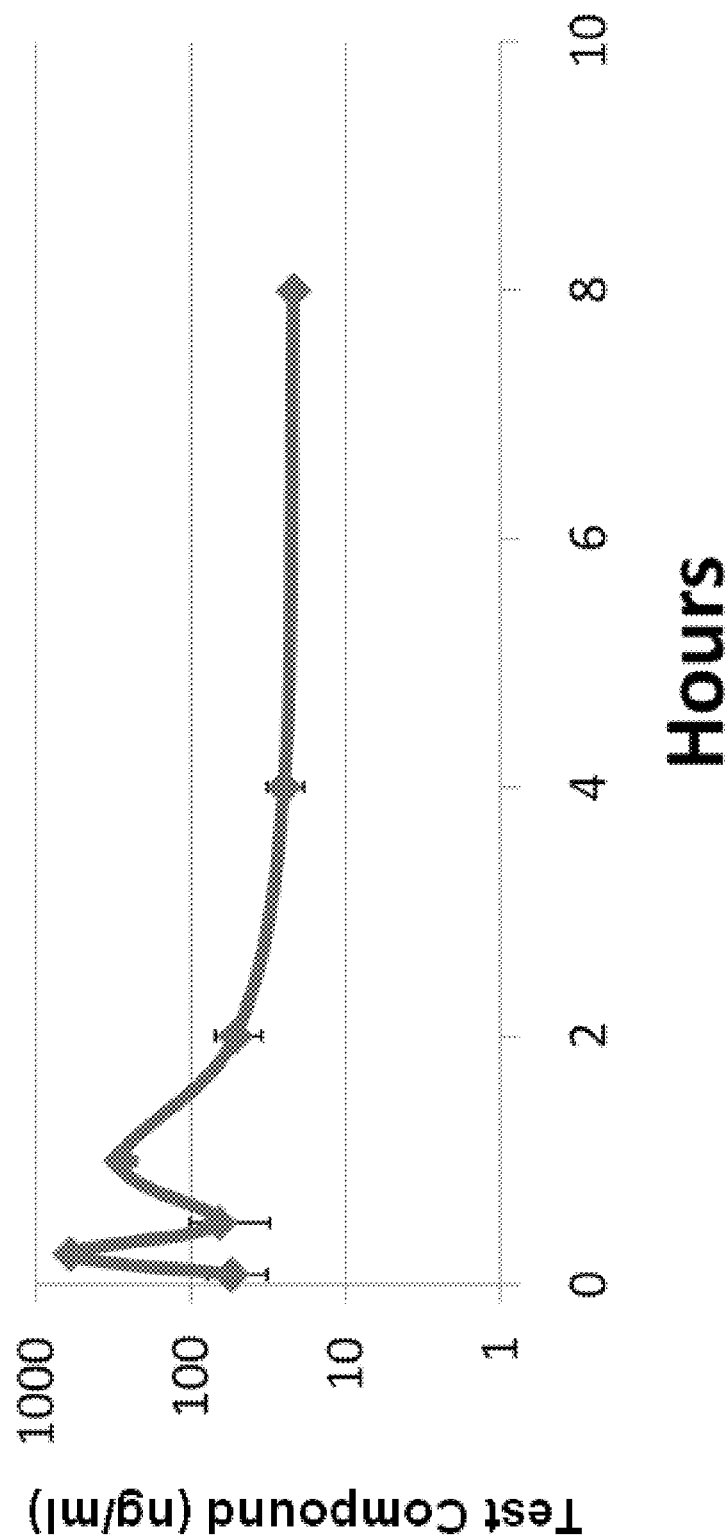
FIG. 16 shows representative data on the pharmacokinetic profile of a representative disclosed compound.

54. Pharmacokinetics of 2-((5-chloro-2-((4-((4-methylpiperazin-1-yl)methyl)phenyl)amino)pyrimidin-4-yl)amino)-N,N-dimethylbenzenesulfonamide Mice were dosed orally with 50 mg/kg of the title compound. Blood was collected at the indicated time points (see FIG. 16). Plasma samples were analyzed by mass spectrometry and standard PK parameters were calculated from these data as shown Table V below.

TABLE V

| | |
| --- | --- |
| T$_{max}$ (hr) | 0.25 |
| C$_{max}$ (ng/mL) | 604 |
| AUC$_{0-t}$ (hr*ng/mL) | 507 |
| T$_{1/2}$ (hr) | 1.1 |

55. Prophetic Assay of Inhibition of Axl Binding

Although, the activity of compounds was routinely assessed the activity assay described above, the selection of a lead compound frequently involves assessment of the compound in secondary assays. The following example of an in vitro effect of the disclosed compounds is prophetic. An examples of a typical in vitro assay methods for a secondary assay to determine the activity of the disclosed compounds in inhibiting binding at the active site of Axl activity is given herein. The disclosed compounds can be assayed using as the secondary assay a time resolved-FRET LanthaScreen Kinase Binding Assay (Invitrogen Corporation, Carlsbad, Calif.). This assay evaluates the ability of the test compound to compete with a fluorescently-labeled tracer molecule to bind in the ATP pocket of a kinase. The assay signal is generated when a Europium-conjugated anti-His tag antibody (Invitrogen) bound to the His-tagged kinase produces a TR-FRET signal with the tracer molecule bound in the ATP pocket of the kinase. In this reaction, 5 µl of test compound is incubated with 5 µl of a kinase/antibody mixture, followed by the addition of 5 µl of Kinase Tracer 236 (Invitrogen). Final concentrations for the assay were (15 µl total volume): 1% DMSO, 5 nM Axl, 2 nM Eu-Anti-His Antibody, and 6 nM Kinase Tracer 236. The Axl enzyme used in this assay is recombinant human Axl kinase (catalytic domain, amino acids 473-894) with a histidine tag (Invitrogen). After 60 minutes of incubation at room temperature, the TR-FRET signal was measured on an EnVision microplate reader.

56. Prophetic In Vivo Activity in a Tumor Xenograft Model

The following example of the in vivo effect of the disclosed compounds are prophetic. Generally agents which inhibit the PI3K/Akt pathway, including Axl kinase inhibitors, display efficacy in preclinical models of cancer. In vivo effects of the compounds described in the preceding examples are expected to be shown in various animal models of cancer known to the skilled person, such as tumor xenograft models. These models are typically conducted in rodent, most often in mouse, but may be conducted in other animal species as is convenient to the study goals. Compounds, products, and compositions disclosed herein are expected to show in vivo effects in various animal models of cancer known to the skilled person, such as mouse tumor xenograft models.

In vivo effects of compounds can be assessed with in a mouse tumor xenograft study, one possible study protocol is described herein. Briefly, cells (2 to 5×10⁶ in 100 culture media) were implanted subcutaneously in the right hind flank athymic nu/nu nude mice (5 to 6 weeks old, 18-22 g). For test compounds of the present invention, a typical cell-line used for the tumor xenograft study would be PSN-1 cells. Other suitable cell-lines for these studies are PANC-1 and PL45 cells. The cells are cultured prior to harvesting for this protocol as described herein.

Following implantation, the tumors are allowed to grow to 100 mm³ before the animals are randomized into treatment groups (e.g. vehicle, positive control and various dose levels of the test compound; the number of animals per group is typically 8-12. Day 1 of study corresponds to the day that the animals receive their first dose. The efficacy of a test compound can be determined in studies of various length dependent upon the goals of the study. Typical study periods are for 14, 21 and 28-days. The dosing frequency (e.g. whether animals are dosed with test compound daily, every other day, every third day or other frequencies) is determined for each study depending upon the toxicity and potency of the test compound. A typical study design would involve dosing daily (M-F) with the test compound with recovery on the weekend. Throughout the study, tumor volumes and body weights are measured twice a week. At the end of the study the animals are euthanized and the tumors harvested and frozen for further analysis.

For example, compounds having a structure represented by a formula:

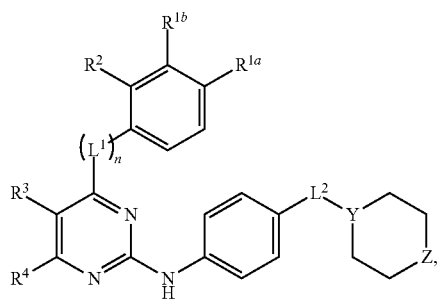

wherein $L^1$ is selected from O and $NR^5$, wherein n is 0 or 1; wherein $R^5$ is selected from is selected from hydrogen and C1-C6 alkyl; wherein $L^2$ is selected from $CH_2$ and $NCH_3$, provided that $L^2$ is $CH_2$ when Y is N; wherein Y is selected from CH or N; wherein Z is selected from O, $NR^6$ and $CH_2$; wherein $R^6$ is selected from hydrogen and $CH_3$; wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalkyl, and $NH(C=O)R^7$; wherein $R^7$ is selected from hydrogen and C1-C6 alkyl; wherein $R^2$ is selected from hydrogen, C1-C6 alkyl, $SO_2R^8$, and $(C=O)R^8$; wherein $R^8$ is selected from hydrogen, C1-C6 alkyl, C3-C6 cycloalkyl, C3-C6 heterocycloalkyl, and $NR^{10}R^{11}$; wherein $R^{10}$ is selected from hydrogen, C1-C6 alkyl, and C3-$C_6$ cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring; wherein $R^3$ is selected from hydrogen, halogen, OH, CN, C1-C6 alkyl, C1-C6 haloalkyl, C1-C6 polyalkyl, C3-C6 cycloalkyl, C3-C6 haloalkyl, C3-C6 polyhaloalkyl, and C3-C6 heterocycloalkyl; and wherein $R^4$ is selected from hydrogen, halogen, $Ar^1$, C1-C6 alkyl, C3-C6 cycloalkyl, and C3-C6 heterocycloalkyl; wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino; wherein $R^{12}$ is selected from C1-C6 alkyl and C3-C6 cycloalkyl; or a pharmaceutically acceptable salt, hydrate, solvate, or polymorph thereof, are expected to show such in vivo effects.

Moreover, compounds prepared using the disclosed synthetic methods are also expected to show such in vivo effects.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

---

What is claimed is:

1. A compound having the following structure (I):

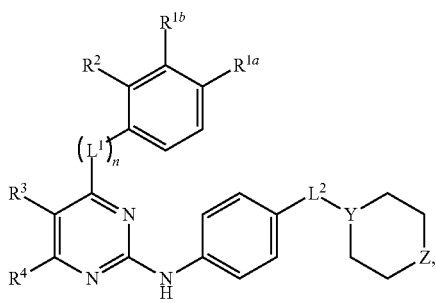

wherein $L^1$ is selected from O and $NR^5$, wherein n is 0 or 1;
wherein $R^5$ is selected from hydrogen and C1-C6 alkyl;
wherein $L^2$ is selected from $CH_2$ and $NCH_3$, provided that $L^2$ is $CH_2$ when Y is N;
wherein Y is selected from CH or N;
wherein Z is selected from $NR^6$ and $CH_2$;
wherein $R^6$ is selected from hydrogen and $CH_3$;
wherein each of $R^{1a}$ and $R^{1b}$ is independently selected from hydrogen, halogen, OH, CN, $SO_2CH_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalky, and $NH(C=O)R^7$;
wherein $R^7$ is selected from hydrogen and C1-C6 alkyl;
wherein $R^2$ is selected from hydrogen, C1-C6 alkyl, $SO_2R^8$ and $C=OR^8$;
wherein $R^8$ is selected from hydrogen, C1-C6 alkyl, C3-C6 cycloalkyl, C3-C6 heterocycloalkyl, and $NR^{10}R^{11}$;
wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring:
wherein $R^3$ is a fluoro; and
wherein $R^4$ is selected from hydrogen, halogen, $Ar^1$, C1-C6 alkyl, C3-C6 cycloalkyl, and C3-C6 heterocycloalkyl;
wherein $Ar^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino;

wherein $R^{12}$ is selected from C1-C6 alkyl and C3-C6 cycloalkyl;

or a pharmaceutically acceptable salt, stereoisomer, hydrate or solvate thereof.

2. The compound of claim 1, wherein $R^{1b}$ is selected from hydrogen and halogen.

3. The compound of claim 1, wherein $R^4$ is hydrogen.

4. The compound of claim 1, wherein the compound is selected from:

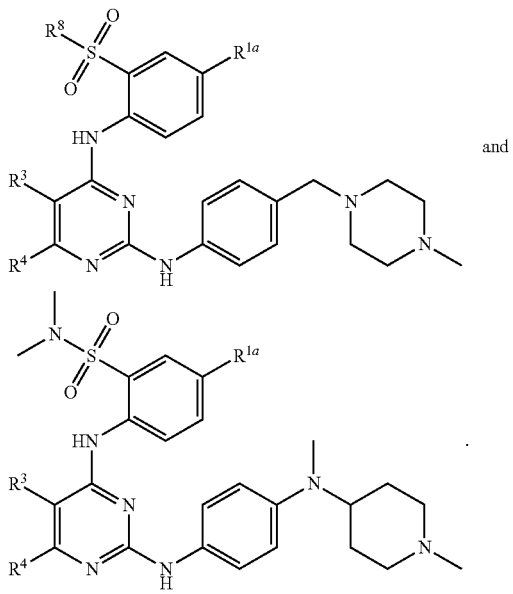

and

5. A method for the treatment of cancers of the lung or pancreas in a mammal, wherein the cancer of the lung or pancreas is associated with AXL receptor kinase dysfunction, wherein the method comprises the step of administering to the mammal an effective amount of at least one compound having the following structure (I):

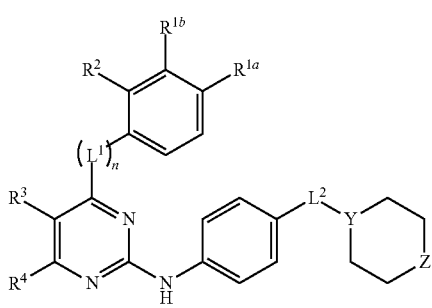

wherein $L^1$ is selected from O and $NR^5$, wherein n is 0 or 1;
wherein $R^5$ is selected from hydrogen and C1-C6 alkyl;
wherein $L^2$ is selected from $CH_2$ and $NCH_3$, provided that $L^2$ is $CH_2$ when Y is N;

wherein Y is selected from CH or N;
wherein Z is selected from $NR^6$ and $CH_2$;
    wherein $R^6$ is selected from hydrogen and $CH_3$;
wherein each of $R^{1a}$ and $R^{1b}$ is independently selected from hydrogen, halogen, OH, CN, $SO_2CH_3$, C1-C6 alkyl, C1-C6 alkoxy, C1-C6 haloalkoxy, C1-C6 polyhaloalkoxy, C1-C6 haloalkyl, C1-C6 polyhaloalkyl, C1-C6 cyanoalky, and $NH(C=O)R^7$;
    wherein $R^7$ is selected from hydrogen and C1-C6 alkyl;
wherein $R^2$ is selected from hydrogen, C1-C6 alkyl, $SO_2R^8$ and $C=OR^8$;
    wherein $R^8$ is selected from hydrogen, C1-C6 alkyl, C3-C6 cycloalkyl, C3-C6 heterocycloalkyl, and $NR^{10}R^{11}$;
        wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring:
wherein $R^3$ is a halogen; and
wherein $R^4$ is selected from hydrogen, halogen, $Ar^1$, C1-C6 alkyl, C3-C6 cycloalkyl, and C3-C6 heterocycloalkyl;
    wherein $Ar^1$ is either phenyl substituted with 0-3 substituents independently selected from cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino;
        wherein $R^{12}$ is selected from C1-C6 alkyl and C3-C6 cycloalkyl;
or a pharmaceutically acceptable salt, stereoisomer, hydrate or solvate thereof.

6. The method of claim 5, further comprising the step of identifying a mammal in need of treatment of a cancer of the lung or pancreas.

7. The method of claim 5, wherein the mammal has been diagnosed with a cancer of the lung or pancreas prior to the administering step.

8. The method of claim 5, wherein the cancer is lung cancer.

9. The method of claim 5, wherein the cancer is pancreatic cancer.

10. The compound of claim 1, wherein $R^{1a}$ and $R^{1b}$ are hydrogen.

11. The compound of claim 1, wherein the compound has one of the following structures:

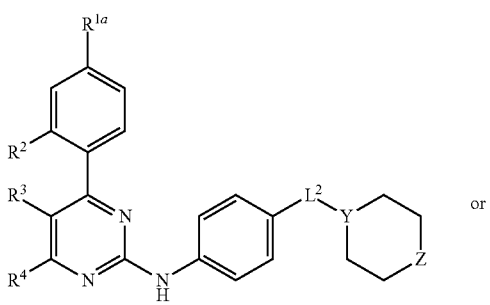

or

-continued
12. The compound of claim 11, wherein $R^4$ is H.
13. The compound of claim 11, wherein Y is N and Z is $NCH_3$.
14. The compound of claim 11, wherein $R^{1a}$ is H or halogen.
15. The compound of claim 11, wherein $R^2$ is —(C=O)$R^8$, —C(=O)$NR^{10}R^{11}$ or —S(=O)$_2R^8$.
16. The compound of claim 15, wherein $R^2$ has one of the following structures:
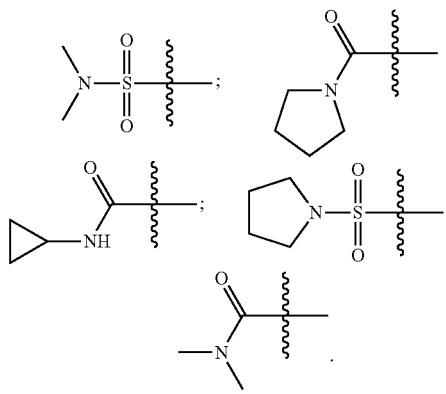
17. A compound having one of the followings structures:
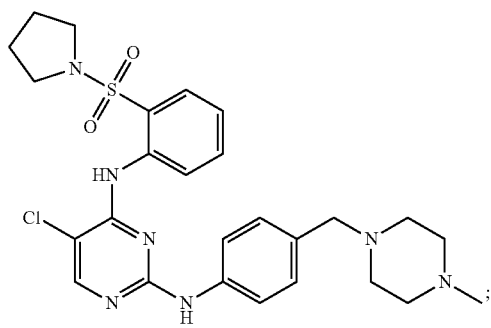
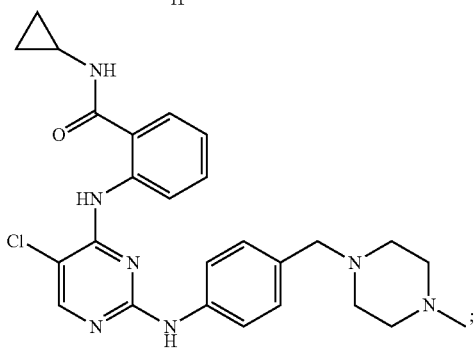
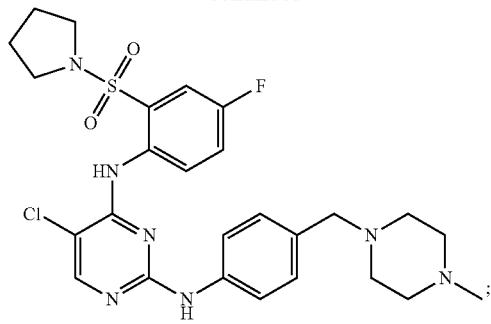
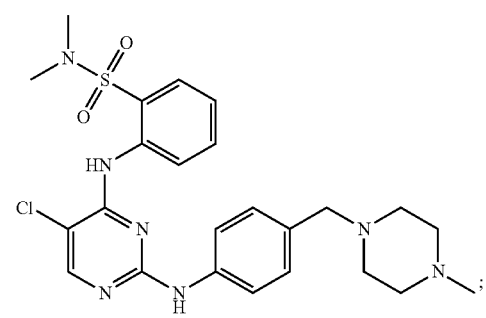
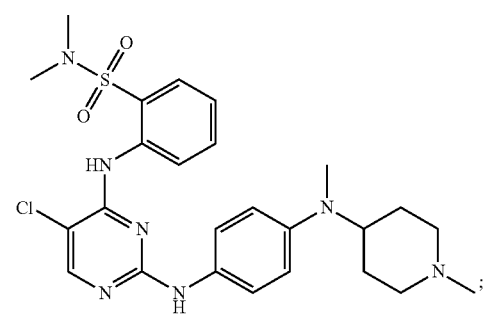
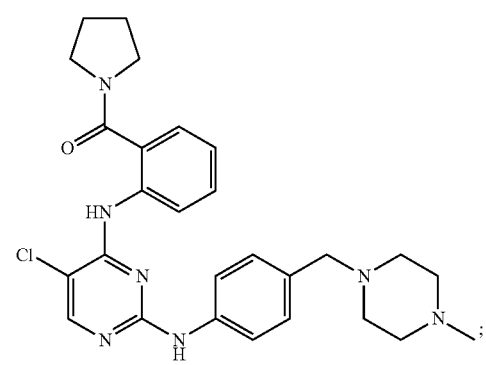
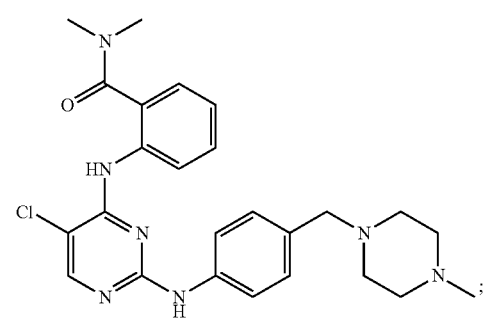

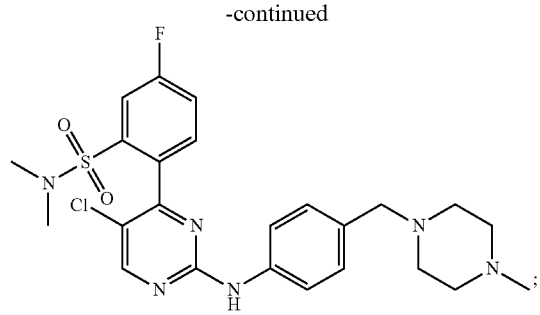

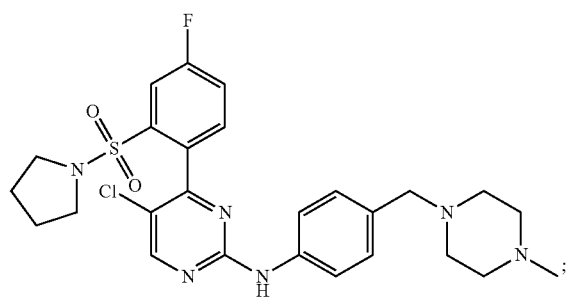

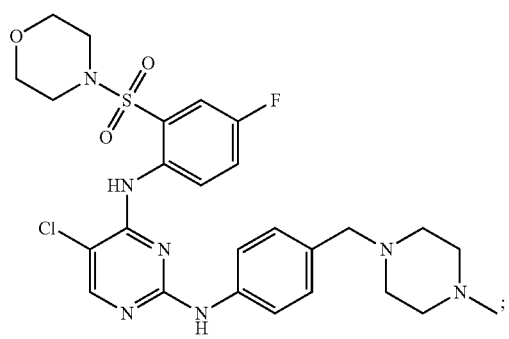

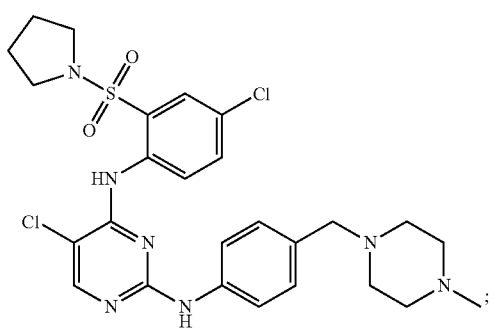

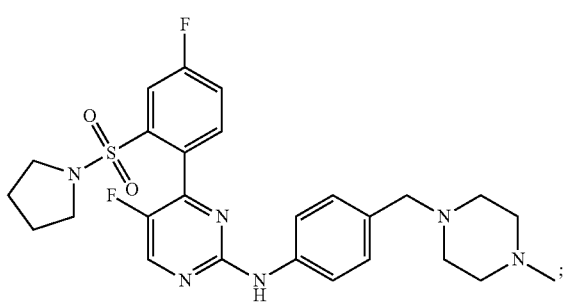

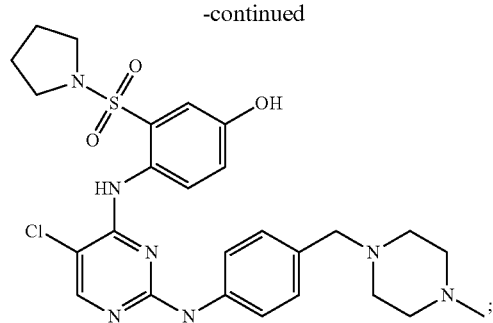

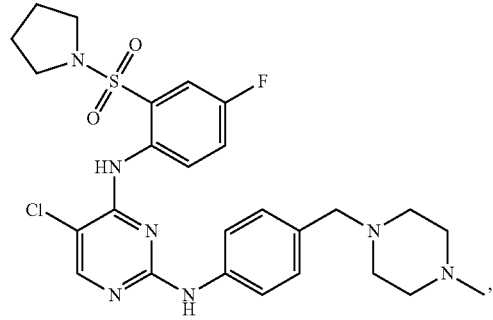

or a pharmaceutically acceptable salt, stereoisomer, hydrate or solvate thereof.

18. The compound of claim 1, wherein $R^{1a}$ is H or halogen.

19. The compound of claim 1, wherein $R^2$ is $SO_2R^8$ and $R^8$ is pyrrolidinyl.

20. The compound of claim 1, wherein $R^2$ is $SO_2R^8$ and $R^8$ is dimethylamino.

21. A compound having one of the following structures:

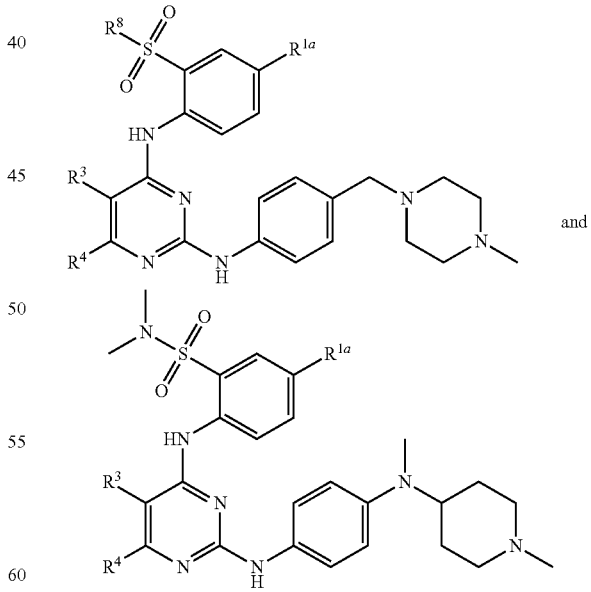

wherein $R^{1a}$ is selected from hydrogen, halogen, OH, CN, $SO_2CH_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalky, and $NH(C=O)R^7$;

wherein $R^7$ is selected from hydrogen and C1-C6 alkyl;
wherein $R^8$ is selected from hydrogen, C1-C6 alkyl, C3-C6 cycloalkyl, C3-C6 heterocycloalkyl, and $NR^{10}R^{11}$;
 wherein $R^{10}$ is selected from hydrogen, C1-C6 alkyl, and C3-C6 cycloalkyl; and wherein $R^{11}$, when present, is selected from hydrogen and C1-C6 alkyl; or $R^{10}$ and $R^{11}$ are covalently bonded and, together with the intermediate nitrogen, comprise an optionally substituted 3-7 membered heterocycloalkyl ring:
wherein $R^3$ is a halogen; and
wherein $R^4$ is selected from hydrogen, halogen, $Ar^1$, C1-C6 alkyl, C3-C6 cycloalkyl, and C3-C6 heterocycloalkyl,
or a pharmaceutically acceptable salt, stereoisomer, hydrate or solvate thereof.

22. The compound of claim 21, wherein $R^3$ is chloro.
23. The compound of claim 21, wherein $R^3$ is fluoro.
24. The compound of claim 21, wherein $R^4$ is hydrogen.
25. The compound of claim 21, wherein $R^{1a}$ is H or halogen.
26. The compound of claim 2, wherein $R^8$ is pyrrolidinyl or dimethylamino.
27. A compound having one of the following structures:

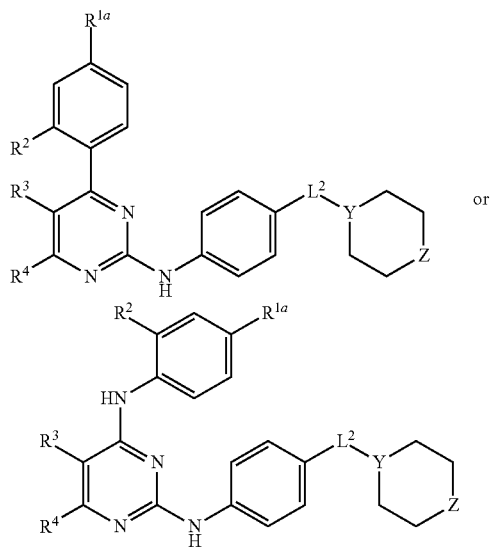

wherein $L^2$ is selected from $CH_2$ and $NCH_3$, provided that $L^2$ is $CH_2$ when Y is N;

wherein Y is selected from CH or N;
wherein Z is selected from $NR^6$ and $CH_2$;
 wherein $R^6$ is selected from hydrogen and $CH_3$;
wherein $R^{1a}$ is selected from hydrogen, halogen, OH, CN, $SO_2CH_3$, C1-C6 alkyl, C1-C6 cyanoalkyl, C1-C6 hydroxyalkyl, C1-C6 alkoxy, C1-C6 haloalkoxy, C1-C6 polyhaloalkoxy, C1-C6 haloalkyl, C1-C6 polyhaloalkyl, C1-C6 cyanoalky, and $NH(C=O)R^7$;
 wherein $R^7$ is selected from hydrogen and C1-C6 alkyl;
 wherein $R^2$ has one of the following structures:

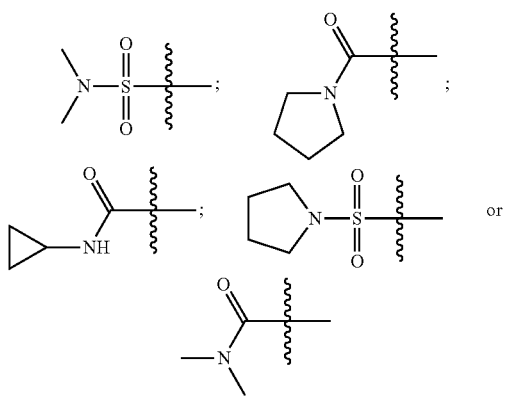

wherein $R^3$ is a halogen; and
wherein $R^4$ is selected from hydrogen, halogen, $Ar^1$, C1-C6 alkyl, C3-C6 cycloalkyl, and C3-C6 heterocycloalkyl;
 wherein $Ar^1$ is either phenyl substituted with 0-3 substituents independently selected from cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino or is monocyclic heteroaryl substituted with 0-3 substituents independently selected from halo, cyano, C1-C6 alkyl, C1-C6 cyanoalkyl, C1-C6 haloalkyoxy, C1-C6 haloalkyl, and C1-C6 polyhaloalkyl, C1-C6 cyanoalkyl, $SO_2R^{12}$, C1-C3 alkyl, C1-C3 alkylamine, and C1-C3 dialkylamino;
  wherein $R^{12}$ is selected from C1-C6 alkyl and C3-C6 cycloalkyl;
or a pharmaceutically acceptable salt, stereoisomer, hydrate or solvate thereof.

28. The compound of claim 27, wherein $R^4$ is hydrogen.
29. The compound of claim 27, wherein $R^3$ is chloro.
30. The compound of claim 27, wherein $R^3$ is fluoro.
31. The compound of claim 27, wherein $R^{1a}$ is H or halogen.

* * * * *

SEQUENCE LISTING

<160> NUMBER OF SEQ ID NOS: 7

<210> SEQ ID NO 1
<211> LENGTH: 21
<212> TYPE: PRT
<213> ORGANISM: Artificial Sequence
<220> FEATURE:
<223> OTHER INFORMATION: Description of Artificial Sequence; note = synthetic construct

<400> SEQUENCE: 1

Leu Gly Glu Gly Glu Phe Gly Val Met Arg Leu Ile Leu Pro Phe Met
1               5                   10                  15

Gly Asn Asp Phe Gly
            20

```
<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 2

Leu Gly Lys Gly Lys Phe Gly Val Leu Arg Leu Tyr Leu Glu Tyr Ala
1               5                   10                  15

Gly Asn Asp Phe Gly
            20

<210> SEQ ID NO 3
<211> LENGTH: 21
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 3

Leu Gly Lys Gly Lys Phe Gly Val Leu Arg Met Tyr Leu Glu Phe Ala
1               5                   10                  15

Gly Asn Asp Phe Gly
            20

<210> SEQ ID NO 4
<211> LENGTH: 270
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 4

Ile Ser Glu Glu Leu Lys Glu Lys Leu Arg Asp Val Met Val Asp Arg
1               5                   10                  15

His Lys Val Ala Leu Gly Lys Thr Leu Gly Glu Gly Glu Phe Gly Ala
            20                  25                  30

Val Met Glu Gly Gln Leu Asn Gln Asp Asp Ser Ile Leu Lys Val Ala
        35                  40                  45

Val Lys Thr Met Lys Ile Ala Ile Cys Thr Arg Ser Glu Leu Glu Asp
    50                  55                  60

Phe Leu Ser Glu Ala Val Cys Met Lys Glu Phe Asp His Pro Asn Val
65                  70                  75                  80

Met Arg Leu Ile Gly Val Cys Phe Gln Gly Ser Glu Arg Glu Ser Phe
                85                  90                  95

Pro Ala Pro Val Val Ile Leu Pro Phe Met Lys His Gly Asp Leu His
            100                 105                 110

Ser Phe Leu Leu Tyr Ser Arg Leu Gly Asp Gln Pro Val Tyr Leu Pro
        115                 120                 125

Thr Gln Met Leu Val Lys Phe Met Ala Asp Ile Ala Ser Gly Met Glu
    130                 135                 140

Tyr Leu Ser Thr Lys Arg Phe Ile His Arg Asp Leu Ala Ala Arg Asn
145                 150                 155                 160

Cys Met Leu Asn Glu Asn Met Ser Val Cys Val Ala Asp Phe Gly Leu
                165                 170                 175

Ser Lys Lys Ile Tyr Asn Gly Asp Tyr Tyr Arg Gln Gly Arg Ile Ala
            180                 185                 190
```

```
Lys Met Pro Val Lys Trp Ile Ala Ile Glu Ser Leu Ala Asp Arg Val
            195                 200                 205

Tyr Thr Ser Lys Ser Asp Val Trp Ser Phe Gly Val Thr Met Trp Glu
        210                 215                 220

Ile Ala Thr Arg Gly Gln Thr Pro Tyr Pro Gly Val Glu Asn Ser Glu
225                 230                 235                 240

Ile Tyr Asp Tyr Leu Arg Gln Gly Asn Arg Leu Lys Gln Pro Ala Asp
                245                 250                 255

Cys Leu Asp Gly Leu Tyr Ala Leu Met Ser Arg Cys Trp Glu
            260                 265                 270

<210> SEQ ID NO 5
<211> LENGTH: 264
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 5

Asn Lys Leu Glu Asp Val Val Ile Asp Arg Asn Leu Leu Ile Leu Gly
1               5                   10                  15

Lys Ile Leu Gly Glu Gly Gly Phe Gly Ser Val Met Glu Gly Asn Leu
            20                  25                  30

Lys Gln Glu Asp Gly Thr Ser Leu Lys Val Ala Val Lys Thr Met Lys
        35                  40                  45

Leu Asp Asn Ser Ser His Arg Glu Ile Glu Glu Phe Leu Ser Glu Ala
    50                  55                  60

Ala Cys Met Lys Asp Phe Ser His Pro Asn Val Ile Arg Leu Leu Gly
65                  70                  75                  80

Val Cys Ile Glu Met Ser Ser Gln Gly Ile Pro Lys Pro Met Val Ile
                85                  90                  95

Leu Pro Phe Met Lys Tyr Gly Asp Leu His Thr Tyr Leu Leu Tyr Ser
            100                 105                 110

Arg Leu Glu Thr Gly Pro Lys His Ile Pro Leu Gln Thr Leu Leu Lys
        115                 120                 125

Phe Met Val Asp Ile Ala Leu Gly Met Glu Tyr Leu Ser Asn Arg Asn
    130                 135                 140

Phe Leu His Arg Asp Leu Ala Ala Arg Asn Cys Met Leu Arg Asp Asp
145                 150                 155                 160

Met Thr Val Cys Val Ala Asp Phe Gly Leu Ser Lys Lys Ile Tyr Ser
                165                 170                 175

Gly Asp Tyr Tyr Arg Gln Gly Arg Ile Ala Lys Met Pro Val Lys Trp
            180                 185                 190

Ile Ala Ile Glu Ser Leu Ala Asp Arg Val Tyr Thr Ser Lys Ser Asp
        195                 200                 205

Val Trp Ala Phe Gly Val Thr Met Trp Glu Ile Arg Thr Arg Gly Met
    210                 215                 220

Thr Pro Tyr Pro Gly Val Gln Asn His Glu Met Tyr Asp Tyr Leu Leu
225                 230                 235                 240

His Gly His Arg Leu Lys Gln Pro Glu Asp Cys Leu Asp Glu Leu Tyr
                245                 250                 255

Glu Ile Met Tyr Ser Cys Trp Arg
            260
```

```
<210> SEQ ID NO 6
<211> LENGTH: 265
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 6

Ala Leu Asn Pro Glu Leu Val Gln Ala Val Gln His Val Val Ile Gly
1               5                   10                  15

Pro Ser Ser Leu Ile Val His Phe Asn Glu Val Ile Gly Arg Gly His
            20                  25                  30

Phe Gly Cys Val Tyr His Gly Thr Leu Leu Asp Asn Asp Gly Lys Lys
        35                  40                  45

Ile His Cys Ala Val Lys Ser Leu Asn Arg Ile Thr Asp Ile Gly Glu
    50                  55                  60

Val Ser Gln Phe Leu Thr Glu Gly Ile Ile Met Lys Asp Phe Ser His
65                  70                  75                  80

Pro Asn Val Leu Ser Leu Leu Gly Ile Cys Leu Arg Ser Glu Gly Ser
                85                  90                  95

Pro Leu Val Val Leu Pro Tyr Met Lys His Gly Asp Leu Arg Asn Phe
            100                 105                 110

Ile Arg Asn Glu Thr His Asn Pro Thr Val Lys Asp Leu Ile Gly Phe
        115                 120                 125

Gly Leu Gln Val Ala Lys Gly Met Lys Tyr Leu Ala Ser Lys Lys Phe
    130                 135                 140

Val His Arg Asp Leu Ala Ala Arg Asn Cys Met Leu Asp Glu Lys Phe
145                 150                 155                 160

Thr Val Lys Val Ala Asp Phe Gly Leu Ala Arg Asp Met Tyr Asp Lys
                165                 170                 175

Glu Tyr Tyr Ser Val His Asn Lys Thr Gly Ala Lys Leu Pro Val Lys
            180                 185                 190

Trp Met Ala Leu Glu Ser Leu Gln Thr Gln Lys Phe Thr Thr Lys Ser
        195                 200                 205

Asp Val Trp Ser Phe Gly Val Leu Leu Trp Glu Leu Met Thr Arg Gly
    210                 215                 220

Ala Pro Pro Tyr Pro Asp Val Asn Thr Phe Asp Ile Thr Val Tyr Leu
225                 230                 235                 240

Leu Gln Gly Arg Arg Leu Leu Gln Pro Glu Tyr Cys Pro Asp Pro Leu
                245                 250                 255

Tyr Glu Val Met Leu Lys Cys Trp His
            260                 265

<210> SEQ ID NO 7
<211> LENGTH: 258
<212> TYPE: PRT
<213> ORGANISM: Artificial Sequence
<220> FEATURE:
<223> OTHER INFORMATION: Description of Artificial Sequence; note =
      synthetic construct

<400> SEQUENCE: 7

Glu Val Ala Arg Glu Lys Ile Thr Met Ser Arg Glu Leu Gly Gln Gly
1               5                   10                  15

Ser Phe Gly Met Val Tyr Glu Gly Val Ala Lys Gly Val Val Lys Asp
            20                  25                  30
```

```
Glu Pro Glu Thr Arg Val Ala Ile Lys Thr Val Asn Glu Ala Ala Ser
    35                  40                  45

Met Arg Glu Arg Ile Glu Phe Leu Asn Glu Ala Ser Val Met Lys Glu
    50                  55                  60

Phe Asn Cys His His Val Val Arg Leu Leu Gly Val Val Ser Gln Gly
65                  70                  75                  80

Gln Pro Thr Leu Val Ile Met Glu Leu Met Thr Arg Gly Asp Leu Lys
                85                  90                  95

Ser Tyr Leu Arg Ser Leu Arg Pro Glu Met Glu Asn Asn Pro Val Leu
                100                 105                 110

Ala Pro Pro Ser Leu Ser Lys Met Ile Gln Met Ala Gly Glu Ile Ala
            115                 120                 125

Asp Gly Met Ala Tyr Leu Asn Ala Asn Lys Phe Val His Arg Asp Leu
    130                 135                 140

Ala Ala Arg Asn Cys Met Val Ala Glu Asp Phe Thr Val Lys Ile Gly
145                 150                 155                 160

Asp Phe Gly Met Thr Arg Asp Ile Tyr Glu Thr Asp Tyr Tyr Arg Lys
                165                 170                 175

Gly Gly Lys Gly Leu Leu Pro Val Arg Trp Met Ser Pro Glu Ser Leu
                180                 185                 190

Lys Asp Gly Val Phe Thr Thr Tyr Ser Asp Val Trp Ser Phe Gly Val
    195                 200                 205

Val Leu Trp Glu Ile Ala Thr Leu Ala Glu Gln Pro Tyr Gln Gly Leu
        210                 215                 220

Ser Asn Glu Gln Val Leu Arg Phe Val Met Glu Gly Gly Leu Leu Asp
225                 230                 235                 240

Lys Pro Asp Asn Cys Pro Asp Met Leu Phe Glu Leu Met Arg Met Cys
                245                 250                 255

Trp Gln
```